US009783806B2

(12) United States Patent
Butler et al.

(10) Patent No.: US 9,783,806 B2
(45) Date of Patent: Oct. 10, 2017

(54) TMPRSS6 IRNA COMPOSITIONS AND METHODS OF USE THEREOF

(71) Applicant: Alnylam Pharmaceuticals, Inc., Cambridge, MA (US)

(72) Inventors: James Butler, Lynnfield, MA (US); Brian Bettencourt, Groton, MA (US); Kallanthottathil G. Rajeev, Wayland, MA (US); Martin Maier, Belmont, MA (US); Klaus Charisse, Acton, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/947,025

(22) Filed: Nov. 20, 2015

(65) Prior Publication Data

US 2016/0145629 A1 May 26, 2016

Related U.S. Application Data

(63) Continuation of application No. PCT/US2014/039149, filed on May 22, 2014.

(60) Provisional application No. 61/912,988, filed on Dec. 6, 2013, provisional application No. 61/826,178, filed on May 22, 2013.

(51) Int. Cl.
| | | |
|---|---|---|
| *C07H 21/02* | (2006.01) | |
| *C07H 21/04* | (2006.01) | |
| *A61K 48/00* | (2006.01) | |
| *C12N 15/113* | (2010.01) | |
| *C12N 9/64* | (2006.01) | |

(52) U.S. Cl.
CPC ........ *C12N 15/1138* (2013.01); *C12N 9/6424* (2013.01); *C12N 15/1137* (2013.01); *C12N 2310/11* (2013.01); *C12N 2310/14* (2013.01); *C12N 2310/315* (2013.01); *C12N 2310/316* (2013.01); *C12N 2310/321* (2013.01); *C12N 2310/322* (2013.01); *C12N 2310/343* (2013.01); *C12N 2310/351* (2013.01); *C12N 2310/3521* (2013.01); *C12N 2310/3533* (2013.01); *C12N 2320/30* (2013.01)

(58) Field of Classification Search
CPC .... C12N 2310/11; C12N 15/113; A61K 48/00
See application file for complete search history.

(56) References Cited

U.S. PATENT DOCUMENTS

| | | |
|---|---|---|
| 2007/0093443 A1 | 4/2007 | Madison et al. |
| 2009/0191263 A1 | 7/2009 | Reich et al. |
| 2009/0192104 A1 | 7/2009 | McSwiggen et al. |
| 2014/0194489 A1 | 7/2014 | Bumcrot et al. |
| 2014/0288158 A1 | 9/2014 | Rajeev et al. |

FOREIGN PATENT DOCUMENTS

| | | |
|---|---|---|
| EP | 1752536 A1 | 2/2007 |
| WO | WO-9813526 A1 | 4/1998 |
| WO | WO-2004/045543 A2 | 6/2004 |
| WO | WO-2009073809 A2 | 6/2009 |
| WO | WO-2010033246 A1 | 3/2010 |
| WO | WO-2010148013 A2 | 12/2010 |
| WO | WO-2012135246 A2 | 10/2012 |
| WO | WO-2013070786 A1 | 5/2013 |
| WO | WO-2016085852 A1 | 6/2016 |

OTHER PUBLICATIONS

Elbashir et al. EMBO, 6877-6888, 2001.*
D'Aquino, KE et al., The protein kinase Kin4 inhibits exit from mitosis in response to spindle position defects. Mol Cell. Jul. 22, 2005;19(2):223-34.
Finberg, K et al., Down-regulation of Bmp/Smad signaling by Tmprss6 is required for maintenance of systemic iron homeostasis. Blood. May 6, 2010;115(18):3817-26. doi:10.1182/blood-2009-05-224808. Epub Mar. 3, 2010.
Lakhal, S et al., Regulation of type II transmembrane serine proteinase TMPRSS6 by hypoxia-inducible factors: new link between hypoxia signaling and iron homeostasis. J Biol Chem. Feb. 11, 2011;286(6):4090-7. Epub Oct. 21, 2010.
Maxon et al., Matriptase-2- and proprotein convertase-cleaved forms of hemojuvelin have different roles in the down-regulation of hepcidin expression. J Biol Chem. Dec. 10, 2010;285(50):39021-8. doi:10.1074/jbc.M110.183160. Epub Oct. 11, 2010.
NCBI_NM_153609.2, *Homo sapiens* transmembrane protease, serine 6 (TMPRSS6), mRNA. Nov. 18, 2006. Version available on PRI Apr. 28, 2012 per sequence retreived in International Search Report on May 30, 2012. Retreived on Feb. 26, 2016 at http://www.ncbi.nlm.nih.gov/nuccore/56682967?sat=15&satkey=9882477.
Sisay et al., Identification of the first low-molecular-weight inhibitors of matriptase-2. J Med Chem. Aug. 12, 2010;53(15):5523-35. doi:10.1021/jm100183e.
International Search Report and Written Opinion for International Application No. PCT/US2014/039149, dated Sep. 1, 2014.
GenBank Acession NM_001130556; Aug. 28, 2012 [online] downloaded from: http://www.ncbi.nlm.nih.gov/nuccore/NM_001130556/ on Jan. 30, 2017.
GenBank Acession CU691658 ; Feb. 23, 2008 [online] downloaded from: http://www.ncbi.nlm.nih.gov/nuccore/CU691658 on Jan. 30, 2017.
GenBank Acession CU013044; Oct. 7, 2008 [online] downloaded from: http://www.ncbi.nlm.nih.gov/nuccore/CU013044/ on Jan. 30, 2017.
GenBank Acession AY358398; Oct. 3, 2003 [online] downloaded from: http://www.ncbi.nlm.nih.gov/nuccore/37181920/ on Jan. 30, 2017.

(Continued)

*Primary Examiner* — Amy Bowman
(74) *Attorney, Agent, or Firm* — McCarter & English, LLP; Maria Laccotripe Zacharakis; Deborah L. Nagle

(57) ABSTRACT

The invention relates to RNAi agents, e.g., double-stranded RNAi agents, targeting the TMPRSS6 gene, and methods of using such RNAi agents to inhibit expression of TMPRSS6 and methods of treating subjects having a TMPRSS6 associated disorder, e.g., an iron overload associated disorder, such as β-thalassemia or hemochromatosis.

30 Claims, 19 Drawing Sheets

(56) References Cited

OTHER PUBLICATIONS

GenBank Acession CR456446; Oct. 16, 2008 [online] downloaded from: http://www.ncbi.nlm.nih.gov/nuccore/CR456446/ on Jan. 30, 2017.
GenBank Acession HV848938; Nov. 15, 2012 [online] downloaded from: http://www.ncbi.nlm.nih.gov/nuccore/HV848938 on Jan. 30, 2017.
GenBank Acession HV784394; Nov. 15, 2012 [online] downloaded from: http://www.ncbi.nlm.nih.gov/nuccore/HV784394 on Jan. 30, 2017.
GenBank Acession HI141555; Nov. 2, 2010 [online] downloaded from: http://www.ncbi.nlm.nih.gov/nuccore/HI141555 on Jan. 30, 2017.
GenBank Acession GX268669; Aug. 13, 2010 [online] downloaded from: http://www.ncbi.nlm.nih.gov/nuccore/303211976 on Jan. 30, 2017.
GenBank Acession DM472417; Jan. 21, 2010 [online] downloaded from: http://www.ncbi.nlm.nih.gov/nuccore/DM472417 on Jan. 30, 2017.
GenBank Acession DM180171; Aug. 26, 2009 [online] downloaded from: http://www.ncbi.nlm.nih.gov/nuccore/DM180171 on Jan. 30, 2017.
GenBank Acession DM117477; Jun. 18, 2009 [online] downloaded from: http://www.ncbi.nlm.nih.gov/nuccore/DM117477 on Jan. 30, 2017.
GenBank Acession FB762896; Dec. 18, 2008 [online] downloaded from: http://www.ncbi.nlm.nih.gov/nuccore/FB762896 on Jan. 30, 2017.
GenBank Acession DJ429262; Jun. 11, 2008 [online] downloaded from: http://www.ncbi.nlm.nih.gov/nuccore/DJ429262 on Jan. 30, 2017.
GenBank Acession DI008490; Feb. 21, 2008 [online] downloaded from: http://www.ncbi.nlm.nih.gov/nuccore/DI008490 on Jan. 30, 2017.
GenBank Acession DI066240; Feb. 21, 2008 [online] downloaded from: http://www.ncbi.nlm.nih.gov/nuccore/DI066240 on Jan. 30, 2017.

* cited by examiner

```
SEQ ID NO:1
>gi|56682967|ref|NM_153609.2| Homo sapiens transmembrane protease,
serine 6 (TMPRSS6), mRNA
CTTGAGCCAGACCCAGTCCAGCTCTGGTGCCTGCCCTCTGGTGCGAGCTGACCTGAGATGCACTTCCCTC
CTCTGTGAGCTGTCTCGGCACCCACTTGCAGTCACTGCCGCCTGATGTTGTTACTCTTCCACTCCAAAAG
GATGCCCGTGGCCGAGGCCCCCAGGTGGCTGGCGGGCAGGGGACGGAGGTGATGGCGAGGAAGCGGAG
CCGGAGGGGATGTTCAAGGCCTGTGAGGACTCCAAGAGAAAAGCCCGGGGCTACCTCCGCCTGGTGCCCC
TGTTTGTGCTGCTGGCCCTGCTCGTGCTGGCTTCGGCGGGGGTGCTACTCTGGTATTTCCTAGGGTACAA
GGCGGAGGTGATGGTCAGCCAGGTGTACTCAGGCAGTCTGCGTGTACTCAATCGCCACTTCTCCCAGGAT
CTTACCCGCCGGGAATCTAGTGCCTTCCGCAGTGAAACCGCCAAAGCCCAGAAGATGCTCAAGGAGCTCA
TCACCAGCACCCGCCTGGGAACTTACTACAACTCCAGCTCCGTCTATTCCTTTGGGGAGGGACCCCTCAC
CTGCTTCTTCTGGTTCATTCTCCAAATCCCCGAGCACCGCCGGCTGATGCTGAGCCCCGAGGTGGTGCAG
GCACTGCTGGTGGAGGAGCTGCTGTCCACAGTCAACAGCTCGGCTGCCGTCCCTACAGGGCCGAGTACG
AAGTGGACCCCGAGGGCCTAGTGATCCTGGAAGCCAGTGTGAAAGACATAGCTGCATTGAATTCCACGCT
GGGTTGTTACCGCTACAGCTACGTGGGCCAGGGCCAGGTCCTCCGGCTGAAGGGGCCTGACCACCTGGCC
TCCAGCTGCCTGTGGCACCTGCAGGGCCCAAGGACCTCATGCTCAAACTCCGGCTGGAGTGGACGCTGG
CAGAGTGCCGGGACCGACTGGCCATGTATGACGTGGCCGGGCCCCTGGAGAAGAGGCTCATCACCTCGGT
GTACGGCTGCAGCCGCCAGGAGCCCGTGGTGGAGGTTCTGGCGTCGGGGGCCATCATGGCGGTCGTCTGG
AAGAAGGGCCTGCACAGCTACTACGACCCCTTCGTGCTCTCCGTGCAGCCGGTGGTCTTCCAGGCCTGTG
AAGTGAACCTGACGCTGGACAACAGGCTCGACTCCCAGGGCGTCCTCAGCACCCCGTACTTCCCAGCTA
CTACTCGCCCCAAACCCACTGCTCCTGGCACCTCACGGTGCCCTCTCTGGACTACGGCTTGGCCCTCTGG
TTTGATGCCTATGCACTGAGGAGGCAGAAGTATGATTTGCCGTGCACCCAGGGCAGTGGACGATCCAGA
ACAGGAGGCTGTGTGGCTTGCGCATCCTGCAGCCCTACGCCGAGAGGATCCCCGTGGTGGCCACGGCCGG
GATCACCATCAACTTCACCTCCCAGATCTCCCTCACCGGGCCCGGTGTGCGGGTGCACTATGGCTTGTAC
AACCAGTCGGACCCCTGCCCTGGAGAGTTCCTCTGTTCTGTGAATGGACTCTGTGTCCCTGCCTGTGATG
GGGTCAAGGACTGCCCCAACGGCCTGGATGAGAGAAACTGCGTTTGCAGAGCCACATTCCAGTGCAAAGA
GGACAGCACATGCATCTCACTGCCCAAGGTCTGTGATGGGCAGCCTGATTGTCTCAACGGCAGCGACGAA
GAGCAGTGCCAGGAAGGGGTGCCATGTGGGACATTCACCTTCCAGTGTGAGGACCGGAGCTGCGTGAAGA
AGCCCAACCCGCAGTGTGATGGCGGCCCGACTGCAGGGACGGCTCGGATGAGGAGCACTGTGACTGTGG
CCTCCAGGGCCCCTCCAGCCGCATTGTTGGTGGAGCTGTGTCCTCCGAGGGTGAGTGGCCATGGCAGGCC
AGCCTCCAGGTCGGGGTCGACACATCTGTGGGGGGGCCCTCATCGCTGACCGCTGGGTGATAACAGCTG
CCCACTGCTTCCAGGAGGACAGCATGGCCTCCACGGTGCTGTGGACCGTGTTCCTGGGCAAGGTGTGGCA
GAACTCGCGCTGGCCTGGAGAGGTGTCCTTCAAGGTGAGCCGCCTGCTCCTGCACCCGTACCACGAAGAG
GACAGCCATGACTACGACGTGGCGCTGCTGCAGCTCGACCACCCGGTGGTGCGCTCGGCCGCCGTGCGCC
CCGTCTGCCTGCCCGCGCGCTCCCACTTCTTCGAGCCCGGCCTGCACTGCTGGATTACGGGCTGGGGCGC
CTTGCGCGAGGGCGGCCCCATCAGCAACGCTCTGCAGAAAGTGGATGTGCAGTTGATCCCACAGGACCTG
TGCAGCGAGGTCTATCGCTACCAGGTGACGCCACGCATGCTGTGTGCCGGCTACCGCAAGGGCAAGAAGG
ATGCCTGTCAGGGTGACTCAGGTGGTCCGCTGGTGTGCAAGGCACTCAGTGGCCGCTGGTTCCTGGCGGG
GCTGGTCAGCTGGGGCCTGGGCTGTGGCCGGCCTAACTACTTCGGCGTCTACACCCGCATCACAGGTGTG
ATCAGCTGGATCCAGCAAGTGGTGACCTGAGGAACTGCCCCCCTGCAAAGCAGGGCCCACCTCCTGGACT
CAGAGAGCCCAGGCAACTGCCAAGCAGGGGACAAGTATTCTGGCGGGGGTGGGGGAGAGAGCAGGCC
CTGTGGTGGCAGGAGGTGGCATCTTGTCTCGTCCCTGATGTCTGCTCCAGTGATGGCAGGAGGATGGAGA
AGTGCCAGCAGCTGGGGGTCAAGACGTCCCCTGAGGACCCAGGCCCACACCCAGCCCTTCTGCCTCCCAA
TTCTCTCTCCTCCGTCCCCTTCCTCCACTGCTGCCTAATGCAAGGCAGTGGCTCAGCAGCAAGAATGCTG
GTTCTACATCCCGAGGAGTGTCTGAGGTGCGCCCCACTCTGTACAGAGGCTGTTTGGGCAGCCTTGCCTC
CAGAGAGCAGATTCCAGCTTCGGAAGCCCCTGGTCTAACTTGGGATCTGGAATGGAAGGTGCTCCCATC
GGAGGGGACCCTCAGAGCCCTGGAGACTGCCAGGTGGGCCTGCTGCCACTGTAAGCCAAAAGGTGGGGAA
GTCCTGACTCCAGGGTCCTTGCCCCACCCCTGCCTGCCACCTGGGCCCTCACAGCCCAGACCCTCACTGG
GAGGTGAGCTCAGCTGCCCTTTGGAATAAAGCTGCCTGATCAAAAAAAAAAAAAAAAAAAAAA
```

Figure 8

SEQ ID NO:2
>gi|125656151|ref|NM_027902.2| Mus musculus transmembrane serine
protease 6 (Tmprss6), mRNA
AGTTTCATTGTCGCCCTGGACCTGACAGGAGAGGCCCATGGAACTTGGGGCCACAGGCCACAAGGGACAA
GGGCCAGACACCCCAGCCATGGCTCCAGGCCATTGATCCAACCTAAGCTGGCCAGTTGGGGGTGGAAAGA
CCTTGGCCTGGATAAACAGAGGCCTCCAGGCCTGTGTGCAGGCCCGGCACCTACCTTCCACTCTTGAAGA
TGCCGAGATGTTTCCAGCTCCCTGTTCTACCAGGATGCCCACCACCGAGGTCCCCCAAGCGGCTGATGG
TCAGGGCGATGCGGGTGATGGAGAGGAAGCTGCTGAGCCAGAGGGGAAGTTCAAGCCCCCAAAAAACACC
AAGAGAAAAAACCGGGACTACGTCCGCTTCACGCCACTGTTGCTGGTCTTGGCTGCGCTGGTCTCAGCAG
GGGTCATGCTTTGGTATTTCCTAGGGTACAAAGCGGAAGTGACCGTAAGCCAGGTGTACTCTGGCAGCCT
CCGGGTGCTCAACCGTCATTTCTCCCAGGACCTGGGCCGACGGGAGTCTATTGCTTTCCGCAGTGAATCT
GCCAAAGCCCAGAAGATGCTCCAAGAACTGGTTGCCAGCACCCGCCTGGGTACTTACTACAACTCTAGTT
CTGTCTACTCCTTTGGGGAGGGACCCCTCACCTGCTTCTTCTGGTTTATCCTTGACATCCCTGAGTACCA
GCGACTGACCCTGAGCCCTGAAGTAGTGCGCGAGCTCCTGGTGGATGAGCTACTGTCCAACAGCTCAACC
CTGGCTTCCTATAAGACCGAATATGAGGTGGACCCGGAAGGCCTGGTGATCCTGGAAGCCAGTGTGAACG
ACATAGTCGTACTGAATTCCACGCTGGGCTGTTATCGCTACAGCTATGTGAACCCAGGCCAGGTCCTCCC
ATTGAAGGGGCCTGACCAGCAGACCACAAGCTGCCTGTGGCATCTGCAAGGGCCCGAAGACCTCATGATC
AAAGTGCGGCTGGAGTGGACCCGGGTCGATTGCAGAGACAGGGTGGCGATGTACGACGCAGCTGGGCCCC
TGGAGAAGAGACTTATCACCTCGGTCTATGGGTGCAGCCGCCAGGAACCTGTGATGGAGGTGCTGGCATC
GGGCTCCGTCATGGCCGTGGTGTGGAAAAAGGGCATGCATAGCTACTATGACCCTTTCCTGCTCTCAGTG
AAGTCTGTGGCCTTCCAGGACTGCCAGGTGAACCTGACACTGGAGGGCCGGCTGGACACACAGGGCTTCC
TCCGTACACCCTACTACCCCAGTTACTACTCTCCCAGTACCCACTGCTCCTGGCATCTCACGGTACCCTC
TCTGGACTACGGCTTGGCGCTCTGGTTCGATGCCTACGCACTGAGGAGGCAGAAGTACAACCGACTGTGT
ACTCAGGGCCAGTGGATGATCCAGAACAGGAGGCTGTGTGGCTTCCGTACCCTGCAGCCATATGCTGAGA
GGATCCCCATGGTGGCCTCAGATGGTGTCACCATCAACTTCACCTCCCAGATCTCCCTCACAGGCCCGGG
TGTGCAAGTGTACTACAGCTTGTACAACCAATCAGACCCCTGCCCTGGTGAGTTCCTCTGCTCTGTGAAT
GGACTGTGTGTCCCTGCGTGTGACGGGATCAAGGACTGCCCCAATGGCCTGGATGAGAGAAACTGTGTCT
GCAGAGCCATGTTCCAGTGCCAAGAGGACAGCACGTGCATTTCACTGCCTAGAGTCTGTGACCGGCAGCC
CGACTGTCTCAATGGCAGTGACGAAGAACAGTGCCAAGAAGGAGTGCCCTGTGGGACATTCACTTTCCAG
TGTGAGGACCGGAGCTGTGTGAAGAAGCCCAACCCAGAGTGTGACGGCCAGTCAGATTGCAGAGACGGCT
CAGATGAGCAACACTGTGACTGTGGCCTCCAGGGCCTCTCCAGCCGTATTGTGGGCGGGACCGTGTCCTC
CGAGGGTGAGTGGCCATGGCAGGCCAGCCTCCAGATTCGGGGTCGACACATCTGTGGGGGGCTCTCATC
GCTGACCGCTGGGTCATAACGGCCGCCCACTGCTTCCAGGAGGACAGCATGGCCTCCCCGAAGCTGTGGA
CCGTGTTCCTGGGAAAGATGCGGCAGAACTCGCGCTGGCCAGGCGAGGTGTCCTTCAAGGTGAGCCGTCT
GTTCCTGCACCCGTACCACGAGGAGGACAGCCATGACTACGACGTGGCCCTGCTGCAGCTCGACCACCCC
GTGGTGTACTCGGCCACTGTGCGCCCGTCTGCCTGCCTGCCCGCTCCCACTTCTTTGAGCCAGGCCAGC
ACTGCTGGATCACAGGCTGGGGAGCCCAGCGAGAGGGTGGTCCGGTGAGCAACACCCTGCAGAAGGTGGA
CGTACAGCTGGTCCCTCAGGACCTCTGCAGTGAGGCCTACCGCTACCAGGTGTCCCCACGCATGCTCTGT
GCTGGCTACCGCAAGGGCAAGAAAGATGCCTGCCAGGGTGACTCTGGAGGCCCACTGGTTTGCAGGGAGC
CCAGTGGCCGCTGGTTCCTGGCAGGGTTGGTTAGCTGGGGCCTGGGCTGTGGCCGACCCAATTTCTTTGG
CGTCTACACCCGTGTCACACGTGTGATCAACTGGATCCAGCAGGTGCTGACCTGAGGGCTGTTCTACAGA
GCTGGACCTGCCTCCAGGCCAAGTTCAGGGTGTCCACCCAGCCAGGACACAAGTATTCTGGGGCAAGTGA
CCCTGCTAAGGCCTGTTTCCCTCAGGCCTACCCCAGTGACAGTACAGAGAAGGATGTCAGCTGGTGGTTA
GGATGCCTCCTGAGGTCCAGGGGCCAGCCTCGGCTAGGTTTCACTTCTAACCCTTTCTTATTCTAGTCCT
TTCCCCTCCCTGCTCCTACCACTGTTTTGGAGTGGGGTCTGGCGGCCATGACCTTGGCCTCCGGGTCTCT
GTAGGAAAGAAAGAATCCTTCCCCTTGCAAAAGCCTCTTGGGGGAACTGCACAGAGAAAGAAGGTGCCTC
TATCAAGGCTCTATCAGAGCCCTTGAGTCTGCCAAGTGGGCTGTACTCTAAGCCAAATCACCGGGCAGCC
TCAGCTGCAGATGCCTGCTGAAGCTCTGCCTGCTACAGGGGCCTCCCTGCCATTCACTGGAGGCCCACTG
TCTGTTCTGGGAATAAAGCACTTGACCAAGCCCTGACACTGAAAAAAAAAAAAAAA

Figure 9

SEQ ID NO:3
>gi|194474097|ref|NM_001130556.1| Rattus norvegicus transmembrane
protease, serine 6 (Tmprss6), mRNA
ATTGTCCGTCCTGGACCTGACAGGAGGCCCATGGAACTTGGGGCCACAGGCCACGAGGGACAAGGGCCAG
ACACCCCAGTCATGGTTCCAGGCTATTGATCCAACCTAAGCTGGCCAGTTGTGGGTGGAGAGACCTTGGC
CTGGATAAACAGAGGCCTCCAGGCCTGTGTTCAGGCCCAGCACCTACCTTCCACTCTTGAAGATGCCAAG
ATGTTTCCAGCTCCCCTGTTCTACCAGGATGCCCACCGCTGAGGTTCCCCAAGCAGCTGGTGGTCAGGGT
GATGGAGGTGATGGAGAGGAAGCTGCAGAGCCAGAGGGGGTGTTCAAGGCCCCAGAAACGCCAAGAGAA
AAGACAGGGACTACGTCCGCTTCACACCACTGTTGCTGGTCTTGGCTGCGTTGGCTTCGGCAGGAGTCAT
GCTCTGGTATTTCCTAGGGTACAAGGCGGAAGTGACCATAAGCCAGGTGTACTCTGGCAGCCTCCGGGTG
CTCAACCGCCATTTTTCACAGGACTTGGCCCGACGGGAGTCTATTGCTTTCCGCACTGAAACTGCCAAAG
CCCAGAAGATGTTCCAAGAGCTGGTTGCCAGCACCCGCTTGGGTACTTACTACAACTCCAGTTCCATCTA
CGCCTTTGGGGAGGGACCCCTTATCTGCTTCTTCTGGTTCATCCTTGACATCCCCGAGTACCAGCGACTG
ACCCTGAGCCCTGAGGTGGTGCGCGAGCTCCTGGTGGGTGAGCTACTGTCCAACAGCTCAGCCTTGGCTT
CCTATAGGACCGAATATGAGGTGGACCCGGAAGGCCTGGTGATACTAGAAGCCAGCGTGAACGACATAGT
CGTACTGAATTCCACGCTGGGCTGTTACCGCTACAGCTACGTGAACCCGGGCCAGGTCCTCCGGTTGAGG
GGGCCCGACCAGCAGACCACTAGCTGCCTGTGGCACCTGCAGGGGCCCGAGGACCTCATGCTCAAAGTGC
AGCTAGAGTGGACTCGGGTTGATTGCAGAGACAGGGTGGCGATGTACGACGCAGCTGGGCCCCTGGAGAA
GAGACTTATCACCTCGGTCTATGGGTGCAGCCGCCAGGAACCCGTGATGGAGGTGCTGGCGTCGGGCTCT
GTCATGGCCGTGGTGTGGAAGAAGGGCTTGCATAGCTTCTATGACCCTTTTCTGCTCTCAGTGAAGTCTG
TGGCCTTCCAGGACTGCCAGGTGAACCTGACCCTGGAAGGCCGGCTGGATCCACAGGGCTTCCTCCGTAC
ACCCTACTACCCCAGTTACTACTCGCCCAGTACCCACTGCTCCTGGCATCTCACGGTTCCCTCTCTGGAC
TATGGCTTGGCACTCTGGTTTGACGCCTATGCACTGAGGAGGCAGAAGTACAACCTACTATGTACTCAGG
GCCAGTGGATGATCCAGAACAGGAGGCTATGTGGCTTCCGTACCCTGCAGCCATATGCTGAGAGGATCCC
CGTGGTGGCCTCGGATGGTATCACCATCAACTTCACCTCCCAGATCTCCCTCACAGGCCCGGGTGTGCAA
GTGTACTACAGCTTGTACAACCAATCAGACCCCTGCCCTGGAGAGTTCCTCTGCTCTGTGAATGGATTGT
GTGTCCCTGCTTGTGACGGAATCAAGGACTGCCCCAACGGCCTGGATGAGAGGAACTGTGTCTGCAGAGC
CATGTTCCAGTGCCAAGAGGACAGCACGTGCATCTCACTGCCGAGAGTCTGTGACCGGCAGCCCGACTGT
CTCAATGGTAGCGACGAAGAGCAGTGCCAAGAAGGAGTGCCCTGTGGGACATTCACTTTCCAGTGTGAGG
ACCGGAGCTGTGTGAAGAAGCCCAACCCCGAGTGTGACGGGCAGGCAGACTGCAGGGATGGCTCGGATGA
GGAGCACTGTGACTGTGGCCTCCAGGGCCCCTCCAGCCGCATTGTGGGCGGGGCCATGTCCTCGGAGGGT
GAGTGGCCCTGGCAGGCCAGTCTCCAGATTCGGGGTCGACACATCTGTGGGGGGGCTCTCATCGCTGACC
GCTGGGTCATAACAGCCGCTCACTGCTTCCAGGAGGACAGCATGGCCTCCCCGAGGCTGTGGACCGTGTT
TCTGGGAAAGATCGGCAGAATTCACGCTGGCCGGGCGAGGTGTCCTTCAAGGTGAGCCGCCTGTTCCTG
CACCCGTATCATGAGGAGGACAGCCATGACTACGACGTGGCCCTGCTGCAGCTGGACCACCCTGTGGTGT
ACTCGGCCACCGTGCGCCCCGTCTGCCTGCCCGCACGCTCTCACTTCTTTGAGCCAGGCCAGCACTGCTG
GATCACAGGCTGGGGAGCCCAGCGAGAGGGTGGTCCTGGTAGCAGCACCCTTCAGAAGGTGGATGTGCAA
CTGATCCCTCAGGACCTGTGCAATGAGGCCTACCGTTACCAGGTGACCCCACGCATGCTCTGTGCTGGTT
ATCGCAAGGGCAAGAAAGATGCCTGCCAGGGCGACTCTGGAGGCCCACTGGTTTGCAAGGAGCCCAGGTG
ACCACCCAGCCAGGGCACAAGTATTCTGGGGCGAGCGACCCTGCTAAGGCCTGTCCCCTCATGCCTACCC
CAGGGACAGTACAGAGAAGGATGTCAGCTGGTGGTTAGGATGCCTCCAGGGGCTAGCCTCAGCTCGGCTT
CACTTCCAACCCTTTCTTATTCTAGTCCTTTCCCCTCTCCCCTCCTACTGCTGTTTTGGGGTGGGGTCTG
GTGGCAATGATGCTGGTTCCAAGGTCTGTGGGAAAGTAAGATTCCTTCCCCTTGCAAAAGCCTCTAGGGG
GAACTGGATCCGAGAAAGAAGGTGCCTCTATCAAGGCTCTGTCAGAGCCCTTGAGACTGCCAAGTAGGGC
CATACCGTAAGCCAAATCATGGGGCAGCCTCAGCTGCGGGTGCCTGCTGTGCTCTGCCTGCTACAGGGCC
CTCCCTGCCATTCACTGGAGCCCACTGTCTGTTCCGGAAATAAAGCAGTTGGCCAAGC

Figure 10

SEQ ID NO:4
>gi|297260989|ref|XM_001085203.2| PREDICTED: Macaca mulatta
transmembrane protease, serine 6, transcript variant 3 (TMPRSS6), mRNA
CAGGATGCCTGTGGCCAAGGCCCCCCAGGTGGCTGGTGGGCAGGGGGACGGAGGTGATGGCGAGGAAGCG
GAGCCAGAGGGGATGTTCGAGGCCCGTGAGGACTCCAAGAGAAAAGCCCGGGGCTACCTCCGCCTGGCGC
CCCTGTGGCTGACCCTGGTTGTGCTGACTTCAGTGGGGGTGCTACTCTGGTATTTCCTAGGGTACAAGGC
GGAGGTGACGGTCAGCCAGGTGTACTCAGGCAGCCTGCGCGTGCTCAATCGCCACTTCTCCCAGGATCTT
ACCCGCCGGGAATCCAGTGCCTTCCGCAGTGAAACCGCCAAAGCCCAGAAGATGCTCAAGGAGCTCATCG
CCAGCACCCGCCTGGGAACTTATTACAACTCCAGCTCCGTCTATTCCTTTGGGGAGGGACCGCTCACCTG
CTTCTTCTGGTTCATTCTCCAAATCCCCGAGCACCGCCGGCTGATGCTGAGCCCCGAGGTGGTGCAGGCA
CTGCTGGTGGAGGAGCTGCTGTCCACAGTCAACAGCTCGGCGGCTGTCCCCTACAGGGCCGAGTACGAAG
TGGACCCCGAGGGCCTAGTGATCCTAGAAGCCAGTGTGAAAGACATAGCTGCACTGAATTCCACGCTGGG
TTGTTACCGCTACAGCTACGTGGGCCAGGGTCAGGTCCTCCGGCTGAAGGGACCCGACCACCTGGCCTCC
AGCTGCCTGTGGCACCTGCAGGGCCCCGAAGACCTCATGCTGAAACTCCGGCTGGAGTGGACGCTGGCCG
AGTGCCGGGACCGACTGGCCATGTATGACGTGGCTGGGCCCCTGGAGAAGAGGCTCATCACCTCGGTGTA
TGGCTGCAGCCGCCAGGAGCCTGTGGTGGAAGTCCTGGCATCGGGGGCCATCATGGCGGTGGTCTGGAAG
AAGGGCCTGCACAGCTACTACGACCCCTTTATGCTCTCCGTGCAGTCGGTGGTCTTCCAGGCCTGCGAGG
TAAACCTGACGCTGGATGACAGGCTGGACTCCCAGGGCGTCCTCAGCACCCCGTACTTCCCCAGCTACTA
CTCGCCCCGAACCCACTGCTCCTGGCACCTCACGGTGCCCTCTCTGGACTACGGCTTGGCCCTCTGGTTT
GACGCCTACGCACTGCGGAGGCAGAAGTATGATTTGCCGTGCACCCAGGGCCAGTGGACGATCCAGAACA
GGAGGCTGTGTGGCCTGCGCATCCTGCAGCCTTACGCCGAGAGGATCCCCGTGGTGGCCACGGCCGGCAT
CACCATCAATTTCACCTCCCAGATCTCCCTCACAGGGCCTGGTGTGCGGGTGCACTATGGCTTGTACAAC
CAGTCGGACCCCTGCCCTGGAGAGTTCCTCTGCTCTGTGAACGGACTCTGCGTCCCTGCCTGTGATGGGG
TCAAGGACTGCCCCAACGGCCTGGATGAGAGAAACTGCGTTTGCAGAGCCACATTCCAGTGCCAAGAGGA
CAGCACGTGCATCTCACTGCTTAAGGTCTGTGACGGGCAGCCTGACTGTCTCAACGGCAGCGATGAAGAG
CGGTGCCAGGAAGGGGTGCCCTGCGGGACATTCACCTTCCAGTGTGAGGACCAGAGCTGCGTGAAGAAGC
CCAACCCACAGTGTGATGGGCGGCCCGACTGCAGGGACGGCTCAGACGAGCAGCACTGTGACTGTGGCCT
CCAGGGCCCCTCCAGTCGCATTGTTGGTGGGGCCGTGTCCTCCGAGGGTGAGTGGCCATGGCAGGCCAGC
CTCCAGGTTCGGGGTCGACACATCTGTGGGGCGCCCTCATCGCTGACCGCTGGGTGATAACAGCTGCCC
ATTGCTTCCAGGAGGACAGCATGGCCTCCCCGGCGCTGTGGACGGTGTTCCTGGGCAAGGTGTGGCAGAA
CTCGCGCTGGCCTGGAGAGGTGTCCTTCAAGGTGAGCCGCCTACTCCTGCATCCGTATCACGAAGAGGAC
AGCCACGACTACGACGTGGCGCTGTTGCAGCTCGACCACCCGGTGGTGCGCTCGGCCGCCGTGCGTCCAG
TCTGCCTGCCCGCGCGCTCCCACTTCTTCGAACCCGGCCTGCACTGCTGGATCACTGGCTGGGGCGCCCT
GCGCGAAGGCGGCCCCACCAGCAATGCTCTGCAGAAAGTGGACGTGCAGTTGATCCCACAGGACCTGTGC
AGCGAGGCCTATCGCTACCAGGTGACGCCACGCATGCTGTGTGCCGGCTACCGCAAGGGCAAGAAGGATG
CCTGCCAGGGTGACTCGGGTGGTCCGCTGGTATGCAAGGCACTCAGTGGCCGCTGGTTCCTGGCAGGGCT
GGTCAGCTGGGGCCTGGGCTGTGGCCGGCCTAACTACTTCGGCGTCTACACCCGCATCACAGGTGTGATC
GGCTGGATCCAGCAAGTGGTGACCTGAGGAACTGCCCCCCTGCAGAGCAGGTCCCACCTC

Figure 11

SEQ ID NO:5
>gi|109094061|ref|XM_001085319.1| PREDICTED: Macaca mulatta similar to
transmembrane protease, serine 6, transcript variant 4 (LOC696094), mRNA
CTTGAGCCACACCCAGTCCAGCTCTGGTGCCTGCCCTCTGGGGTGAGCTGCCTTGAGATGCACTTCGCTC
CTCTGTGAACTGTCTCGGCACCCACTTCCGGTCACTGCCGCCTGATGTTGTTACTCTTCCACTCTGAAAG
GATGCCTGTGGCCAAGGCCCCCAGGTGGCTGGTGGGCAGGGGACGGAGGTGATGGCGAGGAAGCGGAG
CCAGAGGGGATGTTCGAGGCCCGTGAGGACTCCAAGAGAAAAGCCCGGGGCTACCTCCGCCTGGCGCCCC
TGTGGCTGACCCTGGTTGTGCTGACTTCAGTGGGGGTGCTACTCTGGTATTTCCTAGGGTACAAGGCGGA
GGTGACGGTCAGCCAGGTGTACTCAGGCAGCCTGCGCGTGCTCAATCGCCACTTCTCCCAGGATCTTACC
CGCCGGGAATCCAGTGCCTTCCGCAGTGAAACCGCCAAAGCCCAGAAGATGCTCAAGGAGCTCATCGCCA
GCACCCGCCTGGGAACTTATTACAACTCCAGCTCCGTCTATTCCTTTGGGGAGGGACCGCTCACCTGCTT
CTTCTGGTTCATTCTCCAAATCCCCGAGCACCGCCGGCTGATGCTGAGCCCCGAGGTGGTGCAGGCACTG
CTGGTGGAGGAGCTGCTGTCCACAGTCAACAGCTCGGCGGCTGTCCCCTACAGGGCCGAGTACGAAGTGG
ACCCCGAGGGCCTAGTGATCCTAGAAGCCAGTGTGAAAGACATAGCTGCACTGAATTCCACGCTGGGTTG
TTACCGCTACAGCTACGTGGGCCAGGGTCAGGTCCTCCGGCTGAAGGGACCCGACCACCTGGCCTCCAGC
TGCCTGTGGCACCTGCAGGGCCCCGAAGACCTCATGCTGAAACTCCGGCTGGAGTGGACGCTGGCCGAGT
GCCGGGACCGACTGGCCATGTATGACGTGGCTGGGCCCTGGAGAAGAGGCTCATCACCTCGGTGTATGG
CTGCAGCCGCCAGGAGCCTGTGGTGGAAGTCCTGGCATCGGGGGCCATCATGGCGGTGGTCTGGAAGAAG
GGCCTGCACAGCTACTACGACCCCTTTATGCTCTCCGTGCAGTCGGTGGTCTTCCAGGCCTGCGAGGTAA
ACCTGACGCTGGATGACAGGCTGGACTCCCAGGGCGTCCTCAGCACCCCGTACTTCCCCAGCTACTACTC
GCCCCGAACCCACTGCTCCTGGCACCTCACGGTGCCCTCTCTGGACTACGGCTTGGCCCTCTGGTTTGAC
GCCTACGCACTGCGGAGGCAGAAGTATGATTTGCCGTGCACCCAGGGCAGTGGACGATCCAGAACAGGA
GGCTGTGTGGCCTGCGCATCCTGCAGCCTTACGCCGAGAGGATCCCCGTGGTGGCCACGGCCGGCATCAC
CATCAATTTCACCTCCCAGATCTCCCTCACAGGGCCTGGTGTGCGGGTGCACTATGGCTTGTACAACCAG
TCGGACCCCTGCCCTGGAGAGTTCCTCTGCTCTGTGAACGGACTCTGCGTCCCTGCCTGTGATGGGGTCA
AGGACTGCCCCAACGGCCTGGATGAGAGAAACTGCGTTTGCAGAGCCACATTCCAGTGCCAAGAGGACAG
CACGTGCATCTCACTGCTTAAGGTCTGTGACGGGCAGCCTGACTGTCTCAACGGCAGCGATGAAGAGCGG
TGCCAGGAAGGGGTGCCCTGCGGGACATTCACCTTCCAGTGTGAGGACCAGAGCTGCGTGAAGAAGCCCA
ACCCACAGTGTGATGGGCGGCCCGACTGCAGGGACGGCTCAGACGAGCAGCACTGTGACTGTGGCCTCCA
GGGCCCCTCCAGTCGCATTGTTGGTGGGGCCGTGCCTCCGAGGGTGAGTGGCCATGGCAGGCCAGCCTC
CAGGTTCGGGGTCGACACATCTGTGGGGCGCCCTCATCGCTGACCGCTGGGTGATAACAGCTGCCCATT
GCTTCCAGGAGGACAGCATGGCCTCCCCGGCGCTGTGGACGGTGTTCCTGGGCAAGGTGTGGCAGAACTC
GCGCTGGCCTGGAGAGGTGTCCTTCAAGGTGAGCCGCCTACTCCTGCATCCGTATCACGAAGAGGACAGC
CACGACTACGACGTGGCGCTGTTGCAGCTCGACCACCCGGTGGTGCGCTCGGCCGCCGTGCGTCCAGTCT
GCCTGCCCGCGCGCTCCCACTTCTTCGAACCCGGCCTGCACTGCTGGATCACTGGCTGGGGCGCCCTGCG
CGAAGGCGGCCCCACCAGCAATGCTCTGCAGAAAGTGGACGTGCAGTTGATCCCACAGGACCTGTGCAGC
GAGGCCTATCGCTACCAGGTGACGCCACGCATGCTGTGTGCCGGCTACCGCAAGGGCAAGAAGGATGCCT
GCCAGGGTGACTCGGGTGGTCCGCTGGTATGCAAGGCACTCAGTGGCCGCTGGTTCCTGGCAGGGCTGGT
CAGCTGGGGCCTGGGCTGTGGCCGGCCTAACTACTTCGGCGTCTACACCCGCATCACAGGTGTGATCGGC
TGGATCCAGCAAGTGGTGACCTGAGGAACTGCCCCCCTGCAGAGCAGGTCCCACCTCTTGGACTCAGAGA
GCCCAGGGCAATTGCCAAGCAGGGGGACAAGTATTCTGGGGGGAGGGGGCGCGAGCAGGCCCTGTGGTG
GCAGGAGGTGGCATCTTGTCTTGTCCCTGATGTCTGCTCCAGTGATGGCAGGAGGATGGAGGAGTGCCAG
CAGCTGGGGGTCAAGACGTCCCCTAGGGACCCAGGCCCACACCCAGCCCTTCTGCCTCCCGATTCTCTCT
CCTCTGTCCCCTTCCTCCACTGCTGCCTATTGCAAGGAAGTGGCTCAGCAGCAAGAATGCTGGCTCTACG
TCCCCAGGAGTGTCTGAGCTGTGCCCCACTCTGTACAGAGGCTGCTTGGGCAGCCTTGCCTCTAGAGAGC
AGATGCCAGCTTCGGAAGCCCCTGGTCTAACTTGGGATCTGGGAATGGAAGGTGCCCCCATAGGAGGGGA
CCCTCACAGCCCCGGGGACTGCCAGGTGGGCCGGCTGCCACCGTAAGCCAAAAAAGGTGGGGAAGCCCTG
ACTCCAAGGTCCTTGCCCCACCCCTGCCTGCCACCTGGCCCCTCACAGCCCAGACCCTCACCGGCAGGTG
AGCTCAGCTGCCCTTTGGAATAAAGCTGCCTGATCCAA

Figure 12

SEQ ID NO:6
Reverse Complement of >gi|56682967|ref|NM_153609.2| Homo sapiens
transmembrane protease, serine 6 (TMPRSS6), mRNA
TTTTTTTTTTTTTTTTTTTTGATCAGGCAGCTTTATTCCAAAGGGCAGCTGAGCTCACCTCCCAGTGAGGG
TCTGGGCTGTGAGGGCCCAGGTGGCAGGCAGGGGTGGGGCAAGGACCCTGGAGTCAGGACTTCCCCACCTTT
TGGCTTACAGTGGCAGCAGGCCCACCTGGCAGTCTCCAGGGCTCTGAGGGTCCCCTCCGATGGGAGCACCTT
CCATTCCCAGATCCCAAGTTAGACCAGGGGCTTCCGAAGCTGGAATCTGCTCTCTGGAGGCAAGGCTGCCCA
AACAGCCTCTGTACAGAGTGGGGCGCACCTCAGACACTCCTCGGGATGTAGAACCAGCATTCTTGCTGCTGA
GCCACTGCCTTGCATTAGGCAGCAGTGGAGGAAGGGGACGGAGGAGAGAGAATTGGGAGGCAGAAGGGCTGG
GTGTGGGCCTGGGTCCTCAGGGGACGTCTTGACCCCAGCTGCTGGCACTTCTCCATCCTCCTGCCATCACT
GGAGCAGACATCAGGGACGAGACAAGATGCCACCTCCTGCCACCACAGGGCCTGCTCTCTCCCCCACCCCCC
GCCAGAATACTTGTCCCCCTGCTTGGCAGTTGCCCTGGGCTCTCTGAGTCCAGGAGGTGGGCCCTGCTTTGC
AGGGGGGCAGTTCCTCAGGTCACCACTTGCTGGATCCAGCTGATCACACCTGTGATGCGGGTGTAGACGCCG
AAGTAGTTAGGCCGGCCACAGCCCAGGCCCCAGCTGACCAGCCCCGCCAGGAACCAGCGGCCACTGAGTGCC
TTGCACACCAGCGGACCACCTGAGTCACCCTGACAGGCATCCTTCTTGCCCTTGCGGTAGCCGGCACACAGC
ATGCGTGGCGTCACCTGGTAGCGATAGACCTCGCTGCACAGGTCCTGTGGGATCAACTGCACATCCACTTTC
TGCAGAGCGTTGCTGATGGGCCGCCCTCGCGCAAGGCGCCCCAGCCCGTAATCCAGCAGTGCAGGCCGGGC
TCGAAGAAGTGGGAGCGCGCGGGCAGGCAGACGGGGCGCACGGCGGCCGAGCGCACCACCGGGTGGTCGAGC
TGCAGCAGCGCCACGTCGTAGTCATGGCTGTCCTCTTCGTGGTACGGGTGCAGGAGCAGGCGGCTCACCTTG
AAGGACACCTCTCCAGGCCAGCGCGAGTTCTGCCACACCTTGCCCAGGAACACGGTCCACAGCACCGTGGAG
GCCATGCTGTCCTCCTGGAAGCAGTGGGCAGCTGTTATCACCCAGCGGTCAGCGATGAGGGCCCCCCCACAG
ATGTGTCGACCCCGAACCTGGAGGCTGGCCTGCCATGGCCACTCACCCTCGGAGGACACAGCTCCACCAACA
ATGCGGCTGGAGGGCCCTGGAGGCCACAGTCACAGTGCTCCTCATCCGAGCCGTCCCTGCAGTCGGGCCGC
CCATCACACTGCGGGTTGGGCTTCTTCACGCAGCTCCGGTCCTCACACTGGAAGGTGAATGTCCCACATGGC
ACCCCTTCCTGGCACTGCTCTTCGTCGCTGCCGTTGAGACAATCAGGCTGCCCATCACAGACCTTGGGCAGT
GAGATGCATGTGCTGTCCTCTTTGCACTGGAATGTGGCTCTGCAAACGCAGTTTCTCTCATCCAGGCCGTTG
GGGCAGTCCTTGACCCCATCACAGGCAGGGACACAGAGTCCATTCACAGAACAGAGGAACTCTCCAGGGCAG
GGGTCCGACTGGTTGTACAAGCCATAGTGCACCCGCACACCGGGCCCGGTGAGGGAGATCTGGGAGGTGAAG
TTGATGGTGATCCCGGCCGTGGCCACCACGGGGATCCTCTCGGCGTAGGGCTGCAGGATGCGCAAGCCACAC
AGCCTCCTGTTCTGGATCGTCCACTGGCCCTGGGTGCACGGCAAATCATACTTCTGCCTCCTCAGTGCATAG
GCATCAAACCAGAGGGCCAAGCCGTAGTCCAGAGAGGGCACCGTGAGGTGCCAGGAGCAGTGGGTTTGGGC
GAGTAGTAGCTGGGGAAGTACGGGGTGCTGAGGACGCCCTGGGAGTCGAGCCTGTTGTCCAGCGTCAGGTTC
ACTTCACAGGCCTGGAAGACCACCGGCTGCACGGAGAGCACGAAGGGGTCGTAGTAGCTGTGCAGGCCCTTC
TTCCAGACGACCGCCATGATGGCCCCCGACGCCAGAACCTCCACCACGGGCTCCTGGCGGCTGCAGCCGTAC
ACCGAGGTGATGAGCCTCTTCTCCAGGGGCCCGGCCACGTCATACATGGCCAGTCGGTCCCGGCACTCTGCC
AGCGTCCACTCCAGCCGGAGTTTGAGCATGAGGTCCTTGGGGCCCTGCAGGTGCCACAGGCAGCTGGAGGCC
AGGTGGTCAGGCCCCTTCAGCCGGAGGACCTGGCCCTGGCCCACGTAGCTGTAGCGGTAACAACCCAGCGTG
GAATTCAATGCAGCTATGTCTTTCACACTGGCTTCCAGGATCACTAGGCCCTCGGGGTCCACTTCGTACTCG
GCCCTGTAGGGACGGCAGCCGAGCTGTTGACTGTGGACAGCAGCTCCTCCACCAGCAGTGCCTGCACCACC
TCGGGGCTCAGCATCAGCCGGCGGTGCTCGGGGATTTGGAGAATGAACCAGAAGAAGCAGGTGAGGGGTCCC
TCCCCAAAGGAATAGACGGAGCTGGAGTTGTAGTAAGTTCCCAGGCGGGTGCTGGTGATGAGCTCCTTGAGC
ATCTTCTGGGCTTTGCGGTTTCACTGCGGAAGGCACTAGATTCCCGGCGGGTAAGATCCTGGGAGAAGTGG
CGATTGAGTACACGCAGACTGCCTGAGTACACCTGGCTGACCATCACCTCCGCCTTGTACCCTAGGAAATAC
CAGAGTAGCACCCCGCCGAAGCCAGCACGAGCAGGGCAGCAGCACAAACAGGGGCACCAGGCGGAGGTAG
CCCCGGGCTTTTCTCTTGGAGTCCTCACAGGCCTTGAACATCCCTCCGGCTCCGCTTCCTCGCCATCACCT
CCGTCCCCTGCCCGCCAGCCACCTGGGGGGCCTCGGCCACGGGCATCCTTTTGGAGTGGAAGAGTAACAAC
ATCAGGCGGCAGTGACTGCAAGTGGGTGCCGAGACAGCTCACAGAGGAGGGAAGTGCATCTCAGGTCAGCTC
GCACCAGAGGGCAGGCACCAGAGCTGGACTGGGTCTGGCTCAAG

Figure 13

SEQ ID NO:7
Reverse Complement of >gi|125656151|ref|NM_027902.2| Mus musculus
transmembrane serine protease 6 (Tmprss6), mRNA
TTTTTTTTTTTTTTCAGTGTCAGGGCTTGGTCAAGTGCTTTATTCCCAGAACAGACAGTGGGCCTCCAGTG
AATGGCAGGGAGGCCCCTGTAGCAGGCAGAGCTTCAGCAGGCATCTGCAGCTGAGGCTGCCCGGTGATTTGG
CTTAGAGTACAGCCCACTTGGCAGACTCAAGGGCTCTGATAGAGCCTTGATAGAGGCACCTTCTTTCTCTGT
GCAGTTCCCCCAAGAGGCTTTTGCAAGGGGAAGGATTCTTTCTTTCCTACAGAGACCCGGAGGCCAAGGTCA
TGGCCGCCAGACCCCACTCCAAAACAGTGGTAGGAGCAGGGAGGGAAAGGACTAGAATAAGAAAGGGTTAG
AAGTGAAACCTAGCCGAGGCTGGCCCCTGGACCTCAGGAGGCATCCTAACCACCAGCTGACATCCTTCTCTG
TACTGTCACTGGGGTAGGCCTGAGGGAAACAGGCCTTAGCAGGGTCACTTGCCCCAGAATACTTGTGTCCTG
GCTGGGTGGACACCCTGAACTTGGCCTGGAGGCAGGTCCAGCTCTGTAGAACAGCCCTCAGGTCAGCACCTG
CTGGATCCAGTTGATCACACGTGTGACACGGGTGTAGACGCCAAAGAAATTGGGTCGGCCACAGCCCAGGCC
CCAGCTAACCAACCCTGCCAGGAACCAGCGGCCACTGGGCTCCTGCAAACCAGTGGGCCTCCAGAGTCACC
CTGGCAGGCATCTTTCTTGCCCTTGCGGTAGCCAGCACAGAGCATGCGTGGGGACACCTGGTAGCGGTAGGC
CTCACTGCAGAGGTCCTGAGGGACCAGCTGTACGTCCACCTTCTGCAGGGTGTTGCTCACCGGACCACCCTC
TCGCTGGGCTCCCCAGCCTGTGATCCAGCAGTGCTGGCCTGGCTCAAAGAAGTGGGAGCGGGCAGGCAGGCA
GACGGGGCGCACAGTGGCCGAGTACACCACGGGGTGGTCGAGCTGCAGCAGGGCCACGTCGTAGTCATGGCT
GTCCTCCTCGTGGTACGGGTGCAGGAACAGACGGCTCACCTTGAAGGACACCTCGCCTGGCCAGCGCGAGTT
CTGCCGCATCTTTCCCAGGAACACGGTCCACAGCTTCGGGGAGGCCATGCTGTCCTCCTGGAAGCAGTGGGC
GGCCGTTATGACCCAGCGGTCAGCGATGAGAGCCCCCCACAGATGTGTCGACCCCGAATCTGGAGGCTGGC
CTGCCATGGCCACTCACCCTCGGAGGACACGGTCCCGCCCACAATACGGCTGGAGAGGCCCTGGAGGCCACA
GTCACAGTGTTGCTCATCTGAGCCGTCTCTGCAATCTGACTGGCCGTCACACTCTGGGTTGGGCTTCTTCAC
ACAGCTCCGGTCCTCACACTGGAAAGTGAATGTCCCACAGGGCACTCCTTCTTGGCACTGTTCTTCGTCACT
GCCATTGAGACAGTCGGGCTGCCGGTCACAGACTCTAGGCAGTGAAATGCACGTGCTGTCCTCTTGGCACTG
GAACATGGCTCTGCAGACACAGTTTCTCTCATCCAGGCCATTGGGGCAGTCCTTGATCCCGTCACACGCAGG
GACACACAGTCCATTCACAGAGCAGAGGAACTCACCAGGGCAGGGGTCTGATTGGTTGTACAAGCTGTAGTA
CACTTGCACACCCGGGCCTGTGAGGGAGATCTGGGAGGTGAAGTTGATGGTGACACCATCTGAGGCCACCAT
GGGGATCCTCTCAGCATATGGCTGCAGGGTACGGAAGCCACACAGCCTCCTGTTCTGGATCATCCACTGGCC
CTGAGTACACAGTCGGTTGTACTTCTGCCTCCTCAGTGCGTAGGCATCGAACCAGAGCGCCAAGCCGTAGTC
CAGAGAGGGTACCGTGAGATGCCAGGAGCAGTGGGTACTGGGAGAGTAGTAACTGGGGTAGTAGGGTGTACG
GAGGAAGCCCTGTGTGTCCAGCCGGCCCTCCAGTGTCAGGTTCACCTGGCAGTCCTGGAAGGCCACAGACTT
CACTGAGAGCAGGAAAGGGTCATAGTAGCTATGCATGCCCTTTTCCACACCACGGCCATGACGGAGCCCGA
TGCCAGCACCTCCATCACAGGTTCCTGGCGGCTGCACCCATAGACCGAGGTGATAAGTCTCTTCTCCAGGGG
CCCAGCTGCGTCGTACATCGCCACCCTGTCTCTGCAATCGACCCGGGTCCACTCCAGCCGCACTTTGATCAT
GAGGTCTTCGGGCCCTTGCAGATGCCACAGGCAGCTTGTGGTCTGCTGGTCAGGCCCCTTCAATGGGAGGAC
CTGGCCTGGGTTCACATAGCTGTAGCGATAACAGCCCAGCGTGGAATTCAGTACGACTATGTCGTTCACACT
GGCTTCCAGGATCACCAGGCCTTCCGGGTCCACCTCATATTCGGTCTTATAGGAAGCCAGGGTTGAGCTGTT
GGACAGTAGCTCATCCACCAGGAGCTCGCGCACTACTTCAGGGCTCAGGGTCAGTCGCTGGTACTCAGGGAT
GTCAAGGATAAACCAGAAGAAGCAGGTGAGGGGTCCCTCCCCAAAGGAGTAGACAGAACTAGAGTTGTAGTA
AGTACCCAGGCGGGTGCTGGCAACCAGTTCTTGGAGCATCTTCTGGGCTTTGGCAGATTCACTGCGGAAAGC
AATAGACTCCCGTCGGCCCAGGTCCTGGGAGAAATGACGGTTGAGCACCCGGAGGCTGCCAGAGTACACCTG
GCTTACGGTCACTTCCGCTTTGTACCCTAGGAAATACCAAAGCATGACCCCTGCTGAGACCAGCGCAGCCAA
GACCAGCAACAGTGGCGTGAAGCGGACGTAGTCCCGGTTTTTTCTCTTGGTGTTTTTGGGGGCTTGAACTT
CCCCTCTGGCTCAGCAGCTTCCTCTCCATCACCCGCATCGCCCTGACCATCAGCCGCTTGGGGGACCTCGGT
GGTGGGCATCCTGGTAGAACAGGGGAGCTGGAAACATCTCGGCATCTTCAAGAGTGGAAGGTAGGTGCCGGG
CCTGCACACAGGCCTGGAGGCCTCTGTTTATCCAGGCCAAGGTCTTTCCACCCCCAACTGGCCAGCTTAGGT
TGGATCAATGGCCTGGAGCCATGGCTGGGGTGTCTGGCCCTTGTCCCTTGTGGCCTGTGGCCCCAAGTTCCA
TGGGCCTCTCCTGTCAGGTCCAGGGCGACAATGAAACT

Figure 14

SEQ ID NO:8
Reverse Complement of >gi|194474097|ref|NM_001130556.1| Rattus
norvegicus transmembrane protease, serine 6 (Tmprss6), mRNA
GCTTGGCCAACTGCTTTATTTCCGGAACAGACAGTGGGCCTCCAGTGAATGGCAGGGAGGGCCCTGTAGCAG
GCAGAGCACAGCAGGCACCCGCAGCTGAGGCTGCCCCATGATTTGGCTTACGGTATGGCCCTACTTGGCAGT
CTCAAGGGCTCTGACAGAGCCTTGATAGAGGCACCTTCTTTCTCGGATCCAGTTCCCCCTAGAGGCTTTTGC
AAGGGGAAGGAATCTTACTTTCCCACAGACCTTGGAACCAGCATCATTGCCACCAGACCCCACCCCAAAACA
GCAGTAGGAGGGGAGAGGGGAAAGGACTAGAATAAGAAAGGGTTGGAAGTGAAGCCGAGCTGAGGCTAGCCC
CTGGAGGCATCCTAACCACCAGCTGACATCCTTCTCTGTACTGTCCCTGGGGTAGGCATGAGGGGACAGGCC
TTAGCAGGGTCGCTCGCCCCAGAATACTTGTGCCCTGGCTGGGTGGTCACCTGGGCTCCTTGCAAACCAGTG
GGCCTCCAGAGTCGCCCTGGCAGGCATCTTTCTTGCCCTTGCGATAACCAGCACAGAGCATGCGTGGGGTCA
CCTGGTAACGGTAGGCCTCATTGCACAGGTCCTGAGGGATCAGTTGCACATCCACCTTCTGAAGGGTGCTGC
TACCAGGACCACCCTCTCGCTGGGCTCCCCAGCCTGTGATCCAGCAGTGCTGGCCTGGCTCAAAGAAGTGAG
AGCGTGCGGGCAGGCAGACGGGGCGCACGGTGGCCGAGTACACCACAGGGTGGTCCAGCTGCAGCAGGGCCA
CGTCGTAGTCATGGCTGTCCTCCTCATGATACGGGTGCAGGAACAGGCGGCTCACCTTGAAGGACACCTCGC
CCGGCCAGCGTGAATTCTGCCGCATCTTTCCCAGAAACACGGTCCACAGCCTCGGGGAGGCCATGCTGTCCT
CCTGGAAGCAGTGAGCGGCTGTTATGACCCAGCGGTCAGCGATGAGAGCCCCCCACAGATGTGTCGACCCC
GAATCTGGAGACTGGCCTGCCAGGGCCACTCACCCTCCGAGGACATGGCCCCGCCCACAATGCGGCTGGAGG
GGCCCTGGAGGCCACAGTCACAGTGCTCCTCATCCGAGCCATCCCTGCAGTCTGCCTGCCCGTCACACTCGG
GGTTGGGCTTCTTCACACAGCTCCGGTCCTCACACTGGAAAGTGAATGTCCCACAGGGCACTCCTTCTTGGC
ACTGCTCTTCGTCGCTACCATTGAGACAGTCGGGCTGCCGGTCACAGACTCTCGGCAGTGAGATGCACGTGC
TGTCCTCTTGGCACTGGAACATGGCTCTGCAGACACAGTTCCTCTCATCCAGGCCGTTGGGGCAGTCCTTGA
TTCCGTCACAAGCAGGGACACACAATCCATTCACAGAGCAGAGGAACTCTCCAGGGCAGGGTCTGATTGGT
TGTACAAGCTGTAGTACACTTGCACACCCGGGCCTGTGAGGGAGATCTGGGAGGTGAAGTTGATGGTGATAC
CATCCGAGGCCACCACGGGGATCCTCTCAGCATATGGCTGCAGGGTACGGAAGCCACATAGCCTCCTGTTCT
GGATCATCCACTGGCCCTGAGTACATAGTAGGTTGTACTTCTGCCTCCTCAGTGCATAGGCGTCAAACCAGA
GTGCCAAGCCATAGTCCAGAGAGGGAACCGTGAGATGCCAGGAGCAGTGGGTACTGGGCGAGTAGTAACTGG
GGTAGTAGGGTGTACGGAGGAAGCCCTGTGGATCCAGCCGGCCTTCCAGGGTCAGGTTCACCTGGCAGTCCT
GGAAGGCCACAGACTTCACTGAGAGCAGAAAAGGGTCATAGAAGCTATGCAAGCCCTTCTTCCACACCACGG
CCATGACAGAGCCCGACGCCAGCACCTCCATCACGGGTTCCTGGCGGCTGCACCCATAGACCGAGGTGATAA
GTCTCTTCTCCAGGGGCCCAGCTGCGTCGTACATCGCCACCCTGTCTCTGCAATCAACCCGAGTCCACTCTA
GCTGCACTTTGAGCATGAGGTCCTCGGGCCCTGCAGGTGCCACAGGCAGCTAGTGGTCTGCTGGTCGGGCC
CCCTCAACCGGAGGACCTGGCCCGGGTTCACGTAGCTGTAGCGGTAACAGCCCAGCGTGGAATTCAGTACGA
CTATGTCGTTCACGCTGGCTTCTAGTATCACCAGGCCTTCCGGGTCCACCTCATATTCGGTCCTATAGGAAG
CCAAGGCTGAGCTGTTGGACAGTAGCTCACCCACCAGGAGCTCGCGCACCACCTCAGGGCTCAGGGTCAGTC
GCTGGTACTCGGGGATGTCAAGGATGAACCAGAAGAAGCAGATAAGGGGTCCCTCCCCAAAGGCGTAGATGG
AACTGGAGTTGTAGTAAGTACCCAAGCGGGTGCTGGCAACCAGCTCTTGGAACATCTTCTGGGCTTTGGCAG
TTTCAGTGCGGAAAGCAATAGACTCCCGTCGGGCCAAGTCCTGTGAAAAATGGCGGTTGAGCACCCGGAGGC
TGCCAGAGTACACCTGGCTTATGGTCACTTCCGCCTTGTACCCTAGGAAATACCAGAGCATGACTCCTGCCG
AAGCCAACGCAGCCAAGACCAGCAACAGTGGTGTGAAGCGGACGTAGTCCCTGTCTTTTCTCTTGGCGTTTC
TGGGGGCCTTGAACACCCCTCTGGCTCTGCAGCTTCCTCTCCATCACCTCCATCACCCTGACCACCAGCTG
CTTGGGGAACCTCAGCGGTGGGCATCCTGGTAGAACAGGGGAGCTGGAAACATCTTGGCATCTTCAAGAGTG
GAAGGTAGGTGCTGGGCCTGAACACAGGCCTGGAGGCCTCTGTTTATCCAGGCCAAGGTCTCTCCACCCACA
ACTGGCCAGCTTAGGTTGGATCAATAGCCTGGAACCATGACTGGGGTGTCTGGCCCTTGTCCCTCGTGGCCT
GTGGCCCCAAGTTCCATGGGCCTCCTGTCAGGTCCAGGACGGACAAT

Figure 15

SEQ ID NO:9
Reverse Complement of >gi|297260989|ref|XM_001085203.2| PREDICTED:
Macaca mulatta transmembrane protease, serine 6, transcript variant 3
(TMPRSS6), mRNA
GAGGTGGGACCTGCTCTGCAGGGGGGCAGTTCCTCAGGTCACCACTTGCTGGATCCAGCCGATCACACCTGT
GATGCGGGTGTAGACGCCGAAGTAGTTAGGCCGGCCACAGCCCAGGCCCCAGCTGACCAGCCCTGCCAGGAA
CCAGCGGCCACTGAGTGCCTTGCATACCAGCGGACCACCCGAGTCACCCTGGCAGGCATCCTTCTTGCCCTT
GCGGTAGCCGGCACACAGCATGCGTGGCGTCACCTGGTAGCGATAGGCCTCGCTGCACAGGTCCTGTGGGAT
CAACTGCACGTCCACTTTCTGCAGAGCATTGCTGGTGGGGCCGCCTTCGCGCAGGGCGCCCCAGCCAGTGAT
CCAGCAGTGCAGGCCGGGTTCGAAGAAGTGGGAGCGCGCGGGCAGGCAGACTGGACGCACGGCGGCCGAGCG
CACCACCGGGTGGTCGAGCTGCAACAGCGCCACGTCGTAGTCGTGGCTGTCCTCTTCGTGATACGGATGCAG
GAGTAGGCGGCTCACCTTGAAGGACACCTCTCCAGGCAGCGCGAGTTCTGCCACACCTTGCCCAGGAACAC
CGTCCACAGCGCCGGGGAGGCCATGCTGTCCTCCTGGAAGCAATGGGCAGCTGTTATCACCCAGCGGTCAGC
GATGAGGGCGCCCCCACAGATGTGTCGACCCCGAACCTGGAGGCTGGCCTGCCATGGCCACTCACCCTCGGA
GGACACGGCCCCACCAACAATGCGACTGGAGGGGCCTGGAGGCCACAGTCACAGTGCTGCTCGTCTGAGCC
GTCCCTGCAGTCGGGCCGCCCATCACACTGTGGGTTGGCTTCTTCACGCAGCTCTGGTCCTCACACTGGAA
GGTGAATGTCCCGCAGGGCACCCCTTCCTGGCACCGCTCTTCATCGCTGCCGTTGAGACAGTCAGGCTGCCC
GTCACAGACCTTAAGCAGTGAGATGCACGTGCTGTCCTCTTGGCACTGGAATGTGGCTCTGCAAACGCAGTT
TCTCTCATCCAGGCCGTTGGGCAGTCCTTGACCCCATCACAGGCAGGGACGCAGAGTCCGTTCACAGAGCA
GAGGAACTCTCCAGGGCAGGGGTCCGACTGGTTGTACAAGCCATAGTGCACCCGCACACCAGGCCCTGTGAG
GGAGATCTGGGAGGTGAAATTGATGGTGATGCCGGCCGTGGCCACCACGGGGATCCTCTCGGCGTAAGGCTG
CAGGATGCGCAGGCCACACAGCCTCCTGTTCTGGATCGTCCACTGGCCCTGGGTGCACGGCAAATCATACTT
CTGCCTCCGCAGTGCGTAGGCGTCAAACCAGAGGGCCAAGCCGTAGTCCAGAGAGGGCACCGTGAGGTGCCA
GGAGCAGTGGGTTCGGGGCGAGTAGTAGCTGGGAAGTACGGGGTGCTGAGGACGCCCTGGGAGTCCAGCCT
GTCATCCAGCGTCAGGTTTACCTCGCAGGCCTGGAAGACCACCGACTGCACGAGAGCATAAAGGGGTCGTA
GTAGCTGTGCAGGCCCTTCTTCCAGACCACCGCCATGATGGCCCCGATGCCAGGACTTCCACCACAGGCTC
CTGGCGGCTGCAGCCATACACCGAGGTGATGAGCCTCTTCTCCAGGGGCCCAGCCACGTCATACATGGCCAG
TCGGTCCCGGCACTCGGCCAGCGTCCACTCCAGCCGGAGTTTCAGCATGAGGTCTTCGGGGCCCTGCAGGTG
CCACAGGCAGCTGGAGGCCAGGTGGTCGGGTCCCTTCAGCCGGAGGACCTGACCCTGGCCCACGTAGCTGTA
GCGGTAACAACCCAGCGTGGAATTCAGTGCAGCTATGTCTTTCACACTGGCTTCTAGGATCACTAGGCCCTC
GGGGTCCACTTCGTACTCGGCCCTGTAGGGGACAGCCGCCGAGCTGTTGACTGTGGACAGCAGCTCCTCCAC
CAGCAGTGCCTGCACCACCTCGGGGCTCAGCATCAGCCGGCGGTGCTCGGGGATTTGGAGAATGAACCAGAA
GAAGCAGGTGAGCGGTCCCTCCCCAAAGGAATAGACGGAGCTGGAGTTGTAATAAGTTCCCAGGCGGGTGCT
GGCGATGAGCTCCTTGAGCATCTTCTGGGCTTTGGCGGTTTCACTGCGGAAGGCACTGGATTCCCGGCGGGT
AAGATCCTGGGAGAAGTGGCGATTGAGCACGCGCAGGCTGCCTGAGTACACCTGGCTGACCGTCACCTCCGC
CTTGTACCCTAGGAAATACCAGAGTAGCACCCCCACTGAAGTCAGCACAACCAGGGTCAGCCACAGGGGCGC
CAGGCGGAGGTAGCCCCGGGCTTTTCTCTTGGAGTCCTCACGGGCCTCGAACATCCCCTCTGGCTCCGCTTC
CTCGCCATCACCTCCGTCCCCTGCCCACCAGCCACCTGGGGGCCTTGGCCACAGGCATCCTG

Figure 16

SEQ ID NO:10
Reverse Complement of >gi|109094061|ref|XM_001085319.1| PREDICTED:
Macaca mulatta similar to transmembrane protease, serine 6, transcript
variant 4 (LOC696094), mRNA
TTGGATCAGGCAGCTTTATTCCAAAGGGCAGCTGAGCTCACCTGCCGGTGAGGGTCTGGGCTGTGAGGGGCC
AGGTGGCAGGCAGGGGTGGGGCAAGGACCTTGGAGTCAGGGCTTCCCCACCTTTTTTGGCTTACGGTGGCAG
CCGGCCCACCTGGCAGTCCCCGGGGCTGTGAGGGTCCCCTCCTATGGGGGCACCTTCCATTCCCAGATCCCA
AGTTAGACCAGGGGCTTCCGAAGCTGGCATCTGCTCTCTAGAGGCAAGGCTGCCCAAGCAGCCTCTGTACAG
AGTGGGGCACAGCTCAGACACTCCTGGGGACGTAGAGCCAGCATTCTTGCTGCTGAGCCACTTCCTTGCAAT
AGGCAGCAGTGGAGGAAGGGGACAGAGGAGAGAGAATCGGGAGGCAGAAGGGCTGGGTGTGGGCCTGGGTCC
CTAGGGGACGTCTTGACCCCCAGCTGCTGGCACTCCTCCATCCTCCTGCCATCACTGGAGCAGACATCAGGG
ACAAGACAAGATGCCACCTCCTGCCACCACAGGGCCTGCTCGCGCCCCCCTCCCCCCAGAATACTTGTCCCC
CTGCTTGGCAATTGCCCTGGGCTCTCTGAGTCCAAGAGGTGGGACCTGCTCTGCAGGGGGGCAGTTCCTCAG
GTCACCACTTGCTGGATCCAGCCGATCACACCTGTGATGCGGGTGTAGACGCCGAAGTAGTTAGGCCGGCCA
CAGCCCAGGCCCCAGCTGACCAGCCCTGCCAGGAACCAGCGGCCACTGAGTGCCTTGCATACCAGCGGACCA
CCCGAGTCACCCTGGCAGGCATCCTTCTTGCCCTTGCGGTAGCCGGCACACAGCATGCGTGGCGTCACCTGG
TAGCGATAGGCCTCGCTGCACAGGTCCTGTGGGATCAACTGCACGTCCACTTTCTGCAGAGCATTGCTGGTG
GGGCCGCCTTCGCGCAGGGCGCCCCAGCCAGTGATCCAGCAGTGCAGGCCGGGTTCGAAGAAGTGGGAGCGC
GCGGGCAGGCAGACTGGACGCACGGCGGCCGAGCGCACCACCGGGTGGTCGAGCTGCAACAGCGCCACGTCG
TAGTCGTGGCTGTCCTCTTCGTGATACGGATGCAGGAGTAGGCGGCTCACCTTGAAGGACACCTCTCCAGGC
CAGCGCGAGTTCTGCCACACCTTGCCCAGGAACACCGTCCACAGCGCCGGGGAGGCCATGCTGTCCTCCTGG
AAGCAATGGGCAGCTGTTATCACCCAGCGGTCAGCGATGAGGGCGCCCCCACAGATGTGTCGACCCCGAACC
TGGAGGCTGGCCTGCCATGGCCACTCACCCTCGGAGGACACGGCCCCACCAACAATGCGACTGGAGGGGCCC
TGGAGGCCACAGTCACAGTGCTGCTCGTCTGAGCCGTCCCTGCAGTCGGGCCGCCCATCACACTGTGGGTTG
GGCTTCTTCACGCAGCTCTGGTCCTCACACTGGAAGGTGAATGTCCCGCAGGGCACCCCTTCCTGGCACCGC
TCTTCATCGCTGCCGTTGAGACAGTCAGGCTGCCCGTCACAGACCTTAAGCAGTGAGATGCACGTGCTGTCC
TCTTGGCACTGGAATGTGGCTCTGCAAACGCAGTTTCTCTCATCCAGGCCGTTGGGGCAGTCCTTGACCCCA
TCACAGGCAGGGACGCAGAGTCCGTTCACAGAGCAGAGGAACTCTCCAGGGCAGGGTCCGACTGGTTGTAC
AAGCCATAGTGCACCCGCACACCAGGCCCTGTGAGGGAGATCTGGAGGTGAAATTGATGGTGATGCCGGCC
GTGGCCACCACGGGGATCCTCTCGGCGTAAGGCTGCAGGATGCGCAGGCCACACAGCCTCCTGTTCTGGATC
GTCCACTGGCCCTGGGTGCACGGCAAATCATACTTCTGCCTCCGCAGTGCGTAGGCGTCAAACCAGAGGGCC
AAGCCGTAGTCCAGAGAGGGCACCGTGAGGTGCCAGGAGCAGTGGGTTCGGGGCGAGTAGTAGCTGGGGAAG
TACGGGGTGCTGAGGACGCCCTGGGAGTCCAGCCTGTCATCCAGCGTCAGGTTTACCTCGCAGGCCTGGAAG
ACCACCGACTGCACGGAGAGCATAAAGGGGTCGTAGTAGCTGTGCAGGCCCTTCTTCAGACCACCGCCATG
ATGGCCCCCGATGCCAGGACTTCCACCACAGGCTCCTGCGGCTGCAGCCATACACCGAGGTGATGAGCCTC
TTCTCCAGGGGCCCAGCCACGTCATACATGGCCAGTCGGTCCCGGCACTCGGCCAGCGTCCACTCCAGCGG
AGTTTCAGCATGAGGTCTTCGGGGCCCTGCAGGTGCCACAGGCAGCTGGAGGCCAGGTGGTCGGGTCCCTTC
AGCCGGAGGACCTGACCCTGGCCCACGTAGCTGTAGCGGTAACAACCCAGCGTGGAATTCAGTGCAGCTATG
TCTTTCACACTGGCTTCTAGGATCACTAGGCCCTCGGGGTCCACTTCGTACTCGGCCCTGTAGGGGACAGCC
GCCGAGCTGTTGACTGTGGACAGCAGCTCCTCCACCAGCAGTGCCTGCACCACCTCGGGGCTCAGCATCAGC
CGGCGGTGCTCGGGGATTTGGAGAATGAACCAGAAGAAGCAGGTGAGCGGTCCCTCCCCAAAGGAATAGACG
GAGCTGGAGTTGTAATAAGTTCCCAGGCGGGTGCTGGCGATGAGCTCCTTGAGCATCTTCTGGGCTTTGGCG
GTTTCACTGCGGAAGGCACTGGATTCCCGGCGGGTAAGATCCTGGGAGAAGTGGCGATTGAGCACGCGCAGG
CTGCCTGAGTACACCTGGCTGACCGTCACCTCCGCCTTGTACCCTAGGAAATACCAGAGTAGCACCCCCACT
GAAGTCAGCACAACCAGGGTCAGCCACAGGGGCGCCAGGCGGAGGTAGCCCCGGGCTTTTCTCTTGGAGTCC
TCACGGGCCTCGAACATCCCCTCTGGCTCCGCTTCCTCGCCATCACCTCCGTCCCCCTGCCCACCAGCCACC
TGGGGGGCCTTGGCCACAGGCATCCTTTCAGAGTGGAAGAGTAACAACATCAGGCGGCAGTGACCGGAAGTG
GGTGCCGAGACAGTTCACAGAGGAGCGAAGTGCATCTCAAGGCAGCTCACCCCAGAGGGCAGGCACCAGAGC
TGGACTGGGTGTGGCTCAAG

Figure 17

TMPRSS6 IRNA COMPOSITIONS AND METHODS OF USE THEREOF

RELATED APPLICATIONS

This application is a 35 §U.S.C. 111(a) continuation application which claims the benefit of priority to PCT/US2014/039149, filed on May 22, 2014, U.S. Provisional Patent Application No. 61/826,178, filed on May 22, 2013, and U.S. Provisional Patent Application No. 61/912,988, filed on Dec. 6, 2013. The entire contents of each of the foregoing patent applications are hereby incorporated herein by reference.

SEQUENCE LISTING

The instant application contains a Sequence Listing which has been submitted electronically in ASCII format and is hereby incorporated by reference in its entirety. Said ASCII copy, created on Nov. 11, 2015, is named Seq_List_00703.txt and is 449,665 bytes in size.

BACKGROUND OF THE INVENTION

TMPRSS6 (Transmembrane Protease, Serine 6) gene encodes TMPRSS6, also known as matriptase-2, a type II serine protease. It is primarily expressed in the liver, although high levels of TMPRSS6 mRNA are also found in the kidney, with lower levels in the uterus and much smaller amounts detected in many other tissues (Ramsay et al., *Haematologica* (2009), 94(6), 840-849). TMPRSS6 plays a role in iron homeostatis by binding and proteolytically degrading the hepcidin activator and BMP co-receptor HJV (hemojuvelin), which causes down-regulation of hepcidin levels.

TMPRSS6 consists of a short N-terminal intracytoplasmic tail, a type II transmembrane domain, a stem region composed of two extracellular CUB (complement factor Cls/Clr, urchin embryonic growth factor and BMP (bone morphogenetic protein)) domains, three LDLR (low-density-lipoprotein receptor class A) domains, and a C-terminal trypsin-like serine protease domain. There are also consensus sites for N-glycosylation in the extracellular domain, and a potential phosphorylation site in the intracytoplasmic tail region.

Numerous disorders can be associated with iron overload, a condition characterized by increased levels of iron. Iron overload can result in excess iron deposition in various tissues and can lead to tissue and organ damage. Accordingly, methods for effective treatment of disorders associated with iron overload are currently needed.

SUMMARY OF THE INVENTION

The present invention provides compositions comprising RNAi agents, e.g., double-stranded iRNA agents, targeting TMPRSS6. The present invention also provides methods using the compositions of the invention for inhibiting TMPRSS6 expression and for treating TMPRSS6 associated disorders, e.g., iron overload associated disorders, such as thalassemia, e.g., β-thalassemia, or hemochromatosis.

Accordingly, in one aspect, the present invention provides RNAi agents, e.g., double-stranded RNAi agents, capable of inhibiting the expression of TMPRSS6 (matriptase-2) in a cell, wherein the double stranded RNAi agent comprises a sense strand and an antisense strand forming a double-stranded region, wherein the sense strand comprises at least 15 contiguous nucleotides differing by no more than 3 nucleotides from any one of the nucleotide sequences of SEQ ID NO:1, SEQ ID NO:2, or SEQ ID NO:3, SEQ ID NO:4, or SEQ ID NO:5, and the antisense strand comprises at least 15 contiguous nucleotides differing by no more than 3 nucleotides from any one of the nucleotide sequences of SEQ ID NO:6, SEQ ID NO:7, or SEQ ID NO:8, SEQ ID NO:9, or SEQ ID NO:10, wherein substantially all of the nucleotides of the sense strand and substantially all of the nucleotides of the antisense strand are modified nucleotides, and wherein the sense strand is conjugated to a ligand attached at the 3'-terminus.

In one embodiment, all of the nucleotides of said sense strand and all of the nucleotides of said antisense strand are modified nucleotides.

In one embodiment, the sense strand and the antisense strand comprise a region of complementarity which comprises at least 15 contiguous nucleotides differing by no more than 3 nucleotides from any one of the antisense sequences listed in any one of Tables 1, 2, 4, 5, 8, 10, and 12.

In one embodiment, at least one of the modified nucleotides is selected from the group consisting of a 3'-terminal deoxy-thymine (dT) nucleotide, a 2'-O-methyl modified nucleotide, a 2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, a non-natural base comprising nucleotide, a nucleotide comprising a 5'-phosphorothioate group, a nucleotide comprising a 5' phosphate or 5' phosphate mimic (see, e.g., PCT Publication No. WO 2011/005860), and a terminal nucleotide linked to a cholesteryl derivative or a dodecanoic acid bisdecylamide group.

In one embodiment, at least one strand comprises a 3' overhang of at least 1 nucleotide. In another embodiment, at least one strand comprises a 3' overhang of at least 2 nucleotides.

In another aspect, the present invention provides RNAi agents, e.g., double-stranded RNAi agents, capable of inhibiting the expression of TMPRSS6 (matriptase-2) in a cell, wherein the double stranded RNAi agent comprises a sense strand complementary to an antisense strand, wherein the antisense strand comprises a region complementary to part of an mRNA encoding TMPRSS6, wherein each strand is about 14 to about 30 nucleotides in length, wherein the double stranded RNAi agent is represented by formula (III):

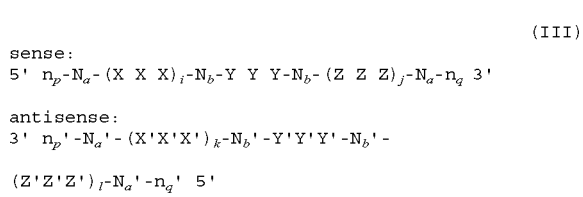

wherein:
i, j, k, and l are each independently 0 or 1;
p, p', q, and q' are each independently 0-6;
each $N_a$ and $N_a'$ independently represents an oligonucleotide sequence comprising 0-25 nucleotides which are either modified or unmodified or combinations thereof, each sequence comprising at least two differently modified nucleotides;
each $N_b$ and $N_b'$ independently represents an oligonucleotide sequence comprising 0-10 nucleotides which are either modified or unmodified or combinations thereof;
each $n_p$, $n_p'$, $n_q$, and $n_q'$, each of which may or may not be present, independently represents an overhang nucleotide;
XXX, YYY, ZZZ, X'X'X', Y'Y'Y', and Z'Z'Z' each independently represent one motif of three identical modifications on three consecutive nucleotides;

modifications on $N_b$ differ from the modification on Y and modifications on $N_b'$ differ from the modification on Y'; and wherein the sense strand is conjugated to at least one ligand.

In one embodiment, i is 0; j is 0; i is 1; j is 1; both i and j are 0; or both i and j are 1. In another embodiment, k is 0; l is 0; k is 1; l is 1; both k and l are 0; or both k and l are 1.

In one embodiment, XXX is complementary to X'X'X', YYY is complementary to Y'Y'Y', and ZZZ is complementary to Z'Z'Z'.

In one embodiment, YYY motif occurs at or near the cleavage site of the sense strand.

In one embodiment, Y'Y'Y' motif occurs at the 11, 12 and 13 positions of the antisense strand from the 5'-end.

In one embodiment, Y is 2'-O-methyl.

In one embodiment, formula (III) is represented by formula (IIIa):

(IIIa)
```
sense:
5'  n_p-N_a-Y Y Y-N_a-n_q  3' antisense:
3'  n_p'-N_a'-Y'Y'Y'-N_a'-n_q'  5'.
```

In another embodiment, formula (III) is represented by formula (IIIb):

(IIIb)
```
sense:
5'  n_p-N_a-Y Y Y-N_b-Z Z Z-N_a-n_q  3' antisense:
3'  n_p'-N_a'-Y'Y'Y'-N_b'-Z'Z'Z'-N_a'-n_q'  5'
``` wherein each $N_b$ and $N_b'$ independently represents an oligonucleotide sequence comprising 1-5 modified nucleotides.

In yet another embodiment, formula (III) is represented by formula (IIIc):

(IIIc)
```
sense:
5'  n_p-N_a-X X X-N_b-Y Y Y-N_a-n_q  3' antisense:
3'  n_p'-N_a'-X'X'X'-N_b'-Y'Y'Y'-N_a'-n_q'  5'
``` wherein each $N_b$ and $N_b'$ independently represents an oligonucleotide sequence comprising 1-5 modified nucleotides.

In one embodiment, formula (III) is represented by formula (IIId):

(IIId)
```
sense:
5'  n_p-N_a-X X X-N_b-Y Y Y-N_b-Z Z Z-N_a-n_q  3' antisense:
3'  n_p'-N_a'-X'X'X'-N_b'-Y'Y'Y'-N_b'-Z'Z'Z'-N_a'-n_q'  5'
``` wherein each $N_b$ and $N_b'$ independently represents an oligonucleotide sequence comprising 1-5 modified nucleotides and each $N_a$ and $N_a'$ independently represents an oligonucleotide sequence comprising 2-10 modified nucleotides.

In one embodiment, the double-stranded region is 15-30 nucleotide pairs in length. In another embodiment, the double-stranded region is 17-23 nucleotide pairs in length. In yet another embodiment, the double-stranded region is 17-25 nucleotide pairs in length. In one embodiment, the double-stranded region is 23-27 nucleotide pairs in length. In another embodiment, the double-stranded region is 19-21 nucleotide pairs in length. In another embodiment, the double-stranded region is 21-23 nucleotide pairs in length. In one embodiment, each strand has 15-30 nucleotides. In another embodiment, each strand has 19-30 nucleotides.

In one embodiment, the modifications on the nucleotides are selected from the group consisting of LNA, HNA, CeNA, 2'-methoxyethyl, 2'-O-alkyl, 2'-O-allyl, 2'-C-allyl, 2'-fluoro, 2'-deoxy, 2'-hydroxyl, and combinations thereof. In another embodiment, the modifications on the nucleotides are 2'-O-methyl or 2'-fluoro modifications.

In one embodiment, the ligand is one or more GalNAc derivatives attached through a bivalent or trivalent branched linker. In another embodiment, the ligand is

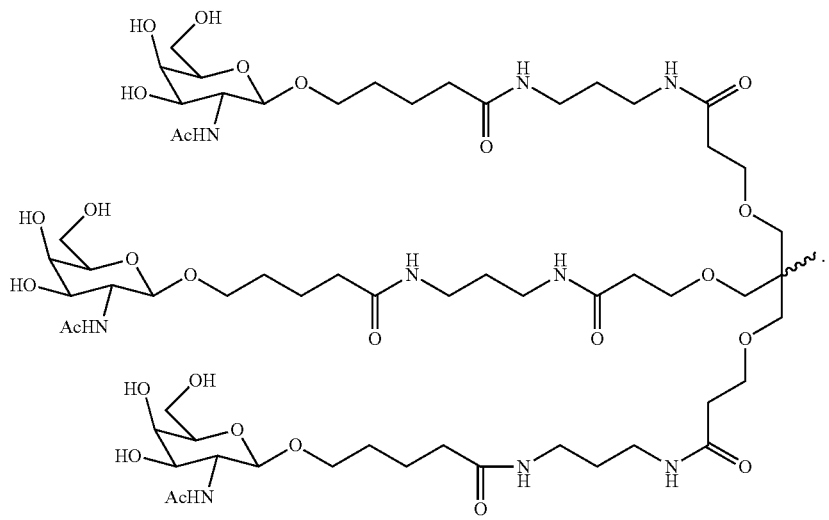 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the ligand is attached to the 3' end of the sense strand.

In one embodiment, the RNAi agent is conjugated to the ligand as shown in the following schematic In one embodiment, q'=0, p=0, q=0, and p' overhang nucleotides are complementary to the target mRNA. In another embodiment, q'=0, p=0, q=0, and p' overhang nucleotides are non-complementary to the target mRNA.

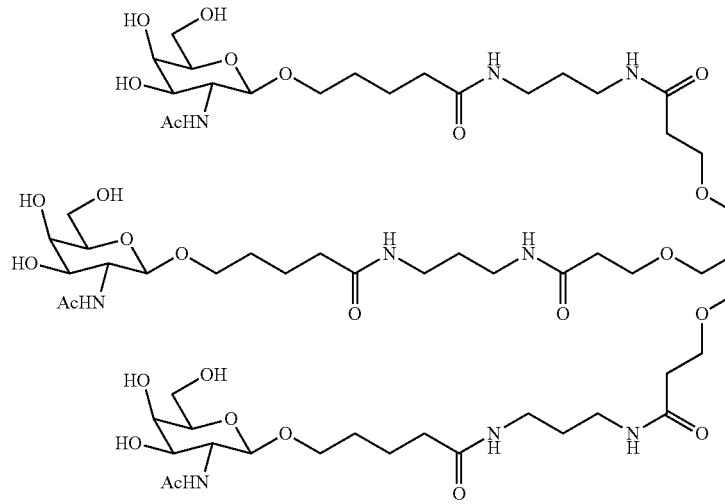

wherein X is O or S. In a specific embodiment, X is O.

In one embodiment, the agent further comprises at least one phosphorothioate or methylphosphonate internucleotide linkage.

In one embodiment, the phosphorothioate or methylphosphonate internucleotide linkage is at the 3'-terminus of one strand. In one embodiment, the strand is the antisense strand. In another embodiment, the strand is the sense strand.

In one embodiment, the phosphorothioate or methylphosphonate internucleotide linkage is at the 5'-terminus of one strand. In one embodiment, the strand is the antisense strand. In another embodiment, the strand is the sense strand.

In one embodiment, the phosphorothioate or methylphosphonate internucleotide linkage is at the both the 5'- and 3'-terminus of one strand. In one embodiment, the strand is the antisense strand.

In one embodiment, the RNAi agent comprises 6-8 phosphorothioate internucleotide linkages.

In one embodiment, the antisense strand comprises two phosphorothioate internucleotide linkages at the 5'-terminus and two phosphorothioate internucleotide linkages at the 3'-terminus, and the sense strand comprises at least two phosphorothioate internucleotide linkages at either the 5'-terminus or the 3'-terminus.

In one embodiment, the base pair at the 1 position of the 5'-end of the antisense strand of the duplex is an AU base pair.

In one embodiment, the Y nucleotides contain a 2'-fluoro modification.

In one embodiment, the Y' nucleotides contain a 2'-O-methyl modification.

In one embodiment, p'>0. In another embodiment, p'=2.

In one embodiment, the sense strand has a total of 21 nucleotides and the antisense strand has a total of 23 nucleotides.

In one embodiment, at least one $n_p$' is linked to a neighboring nucleotide via a phosphorothioate linkage.

In one embodiment, all $n_p$' are linked to neighboring nucleotides via phosphorothioate linkages.

In one embodiment, the RNAi agent is selected from the group of RNAi agents listed in any one of Tables 1, 2, 4, 5, 8, 10, and 12.

In one embodiment, the RNAi agent is AD-59743. In another embodiment, the RNAi agent is AD-60940.

In one aspect, the present invention provides double stranded RNAi agents for inhibiting expression of TMPRSS6 in a cell, wherein the double stranded RNAi agent comprises a sense strand and an antisense strand forming a double stranded region, wherein the sense strand comprises at least 15 contiguous nucleotides differing by no more than 3 nucleotides from any one of the nucleotide sequences of SEQ ID NO:1, SEQ ID NO:2, or SEQ ID NO:3, SEQ ID NO:4, or SEQ ID NO:5, and the antisense strand comprises at least 15 contiguous nucleotides differing by no more than 3 nucleotides from any one of the nucleotide sequences of SEQ ID NO:6, SEQ ID NO:7, or SEQ ID NO:8, SEQ ID NO:9, or SEQ ID NO:10, wherein substantially all of the nucleotides of the sense strand comprise a modification selected from the group consisting of a 2'-O-methyl modification and a 2'-fluoro modification, wherein the sense strand comprises two phosphorothioate internucleotide linkages at the 5'-terminus, wherein substantially all of the nucleotides of the antisense strand comprise a modification selected from the group consisting of a 2'-O-methyl modification and a 2'-fluoro modification, wherein the antisense strand comprises two phosphorothioate internucleotide linkages at the 5'-terminus and two phosphorothioate internucleotide linkages at the 3'-terminus, and wherein the sense strand is conjugated to one or more GalNAc derivatives attached through a branched bivalent or trivalent linker at the 3'-terminus.

In one embodiment, all of the nucleotides of the sense strand and all of the nucleotides of the antisense strand comprise a modification.

In another aspect, the present invention provides RNAi agents, e.g., double stranded RNAi agents, capable of inhibiting the expression of TMPRSS6 (matriptase-2) in a cell, wherein the double stranded RNAi agent comprises a sense strand complementary to an antisense strand, wherein the antisense strand comprises a region complementary to part of an mRNA encoding TMPRSS6, wherein each strand is about 14 to about 30 nucleotides in length, wherein the double stranded RNAi agent is represented by formula (III):

(III)
sense:
5' $n_p$-$N_a$-(X X X)$_i$-$N_b$-Y Y Y-$N_b$-(Z Z Z)$_j$-$N_a$-$n_q$ 3'
antisense:
3' $n_p'$-$N_a'$-(X'X'X')$_k$-$N_b'$-Y'Y'Y'-$N_b'$-
(Z'Z'Z')$_l$-$N_a'$-$n_q'$ 5' wherein:

i, j, k, and l are each independently 0 or 1;

p, p', q, and q' are each independently 0-6;

each $N_a$ and $N_a'$ independently represents an oligonucleotide sequence comprising 0-25 nucleotides which are either modified or unmodified or combinations thereof, each sequence comprising at least two differently modified nucleotides;

each $N_b$ and $N_b'$ independently represents an oligonucleotide sequence comprising 0-10 nucleotides which are either modified or unmodified or combinations thereof;

each $n_p$, $n_p'$, $n_q$, and $n_q'$, each of which may or may not be present independently represents an overhang nucleotide;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b'$ differ from the modification on Y'; and wherein the sense strand is conjugated to at least one ligand.

In yet another aspect, the present invention provides RNAi agents, e.g., double stranded RNAi agents, capable of inhibiting the expression of TMPRSS6 (matriptase-2) in a cell, wherein the double stranded RNAi agent comprises a sense strand complementary to an antisense strand, wherein the antisense strand comprises a region complementary to part of an mRNA encoding TMPRSS6, wherein each strand is about 14 to about 30 nucleotides in length, wherein the double stranded RNAi agent is represented by formula (III):

(III)
sense:
5' $n_p$-$N_a$-(X X X)$_i$-$N_b$-Y Y Y-$N_b$-(Z Z Z)$_j$-$N_a$-$n_q$ 3'
antisense:
3' $n_p'$-$N_a'$-(X'X'X')$_k$-$N_b'$-Y'Y'Y'-$N_b'$-(Z'Z'Z')$_l$-$N_a'$-
$n_q'$ 5' wherein:

i, j, k, and l are each independently 0 or 1;

each $n_p$, $n_q$, and $n_q'$, each of which may or may not be present, independently represents an overhang nucleotide;

p, q, and q' are each independently 0-6;

$n_p'$>0 and at least one $n_p'$ is linked to a neighboring nucleotide via a phosphorothioate linkage;

each $N_a$ and $N_a'$ independently represents an oligonucleotide sequence comprising 0-25 nucleotides which are either modified or unmodified or combinations thereof, each sequence comprising at least two differently modified nucleotides;

each $N_b$ and $N_b'$ independently represents an oligonucleotide sequence comprising 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b'$ differ from the modification on Y'; and wherein the sense strand is conjugated to at least one ligand.

In a further aspect, the present invention provides RNAi agents, e.g., double stranded RNAi agents, capable of inhibiting the expression of TMPRSS6 (matriptase-2) in a cell, wherein the double stranded RNAi agent comprises a sense strand complementary to an antisense strand, wherein the antisense strand comprises a region complementary to part of an mRNA encoding TMPRSS6, wherein each strand is about 14 to about 30 nucleotides in length, wherein the double stranded RNAi agent is represented by formula (III):

(III)
sense:
5' $n_p$-$N_a$-(X X X)$_i$-$N_b$-Y Y Y-$N_b$-(Z Z Z)$_j$-$N_a$-$n_q$ 3'
antisense:
3' $n_p'$-$N_a'$-(X'X'X')$_k$-$N_b'$-Y'Y'Y'-$N_b'$-(Z'Z'Z')$_l$-$N_a'$-
$n_q'$ 5' wherein:

i, j, k, and l are each independently 0 or 1;

each $n_p$, $n_q$, and $n_q'$, each of which may or may not be present, independently represents an overhang nucleotide;

p, q, and q' are each independently 0-6;

$n_p'$>0 and at least one $n_p'$ is linked to a neighboring nucleotide via a phosphorothioate linkage;

each $N_a$ and $N_a'$ independently represents an oligonucleotide sequence comprising 0-25 nucleotides which are either modified or unmodified or combinations thereof, each sequence comprising at least two differently modified nucleotides;

each $N_b$ and $N_b'$ independently represents an oligonucleotide sequence comprising 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b'$ differ from the modification on Y'; and wherein the sense strand is conjugated to at least one ligand, wherein the ligand is one or more GalNAc derivatives attached through a bivalent or trivalent branched linker.

In another aspect, the present invention provides RNAi agents, e.g., double stranded RNAi agents capable of inhibiting the expression of TMPRSS6 (matriptase-2) in a cell, wherein the double stranded RNAi agent comprises a sense strand complementary to an antisense strand, wherein the antisense strand comprises a region complementary to part of an mRNA encoding TMPRSS6, wherein each strand is about 14 to about 30 nucleotides in length, wherein the double stranded RNAi agent is represented by formula (III):

(III)
sense:
5' $n_p$-$N_a$-(X X X)$_i$-$N_b$-Y Y Y-$N_b$-(Z Z Z)$_j$-$N_a$-$n_q$ 3' antisense:
3' $n_p'$-$N_a'$-(X'X'X')$_k$-$N_b'$-Y'Y'Y'-$N_b'$-(Z'Z'Z')$_l$-$N_a'$-$n_q'$ 5' wherein:

i, j, k, and l are each independently 0 or 1;

each $n_p$, $n_q$, and $n_q'$, each of which may or may not be present, independently represents an overhang nucleotide;

p, q, and q' are each independently 0-6;

$n_p'>0$ and at least one $n_p'$ is linked to a neighboring nucleotide via a phosphorothioate linkage;

each $N_a$ and $N_a'$ independently represents an oligonucleotide sequence comprising 0-25 nucleotides which are either modified or unmodified or combinations thereof, each sequence comprising at least two differently modified nucleotides;

each $N_b$ and $N_b'$ independently represents an oligonucleotide sequence comprising 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b'$ differ from the modification on Y';

wherein the sense strand comprises at least one phosphorothioate linkage; and wherein the sense strand is conjugated to at least one ligand, wherein the ligand is one or more GalNAc derivatives attached through a bivalent or trivalent branched linker.

In yet another aspect, the present invention provides RNAi agents, e.g., double stranded RNAi agents, capable of inhibiting the expression of TMPRSS6 (matriptase-2) in a cell, wherein the double stranded RNAi agent comprises a sense strand complementary to an antisense strand, wherein the antisense strand comprises a region complementary to part of an mRNA encoding TMPRSS6, wherein each strand is about 14 to about 30 nucleotides in length, wherein the double stranded RNAi agent is represented by formula (III):

(IIIa)
sense: 5' $n_p$-$N_a$-Y Y Y-$N_a$-$n_q$ 3' antisense: 3' $n_p'$-$N_a'$-Y'Y'Y'-$N_a'$-$n_q'$ 5' wherein:

each $n_p$, $n_q$, and $n_q'$, each of which may or may not be present, independently represents an overhang nucleotide;

p, q, and q' are each independently 0-6;

$n_p'>0$ and at least one $n_p'$ is linked to a neighboring nucleotide via a phosphorothioate linkage;

each $N_a$ and $N_a'$ independently represents an oligonucleotide sequence comprising 0-25 nucleotides which are either modified or unmodified or combinations thereof, each sequence comprising at least two differently modified nucleotides;

YYY and Y'Y'Y' each independently represent one motif of three identical modifications on three consecutive nucleotides, and wherein the modifications are 2'-O-methyl or 2'-fluoro modifications;

wherein the sense strand comprises at least one phosphorothioate linkage; and wherein the sense strand is conjugated to at least one ligand, wherein the ligand is one or more GalNAc derivatives attached through a bivalent or trivalent branched linker.

In one embodiment, the present invention provides RNAi agent selected from the group of RNAi agents listed in any one of Tables 1, 2, 4, 5, 8, 19, and 12.

In one aspect, the present invention provides compositions comprising a modified antisense polynucleotide agent, wherein the agent is capable of inhibiting the expression of TMPRSS6 in a cell, and comprises a sequence complementary to a sense sequence selected from the group of the sequences listed in any one of Tables 1, 2, 4, 5, 8, 10, and 12, wherein the polynucleotide is about 14 to about 30 nucleotides in length.

The present invention also provides cells, vectors, host cells, and pharmaceutical compositions comprising, e.g., the double stranded RNAi agents of the invention.

In some embodiments, the RNAi agent is administered using a pharmaceutical composition.

In preferred embodiments, the RNAi agent is administered in a solution. In some such embodiments, the siRNA is administered in an unbuffered solution. In one embodiment, the siRNA is administered in water. In other embodiments, the siRNA is administered with a buffer solution, such as an acetate buffer, a citrate buffer, a prolamine buffer, a carbonate buffer, or a phosphate buffer or any combination thereof. In some embodiments, the buffer solution is phosphate buffered saline (PBS).

In one embodiment, the pharmaceutical compositions further comprise a lipid formulation. In one embodiment, the lipid formulation comprises a LNP, or XTC. In another embodiment, the lipid formulation comprises a MC3.

In one aspect, the present invention provides methods of inhibiting TMPRSS6 expression in a cell. The methods include contacting the cell with an RNAi agent, e.g., a double stranded RNAi agent, or a modified antisense polynucleotide agent of the invention, or vector of the invention, or a pharmaceutical composition of the invention; and maintaining the cell produced in step (a) for a time sufficient to obtain degradation of the mRNA transcript of a TMPRSS6 gene, thereby inhibiting expression of the TMPRSS6 gene in the cell.

In one embodiment, the cell is within a subject.

In one embodiment, the subject is a human.

In one embodiment, the TMPRSS6 expression is inhibited by at least about 30%, 35%, 40%, 45%, 50%, 55%, 60%, 65%, 70%, 75%, 80%, 85%, 90%, 95%, 98%, or 100%.

In another embodiment, hepcidin gene expression is increased by at least about 1.5-fold, about 2-fold, about 3-fold, about 4-fold, or about 5-fold.

In yet another embodiment, serum hepcidin concentration is increased by at least about 10%, about 25%, about 50%, about 100%, about 150%, about 200%, about 250%, or about 300%.

In one embodiment, serum iron concentration is decreased by at least about 20%, about 30%, about 40%, about 50%, about 60%, about 70%, about 80%, about 90%, about 95%, about 98% or about 100%.

In another embodiment, a percent transferrin saturation is decreased by at least about 20%, about 30%, about 40%, about 50%, about 60%, about 70%, about 80%, about 90%, about 95%, about 98% or about 100%.

In another aspect, the present invention provides methods of treating a subject having a disorder mediated by, or associated with, TMPRSS6 expression. The methods include administering to the subject a therapeutically effective amount of an RNAi agent, e.g., a double stranded RNAi agent, of the invention, or a modified antisense polynucleotide agent of the invention, or a vector of the invention, or a pharmaceutical composition of the invention, thereby treating the subject.

In one aspect, the present invention provides methods of treating a subject having a TMPRSS6-associated disorder. The methods include subcutaneously administering to the subject a therapeutically effective amount of a double stranded RNAi agent, wherein the double stranded RNAi agent comprises a sense strand and an antisense strand forming a double stranded region, wherein the sense strand comprises at least 15 contiguous nucleotides differing by no more than 3 nucleotides from any one of the nucleotide sequences of SEQ ID NO:1, SEQ ID NO:2, or SEQ ID NO:3, SEQ ID NO:4, or SEQ ID NO:5, and the antisense strand comprises at least 15 contiguous nucleotides differing by no more than 3 nucleotides from any one of the nucleotide sequences of SEQ ID NO:6, SEQ ID NO:7, or SEQ ID NO:8, SEQ ID NO:9, or SEQ ID NO:10, wherein substantially all of the nucleotides of the antisense strand comprise a modification selected from the group consisting of a 2'-O-methyl modification and a 2'-fluoro modification, wherein the antisense strand comprises two phosphorothioate internucleotide linkages at the 5'-terminus and two phosphorothioate internucleotide linkages at the 3'-terminus, wherein substantially all of the nucleotides of the sense strand comprise a modification selected from the group consisting of a 2'-O-methyl modification and a 2'-fluoro modification, wherein the sense strand comprises two phosphorothioate internucleotide linkages at the 5'-terminus and, wherein the sense strand is conjugated to one or more GalNAc derivatives attached through a branched bivalent or trivalent linker at the 3'-terminus, thereby treating the subject. In one embodiment, all of the nucleotides of the sense strand and all of the nucleotides of the antisense strand comprise a modification.

In one embodiment, the subject is a human.

In one embodiment, the subject has a disorder associated with iron overload, e.g., hereditary hemochromatosis, β-thalassemia (e.g., β-thalassemia major and β-thalassemia intermedia) erythropoietic *porphyria*, Parkinson's Disease, Alzheimer's Disease or Friedreich's Ataxia.

In one embodiment, the RNAi agent, e.g., double stranded RNAi agent, is administered at a dose of about 0.01 mg/kg to about 10 mg/kg, about 1 mg/kg to about 10 mg/kg, about 2 mg/kg to about 10 mg/kg, about 3 mg/kg to about 10 mg/kg, about 4 mg/kg to about 10 mg/kg, about 5 mg/kg to about 15 mg/kg, about 6 mg/kg to about 15 mg/kg, about 7 mg/kg to about 15 mg/kg, about 8 mg/kg to about 15 mg/kg, about 9 mg/kg to about 15 mg/kg, about 10 mg/kg to about 20 mg/kg, about 12 mg/kg to about 20 mg/kg, about 13 mg/kg to about 20 mg/kg, about 14 mg/kg to about 20 mg/kg, about 15 mg/kg to about 20 mg/kg, about 16 mg/kg to about 20 mg/kg or about 18 mg/kg to about 20 mg/kg. In particular embodiments, the double stranded RNAi agent is administered at a dose of about 0.1 mg/kg, about 1.0 mg/kg, or about 3.0 mg/kg.

In one embodiment, the RNAi agent, e.g., double stranded RNAi agent, is administered subcutaneously or intravenously.

In one embodiment, the RNAi agent is administered in two or more doses. In a specific embodiment, the RNAi agent is administered at intervals selected from the group consisting of once every about 12 hours, once every about 24 hours, once every about 48 hours, once every about 72 hours, once every about 96 hours, once about every 7 days, or once about every 14 days. In particular embodiments, the RNAi agent is administered once a week for up to 2 weeks, up to 3 weeks, up to 4 weeks, up to 5 weeks, or longer.

In yet another aspect, the present invention provides methods of treating an iron overload associated disorder in a subject. The methods include administering to the subject a therapeutically effective amount of an RNAi agent, e.g., a double stranded RNAi agent, or the vector of the invention, thereby treating the subject.

In one embodiment, the iron overload associated disorder is hemochromatosis. In another embodiment, the iron overload associated disorder is a thalassemia, e.g., β-thalassemia (e.g., β-thalassemia major and β-thalassemia intermiedia), or erythropoietic *porphyria*. In yet another embodiment, the iron overload associated disorder is a neurological disease, e.g., Parkinson's Disease, Alzheimer's Disease or Friedreich's Ataxia.

In one embodiment, the subject is a primate or rodent. In another embodiment, the subject is a human.

In one embodiment, the RNAi agent, e.g., double stranded RNAi agent, is administered at a dose of about 0.01 mg/kg to about 10 mg/kg, about 0.5 mg/kg to about 50 mg/kg, about 10 mg/kg to about 30 mg/kg, about 10 mg/kg to about 20 mg/kg, about 15 mg/kg to about 20 mg/kg, about 15 mg/kg to about 25 mg/kg, about 15 mg/kg to about 30 mg/kg, or about 20 mg/kg to about 30 mg/kg.

In one embodiment, the RNAi agent, e.g., double stranded RNAi agent, is administered subcutaneously or intravenously.

In one embodiment, the RNAi agent is administered in two or more doses. In a specific embodiment, the RNAi agent is administered at intervals selected from the group consisting of once every about 12 hours, once every about 24 hours, once every about 48 hours, once every about 72 hours, once every about 96 hours, once about every 7 days, or once about every 14 days.

In one embodiment, administering results in a decrease in iron levels, ferritin level and/or transferrin saturation level in the subject.

In one embodiment, the methods further comprise determining the iron level in the subject.

In one embodiment, the methods of the invention which include administering an iRNA agent of the invention (or pharmaceutical composition of the invention) to a subject are practiced in combination with administration of additional pharmaceuticals and/or other therapeutic methods. In one embodiment, the methods of the invention further comprise administering an iron chelator, e.g., deferiprone, deferoxamine, and deferasirox, to a subject.

The present invention is further illustrated by the following detailed description and drawings.

BRIEF DESCRIPTION OF THE DRAWINGS

FIG. 8 shows the nucleotide sequence of *Homo sapiens* TMPRSS6 (SEQ ID NO:1).

FIG. 9 shows the nucleotide sequence of *Mus musculus* TMPRSS6 (SEQ ID NO:2).

FIG. 10 shows the nucleotide sequence of *Rattus norvegicus* TMPRSS6 (SEQ ID NO:3).

FIG. 11 shows the nucleotide sequence of *Macaca mulatta* TMPRSS6 (SEQ ID NO:4).

FIG. 12 shows the nucleotide sequence of *Macaca mulatta* TMPRSS6 (SEQ ID NO:5).

FIG. 13 shows the reverse complement of SEQ ID NO:1 (SEQ ID NO:6).

FIG. 14 shows the reverse complement of SEQ ID NO:2 (SEQ ID NO:7).

FIG. 15 shows the reverse complement of SEQ ID NO:3 (SEQ ID NO:8).

FIG. 16 shows the reverse complement of SEQ ID NO:4 (SEQ ID NO:9).

FIG. 17 shows the reverse complement of SEQ ID NO:5 (SEQ ID NO:10).

DETAILED DESCRIPTION OF THE INVENTION

Figure 1:
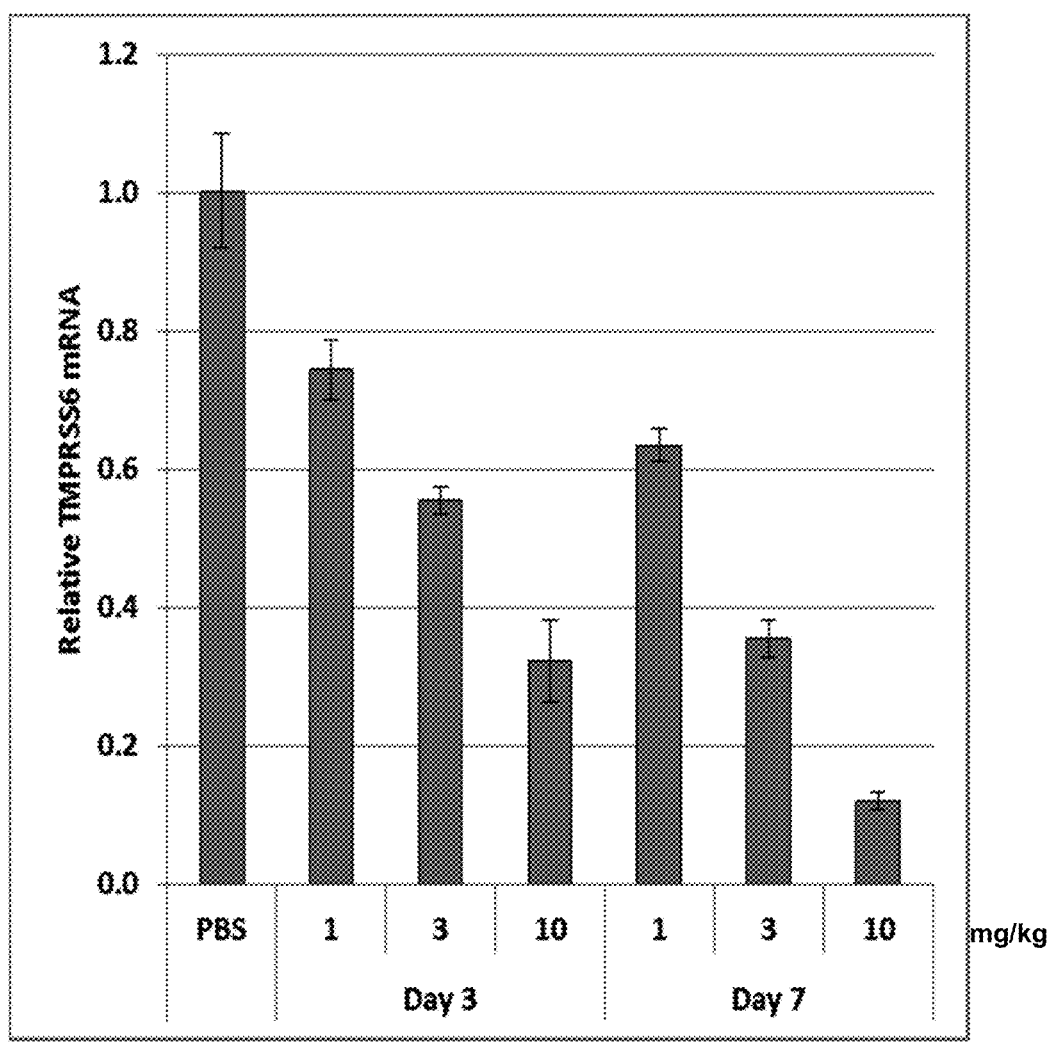
FIG. 1 is a graph showing relative levels of TMPRSS6 mRNA in the liver of wild-type mice following administration of a single dose of 1 mg/kg, 3 mg/kg or 10 mg/kg of the iRNA agent AD-59743.

The present invention provides compositions comprising RNAi agents, e.g., double-stranded iRNA agents, targeting TMPRSS6. The present invention also provides methods using the compositions of the invention for inhibiting TMPRSS6 expression and for treating TMPRSS6 associated disorders, e.g., β-thalassemia or hemochromatosis.

TMPRSS6 plays an important role in iron homeostasis as an inhibitor of HAMP gene expression. The HAMP gene encodes the liver hormone hepcidin, which is a central regulator of iron homeostasis. Hepcidin binds to the iron exporter protein ferroportin (FPN1), which is localized mainly on absorptive enterocytes, hepatocytes and macrophages. Hepcidin binding to the extracellular domain of ferroportin leads to the internalization and degradation of ferroportin, thus decreasing the absorption of dietary iron from the intestine, and the release of iron from macrophages and hepatocytes. HAMP gene expression can be stimulated in response to iron through Bone Morphogenetic Protein (BMP)/Sons of Mothers Against Decapentaplegic (SMAD)-dependent signal transduction cascade mediated by the BMP-co-receptor hemojuvelin (HJV). The key role of TMPRSS6 in HAMP regulation is in the inhibition of BMP-mediated HAMP upregulation. TMPRSS6 inhibits BMP-mediated HAMP upregulation by cleaving the BMP co-receptor HJV, which is essential for BMP-mediated HAMP upregulation; thus preventing BMP signaling, SMAD translocation to the nucleus, and HAMP transcriptional activation.

Several human and mouse studies have confirmed the role of TMPRSS6 in HAMP regulation and iron homeostasis (Du et al. *Science* 2008, Vol. 320, pp 1088-1092; Folgueras et al. *Blood* 2008, Vol. 112, pp 2539-45). Studies have shown that loss of function mutations in TMPRSS6 can lead to the upregulation of hepcidin expression, causing an inherited iron deficiency anemia called iron refractory iron deficiency anemia (IRIDA) (Finberg. Seminars in *Hematology* 2009, Vol. 46, pp 378-86), which is characterized by elevated hepcidin levels, hypochromic microcytic anemia, low mean corpuscular volume (MCV), low transferrin saturation, poor absorption of oral iron, and incomplete response to parenteral iron. However, loss of function mutations in positive regulators of HAMP (e.g., BMP1, BMP4, and HFE) have been shown to downregulate hepcidin expression and cause iron overload disorders (Milet et al. *Am J Hum Gen* 2007, Vol. 81, pp 799-807; Finberg et al. *Blood* 2011, Vol. 117, pp 4590-9). In the primary iron overload disorders, collectively called hereditary hemochromatosis (HH), in anemias characterized by massive ineffective hematopoiesis, and in iron overload (secondary hemochromatosis), such as β-thalassemia intermedia (TI), hepcidin levels are low despite elevated serum iron concentrations and iron stores. A mouse model of β-thalassemia intermedia has demonstrated that the loss of TMPRSS6 expression leads to elevated levels of hepcidin (Finberg 2010 Oral Presentation: "TMPRSS6, an inhibitor of Hepatic BMP/Smad Signaling, is required for Hepcidin Suppression and Iron Loading in a Mouse Model of β-Thalassemia." American Society of Hematology Annual Meeting 2010, Abstract No.: 164).

The present invention describes iRNA agents, compositions and methods for modulating the expression of a TMPRSS6 gene. In certain embodiments, expression of TMPRSS6 is reduced or inhibited using a TMPRSS6-specific iRNA agent, thereby leading to increase HAMP expression, and decreased serum iron levels. Thus, inhibition of TMPRSS6 gene expression or activity using the iRNA compositions featured in the invention can be a useful approach to therapies aimed at reducing the iron levels in a subject. Such inhibition can be useful for treating iron overload associated disorders, such as hemochromatosis or thalassemia, e.g., β-thalassemia (e.g., β-thalassemia major and β-thalassemia intermiedia).

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise.

As used herein, "TMPRSS6" refers to the type II plasma membrane serine protease (TTSP) gene or protein. TMPRSS6 is also known as matriptase-2, IRIDA (iron refractory iron-deficiency anemia), transmembrane protease serine 6, type II transmembrane serine protease 6, and membrane-bound mosaic serine proteinase matriptase-2. TMPRSS6 is a serine protease Type II transmembrane protein of approximately 899 amino acids in length. TMPRSS6 contains multiple domains, e.g., a short endo domain, a transmembrane domain, a sea urchin sperm protein/enteropeptidase domain/agrin (SEA) domain, two complement factor/urchin embryonic growth factor/BMP domains (CUB), three LDL-R class a domains (LDLa), and a trypsin-like serine protease domain with conserved His-Asp-Ser triad (HDS). The term "TMPRSS6" includes human TMPRSS6, the amino acid and nucleotide sequence of which may be found in, for example, GenBank Accession No. GI:56682967; mouse TMPRSS6, the amino acid and nucleotide sequence of which may be found in, for example, GenBank Accession No. GI:125656151; rat TMPRSS6, the amino acid and nucleotide sequence of which may be found in, for example, GenBank Accession No. GI:194474097; rhesus TMPRSS6, the amino acid and nucleotide sequence of which may be found in, for example, GenBank Accession No. XM_001085203.2 (GI:297260989) and XM_001085319.1 (GI:109094061). Additional examples of AGT mRNA sequences are readily available using publicly available databases, e.g., GenBank, UniProt, OMIM, and the *Macaca* genome project web site.

The term "TMPRSS6," as used herein, also refers to naturally occurring DNA sequence variations of the TMPRSS6 gene, such as a single nucleotide polymorphism (SNP) in the TMPRSS6 gene. Exemplary SNPs may be found in the dbSNP database available at www.ncbi.nlm.nih.gov/projects/SNP.

As used herein, "target sequence" refers to a contiguous portion of the nucleotide sequence of an mRNA molecule formed during the transcription of a TMPRSS6 gene, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature.

"G," "C," "A" and "U" each generally stand for a nucleotide that contains guanine, cytosine, adenine, and uracil as a base, respectively. "T" and "dT" are used interchangeably herein and refer to a deoxyribonucleotide wherein the nucleobase is thymine, e.g., deoxyribothymine, 2'-deoxythymidine or thymidine. However, it will be understood that the term "ribonucleotide" or "nucleotide" or "deoxyribonucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

The terms "iRNA", "RNAi agent," "iRNA agent,", "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of TMPRSS6 in a cell, e.g., a cell within a subject, such as a mammalian subject.

In one embodiment, an RNAi agent of the invention includes a single stranded RNA that interacts with a target RNA sequence, e.g., a TMPRSS6 target mRNA sequence, to direct the cleavage of the target RNA. Without wishing to be bound by theory, it is believed that long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). Thus, in one aspect the invention relates to a single stranded RNA (siRNA) generated within a cell and which promotes the formation of a RISC complex to effect silencing of the target gene, i.e., a TMPRSS6 gene. Accordingly, the term "siRNA" is also used herein to refer to an RNAi as described above.

In another embodiment, the RNAi agent may be a single-stranded siRNA that is introduced into a cell or organism to inhibit a target mRNA. Single-stranded RNAi agents bind to the RISC endonuclease Argonaute 2, which then cleaves the target mRNA. The single-stranded siRNAs are generally 15-30 nucleotides and are chemically modified. The design and testing of single-stranded siRNAs are described in U.S. Pat. No. 8,101,348 and in Lima et al., (2012) *Cell* 150: 883-894, the entire contents of each of which are hereby incorporated herein by reference. Any of the antisense nucleotide sequences described herein may be used as a single-stranded siRNA as described herein or as chemically modified by the methods described in Lima et al., (2012) *Cell* 150; 883-894.

In yet another embodiment, the present invention provides single-stranded antisense oligonucleotide molecules targeting TMPRSS6. A "single-stranded antisense oligonucleotide molecule" is complementary to a sequence within the target mRNA (i.e., TMPRSS6). Single-stranded antisense oligonucleotide molecules can inhibit translation in a stoichiometric manner by base pairing to the mRNA and physically obstructing the translation machinery, see Dias, N. et al., (2002) *Mol Cancer Ther* 1:347-355. Alternatively, the single-stranded antisense oligonucleotide molecules inhibit a target mRNA by hydridizing to the target and cleaving the target through an RNaseH cleavage event. The single-stranded antisense oligonucleotide molecule may be about 10 to about 30 nucleotides in length and have a sequence that is complementary to a target sequence. For example, the single-stranded antisense oligonucleotide molecule may comprise a sequence that is at least about 10, 11, 12, 13, 14, 15, 16, 17, 18, 19, 20, or more contiguous nucleotides from any one of the antisense nucleotide sequences described herein, e.g., the sequences provided in any one of Tables, 1, 2, 4, 5, 8, 10, and 12, or bind any of the target sites described herein. The single-stranded antisense oligonucleotide molecules may comprise modified RNA, DNA, or a combination thereof.

In another embodiment, an "iRNA" for use in the compositions, uses, and methods of the invention is a double-stranded RNA and is referred to herein as a "double stranded RNAi agent," "double-stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., a TMPRSS6 gene. In some embodiments of the invention, a double-stranded RNA (dsRNA) triggers the degradation of a target RNA, e.g., an mRNA, through a post-transcriptional gene-silencing mechanism referred to herein as RNA interference or RNAi.

In general, the majority of nucleotides of each strand of a dsRNA molecule are ribonucleotides, but as described in detail herein, each or both strands can also include one or more non-ribonucleotides, e.g., a deoxyribonucleotide and/ or a modified nucleotide. In addition, as used in this specification, an "RNAi agent" may include ribonucleotides with chemical modifications; an RNAi agent may include substantial modifications at multiple nucleotides. Such modifications may include all types of modifications disclosed herein or known in the art. Any such modifications, as used in a siRNA type molecule, are encompassed by "RNAi agent" for the purposes of this specification and claims.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi agent may comprise one or more nucleotide overhangs.

In one embodiment, an RNAi agent of the invention is a dsRNA of 24-30 nucleotides that interacts with a target RNA sequence, e.g., a TMPRSS6 target mRNA sequence, to direct the cleavage of the target RNA. Without wishing to be bound by theory, long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature*

409:363). The siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleave the target to induce silencing (Elbashir, et al., (2001) Genes Dev. 15:188).

As used herein, a "nucleotide overhang" refers to the unpaired nucleotide or nucleotides that protrude from the duplex structure of an RNAi agent when a 3'-end of one strand of the RNAi agent extends beyond the 5'-end of the other strand, or vice versa. "Blunt" or "blunt end" means that there are no unpaired nucleotides at that end of the double stranded RNAi agent, i.e., no nucleotide overhang. A "blunt ended" RNAi agent is a dsRNA that is double-stranded over its entire length, i.e., no nucleotide overhang at either end of the molecule. The RNAi agents of the invention include RNAi agents with nucleotide overhangs at one end (i.e., agents with one overhang and one blunt end) or with nucleotide overhangs at both ends.

The term "antisense strand" refers to the strand of a double stranded RNAi agent which includes a region that is substantially complementary to a target sequence (e.g., a human TMPRSS6 mRNA). As used herein, the term "region complementary to part of an mRNA encoding transthyretin" refers to a region on the antisense strand that is substantially complementary to part of a TMPRSS6 mRNA sequence. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. For example, a complementary sequence is sufficient to allow the relevant function of the nucleic acid to proceed, e.g., RNAi. The skilled person will be able to determine the set of conditions most appropriate for a test of complementarity of two sequences in accordance with the ultimate application of the hybridized nucleotides.

Sequences can be "fully complementary" with respect to each when there is base-pairing of the nucleotides of the first nucleotide sequence with the nucleotides of the second nucleotide sequence over the entire length of the first and second nucleotide sequences. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary," "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding TMPRSS6) including a 5' UTR, an open reading frame (ORF), or a 3' UTR. For example, a polynucleotide is complementary to at least a part of a TMPRSS6 mRNA if the sequence is substantially complementary to a non-interrupted portion of an mRNA encoding TMPRSS6.

The term "inhibiting," as used herein, is used interchangeably with "reducing," "silencing," "downregulating," "suppressing" and other similar terms, and includes any level of inhibition.

The phrase "inhibiting expression of a TMPRSS6," as used herein, includes inhibition of expression of any TMPRSS6 gene (such as, e.g., a mouse TMPRSS6 gene, a rat TMPRSS6 gene, a monkey TMPRSS6 gene, or a human TMPRSS6 gene) as well as variants, (e.g., naturally occurring variants), or mutants of a TMPRSS6 gene. Thus, the TMPRSS6 gene may be a wild-type TMPRSS6 gene, a mutant TMPRSS6 gene, or a transgenic TMPRSS6 gene in the context of a genetically manipulated cell, group of cells, or organism.

"Inhibiting expression of a TMPRSS6 gene" includes any level of inhibition of a TMPRSS6 gene, e.g., at least partial suppression of the expression of a TMPRSS6 gene, such as an inhibition of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%.

The expression of a TMPRSS6 gene may be assessed based on the level of any variable associated with TMPRSS6 gene expression, e.g., TMPRSS6 mRNA level, TMPRSS6 protein level, hepcidin mRNA level, hepcidin protein level, or iron levels in tissues or serum. Inhibition may be assessed by a decrease in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

The phrase "contacting a cell with a double stranded RNAi agent," as used herein, includes contacting a cell by any possible means. Contacting a cell with a double stranded RNAi agent includes contacting a cell in vitro with the RNAi agent or contacting a cell in vivo with the RNAi agent. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, the bloodstream or the subcutaneous space, such that the agent will subsequently reach the tissue where the cell to be contacted is located. For example, the RNAi agent may contain and/or be coupled to a ligand, e.g., a GalNAc3 ligand, that directs the RNAi agent to a site of interest, e.g., the liver. Combinations of in vitro and in vivo methods of contacting are also possible. In connection with the methods of the invention, a cell might also be contacted in vitro with an RNAi agent and subsequently transplanted into a subject.

A "patient" or "subject," as used herein, is intended to include either a human or non-human animal, preferably a mammal, e.g., human or a monkey. Most preferably, the subject or patient is a human.

A "TMPRSS6 associated disorder", as used herein, is intended to include any disorder that can be treated or prevented, or the symptoms of which can be alleviated, by inhibiting the expression of TMPRSS6. In some embodiments, the TMPRSS6 associated disorder is also associated with iron overload, a condition characterized by elevated iron levels, or iron dysregulation. Iron overload may be caused, for example, by hereditary conditions, by elevated iron uptake from diet, or by excess iron administered parenterally that includes intravenous injection of excess iron, and transfusional iron overload.

TMPRSS6 associated disorders include, but are not limited to, hereditary hemochromatosis, idiopathic hemochromatosis, primary hemochromatosis, secondary hemochromatosis, severe juvenile hemochromatosis, neonatal hemochromatosis, sideroblastic anemia, hemolytic anemia, dyserythropoietic anemia, sickle-cell anemia, hemoglobinopathy, thalassemia (e.g., β-thalassemia and α-thalassemia), chronic liver diseases, *porphyria* cutanea tarda, erythropoietic *porphyria*, atransferrinemia, hereditary tyrosinemia, cerebrohepatorenal syndrome, idiopathic pulmonary hemosiderosis, renal hemosiderosis.

TMPRSS6 associated disorders include disorders associated with oral administration of excess iron, transfusional iron overload and intravenous injection of excess iron.

TMPRSS6 associated disorders also include disorders with symptoms that are associated with or may be caused by iron overload. Such symptoms include increased risk for liver disease (cirrhosis, cancer), heart attack or heart failure, diabetes mellitus, osteoarthritis, osteoporosis, metabolic syndrome, hypothyroidism, hypogonadism, and in some cases premature death. In one embodiment, TMPRSS6 associated disorders include neurodegenerative disorders associated with iron overload and/or iron dysregulation, such as Alzheimer's Disease, Parkinson's Disease, Huntington's Disease, Friedreich's Ataxia, epilepsy and multiple sclerosis. Administration of an iRNA that targets TMPRSS6, e.g., an iRNA described in any one of Tables 1, 2, 4, 5, 8, 10, and 12 can treat one or more of these symptoms, or prevent the development or progression of a disease or disorder that is aggravated by increased iron levels.

In one embodiment, a TMPRSS6 associated disorder is a β-thalassemia. A β-thalassemia is any one of a group of hereditary disorders characterized by a genetic deficiency in the synthesis of beta-globin chains. In the homozygous state, beta thalassemia ("thalassemia major") causes severe, transfusion-dependent anemia. In the heterozygous state, the beta thalassemia trait ("thalassemia minor") causes mild to moderate microcytic anemia.

"Thalassemia intermedia" is a β-thalassemia that results in subjects in whom the clinical severity of the disease is somewhere between the mild symptoms of β-thalassemia minor and the β-thalassemia major. The diagnosis is a clinical one that is based on the patient maintaining a satisfactory hemoglobin (Hb) level of at least 6-7 g/dL at the time of diagnosis without the need for regular blood transfusions.

In one embodiment, a β-thalassemia is thalassemia major. In another embodiment, a β-thalassemia is thalassemia intermedia.

"Therapeutically effective amount," as used herein, is intended to include the amount of an RNAi agent that, when administered to a patient for treating a TMPRSS6 associated disease, is sufficient to effect treatment of the disease (e.g., by diminishing, ameliorating or maintaining the existing disease or one or more symptoms of disease). The "therapeutically effective amount" may vary depending on the RNAi agent, how the agent is administered, the disease and its severity and the history, age, weight, family history, genetic makeup, stage of pathological processes mediated by TMPRSS6 expression, the types of preceding or concomitant treatments, if any, and other individual characteristics of the patient to be treated.

"Prophylactically effective amount," as used herein, is intended to include the amount of an RNAi agent that, when administered to a subject who does not yet experience or display symptoms of a TMPRSS6-associated disease, but who may be predisposed to the disease, is sufficient to prevent or ameliorate the disease or one or more symptoms of the disease. Ameliorating the disease includes slowing the course of the disease or reducing the severity of later-developing disease. The "prophylactically effective amount" may vary depending on the RNAi agent, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylacticaly effective amount" also includes an amount of an RNAi agent that produces some desired local or systemic effect at a reasonable benefit/risk ratio applicable to any treatment. RNAi gents employed in the methods of the present invention may be administered in a sufficient amount to produce a reasonable benefit/risk ratio applicable to such treatment.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In preferred embodiments, a "sample derived from a subject" refers to blood or plasma drawn from the subject. In further embodiments, a "sample derived from a subject" refers to liver tissue (or subcomponents thereof) derived from the subject.

II. iRNAs of the Invention

Described herein are improved double-stranded RNAi agents which inhibit the expression of a TMPRSS6 gene in a cell, such as a cell within a subject, e.g., a mammal, such as a human having a TMPRSS6 associated disorder, e.g., β-thalassemia (e.g., β-thalassemia major and β-thalassemia intermiedia) or hemochromatosis, and uses of such double-stranded RNAi agents.

Accordingly, the invention provides double-stranded RNAi agents with chemical modifications capable of inhibiting the expression of a target gene (i.e., a TMPRSS6 gene) in vivo. In certain aspects of the invention, substantially all of the nucleotides of an iRNA of the invention are modified. In other embodiments of the invention, all of the nucleotides of an iRNA of the invention are modified. iRNAs of the invention in which "substantially all of the nucleotides are modified" are largely but not wholly modified and can include not more than 5, 4, 3, 2, or 1 unmodified nucleotides.

The RNAi agent comprises a sense strand and an antisense strand. Each strand of the RNAi agent may range from 12-30 nucleotides in length. For example, each strand may be between 14-30 nucleotides in length, 17-30 nucleotides in length, 19-30 nucleotides in length, 25-30 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length.

The sense strand and antisense strand typically form a duplex double stranded RNA ("dsRNA"), also referred to herein as an "RNAi agent." The duplex region of an RNAi agent may be 12-30 nucleotide pairs in length. For example, the duplex region can be between 14-30 nucleotide pairs in length, 17-30 nucleotide pairs in length, 27-30 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotides in length.

In one embodiment, the RNAi agent may contain one or more overhang regions and/or capping groups at the 3'-end, 5'-end, or both ends of one or both strands. The overhang can be 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In one embodiment, the nucleotides in the overhang region of the RNAi agent can each independently be a modified or unmodified nucleotide including, but no limited to 2'-sugar modified, such as, 2-F, 2'-O-methyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be another sequence.

The 5'- or 3'-overhangs at the sense strand, antisense strand or both strands of the RNAi agent may be phosphorylated. In some embodiments, the overhang region(s) contains two nucleotides having a phosphorothioate between the two nucleotides, where the two nucleotides can be the same or different. In one embodiment, the overhang is present at the 3'-end of the sense strand, antisense strand, or both strands. In one embodiment, this 3'-overhang is present in the antisense strand. In one embodiment, this 3'-overhang is present in the sense strand.

The RNAi agent may contain only a single overhang, which can strengthen the interference activity of the RNAi, without affecting its overall stability. For example, the single-stranded overhang may be located at the 3'-terminal end of the sense strand or, alternatively, at the 3'-terminal end of the antisense strand. The RNAi may also have a blunt end, located at the 5'-end of the antisense strand (or the 3'-end of the sense strand) or vice versa. Generally, the antisense strand of the RNAi has a nucleotide overhang at the 3'-end, and the 5'-end is blunt. While not wishing to be bound by theory, the asymmetric blunt end at the 5'-end of the antisense strand and 3'-end overhang of the antisense strand favor the guide strand loading into RISC process.

Any of the nucleic acids featured in the invention can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and US Pat RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in iRNAs, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., Science, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)—ON[($CH_2$)$_n$$CH_3$)]$_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O($CH_2$)$_2$ON($CH_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$.

Other modifications include 2'-methoxy (2'-$OCH_3$), 2'-aminopropoxy (2'-$OCH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12): 3185-3193).

Representative U.S. patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

A. Modified iRNAs Comprising Motifs of the Invention

In certain aspects of the invention, the double-stranded RNAi agents of the invention include agents with chemical modifications as disclosed, for example, in U.S. Provisional Application No. 61/561,710, filed on Nov. 18, 2011, or in PCT/US2012/065691, filed on Nov. 16, 2012, the entire contents of each of which are incorporated herein by reference.

As shown herein and in Provisional Application No. 61/561,710, a superior result may be obtained by introducing one or more motifs of three identical modifications on three consecutive nucleotides into a sense strand and/or antisense strand of a RNAi agent, particularly at or near the cleavage site. In some embodiments, the sense strand and antisense strand of the RNAi agent may otherwise be completely modified. The introduction of these motifs interrupts the modification pattern, if present, of the sense and/or antisense strand. The RNAi agent may be optionally conjugated with a GalNAc derivative ligand, for instance on the sense strand. The resulting RNAi agents present superior gene silencing activity.

More specifically, it has been surprisingly discovered that when the sense strand and antisense strand of the double-stranded RNAi agent are modified to have one or more motifs of three identical modifications on three consecutive nucleotides at or near the cleavage site of at least one strand of an RNAi agent, the gene silencing activity of the RNAi agent was superiorly enhanced.

In one embodiment, the RNAi agent is a double ended bluntmer of 19 nucleotides in length, wherein the sense strand contains at least one motif of three 2'-F modifications on three consecutive nucleotides at positions 7, 8, 9 from the 5' end. The antisense strand contains at least one motif of three 2'-O-methyl modifications on three consecutive nucleotides at positions 11, 12, 13 from the 5'end.

In another embodiment, the RNAi agent is a double ended bluntmer of 20 nucleotides in length, wherein the sense strand contains at least one motif of three 2'-F modifications on three consecutive nucleotides at positions 8, 9, 10 from the 5'end. The antisense strand contains at least one motif of three 2'-O-methyl modifications on three consecutive nucleotides at positions 11, 12, 13 from the 5'end.

In yet another embodiment, the RNAi agent is a double ended bluntmer of 21 nucleotides in length, wherein the sense strand contains at least one motif of three 2'-F modifications on three consecutive nucleotides at positions 9, 10, 11 from the 5'end. The antisense strand contains at least one motif of three 2'-O-methyl modifications on three consecutive nucleotides at positions 11, 12, 13 from the 5'end.

In one embodiment, the RNAi agent comprises a 21 nucleotide sense strand and a 23 nucleotide antisense strand, wherein the sense strand contains at least one motif of three 2'-F modifications on three consecutive nucleotides at positions 9, 10, 11 from the 5'end; the antisense strand contains at least one motif of three 2'-O-methyl modifications on three consecutive nucleotides at positions 11, 12, 13 from the 5'end, wherein one end of the RNAi agent is blunt, while the other end comprises a 2 nucleotide overhang. Preferably, the 2 nucleotide overhang is at the 3'-end of the antisense strand. When the 2 nucleotide overhang is at the 3'-end of the antisense strand, there may be two phosphorothioate internucleotide linkages between the terminal three nucleotides, wherein two of the three nucleotides are the overhang nucleotides, and the third nucleotide is a paired nucleotide next to the overhang nucleotide. In one embodiment, the RNAi agent additionally has two phosphorothioate internucleotide linkages between the terminal three nucleotides at both the 5'-end of the sense strand and at the 5'-end of the antisense strand. In one embodiment, every nucleotide in the sense strand and the antisense strand of the RNAi agent, including the nucleotides that are part of the motifs are modified nucleotides. In one embodiment each residue is independently modified with a 2'-O-methyl or 3'-fluoro, e.g., in an alternating motif. Optionally, the RNAi agent further comprises a ligand (preferably GalNAc$_3$).

In one embodiment, the RNAi agent comprises sense and antisense strands, wherein the RNAi agent comprises a first strand having a length which is at least 25 and at most 29 nucleotides and a second strand having a length which is at most 30 nucleotides with at least one motif of three 2'-O-methyl modifications on three consecutive nucleotides at position 11, 12, 13 from the 5' end; wherein the 3' end of the first strand and the 5' end of the second strand form a blunt end and the second strand is 1-4 nucleotides longer at its 3' end than the first strand, wherein the duplex region which is at least 25 nucleotides in length, and the second strand is sufficiently complementary to a target mRNA along at least 19 nucleotide of the second strand length to reduce target gene expression when the RNAi agent is introduced into a mammalian cell, and wherein dicer cleavage of the RNAi agent preferentially results in an siRNA comprising the 3' end of the second strand, thereby reducing expression of the target gene in the mammal. Optionally, the RNAi agent further comprises a ligand.

In one embodiment, the sense strand of the RNAi agent contains at least one motif of three identical modifications on three consecutive nucleotides, where one of the motifs occurs at the cleavage site in the sense strand.

In one embodiment, the antisense strand of the RNAi agent can also contain at least one motif of three identical modifications on three consecutive nucleotides, where one of the motifs occurs at or near the cleavage site in the antisense strand For an RNAi agent having a duplex region of 17-23 nucleotide in length, the cleavage site of the antisense strand is typically around the 10, 11 and 12 positions from the 5'-end. Thus the motifs of three identical modifications may occur at the 9, 10, 11 positions; 10, 11, 12 positions; 11, 12, 13 positions; 12, 13, 14 positions; or 13, 14, 15 positions of the antisense strand, the count starting from the 1$^{st}$ nucleotide from the 5'-end of the antisense strand, or, the count starting from the 1$^{st}$ paired nucleotide within the duplex region from the 5'-end of the antisense strand. The cleavage site in the antisense strand may also change according to the length of the duplex region of the RNAi from the 5'-end.

The sense strand of the RNAi agent may contain at least one motif of three identical modifications on three consecutive nucleotides at the cleavage site of the strand; and the antisense strand may have at least one motif of three identical modifications on three consecutive nucleotides at or near the cleavage site of the strand. When the sense strand and the antisense strand form a dsRNA duplex, the sense strand and the antisense strand can be so aligned that one motif of the three nucleotides on the sense strand and one motif of the three nucleotides on the antisense strand have at least one nucleotide overlap, i.e., at least one of the three nucleotides of the motif in the sense strand forms a base pair with at least one of the three nucleotides of the motif in the antisense strand. Alternatively, at least two nucleotides may overlap, or all three nucleotides may overlap.

In one embodiment, the sense strand of the RNAi agent may contain more than one motif of three identical modifications on three consecutive nucleotides. The first motif may occur at or near the cleavage site of the strand and the other motifs may be a wing modification. The term "wing modification" herein refers to a motif occurring at another portion of the strand that is separated from the motif at or near the cleavage site of the same strand. The wing modification is either adjacent to the first motif or is separated by at least one or more nucleotides. When the motifs are immediately adjacent to each other then the chemistry of the motifs are distinct from each other and when the motifs are separated by one or more nucleotide than the chemistries can be the same or different. Two or more wing modifications may be present. For instance, when two wing modifications are present, each wing modification may occur at one end relative to the first motif which is at or near cleavage site or on either side of the lead motif.

Like the sense strand, the antisense strand of the RNAi agent may contain more than one motifs of three identical modifications on three consecutive nucleotides, with at least one of the motifs occurring at or near the cleavage site of the strand. This antisense strand may also contain one or more wing modifications in an alignment similar to the wing modifications that may be present on the sense strand.

In one embodiment, the wing modification on the sense strand or antisense strand of the RNAi agent typically does not include the first one or two terminal nucleotides at the 3'-end, 5'-end or both ends of the strand.

In another embodiment, the wing modification on the sense strand or antisense strand of the RNAi agent typically does not include the first one or two paired nucleotides within the duplex region at the 3'-end, 5'-end or both ends of the strand.

When the sense strand and the antisense strand of the RNAi agent each contain at least one wing modification, the wing modifications may fall on the same end of the duplex region, and have an overlap of one, two or three nucleotides.

When the sense strand and the antisense strand of the RNAi agent each contain at least two wing modifications, the sense strand and the antisense strand can be so aligned that two modifications each from one strand fall on one end of the duplex region, having an overlap of one, two or three nucleotides; two modifications each from one strand fall on the other end of the duplex region, having an overlap of one, two or three nucleotides; two modifications one strand fall on each side of the lead motif, having an overlap of one, two or three nucleotides in the duplex region.

In one embodiment, every nucleotide in the sense strand and antisense strand of the RNAi agent, including the nucleotides that are part of the motifs, may be modified. Each nucleotide may be modified with the same or different modification which can include one or more alteration of one or both of the non-linking phosphate oxygens and/or of one or more of the linking phosphate oxygens; alteration of a constituent of the ribose sugar, e.g., of the 2' hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in many cases it will not. By way of example, a modification may only occur at a 3' or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of a RNA or may only occur in a single strand region of a RNA. For example, a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. For example, it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In one embodiment, each residue of the sense strand and antisense strand is independently modified with LNA, HNA, CeNA, 2'-methoxyethyl, 2'-O-methyl, 2'-O-allyl, 2'-C-allyl, 2'-deoxy, 2'-hydroxyl, or 2'-fluoro. The strands can contain more than one modification. In one embodiment, each residue of the sense strand and antisense strand is independently modified with 2'-O-methyl or 2'-fluoro.

At least two different modifications are typically present on the sense strand and antisense strand. Those two modifications may be the 2'-O-methyl or 2'-fluoro modifications, or others.

In one embodiment, the $N_a$ and/or $N_b$ comprise modifications of an alternating pattern. The term "alternating motif" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AAB-BAABBAABB . . . ," "AABAABAABAAB . . . ," "AAABAAABAAAB . . . ," "AAABBBAAABBB . . . ," or "ABCABCABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABABAB . . . ", "ACACAC . . . " "BDBDBD . . . " or "CDCDCD . . . ," etc.

In one embodiment, the RNAi agent of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 5'-3' of the strand within the duplex region. As another example, the alternating motif in the sense strand may start with "AABBAABB" from 5'-3' of the strand and the alternating motif in the antisense strand may start with "BBAABBAA" from 5'-3' of the strand within the duplex region, so that there is a complete or partial shift of the modification patterns between the sense strand and the antisense strand.

In one embodiment, the RNAi agent comprises the pattern of the alternating motif of 2'-O-methyl modification and 2'-F modification on the sense strand initially has a shift relative to the pattern of the alternating motif of 2'-O-methyl modification and 2'-F modification on the antisense strand initially, i.e., the 2'-O-methyl modified nucleotide on the sense strand base pairs with a 2'-F modified nucleotide on the antisense strand and vice versa. The 1 position of the sense strand may start with the 2'-F modification, and the 1 position of the antisense strand may start with the 2'-O-methyl modification.

The introduction of one or more motifs of three identical modifications on three consecutive nucleotides to the sense strand and/or antisense strand interrupts the initial modification pattern present in the sense strand and/or antisense strand. This interruption of the modification pattern of the sense and/or antisense strand by introducing one or more motifs of three identical modifications on three consecutive nucleotides to the sense and/or antisense strand surprisingly enhances the gene silencing activity to the target gene.

In one embodiment, when the motif of three identical modifications on three consecutive nucleotides is introduced to any of the strands, the modification of the nucleotide next to the motif is a different modification than the modification of the motif. For example, the portion of the sequence containing the motif is " . . . $N_a$YYY$N_b$ . . . ," where "Y" represents the modification of the motif of three identical modifications on three consecutive nucleotide, and "$N_a$" and "$N_b$" represent a modification to the nucleotide next to the motif "YYY" that is different than the modification of Y, and where $N_a$ and $N_b$ can be the same or different modifications. Alternatively, $N_a$ and/or $N_b$ may be present or absent when there is a wing modification present.

The RNAi agent may further comprise at least one phosphorothioate or methylphosphonate internucleotide linkage. The phosphorothioate or methylphosphonate internucleotide linkage modification may occur on any nucleotide of the sense strand or antisense strand or both strands in any position of the strand. For instance, the internucleotide linkage modification may occur on every nucleotide on the sense strand and/or antisense strand; each internucleotide linkage modification may occur in an alternating pattern on the sense strand and/or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In one embodiment, the RNAi comprises a phosphorothioate or methylphosphonate internucleotide linkage modification in the overhang region. For example, the overhang region may contain two nucleotides having a phosphorothioate or methylphosphonate internucleotide linkage between the two nucleotides. Internucleotide linkage modifications also may be made to link the overhang nucleotides with the terminal paired nucleotides within the duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. These terminal three nucleotides may be at the 3'-end of the antisense strand, the 3'-end of the sense strand, the 5'-end of the antisense strand, and/or the 5'end of the antisense strand.

In one embodiment, the 2 nucleotide overhang is at the 3'-end of the antisense strand, and there are two phosphorothioate internucleotide linkages between the terminal three nucleotides, wherein two of the three nucleotides are the overhang nucleotides, and the third nucleotide is a paired nucleotide next to the overhang nucleotide. Optionally, the RNAi agent may additionally have two phosphorothioate internucleotide linkages between the terminal three nucleotides at both the 5'-end of the sense strand and at the 5'-end of the antisense strand.

In one embodiment, the RNAi agent comprises mismatch (es) with the target, within the duplex, or combinations thereof. The mismatch may occur in the overhang region or the duplex region. The base pair may be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In one embodiment, the RNAi agent comprises at least one of the first 1, 2, 3, 4, or 5 base pairs within the duplex regions from the 5'-end of the antisense strand independently selected from the group of: A:U, G:U, I:C, and mismatched pairs, e.g., non-canonical or other than canonical pairings or pairings which include a universal base, to promote the dissociation of the antisense strand at the 5'-end of the duplex.

In one embodiment, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

In one embodiment, the sense strand sequence may be represented by formula (I):

$$5' \quad n_p\text{-}N_a\text{-}(X\ X\ X)_i\text{-}N_b\text{-}Y\ Y\ Y\text{-}N_b\text{-}(Z\ Z\ Z)_j\text{-}N_a\text{-}n_q \quad 3' \quad (I)$$

wherein:

i and j are each independently 0 or 1;

p and q are each independently 0-6;

each $N_a$ independently represents an oligonucleotide sequence comprising 0-25 modified nucleotides, each sequence comprising at least two differently modified nucleotides;

each $N_b$ independently represents an oligonucleotide sequence comprising 0-10 modified nucleotides;

each $n_p$ and $n_q$ independently represent an overhang nucleotide;

wherein Nb and Y do not have the same modification; and

XXX, YYY and ZZZ each independently represent one motif of three identical modifications on three consecutive nucleotides. Preferably YYY is all 2'-F modified nucleotides.

In one embodiment, the $N_a$ and/or $N_b$ comprise modifications of alternating pattern.

In one embodiment, the YYY motif occurs at or near the cleavage site of the sense strand. For example, when the RNAi agent has a duplex region of 17-23 nucleotides in length, the YYY motif can occur at or the vicinity of the cleavage site (e.g.: can occur at positions 6, 7, 8, 7, 8, 9, 8, 9, 10, 9, 10, 11, 10, 11, 12 or 11, 12, 13) of-the sense strand, the count starting from the 1$^{st}$ nucleotide, from the 5'-end; or optionally, the count starting at the 1$^{st}$ paired nucleotide within the duplex region, from the 5'-end.

In one embodiment, i is 1 and j is 0, or i is 0 and j is 1, or both i and j are 1. The sense strand can therefore be represented by the following formulas:

$$5' \quad n_p\text{-}N_a\text{-}YYY\text{-}N_b\text{-}ZZZ\text{-}N_a\text{-}n_q \quad 3'; \quad (Ib)$$

$$5' \quad n_p\text{-}N_a\text{-}XXX\text{-}N_b\text{-}YYY\text{-}N_a\text{-}n_q \quad 3'; \quad (Ic)$$

or $$5' \quad n_p\text{-}N_a\text{-}XXX\text{-}N_b\text{-}YYY\text{-}N_b\text{-}ZZZ\text{-}N_a\text{-}n_q \quad 3'. \quad (Id)$$

When the sense strand is represented by formula (Ib), $N_b$ represents an oligonucleotide sequence comprising 0-10, 0-7, 0-5, 0-4, 0-2 or 0 modified nucleotides. Each $N_a$ independently can represent an oligonucleotide sequence comprising 2-20, 2-15, or 2-10 modified nucleotides.

When the sense strand is represented as formula (Ic), $N_b$ represents an oligonucleotide sequence comprising 0-10, 0-7, 0-10, 0-7, 0-5, 0-4, 0-2 or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2 or 0 modified nucleotides. Preferably, $N_b$ is 0, 1, 2, 3, 4, 5 or 6 Each $N_a$ can independently represent an oligonucleotide sequence comprising 2-20, 2-15, or 2-10 modified nucleotides.

Each of X, Y and Z may be the same or different from each other.

In other embodiments, i is 0 and j is 0, and the sense strand may be represented by the formula:

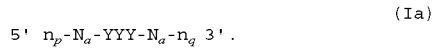
(Ia)

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

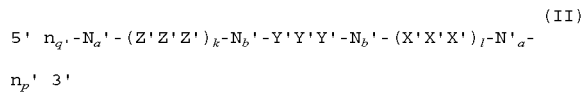
(II)

wherein:
k and l are each independently 0 or 1;
p' and q' are each independently 0-6;
each $N_a'$ independently represents an oligonucleotide sequence comprising 0-25 modified nucleotides, each sequence comprising at least two differently modified nucleotides;
each $N_b'$ independently represents an oligonucleotide sequence comprising 0-10 modified nucleotides;
each $n_p'$ and $n_q'$ independently represent an overhang nucleotide;
wherein $N_b'$ and Y' do not have the same modification; and
X'X'X', Y'Y'Y' and Z'Z'Z' each independently represent one motif of three identical modifications on three consecutive nucleotides.

In one embodiment, the $N_a'$ and/or $N_b'$ comprise modifications of alternating pattern.

The Y'Y'Y' motif occurs at or near the cleavage site of the antisense strand. For example, when the RNAi agent has a duplex region of 17-23 nucleotide in length, the Y'Y'Y' motif can occur at positions 9, 10, 11; 10, 11, 12; 11, 12, 13; 12, 13, 14; or 13, 14, 15 of the antisense strand, with the count starting from the 1st nucleotide, from the 5'-end; or optionally, the count starting at the 1st paired nucleotide within the duplex region, from the 5'-end. Preferably, the Y'Y'Y' motif occurs at positions 11, 12, 13.

In one embodiment, Y'Y'Y' motif is all 2'-OMe modified nucleotides.

In one embodiment, k is 1 and l is 0, or k is 0 and l is 1, or both k and l are 1.

The antisense strand can therefore be represented by the following formulas:

(IIb)

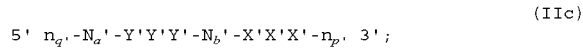
(IIc)
or

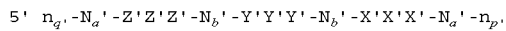
(IId)

When the antisense strand is represented by formula (IIb), $N_b$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IIc), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IId), each $N_b'$ independently represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides. Preferably, $N_b$ is 0, 1, 2, 3, 4, 5 or 6.

In other embodiments, k is 0 and l is 0 and the antisense strand may be represented by the formula:

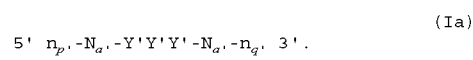
(Ia)

When the antisense strand is represented as formula (IIa), each $N_a'$ independently represents an oligonucleotide sequence comprising 2-20, 2-15, or 2-10 modified nucleotides.

Each of X', Y' and Z' may be the same or different from each other.

Each nucleotide of the sense strand and antisense strand may be independently modified with LNA, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y' and Z', in particular, may represent a 2'-O-methyl modification or a 2'-fluoro modification.

In one embodiment, the sense strand of the RNAi agent may contain YYY motif occurring at 9, 10 and 11 positions of the strand when the duplex region is 21 nt, the count starting from the 1st nucleotide from the 5'-end, or optionally, the count starting at the 1st paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In one embodiment the antisense strand may contain Y'Y'Y' motif occurring at positions 11, 12, 13 of the strand, the count starting from the 1st nucleotide from the 5'-end, or optionally, the count starting at the 1st paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification.

The sense strand represented by any one of the above formulas (Ia), (Ib), (Ic), and (Id) forms a duplex with a antisense strand being represented by any one of formulas (IIa), (IIb), (IIc), and (IId), respectively.

Accordingly, the RNAi agents for use in the methods of the invention may comprise a sense strand and an antisense strand, each strand having 14 to 30 nucleotides, the RNAi duplex represented by formula (III):

(III)

sense:
5' $n_p$-$N_a$-(X X X)$_i$-$N_b$-Y Y Y-$N_b$-(Z Z Z)$_j$-$N_a$-$n_q$ 3' antisense:
3' $n_p'$-$N_a'$-(X'X'X')$_k$-$N_b'$-Y'Y'Y'-$N_b'$-(Z'Z'Z')$_l$-$N_a'$-$n_q'$ 5' wherein:

i, j, k, and l are each independently 0 or 1;

p, p', q, and q' are each independently 0-6;

each $N_a$ and $N_a$ independently represents an oligonucleotide sequence comprising 0-25 modified nucleotides, each sequence comprising at least two differently modified nucleotides;

each $N_b$ and $N_b$ independently represents an oligonucleotide sequence comprising 0-10 modified nucleotides;

wherein each $n_p'$, $n_p$, $n_q'$, and $n_q$, each of which may or may not be present, independently represents an overhang nucleotide; and XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and l is 0; or k is 1 and l is 0; k is 0 and l is 1; or both k and l are 0; or both k and l are 1.

Exemplary combinations of the sense strand and antisense strand forming a RNAi duplex include the formulas below:

(IIIa)
5' $n_p$-$N_a$-Y Y Y-$N_a$-$n_q$ 3'
3' $n_p'$-$N_a'$-Y'Y'Y'-$N_a'n_q'$ 5'

(IIIb)
5' $n_p$-$N_a$-Y Y Y-$N_b$-Z Z Z -$N_a$-$n_q$ 3'
3' $n_p'$-$N_a'$-Y'Y'Y'-$N_b'$-Z'Z'Z'-$N_a'n_q'$ 5'

(IIIc)
5' $n_p$-$N_a$-X X X-$N_b$-Y Y Y-$N_a$-$n_q$ 3'
3' $n_p'$-$N_a'$-X'X'X'-$N_b'$-Y'Y'Y'-$N_a'$-$n_q'$ 5'

(IIId)
5' $n_p$-$N_a$-X X X-$N_b$-Y Y Y-$N_b$-Z Z Z-$N_a$-$n_q$3'
3' $n_p'$-$N_a'$-X'X'X'-$N_b'$-Y'Y'Y'-$N_b'$-Z'Z'Z'-$N_a$-$n_q'$ 5'

When the RNAi agent is represented by formula (IIIa), each $N_a$ independently represents an oligonucleotide sequence comprising 2-20, 2-15, or 2-10 modified nucleotides.

When the RNAi agent is represented by formula (IIIb), each $N_b$ independently represents an oligonucleotide sequence comprising 1-10, 1-7, 1-5 or 1-4 modified nucleotides. Each $N_a$ independently represents an oligonucleotide sequence comprising 2-20, 2-15, or 2-10 modified nucleotides.

When the RNAi agent is represented as formula (IIIc), each $N_b$, $N_b'$ independently represents an oligonucleotide sequence comprising 0-10, 0-7, 0-10, 0-7, 0-5, 0-4, 0-2 or 0 modified nucleotides. Each $N_a$ independently represents an oligonucleotide sequence comprising 2-20, 2-15, or 2-10 modified nucleotides.

When the RNAi agent is represented as formula (IIId), each $N_b$, $N_b'$ independently represents an oligonucleotide sequence comprising 0-10, 0-7, 0-10, 0-7, 0-5, 0-4, 0-2 or 0 modified nucleotides. Each $N_a$, $N_a'$ independently represents an oligonucleotide sequence comprising 2-20, 2-15, or 2-10 modified nucleotides. Each of $N_a$, $N_a'$, $N_b$ and $N_b$ independently comprises modifications of alternating pattern.

Each of X, Y and Z in formulas (III), (IIIa), (IIIb), (IIIc), and (IIId) may be the same or different from each other.

When the RNAi agent is represented by formula (III), (IIIa), (IIIb), (IIIc), and (IIId), at least one of the Y nucleotides may form a base pair with one of the Y' nucleotides. Alternatively, at least two of the Y nucleotides form base pairs with the corresponding Y' nucleotides; or all three of the Y nucleotides all form base pairs with the corresponding Y' nucleotides.

When the RNAi agent is represented by formula (IIIb) or (IIId), at least one of the Z nucleotides may form a base pair with one of the Z' nucleotides. Alternatively, at least two of the Z nucleotides form base pairs with the corresponding Z' nucleotides; or all three of the Z nucleotides all form base pairs with the corresponding Z' nucleotides.

When the RNAi agent is represented as formula (IIIc) or (IIId), at least one of the X nucleotides may form a base pair with one of the X' nucleotides. Alternatively, at least two of the X nucleotides form base pairs with the corresponding X' nucleotides; or all three of the X nucleotides all form base pairs with the corresponding X' nucleotides.

In one embodiment, the modification on the Y nucleotide is different than the modification on the Y' nucleotide, the modification on the Z nucleotide is different than the modification on the Z' nucleotide, and/or the modification on the X nucleotide is different than the modification on the X' nucleotide.

In one embodiment, when the RNAi agent is represented by formula (IIId), the $N_a$ modifications are 2'-O-methyl or 2'-fluoro modifications. In another embodiment, when the RNAi agent is represented by formula (IIId), the $N_a$ modifications are 2'-O-methyl or 2'-fluoro modifications and $n_p'$>0 and at least one $n_p'$ is linked to a neighboring nucleotide a via phosphorothioate linkage. In yet another embodiment, when the RNAi agent is represented by formula (IIId), the $N_a$ modifications are 2'-O-methyl or 2'-fluoro modifications, $n_p'$>0 and at least one $n_p'$ is linked to a neighboring nucleotide via phosphorothioate linkage, and the sense strand is conjugated to one or more GalNAc derivatives attached through a bivalent or trivalent branched linker. In another embodiment, when the RNAi agent is represented by formula (IIId), the $N_a$ modifications are 2'-O-methyl or 2'-fluoro modifications, $n_p'$>0 and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, when the RNAi agent is represented by formula (IIIa), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, the RNAi agent is a multimer containing at least two duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, the RNAi agent is a multimer containing three, four, five, six or more duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, two RNAi agents represented by formula (III), (IIIa), (IIIb), (IIIc), and (IIId) are linked to each other at the 5' end, and one or both of the 3' ends and are optionally conjugated to a ligand. Each of the agents can target the same gene or two different genes; or each of the agents can target same gene at two different target sites.

Various publications describe multimeric RNAi agents that can be used in the methods of the invention. Such publications include WO2007/091269, U.S. Pat. No. 7,858,769, WO2010/141511, WO2007/117686, WO2009/014887 and WO2011/031520 the entire contents of each of which are hereby incorporated herein by reference.

The RNAi agent that contains conjugations of one or more carbohydrate moieties to a RNAi agent can optimize one or more properties of the RNAi agent. In many cases, the carbohydrate moiety will be attached to a modified subunit of the RNAi agent. For example, the ribose sugar of one or more ribonucleotide subunits of a dsRNA agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The RNAi agents may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

In certain specific embodiments, the RNAi agent for use in the methods of the invention is an agent selected from the group of agents listed in any one of Tables 1, 2, 4, 5, 8, 10, and 12. In one embodiment, when the agent is an agent listed in Table 12, the agent may lack a terminal dT.

The present invention further includes double-stranded RNAi agents comprising any one of the sequences listed in any one of Tables 1, 2, 4, 5, 8, 10, and 12 which comprise a 5' phosphate or phosphate mimetic on the antisense strand (see, e.g., PCT Publication No. WO 2011005860). Further, the present invention includes double-stranded RNAi agents comprising any one of the sequences listed in any one of Tables 1, 2, 4, 5, 8, 10, and 12 which include a 2'fluoro group in place of a 2'-OMe group at the 5'end of the sense strand.

These agents may further comprise a ligand.

In one embodiment, the agent is AD-60940 (sense strand: CfsusGfgUfaUfuUfCfCfuAfgGfgUfaCfaAfL96; antisense strand: usUfsgUfaCfcCfuAfggaAfaUfaCfcAfgsasg).

A. Ligands

The double-stranded RNA (dsRNA) agents of the invention may optionally be conjugated to one or more ligands. The ligand can be attached to the sense strand, antisense strand or both strands, at the 3'-end, 5'-end or both ends. For instance, the ligand may be conjugated to the sense strand. In preferred embodiments, the ligand is conjugated to the 3'-end of the sense strand. In one preferred embodiment, the ligand is a GalNAc ligand. In particularly preferred embodiments, the ligand is GalNAc₃:

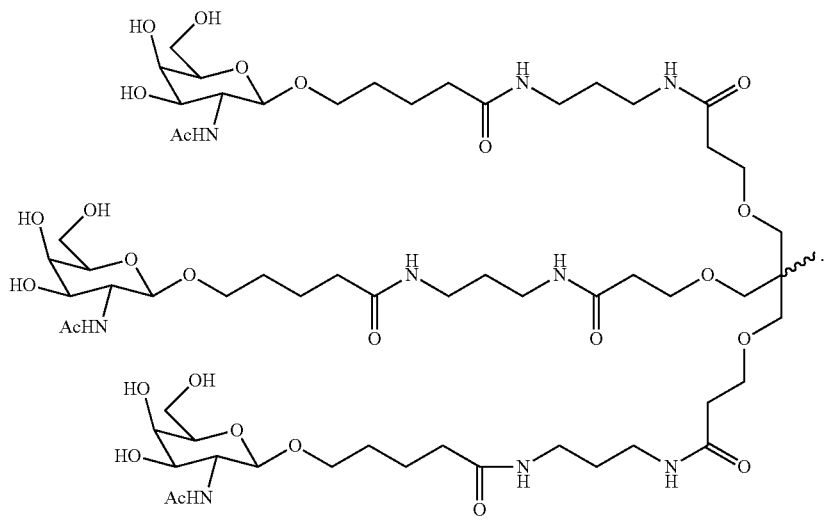 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In some embodiments, the ligand, e.g., GalNAc ligand, is attached to the 3' end of the RNAi agent. In one embodiment, the RNAi agent is conjugated to the ligand, e.g., GalNAc ligand, as shown in the following schematic compartment, tissue, organ or region of the body, as, e.g., compared to a species absent such a ligand. Ligands providing enhanced affinity for a selected target are also termed targeting ligands.

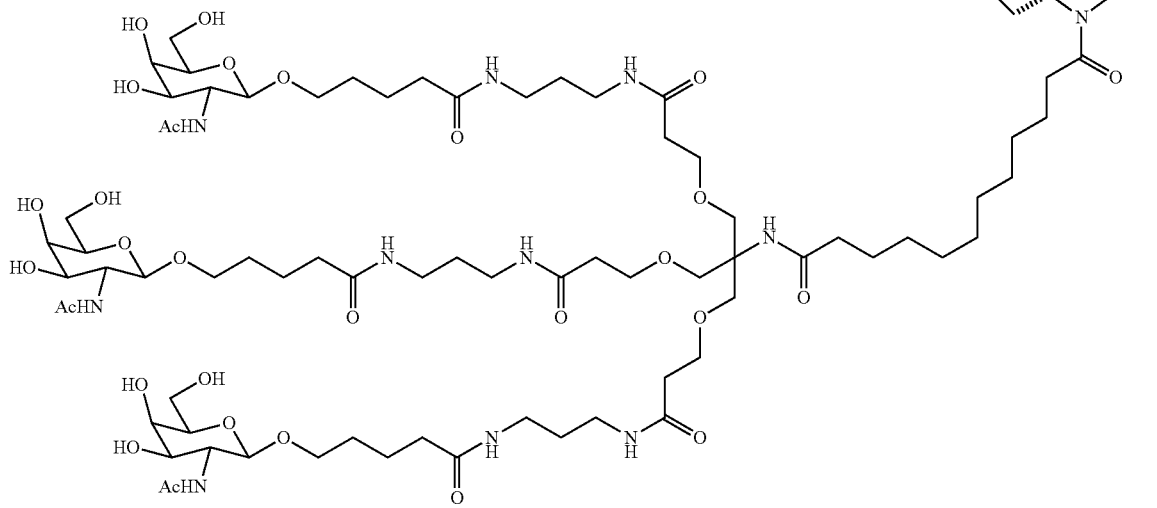

wherein X is O or S. In one embodiment, X is O.

A wide variety of entities can be coupled to the RNAi agents of the present invention. Preferred moieties are ligands, which are coupled, preferably covalently, either directly or indirectly via an intervening tether.

In preferred embodiments, a ligand alters the distribution, targeting or lifetime of the molecule into which it is incorporated. In preferred embodiments a ligand provides an enhanced affinity for a selected target, e.g., molecule, cell or cell type, compartment, receptor e.g., a cellular or organ Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In one embodiment, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GALA peptide (Subbarao et al., *Biochemistry,* 1987, 26: 2964-2972), the EALA peptide (Vogel et al., *J. Am. Chem. Soc.,* 1996, 118: 1581-1586), and their derivatives (Turk et al., *Biochem. Biophys. Acta,* 2002, 1559: 56-68). In one embodiment, the endosomolytic component may contain a chemical group (e.g., an amino acid) which will undergo a change in charge or protonation in response to a change in pH. The endosomolytic component may be linear or branched.

Ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g., an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Other examples of ligands include dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases or a chelator (e.g., EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the oligonucleotide into the cell by, for example, activating an inflammatory response. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include B vitamins, e.g., folic acid, B12, riboflavin, biotin, pyridoxal or other vitamins or nutrients taken up by cancer cells. Also included are HAS, low density lipoprotein (LDL) and high-density lipoprotein (HDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVL-LALLAP (SEQ ID NO: 11). An RFGF analogue (e.g., amino acid sequence AALLPVLLAAP (SEQ ID NO: 12)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ) (SEQ ID NO: 13) and the Drosophila Antennapedia protein (RQIKI-WFQNRRMKWKK) (SEQ ID NO: 14) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized. An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting of an iRNA agent to tumors of a variety of other tissues, including the lung, kidney, spleen, or liver (Aoki et al., Cancer Gene Therapy 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_v\beta_3$ (Haubner et al., Jour. Nucl. Med., 42:326-336, 2001). Peptides that target markers enriched in proliferating cells can be used. For example, RGD containing peptides and peptidomimetics can target cancer cells, in particular cells that exhibit an integrin. Thus, one could use RGD peptides, cyclic peptides containing RGD, RGD peptides that include D-amino acids, as well as synthetic RGD mimics. In addition to RGD, one can use other moieties that target the integrin ligand. Generally, such ligands can be used to control proliferating cells and angiogeneis. Preferred conjugates of this type of ligand target PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In one embodiment, a targeting peptide can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, $H_2A$ peptides, Xenopus peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by $i\pm3$, or $i\pm4$ positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, galactose, mannose, mannose-6P, clusters of sugars such as GalNAc cluster, mannose cluster, galactose cluster, or an apatamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycaboxylates, polycations, masked oligo or poly cations or anions, acetals, polyacetals, ketals/polyketyals, orthoesters, polymers with masked or unmasked cationic or anionic charges, dendrimers with masked or unmasked cationic or anionic charges.

PK modulator stands for pharmacokinetic modulator. PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple phosphorothioate linkages in the backbone are also amenable to the present invention as ligands (e.g., as PK modulating ligands).

In addition, aptamers that bind serum components (e.g., serum proteins) are also amenable to the present invention as PK modulating ligands.

Other ligand conjugates amenable to the invention are described in U.S. patent application Ser. No. 10/916,185, filed Aug. 10, 2004; U.S. Ser. No. 10/946,873, filed Sep. 21, 2004; U.S. Ser. No. 10/833,934, filed Aug. 3, 2007; U.S. Ser. No. 11/115,989 filed Apr. 27, 2005 and U.S. Ser. No. 11/944,227 filed Nov. 21, 2007, which are incorporated by reference in their entireties for all purposes.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

Ligands can be coupled to the oligonucleotides at various places, for example, 3'-end, 5'-end, and/or at an internal position. In preferred embodiments, the ligand is attached to the oligonucleotides via an intervening tether, e.g., a carrier described herein. The ligand or tethered ligand may be present on a monomer when the monomer is incorporated into the growing strand. In some embodiments, the ligand may be incorporated via coupling to a "precursor" monomer after the "precursor" monomer has been incorporated into the growing strand. For example, a monomer having, e.g., an amino-terminated tether (i.e., having no associated ligand), e.g., TAP-$(CH_2)_n NH_2$ may be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction may be incorporated, e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligonucleotides, ligands can be attached to one or both strands. In some embodiments, a double-stranded iRNA agent contains a ligand conjugated to the sense strand. In other embodiments, a double-stranded iRNA agent contains a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

Any suitable ligand in the field of RNA interference may be used, although the ligand is typically a carbohydrate e.g. monosaccharide (such as GalNAc), disaccharide, trisaccharide, tetrasaccharide, polysaccharide.

Linkers that conjugate the ligand to the nucleic acid include those discussed above. For example, the ligand can be one or more GalNAc (N-acetylglucosamine) derivatives attached through a bivalent or trivalent branched linker.

In one embodiment, the dsRNA of the invention is conjugated to a bivalent and trivalent branched linkers include the structures shown in any of formula (IV)-(VII):

Formula (IV)

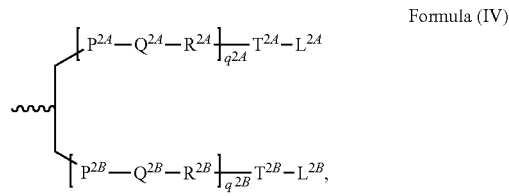

Formula (V)

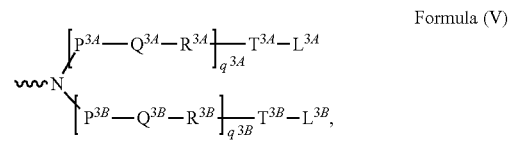

-continued

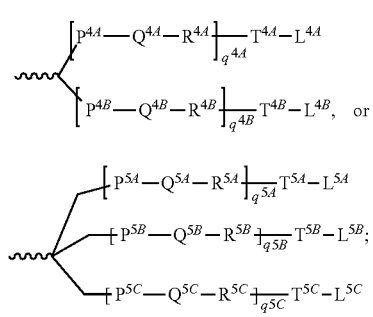

Formula (VI)

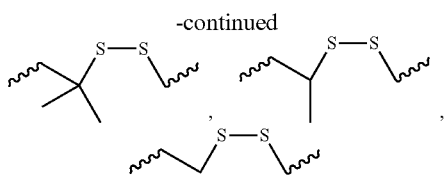

Formula (VII)

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain.

Trivalent conjugating GalNAc derivatives are particularly useful for use with RNAi agents for inhibiting the expression of a target gene, such as those of formula (VII):

wherein:
$q^{2A}$, $q^{2B}$, $q^{3A}$, $q^{3B}$, $q^{4A}$, $q^{4B}$, $q^{5A}$, $q^{5B}$ and $q^{5C}$ represent independently for each occurrence 0-20 and wherein the repeating unit can be the same or different;
$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), $CH_2$, $CH_2NH$ or $CH_2O$;
$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')=C(R''), C≡C or C(O);
$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, —C(O)—CH($R^a$)—NH—, CO, CH=N—O,

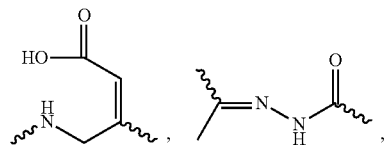

Formula (VII)

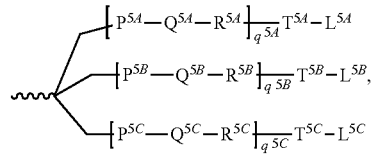

wherein $L^{5A}$, $L^{5B}$ and $L^{5C}$ represent a monosaccharide, such as GalNAc derivative. Examples of suitable bivalent and trivalent branched linker groups conjugating GalNAc derivatives include, but are not limited to, the following compounds:

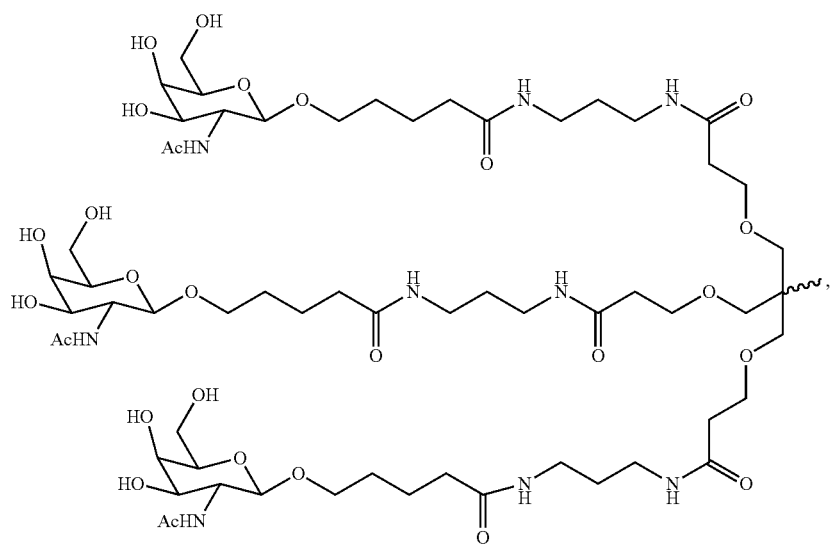

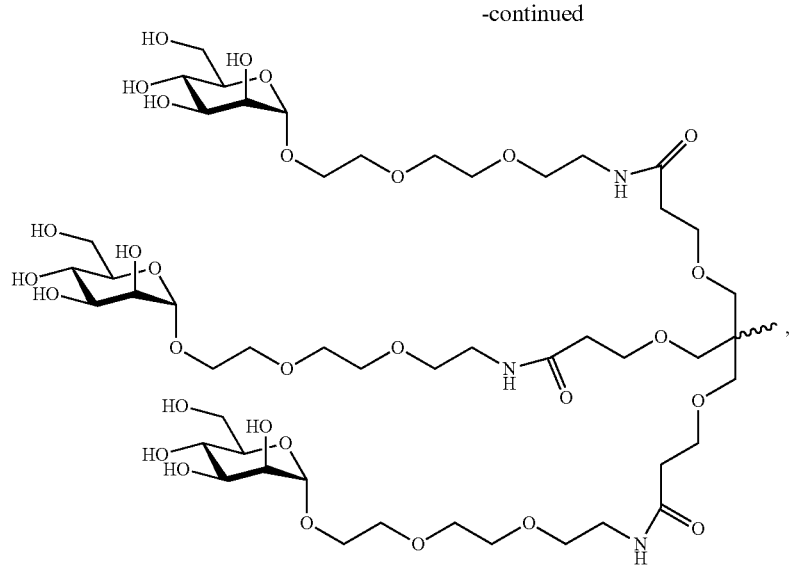
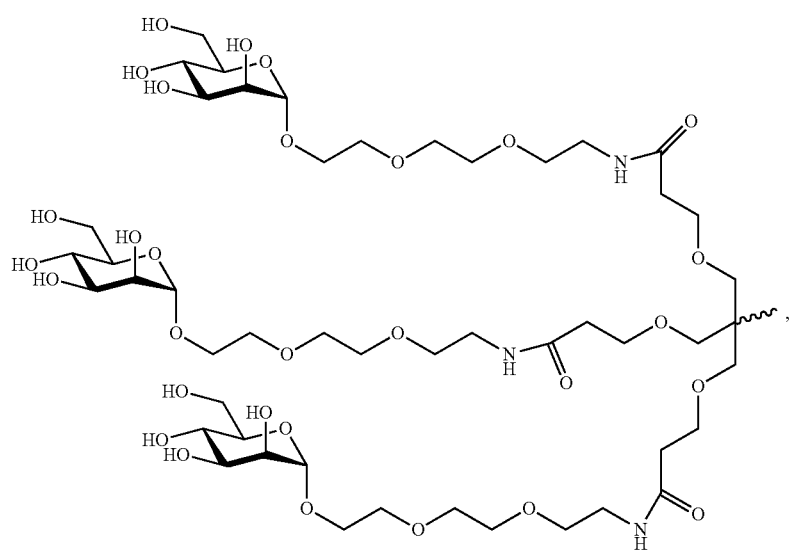
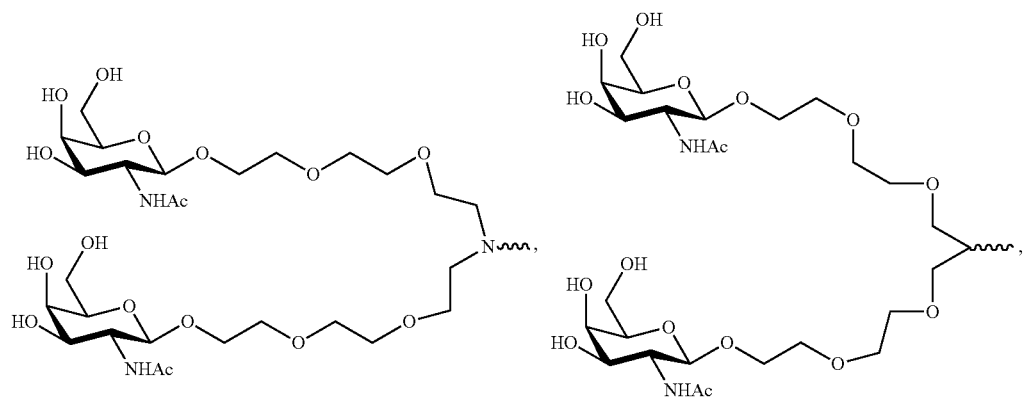

-continued
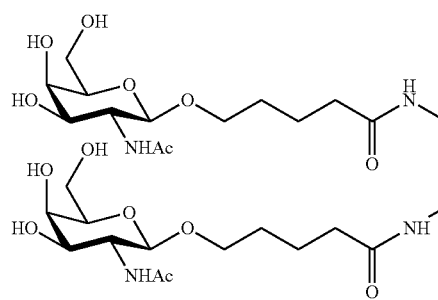
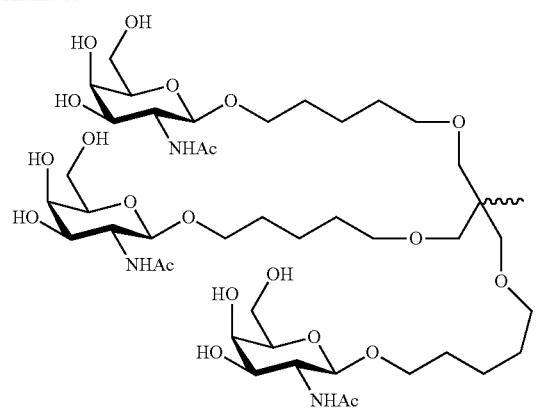
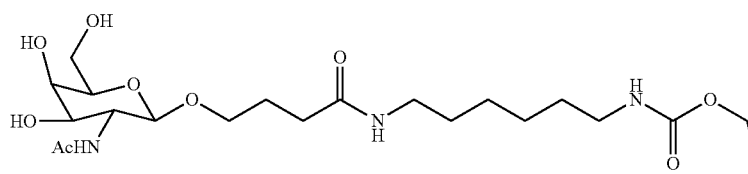
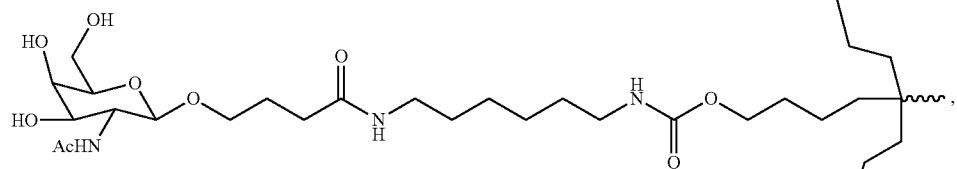
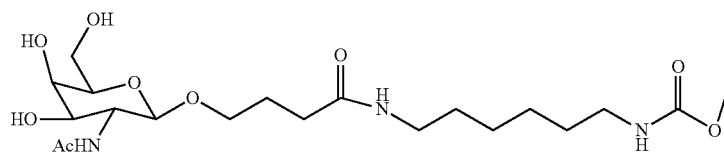
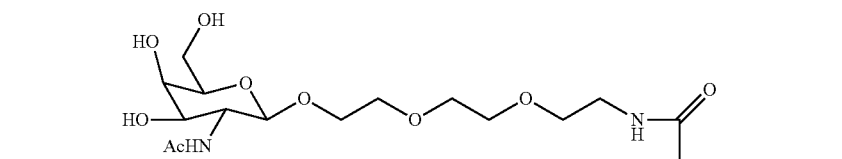
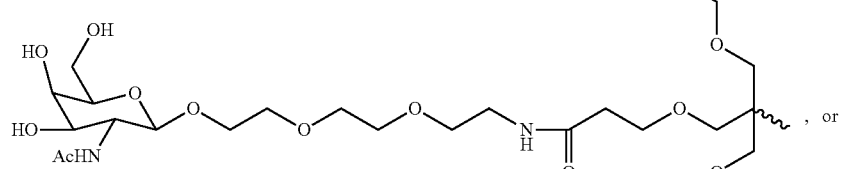
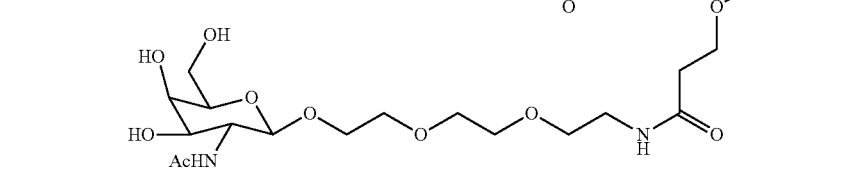

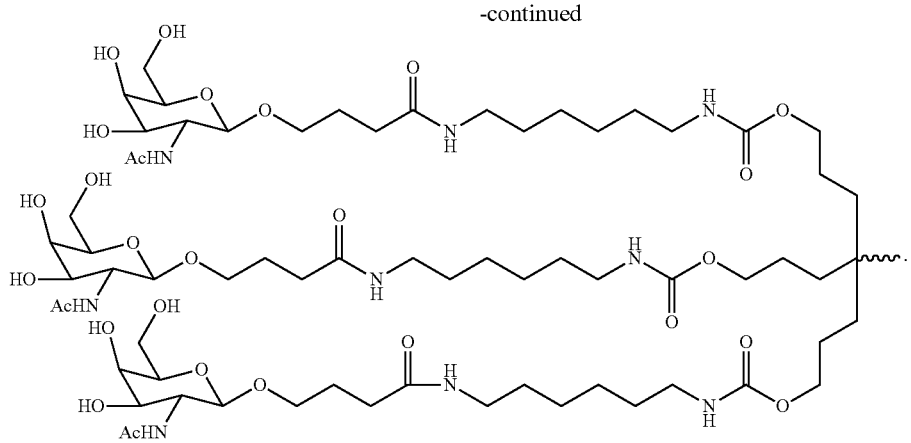

In other embodiments, the RNAi agent for use in the methods of the invention is AD-59743.

III. Delivery of an iRNA of the Invention

The delivery of an iRNA agent of the invention to a cell e.g., a cell within a subject, such as a human subject (e.g., a subject in need thereof, such as a subject having a TMPRSS6 associated disorder, such as a hemochromatosis) can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S. and Julian R L. (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. The non-specific effects of an iRNA can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the iRNA molecule to be administered. Several studies have shown successful knockdown of gene products when an iRNA is administered locally. For example, intraocular delivery of a VEGF dsRNA by intravitreal injection in cynomolgus monkeys (Tolentino, M J., et al (2004) *Retina* 24:132-138) and subretinal injections in mice (Reich, S J., et al (2003) *Mol. Vis.* 9:210-216) were both shown to prevent neovascularization in an experimental model of age-related macular degeneration. In addition, direct intratumoral injection of a dsRNA in mice reduces tumor volume (Pille, J., et al (2005) *Mol. Ther.* 11:267-274) and can prolong survival of tumor-bearing mice (Kim, W J., et al (2006) *Mol. Ther.* 14:343-350; Li, S., et al (2007) *Mol. Ther.* 15:515-523). RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya, Y., et al (2005) *J. Neurophysiol.* 93:594-602) and to the lungs by intranasal administration (Howard, K A., et al (2006) *Mol. Ther.* 14:476-484; Zhang, X., et al (2004) *J. Biol. Chem.* 279:10677-10684; Bitko, V., et al (2005) *Nat. Med.* 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) *Nature* 432:173-178). Conjugation of an iRNA to an aptamer has been shown to inhibit tumor growth and mediate tumor regression in a mouse model of prostate cancer (McNamara, J O., et al (2006) *Nat. Biotechnol.* 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H., et al (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al (2003) *J. Mol. Biol* 327:761-766; Verma, U N., et al (2003) Clin. *Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) *Nature* 441:111-114), cardiolipin (Chien, P Y., et al (2005) *Cancer Gene Ther.* 12:321-328; Pal, A., et al (2005) *Int J. Oncol.* 26:1087-1091), polyethyleneimine (Bonnet M E., et al (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A., et al (2007) *Biochem. Soc. Trans.* 35:61-67; Yoo, H., et al (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

A. Vector Encoded iRNAs of the Invention iRNA targeting the TMPRSS6 gene can be expressed from transcription units inserted into DNA or RNA vectors (see, e.g., Couture, A, et al., *TIG.* (1996), 12:5-10; Skillern, A., et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

iRNA expression plasmids can be transfected into target cells as a complex with cationic lipid carriers (e.g., Oligofectamine) or non-cationic lipid-based carriers (e.g., Transit-TKO™). Multiple lipid transfections for iRNA-mediated knockdowns targeting different regions of a target RNA over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are further described below.

Vectors useful for the delivery of an iRNA will include regulatory elements (promoter, enhancer, etc.) sufficient for expression of the iRNA in the desired target cell or tissue. The regulatory elements can be chosen to provide either constitutive or regulated/inducible expression.

Expression of the iRNA can be precisely regulated, for example, by using an inducible regulatory sequence that is sensitive to certain physiological regulators, e.g., circulating glucose levels, or hormones (Docherty et al., 1994, *FASEB J.* 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the iRNA transgene.

Viral vectors that contain nucleic acid sequences encoding an iRNA can be used. For example, a retroviral vector can be used (see Miller et al., *Meth. Enzymol.* 217:581-599 (1993)). These retroviral vectors contain the components necessary for the correct packaging of the viral genome and integration into the host cell DNA. The nucleic acid sequences encoding an iRNA are cloned into one or more vectors, which facilitate delivery of the nucleic acid into a patient. More detail about retroviral vectors can be found, for example, in Boesen et al., *Biotherapy* 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., *J. Clin. Invest.* 93:644-651 (1994); Kiem et al., *Blood* 83:1467-1473 (1994); Salmons and Gunzberg, *Human Gene Therapy* 4:129-141 (1993); and Grossman and Wilson, *Curr. Opin. in Genetics and Devel.* 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of iRNAs of the invention. Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499-503 (1993) present a review of adenovirus-based gene therapy. Bout et al., *Human Gene Therapy* 5:3-10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431-434 (1991); Rosenfeld et al., *Cell* 68:143-155 (1992); Mastrangeli et al., *J. Clin. Invest.* 91:225-234 (1993); PCT Publication WO94/12649; and Wang, et al., *Gene Therapy* 2:775-783 (1995). A suitable AV vector for expressing an iRNA featured in the invention, a method for constructing the recombinant AV vector, and a method for delivering the vector into target cells, are described in Xia H et al. (2002), *Nat. Biotech.* 20: 1006-1010.

Adeno-associated virus (AAV) vectors may also be used to delivery an iRNA of the invention (Walsh et al., Proc. Soc. Exp. Biol. Med. 204:289-300 (1993); U.S. Pat. No. 5,436,146). In one embodiment, the iRNA can be expressed as two separate, complementary single-stranded RNA molecules from a recombinant AAV vector having, for example, either the U6 or H1 RNA promoters, or the cytomegalovirus (CMV) promoter. Suitable AAV vectors for expressing the dsRNA featured in the invention, methods for constructing the recombinant AV vector, and methods for delivering the vectors into target cells are described in Samulski R et al. (1987), *J. Virol.* 61: 3096-3101; Fisher K J et al. (1996), *J. Virol,* 70: 520-532; Samulski R et al. (1989), *J. Virol.* 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

Another viral vector suitable for delivery of an iRNA of the invention is a pox virus such as a vaccinia virus, for example an attenuated vaccinia such as Modified Virus Ankara (MVA) or NYVAC, an avipox such as fowl pox or canary pox.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes; see, e.g., Rabinowitz J E et al. (2002), *J Virol* 76:791-801, the entire disclosure of which is herein incorporated by reference.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

IV. Pharmaceutical Compositions of the Invention

The present invention also includes pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for treating a TMPRSS6 associated disease or disorder, e.g. hemochromatosis. Such pharmaceutical compositions are formulated based on the mode of delivery. One example is compositions that are formulated for systemic administration via parenteral delivery, e.g., by intravenous (IV) delivery. Another example is compositions that are formulated for direct delivery into the brain parenchyma, e.g., by infusion into the brain, such as by continuous pump infusion.

The pharmaceutical compositions comprising RNAi agents of the invention may be, for example, solutions with or without a buffer, or compositions containing pharmaceutically acceptable carriers. Such compositions include, for example, aqueous or crystalline compositions, liposomal formulations, micellar formulations, emulsions, and gene therapy vectors.

In the methods of the invention, the RNAi agent may be administered in a solution. A free RNAi agent may be administered in an unbuffered solution, e.g., in saline or in water. Alternatively, the free siRNA may also be administered in a suitable buffer solution. The buffer solution may comprise acetate, citrate, prolamine, carbonate, or phosphate, or any combination thereof. In a preferred embodiment, the buffer solution is phosphate buffered saline (PBS). The pH and osmolarity of the buffer solution containing the RNAi agent can be adjusted such that it is suitable for administering to a subject.

In some embodiments, the buffer solution further comprises an agent for controlling the osmolarity of the solution, such that the osmolarity is kept at a desired value, e.g., at the physiologic values of the human plasma. Solutes which can be added to the buffer solution to control the osmolarity include, but are not limited to, proteins, peptides, amino acids, non-metabolized polymers, vitamins, ions, sugars, metabolites, organic acids, lipids, or salts. In some embodiments, the agent for controlling the osmolarity of the solution is a salt. In certain embodiments, the agent for controlling the osmolarity of the solution is sodium chloride or potassium chloride.

The pharmaceutical compositions of the invention may be administered in dosages sufficient to inhibit expression of a TMPRSS6 gene.

In general, a suitable dose of an iRNA of the invention will be in the range of about 0.001 to about 200.0 milligrams per kilogram body weight of the recipient per day, generally in the range of about 1 to 50 mg per kilogram body weight per day. For example, the dsRNA can be administered at about 0.01 mg/kg, about 0.05 mg/kg, about 0.5 mg/kg, about 1 mg/kg, about 1.5 mg/kg, about 2 mg/kg, about 3 mg/kg, about 4 mg/kg, about 5 mg/kg, about 6 mg/kg, about 7 mg/kg, about 8 mg/kg, about 9 mg/kg about 10 mg/kg, about 20 mg/kg, about 30 mg/kg, about 40 mg/kg, or about 50 mg/kg per single dose.

For example, the RNAi agent, e.g., dsRNA, may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the RNAi agent, e.g., dsRNA, is administered at a dose of about 0.1 to about 50 mg/kg, about 0.25 to about 50 mg/kg, about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.1 to about 20 mg/kg, about 0.25 to about 20 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. Values and ranges intermediate to the recited values are also intended to be part of this invention.

For example, the RNAi agent, e.g., dsRNA, may be administered at a dose of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the RNAi agent, e.g., dsRNA, is administered at a dose of about 0.5 to about 50 mg/kg, about 0.75 to about 50 mg/kg, about 1 to about 50 mg/mg, about 1.5 to about 50 mg/kg, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 30 to about 40 mg/kg, about 35 to about 40 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. In one embodiment, the dsRNA is administered at a dose of about 10 mg/kg to about 30 mg/kg. Values and ranges intermediate to the recited values are also intended to be part of this invention.

For example, subjects can be administered a therapeutic amount of iRNA, such as about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

In certain embodiments, for example, when a composition of the invention comprises a dsRNA as described herein and a lipid, subjects can be administered a therapeutic amount of iRNA, such as about 0.01 mg/kg to about 5 mg/kg, about 0.01 mg/kg to about 10 mg/kg, about 0.05 mg/kg to about 5 mg/kg, about 0.05 mg/kg to about 10 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 1 mg/kg to about 5 mg/kg, about 1 mg/kg to about 10 mg/kg, about 1.5 mg/kg to about 5 mg/kg, about 1.5 mg/kg to about 10 mg/kg, about 2 mg/kg to about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg. Values and ranges intermediate to the recited values are also intended to be part of this invention. For example, the dsRNA may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In certain embodiments of the invention, for example, when a double-stranded RNAi agent includes modifications (e.g., one or more motifs of three identical modifications on three consecutive nucleotides, including one such motif at or near the cleavage site of the agent), six phosphorothioate linkages, and a ligand, such an agent is administered at a dose of about 0.01 to about 0.5 mg/kg, about 0.01 to about 0.4 mg/kg, about 0.01 to about 0.3 mg/kg, about 0.01 to about 0.2 mg/kg, about 0.01 to about 0.1 mg/kg, about 0.01 mg/kg to about 0.09 mg/kg, about 0.01 mg/kg to about 0.08 mg/kg, about 0.01 mg/kg to about 0.07 mg/kg, about 0.01 mg/kg to about 0.06 mg/kg, about 0.01 mg/kg to about 0.05 mg/kg, about 0.02 to about 0.5 mg/kg, about 0.02 to about 0.4 mg/kg, about 0.02 to about 0.3 mg/kg, about 0.02 to about 0.2 mg/kg, about 0.02 to about 0.1 mg/kg, about 0.02 mg/kg to about 0.09 mg/kg, about 0.02 mg/kg to about 0.08 mg/kg, about 0.02 mg/kg to about 0.07 mg/kg, about 0.02 mg/kg to about 0.06 mg/kg, about 0.02 mg/kg to about 0.05 mg/kg, about 0.03 to about 0.5 mg/kg, about 0.03 to about 0.4 mg/kg, about 0.03 to about 0.3 mg/kg, about 0.03 to about 0.2 mg/kg, about 0.03 to about 0.1 mg/kg, about 0.03 mg/kg to about 0.09 mg/kg, about 0.03 mg/kg to about 0.08 mg/kg, about 0.03 mg/kg to about 0.07 mg/kg, about 0.03 mg/kg to about 0.06 mg/kg, about 0.03 mg/kg to about 0.05 mg/kg, about 0.04 to about 0.5 mg/kg, about 0.04 to about 0.4 mg/kg, about 0.04 to about 0.3 mg/kg, about 0.04 to about 0.2 mg/kg, about 0.04 to about 0.1 mg/kg, about 0.04 mg/kg to about 0.09 mg/kg, about 0.04 mg/kg to about 0.08 mg/kg, about 0.04 mg/kg to about 0.07 mg/kg, about 0.04 mg/kg to about 0.06 mg/kg, about 0.05 to about 0.5 mg/kg, about 0.05 to about 0.4 mg/kg, about 0.05 to about 0.3 mg/kg, about 0.05 to about 0.2 mg/kg, about 0.05 to about 0.1 mg/kg, about 0.05 mg/kg to about 0.09 mg/kg, about 0.05 mg/kg to about 0.08 mg/kg, or about 0.05 mg/kg to about 0.07 mg/kg. Values and ranges intermediate to the foregoing recited values are also intended to be part of this invention, e.g., the RNAi agent may be administered to the subject at a dose of about 0.015 mg/kg to about 0.45 mg/mg.

For example, the RNAi agent, e.g., RNAi agent in a pharmaceutical composition, may be administered at a dose of about 0.01 mg/kg, 0.0125 mg/kg, 0.015 mg/kg, 0.0175 mg/kg, 0.02 mg/kg, 0.0225 mg/kg, 0.025 mg/kg, 0.0275 mg/kg, 0.03 mg/kg, 0.0325 mg/kg, 0.035 mg/kg, 0.0375 mg/kg, 0.04 mg/kg, 0.0425 mg/kg, 0.045 mg/kg, 0.0475 mg/kg, 0.05 mg/kg, 0.0525 mg/kg, 0.055 mg/kg, 0.0575 mg/kg, 0.06 mg/kg, 0.0625 mg/kg, 0.065 mg/kg, 0.0675 mg/kg, 0.07 mg/kg, 0.0725 mg/kg, 0.075 mg/kg, 0.0775 mg/kg, 0.08 mg/kg, 0.0825 mg/kg, 0.085 mg/kg, 0.0875 mg/kg, 0.09 mg/kg, 0.0925 mg/kg, 0.095 mg/kg, 0.0975 mg/kg, 0.1 mg/kg, 0.125 mg/kg, 0.15 mg/kg, 0.175 mg/kg, 0.2 mg/kg, 0.225 mg/kg, 0.25 mg/kg, 0.275 mg/kg, 0.3 mg/kg, 0.325 mg/kg, 0.35 mg/kg, 0.375 mg/kg, 0.4 mg/kg, 0.425 mg/kg, 0.45 mg/kg, 0.475 mg/kg, or about 0.5 mg/kg. Values intermediate to the foregoing recited values are also intended to be part of this invention.

The pharmaceutical composition can be administered once daily, or the iRNA can be administered as two, three, or more sub-doses at appropriate intervals throughout the day or even using continuous infusion or delivery through a controlled release formulation. In that case, the iRNA contained in each sub-dose must be correspondingly smaller in order to achieve the total daily dosage. The dosage unit can also be compounded for delivery over several days, e.g., using a conventional sustained release formulation which provides sustained release of the iRNA over a several day period. Sustained release formulations are well known in the art and are particularly useful for delivery of agents at a particular site, such as could be used with the agents of the present invention. In this embodiment, the dosage unit contains a corresponding multiple of the daily dose.

In other embodiments, a single dose of the pharmaceutical compositions can be long lasting, such that subsequent doses are administered at not more than 3, 4, or 5 day intervals, or at not more than 1, 2, 3, or 4 week intervals. In some embodiments of the invention, a single dose of the pharmaceutical compositions of the invention is administered once per week. In other embodiments of the invention, a single dose of the pharmaceutical compositions of the invention is administered bi-monthly.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using an appropriate animal model, as described elsewhere herein.

Advances in mouse genetics have generated a number of mouse models for the study of various human diseases, such as a disorder associated with iron overload that would benefit from reduction in the expression of TMPRSS6. Such models can be used for in vivo testing of iRNA, as well as for determining a therapeutically effective dose. Suitable mouse models are known in the art and include, for example, the thalassemic Th3/+ mouse as a model of β-thalassemia (Douet et al., *Am. J. Pathol.* (2011), 178(2):774-83), the HFE knockout mouse as a model of hereditary hemochromatosis (Zhou et al. (1998) *Proc. Natl. Acad. Sci USA*, 85:2492-2497); a Uros(mut248) mouse as a model of congenital erythropoietic *porphyria* (Ged et al. (2006) *Genomics*, 87(1):84-92).

The pharmaceutical compositions of the present invention can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration The iRNA can be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention can be encapsulated within liposomes or can form complexes thereto, in particular to cationic liposomes. Alternatively, iRNAs can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof). Topical formulations are described in detail in U.S. Pat. No. 6,747,014, which is incorporated herein by reference.

A. iRNA Formulations Comprising Membranous Molecular Assemblies

An iRNA for use in the compositions and methods of the invention can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the iRNA composition. The lipophilic material isolates the aqueous interior from an aqueous exterior, which typically does not include the iRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the iRNA are delivered into the cell where the iRNA can specifically bind to a target RNA and can mediate RNAi. In some cases the liposomes are also specifically targeted, e.g., to direct the iRNA to particular cell types.

A liposome containing a RNAi agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The RNAi agent preparation is then added to the micelles that include the lipid component. The cationic groups on the lipid interact with the RNAi agent and condense around the RNAi agent to form a liposome. After condensation, the detergent is removed, e.g., by dialysis, to yield a liposomal preparation of RNAi agent.

If necessary a carrier compound that assists in condensation can be added during the condensation reaction, e.g., by controlled addition. For example, the carrier compound can be a polymer other than a nucleic acid (e.g., spermine or spermidine). pH can also adjusted to favor condensation.

Methods for producing stable polynucleotide delivery vehicles, which incorporate a polynucleotide/cationic lipid complex as structural components of the delivery vehicle, are further described in, e.g., WO 96/37194, the entire contents of which are incorporated herein by reference. Liposome formation can also include one or more aspects of exemplary methods described in Felgner, P. L. et al., *Proc. Natl. Acad. Sci., USA* 8:7413-7417, 1987; U.S. Pat. No. 4,897,355; U.S. Pat. No. 5,171,678; Bangham, et al. *M. Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986). Microfluidization can be used when consistently small (50 to 200 nm) and relatively uniform aggregates are desired (Mayhew, et al. *Biochim. Biophys. Acta* 775:169, 1984). These methods are readily adapted to packaging RNAi agent preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980-985).

Liposomes which are pH-sensitive or negatively-charged, entrap nucleic acids rather than complex with it. Since both the nucleic acid and the lipid are similarly charged, repulsion rather than complex formation occurs. Nevertheless, some nucleic acid is entrapped within the aqueous interior of these liposomes. pH-sensitive liposomes have been used to deliver nucleic acids encoding the thymidine kinase gene to cell monolayers in culture. Expression of the exogenous gene was detected in the target cells (Zhou et al., *Journal of Controlled Release*, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. No. 5,283,185; U.S. Pat. No. 5,171,678; WO 94/00569; WO 93/24640; WO 91/16024; Felgner, *J. Biol. Chem.* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al. *S.T.P. Pharma. Sci.*, 1994, 4(6) 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver RNAi agents to macrophages.

Further advantages of liposomes include: liposomes obtained from natural phospholipids are biocompatible and biodegradable; liposomes can incorporate a wide range of water and lipid soluble drugs; liposomes can protect encapsulated RNAi agents in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of RNAi agent (see, e.g., Felgner, P. L. et al., Proc. Natl. Acad. Sci., USA 8:7413-7417, 1987 and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoyl-phosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., *Biochim. Biophys. Res. Commun.* 179:280, 1991). Lipopolylysine, made by conjugating polylysine to DOPE, has been reported to be effective for transfection in the presence of serum (Zhou, X. et al., *Biochim. Biophys. Acta* 1065:8, 1991). For certain cell lines, these liposomes containing conjugated cationic lipids, are said to exhibit lower toxicity and provide more efficient transfection than the DOTMA-containing compositions.

Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer RNAi agent into the skin. In some implementations, liposomes are used for delivering RNAi agent to epidermal cells and also to enhance the penetration of RNAi agent into dermal tissues, e.g., into skin. For example, the liposomes can be applied topically. Topical delivery of drugs formulated as liposomes to the skin has been documented (see, e.g., Weiner et al., *Journal of Drug Targeting*, 1992, vol. 2, 405-410 and du Plessis et al., *Antiviral Research*, 18, 1992, 259-265; Mannino, R. J. and Fould-Fogerite, S., *Biotechniques* 6:682-690, 1988; Itani, T. et al. *Gene* 56:267-276. 1987; Nicolau, C. et al. *Meth. Enz.* 149:157-176, 1987; Straubinger, R. M. and Papahadjopoulos, D. *Meth. Enz.* 101:512-527, 1983; Wang, C. Y. and Huang, L., *Proc. Natl. Acad. Sci. USA* 84:7851-7855, 1987).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with RNAi agent are useful for treating a dermatological disorder.

Liposomes that include iRNA can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include RNAi agent can be delivered, for example, subcutaneously by infection in order to deliver RNAi agent to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present invention are described in U.S. provisional application Ser. No. 61/018, 616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

The iRNA for use in the methods of the invention can also be provided as micellar formulations. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

B. Lipid Particles iRNAs, e.g., dsRNAs of in the invention may be fully encapsulated in a lipid formulation, e.g., a LNP, or other nucleic acid-lipid particle.

As used herein, the term "LNP" refers to a stable nucleic acid-lipid particle. LNPs contain a cationic lipid, a non-cationic lipid, and a lipid that prevents aggregation of the particle (e.g., a PEG-lipid conjugate). LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; U.S. Publication No. 2010/0324120 and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the invention.

The cationic lipid can be, for example, N,N-dioleyl-N,N-dimethylammonium chloride (DODAC), N,N-distearyl-N,N-dimethylammonium bromide (DDAB), N—(I-(2,3-dioleoyloxy)propyl)-N,N,N-trimethylammonium chloride (DOTAP), N—(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N- dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis (2-hydroxydodecyl)amino)ethyl)(2-hydroxydodecyl)amino) ethyl)piperazin-1-yl)ethylazanediyl)didodecan-2-ol (Tech G1), or a mixture thereof. The cationic lipid can comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference. In one embodiment, the lipid-siRNA particle includes 40% 2,2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/Lipid Ratio.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles can be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98.4HCl (MW 1487) (see U.S. patent application Ser. No. 12/056,230, filed Mar. 26, 2008, which is incorporated herein by reference), Cholesterol (Sigma-Aldrich), and PEG-Ceramide C16 (Avanti Polar Lipids) can be used to prepare lipid-dsRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous dsRNA (e.g., in sodium acetate pH 5) such that the final ethanol concentration is about 35-45% and the final sodium acetate concentration is about 100-300 mM. Lipid-dsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula I

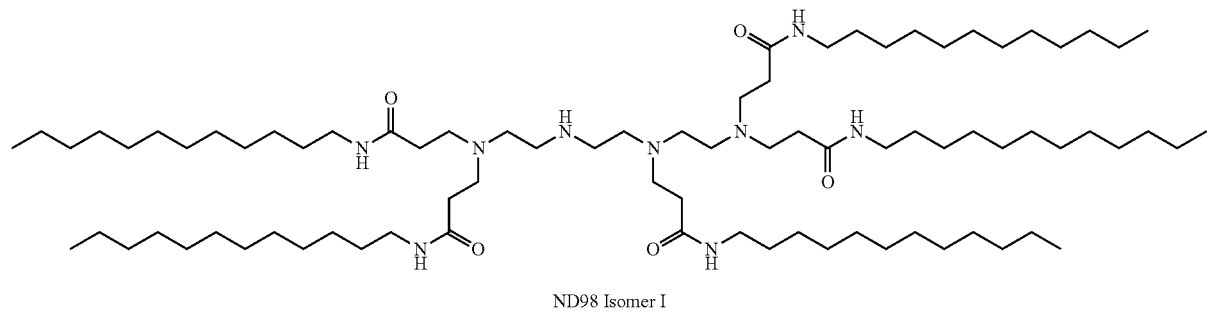

ND98 Isomer I

LNP01 formulations are described, e.g., in International Application Publication No. WO 2008/042973, which is hereby incorporated by reference.

Additional exemplary lipid-dsRNA formulations are described in Table A.

TABLE A

| | Ionizable/Cationic Lipid | cationic lipid/non-cationic lipid/cholesterol/PEG-lipid conjugate Lipid:siRNA ratio |
|---|---|---|
| LNP-1 | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA ~7:1 |
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA ~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine(ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |
| LNP21 | C12-200 | C12-200/DSPC/Chol/PEG-DSG 50/10/38.5/1.5 Lipid:siRNA: 7:1 |
| LNP22 | XTC | XTC/DSPC/Chol/PEG-DSG 50/10/38.5/1.5 Lipid:siRNA: 10:1 |

DSPC: distearoylphosphatidylcholine

DPPC: dipalmitoylphosphatidylcholine

PEG-DMG: PEG-didimyristoyl glycerol (C14-PEG, or PEG-C14) (PEG with avg mol wt of 2000)

PEG-DSG: PEG-distyryl glycerol (C18-PEG, or PEG-C18) (PEG with avg mol wt of 2000)

PEG-cDMA: PEG-carbamoyl-1,2-dimyristyloxypropylamine (PEG with avg mol wt of 2000)

LNP (1,2-Dilinolenyloxy-N,N-dimethylaminopropane (DLinDMA)) comprising formulations are described in International Publication No. WO2009/127060, filed Apr. 15, 2009, which is hereby incorporated by reference.

XTC comprising formulations are described, e.g., in U.S. Provisional Ser. No. 61/148,366, filed Jan. 29, 2009; U.S. Provisional Ser. No. 61/156,851, filed Mar. 2, 2009; U.S. Provisional Serial No. filed Jun. 10, 2009; U.S. Provisional Ser. No. 61/228,373, filed Jul. 24, 2009; U.S. Provisional Ser. No. 61/239,686, filed Sep. 3, 2009, and International Application No. PCT/US2010/022614, filed Jan. 29, 2010, which are hereby incorporated by reference.

MC3 comprising formulations are described, e.g., in U.S. Publication No. 2010/0324120, filed Jun. 10, 2010, the entire contents of which are hereby incorporated by reference. ALNY-100 comprising formulations are described, e.g., International patent application number PCT/US09/63933, filed on Nov. 10, 2009, which is hereby incorporated by reference. C12-200 comprising formulations are described in U.S. Provisional Ser. No. 61/175,770, filed May 5, 2009 and International Application No. PCT/US10/33777, filed May 5, 2010, which are hereby incorporated by reference.

Synthesis of Ionizable/Cationic Lipids

Any of the compounds, e.g., cationic lipids and the like, used in the nucleic acid-lipid particles of the invention can be prepared by known organic synthesis techniques, including the methods described in more detail in the Examples. All substituents are as defined below unless indicated otherwise.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(=O)alkyl, —C(=O)alkenyl, and —C(=O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms can be optionally oxidized, and the nitrogen heteroatom can be optionally quaternized, including bicyclic rings in which any of the above heterocycles are fused to a benzene ring. The heterocycle can be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" means that, when substituted, at least one hydrogen atom is replaced with a substituent. In the case of an oxo substituent (=O) two hydrogen atoms are replaced. In this regard, substituents include oxo, halogen, heterocycle, —CN, —ORx, —NRxRy, —NRxC(=O)Ry, —NRxSO2Ry, —C(=O)Rx, —C(=O)ORx, —C(=O)NRxRy, —SOnRx and —SOnNRxRy, wherein n is 0, 1 or 2, Rx and Ry are the same or different and independently hydrogen, alkyl or heterocycle, and each of said alkyl and heterocycle substituents can be further substituted with one or more of oxo, halogen, —OH, —CN, alkyl, —ORx, heterocycle, —NRxRy, —NRxC(=O)Ry, —NRxSO2Ry, —C(=O)Rx, —C(=O)ORx, —C(=O)NRxRy, —SOnRx and —SOnNRxRy.

"Halogen" means fluoro, chloro, bromo and iodo.

In some embodiments, the methods of the invention can require the use of protecting groups. Protecting group methodology is well known to those skilled in the art (see, for example, Protective Groups in Organic Synthesis, Green, T. W. et al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

Synthesis of Formula A

In some embodiments, nucleic acid-lipid particles of the invention are formulated using a cationic lipid of formula A:

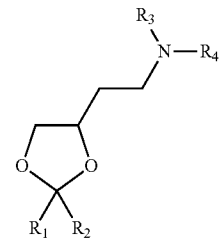

where R1 and R2 are independently alkyl, alkenyl or alkynyl, each can be optionally substituted, and R3 and R4 are independently lower alkyl or R3 and R4 can be taken together to form an optionally substituted heterocyclic ring. In some embodiments, the cationic lipid is XTC (2,2-Dilinoleyl-4-dimethylaminoethyl-[1,3]-dioxolane). In general, the lipid of formula A above can be made by the following Reaction Schemes 1 or 2, wherein all substituents are as defined above unless indicated otherwise.

Scheme 1

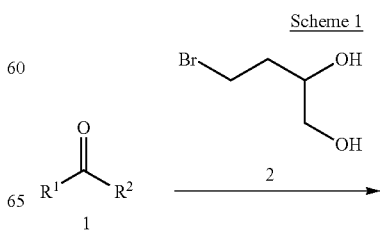

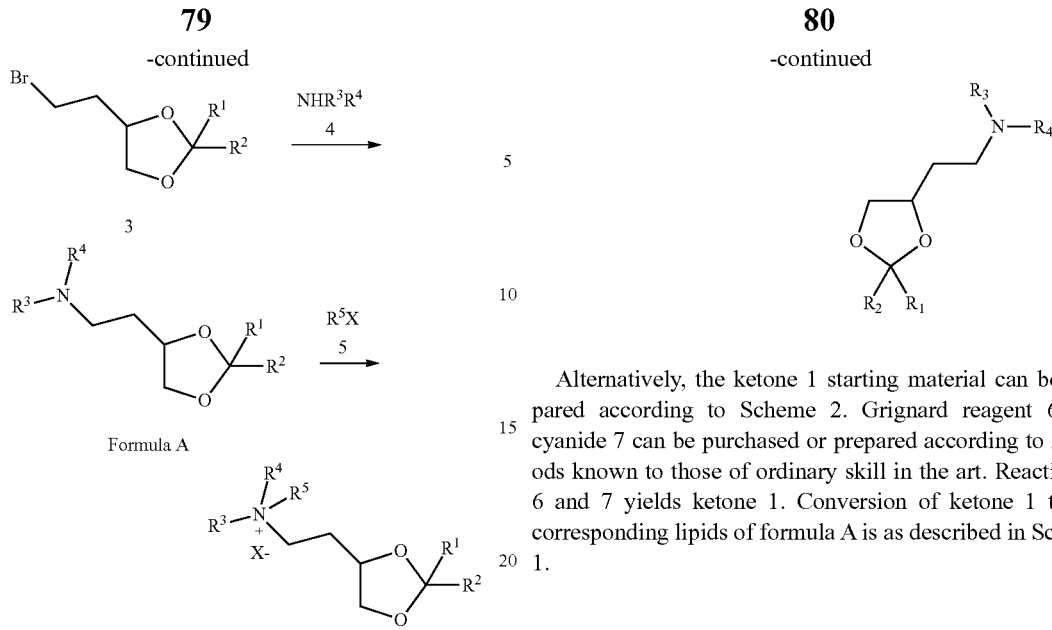

Lipid A, where R1 and R2 are independently alkyl, alkenyl or alkynyl, each can be optionally substituted, and R3 and R4 are independently lower alkyl or R3 and R4 can be taken together to form an optionally substituted heterocyclic ring, can be prepared according to Scheme 1. Ketone 1 and bromide 2 can be purchased or prepared according to methods known to those of ordinary skill in the art. Reaction of 1 and 2 yields ketal 3. Treatment of ketal 3 with amine 4 yields lipids of formula A. The lipids of formula A can be converted to the corresponding ammonium salt with an organic salt of formula 5, where X is anion counter ion selected from halogen, hydroxide, phosphate, sulfate, or the like.

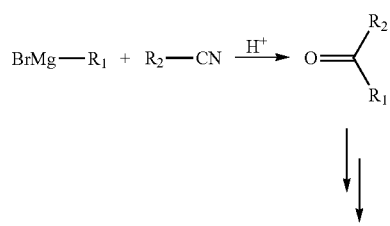

Alternatively, the ketone 1 starting material can be prepared according to Scheme 2. Grignard reagent 6 and cyanide 7 can be purchased or prepared according to methods known to those of ordinary skill in the art. Reaction of 6 and 7 yields ketone 1. Conversion of ketone 1 to the corresponding lipids of formula A is as described in Scheme 1.

Synthesis of MC3

Preparation of DLin-M-C3-DMA (i.e., (6Z,9Z,28Z,31Z)-heptatriaconta-6,9,28,31-tetraen-19-yl 4-(dimethylamino)butanoate) was as follows. A solution of (6Z,9Z,28Z,31Z)-heptatriaconta-6,9,28,31-tetraen-19-ol (0.53 g), 4-N,N-dimethylaminobutyric acid hydrochloride (0.51 g), 4-N,N-dimethylaminopyridine (0.61 g) and 1-ethyl-3-(3-dimethylaminopropyl)carbodiimide hydrochloride (0.53 g) in dichloromethane (5 mL) was stirred at room temperature overnight. The solution was washed with dilute hydrochloric acid followed by dilute aqueous sodium bicarbonate. The organic fractions were dried over anhydrous magnesium sulphate, filtered and the solvent removed on a rotovap. The residue was passed down a silica gel column (20 g) using a 1-5% methanol/dichloromethane elution gradient. Fractions containing the purified product were combined and the solvent removed, yielding a colorless oil (0.54 g). Synthesis of ALNY-100

Synthesis of ketal 519 [ALNY-100] was performed using the following scheme 3:

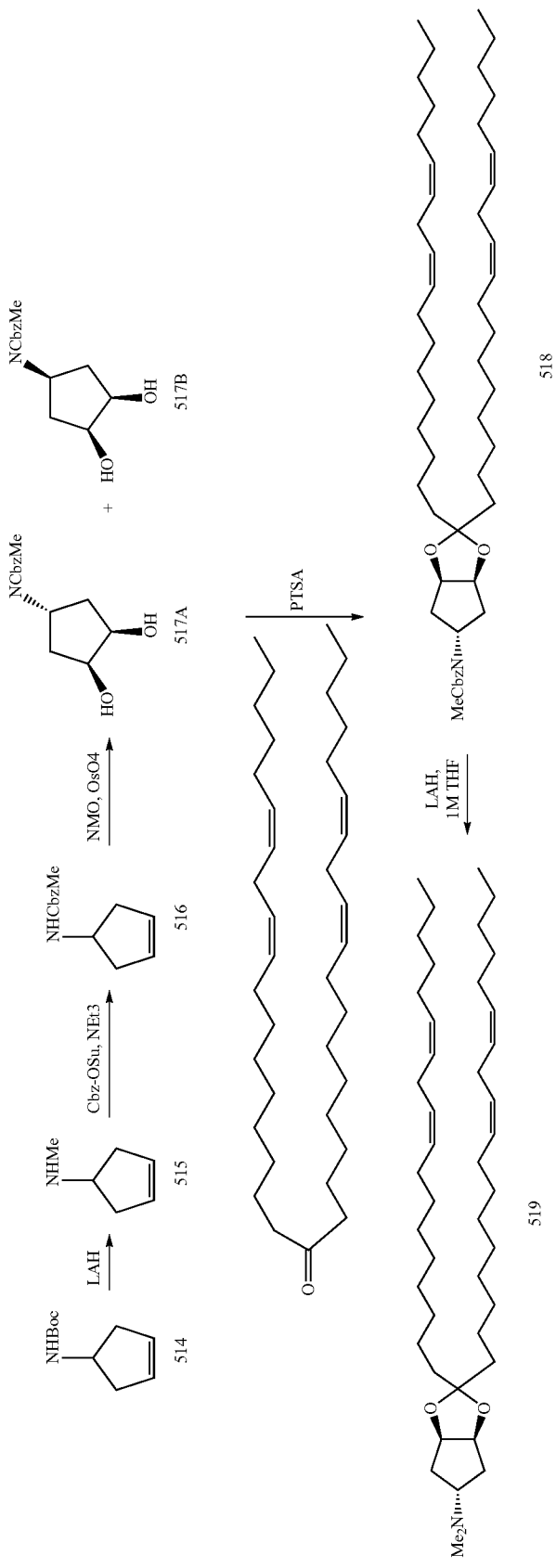

Synthesis of 515

To a stirred suspension of LiAlH4 (3.74 g, 0.09852 mol) in 200 ml anhydrous THF in a two neck RBF (1 L), was added a solution of 514 (10 g, 0.04926 mol) in 70 mL of THF slowly at 0° C. under nitrogen atmosphere. After complete addition, reaction mixture was warmed to room temperature and then heated to reflux for 4 h. Progress of the reaction was monitored by TLC. After completion of reaction (by TLC) the mixture was cooled to 0° C. and quenched with careful addition of saturated Na2SO4 solution. Reaction mixture was stirred for 4 h at room temperature and filtered off. Residue was washed well with THF. The filtrate and washings were mixed and diluted with 400 mL dioxane and 26 mL conc. HCl and stirred for 20 minutes at room temperature. The volatilities were stripped off under vacuum to furnish the hydrochloride salt of 515 as a white solid. Yield: 7.12 g 1H-NMR (DMSO, 400 MHz): δ=9.34 (broad, 2H), 5.68 (s, 2H), 3.74 (m, 1H), 2.66-2.60 (m, 2H), 2.50-2.45 (m, 5H).

Synthesis of 516

To a stirred solution of compound 515 in 100 mL dry DCM in a 250 mL two neck RBF, was added NEt3 (37.2 mL, 0.2669 mol) and cooled to 0° C. under nitrogen atmosphere. After a slow addition of N-(benzyloxy-carbonyloxy)-succinimide (20 g, 0.08007 mol) in 50 mL dry DCM, reaction mixture was allowed to warm to room temperature. After completion of the reaction (2-3 h by TLC) mixture was washed successively with 1N HCl solution (1×100 mL) and saturated NaHCO3 solution (1×50 mL). The organic layer was then dried over anhyd. Na2SO4 and the solvent was evaporated to give crude material which was purified by silica gel column chromatography to get 516 as sticky mass. Yield: 11 g (89%). 1H-NMR (CDCl3, 400 MHz): δ=7.36-7.27 (m, 5H), 5.69 (s, 2H), 5.12 (s, 2H), 4.96 (br., 1H) 2.74 (s, 3H), 2.60 (m, 2H), 2.30-2.25 (m, 2H). LC-MS [M+H]-232.3 (96.94%).

Synthesis of 517A and 517B

The cyclopentene 516 (5 g, 0.02164 mol) was dissolved in a solution of 220 mL acetone and water (10:1) in a single neck 500 mL RBF and to it was added N-methyl morpholine-N-oxide (7.6 g, 0.06492 mol) followed by 4.2 mL of 7.6% solution of OsO4 (0.275 g, 0.00108 mol) in tert-butanol at room temperature. After completion of the reaction (~3 h), the mixture was quenched with addition of solid Na2SO3 and resulting mixture was stirred for 1.5 h at room temperature. Reaction mixture was diluted with DCM (300 mL) and washed with water (2×100 mL) followed by saturated NaHCO3 (1×50 mL) solution, water (1×30 mL) and finally with brine (1×50 mL). Organic phase was dried over an. Na2SO4 and solvent was removed in vacuum. Silica gel column chromatographic purification of the crude material was afforded a mixture of diastereomers, which were separated by prep HPLC. Yield: ~6 g crude 517A—Peak-1 (white solid), 5.13 g (96%). 1H-NMR (DMSO, 400 MHz): δ=7.39-7.31 (m, 5H), 5.04 (s, 2H), 4.78-4.73 (m, 1H), 4.48-4.47 (d, 2H), 3.94-3.93 (m, 2H), 2.71 (s, 3H), 1.72-1.67 (m, 4H). LC-MS—[M+H]-266.3, [M+NH4+]-283.5 present, HPLC-97.86%. Stereochemistry confirmed by X-ray.

Synthesis of 518

Using a procedure analogous to that described for the synthesis of compound 505, compound 518 (1.2 g, 41%) was obtained as a colorless oil. 1H-NMR (CDCl3, 400 MHz): δ=7.35-7.33 (m, 4H), 7.30-7.27 (m, 1H), 5.37-5.27 (m, 8H), 5.12 (s, 2H), 4.75 (m, 1H), 4.58-4.57 (m, 2H), 2.78-2.74 (m, 7H), 2.06-2.00 (m, 8H), 1.96-1.91 (m, 2H), 1.62 (m, 4H), 1.48 (m, 2H), 1.37-1.25 (br m, 36H), 0.87 (m, 6H). HPLC-98.65%.

General Procedure for the Synthesis of Compound 519

A solution of compound 518 (1 eq) in hexane (15 mL) was added in a drop-wise fashion to an ice-cold solution of LAH in THF (1 M, 2 eq). After complete addition, the mixture was heated at 40° C. over 0.5 h then cooled again on an ice bath. The mixture was carefully hydrolyzed with saturated aqueous Na2SO4 then filtered through celite and reduced to an oil. Column chromatography provided the pure 519 (1.3 g, 68%) which was obtained as a colorless oil. 13C NMR δ=130.2, 130.1 (×2), 127.9 (×3), 112.3, 79.3, 64.4, 44.7, 38.3, 35.4, 31.5, 29.9 (×2), 29.7, 29.6 (×2), 29.5 (×3), 29.3 (×2), 27.2 (×3), 25.6, 24.5, 23.3, 226, 14.1; Electrospray MS (+ve): Molecular weight for C44H80NO2 (M+H)+Calc. 654.6. Found 654.6.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total dsRNA concentration in the formulation, as well as the entrapped fraction, is estimated using a dye exclusion assay. A sample of the formulated dsRNA can be incubated with an RNA-binding dye, such as Ribogreen (Molecular Probes) in the presence or absence of a formulation disrupting surfactant, e.g., 0.5% Triton-X100. The total dsRNA in the formulation can be determined by the signal from the sample containing the surfactant, relative to a standard curve. The entrapped fraction is determined by subtracting the "free" dsRNA content (as measured by the signal in the absence of surfactant) from the total dsRNA content. Percent entrapped dsRNA is typically >85%. For LNP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the invention are administered in conjunction with one or more penetration enhancer surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention can be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension can also contain stabilizers.

C. Additional Formulations i. Emulsions

The compositions of the present invention can be prepared and formulated as emulsions. Emulsions are typically heterogeneous systems of one liquid dispersed in another in the form of droplets usually exceeding 0.1 µm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present invention, the compositions of iRNAs and nucleic acids are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191, 105; 7,063,860; 7,070,802; 7,157,099; Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., Pharmaceutical Research, 1994, 11, 1385; Ho et al., J. Pharm. Sci., 1996, 85, 138-143). Often microemulsions can form spontaneously when their components are brought together at ambient temperature. This can be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention can also contain additional components and additives such as sorbitan monostearate (Grill 3), Labrasol, and penetration enhancers to improve the properties of the formulation and to enhance the absorption of the iRNAs and nucleic acids of the present invention. Penetration enhancers used in the microemulsions of the present invention can be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

iii. Microparticles

An RNAi agent of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., *J. Pharm. Exp. Ther.,* 1992, 263, 25; Yamashita et al., *J. Pharm. Sci.,* 1990, 79, 579-583).

Chelating agents, as used in connection with the present invention, can be defined as compounds that remove metallic ions from solution by forming complexes therewith, with the result that absorption of iRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., *J. Control Rel.,* 1990, 14, 43-51).

As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., *J. Pharm. Pharmacol.,* 1987, 39, 621-626).

Agents that enhance uptake of iRNAs at the cellular level can also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen; Carlsbad, Calif.), Lipofectamine 2000™ (Invitrogen; Carlsbad, Calif.), 293Fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPass$^a$ D1 Transfection Reagent (New England Biolabs; Ipswich, Mass., USA), LyoVec™/LipoGen™ (Invitrogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents can be utilized to enhance the penetration of the administered nucleic acids, including glycols such as ethylene glycol and propylene glycol, pyrrols such as 2-pyrrol, azones, and terpenes such as limonene and menthone.

v. Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

vi. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions can contain substances which increase the viscosity of the suspension including, for example, sodium carboxymethylcellulose, sorbitol and/or dextran. The suspension can also contain stabilizers.

In some embodiments, pharmaceutical compositions featured in the invention include (a) one or more iRNA compounds and (b) one or more agents which function by a non-RNAi mechanism and which are useful in treating a bleeding disorder. Examples of such agents include, but are not limited to an anti-inflammatory agent, anti-steatosis agent, anti-viral, and/or anti-fibrosis agent. In addition, other substances commonly used to protect the liver, such as silymarin, can also be used in conjunction with the iRNAs described herein. Other agents useful for treating liver diseases include telbivudine, entecavir, and protease inhibitors such as telaprevir and other disclosed, for example, in Tung et al., U.S. Application Publication Nos. 2005/0148548, 2004/0167116, and 2003/0144217; and in Hale et al., U.S. Application Publication No. 2004/0127488.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the ED50 with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the iRNAs featured in the invention can be administered in combination with other known agents effective in treatment of pathological processes that are mediated by iron overload and that can be treated by inhibiting TMPRSS6 expression. In any event, the administering physician can adjust the amount and timing of iRNA administration on the basis of results observed using standard measures of efficacy known in the art or described herein.

V. Methods for Inhibiting TMPRSS6 Expression

The present invention provides methods of inhibiting expression of TMPRSS6 (matriptase-2) in a cell. The methods include contacting a cell with an RNAi agent, e.g., a double stranded RNAi agent, in an amount effective to inhibit expression of the TMPRSS6 in the cell, thereby inhibiting expression of the TMPRSS6 in the cell.

Contacting of a cell with a double stranded RNAi agent may be done in vitro or in vivo. Contacting a cell in vivo with the RNAi agent includes contacting a cell or group of cells within a subject, e.g., a human subject, with the RNAi agent. Combinations of in vitro and in vivo methods of contacting are also possible. Contacting may be direct or indirect, as discussed above. Furthermore, contacting a cell may be accomplished via a targeting ligand, including any ligand described herein or known in the art. In preferred embodiments, the targeting ligand is a carbohydrate moiety, e.g., a $GalNAc_3$ ligand, or any other ligand that directs the RNAi agent to a site of interest, e.g., the liver of a subject.

The term "inhibiting," as used herein, is used interchangeably with "reducing," "silencing," "downregulating" and other similar terms, and includes any level of inhibition.

The phrase "inhibiting expression of a TMPRSS6" is intended to refer to inhibition of expression of any TMPRSS6 gene (such as, e.g., a mouse TMPRSS6 gene, a rat TMPRSS6 gene, a monkey TMPRSS6 gene, or a human TMPRSS6 gene) as well as variants or mutants of a TMPRSS6 gene. Thus, the TMPRSS6 gene may be a wild-type TMPRSS6 gene, a mutant TMPRSS6 gene, or a transgenic TMPRSS6 gene in the context of a genetically manipulated cell, group of cells, or organism.

"Inhibiting expression of a TMPRSS6 gene" includes any level of inhibition of a TMPRSS6 gene, e.g., at least partial suppression of the expression of a TMPRSS6 gene. The expression of the TMPRSS6 gene may be assessed based on the level, or the change in the level, of any variable associated with TMPRSS6 gene expression, e.g., TMPRSS6 mRNA level, TMPRSS6 protein level, or lipid levels. This level may be assessed in an individual cell or in a group of cells, including, for example, a sample derived from a subject.

Inhibition may be assessed by a decrease in an absolute or relative level of one or more variables that are associated with TMPRSS6 expression compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In some embodiments of the methods of the invention, expression of a TMPRSS6 gene is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%. at least about 95%, at least about 96%, at least about 97%, at least about 98%, or at least about 99%.

Inhibition of the expression of a TMPRSS6 gene may be manifested by a reduction of the amount of mRNA expressed by a first cell or group of cells (such cells may be present, for example, in a sample derived from a subject) in which a TMPRSS6 gene is transcribed and which has or have been treated (e.g., by contacting the cell or cells with an RNAi agent of the invention, or by administering an RNAi agent of the invention to a subject in which the cells are or were present) such that the expression of a TMPRSS6 gene is inhibited, as compared to a second cell or group of cells substantially identical to the first cell or group of cells but which has not or have not been so treated (control cell(s)). In preferred embodiments, the inhibition is assessed by expressing the level of mRNA in treated cells as a percentage of the level of mRNA in control cells, using the following formula:

$$\frac{(mRNA\ in\ control\ cells) - (mRNA\ in\ treated\ cells)}{(mRNA\ in\ control\ cells)} \cdot 100\%$$

Alternatively, inhibition of the expression of a TMPRSS6 gene may be assessed in terms of a reduction of a parameter that is functionally linked to TMPRSS6 gene expression, e.g., TMPRSS6 protein expression, hepcidin gene or protein expression, or iron levels in tissues or serum. TMPRSS6 gene silencing may be determined in any cell expressing TMPRSS6, either constitutively or by genomic engineering, and by any assay known in the art. The liver is the major site of TMPRSS6 expression. Other significant sites of expression include the kidneys and the uterus.

Inhibition of the expression of a TMPRSS6 protein may be manifested by a reduction in the level of the TMPRSS6 protein that is expressed by a cell or group of cells (e.g., the level of protein expressed in a sample derived from a subject). As explained above for the assessment of mRNA suppression, the inhibition of protein expression levels in a treated cell or group of cells may similarly be expressed as a percentage of the level of protein in a control cell or group of cells.

A control cell or group of cells that may be used to assess the inhibition of the expression of a TMPRSS6 gene includes a cell or group of cells that has not yet been contacted with an RNAi agent of the invention. For example, the control cell or group of cells may be derived from an individual subject (e.g., a human or animal subject) prior to treatment of the subject with an RNAi agent.

The level of TMPRSS6 mRNA that is expressed by a cell or group of cells may be determined using any method known in the art for assessing mRNA expression. In one embodiment, the level of expression of TMPRSS6 in a sample is determined by detecting a transcribed polynucleotide, or portion thereof, e.g., mRNA of the TMPRSS6 gene. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (Pre-Analytix, Switzerland). Typical assay formats utilizing ribonucleic acid hybridization include nuclear run-on assays, RT-PCR, RNase protection assays (Melton et al., *Nuc. Acids Res.* 12:7035), Northern blotting, in situ hybridization, and microarray analysis.

In one embodiment, the level of expression of TMPRSS6 is determined using a nucleic acid probe. The term "probe", as used herein, refers to any molecule that is capable of selectively binding to a specific TMPRSS6. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or Northern analyses, polymerase chain reaction (PCR) analyses and probe arrays. One method for the determination of mRNA levels involves contacting the isolated mRNA with a nucleic acid molecule (probe) that can hybridize to TMPRSS6 mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in determining the level of TMPRSS6 mRNA.

An alternative method for determining the level of expression of TMPRSS6 in a sample involves the process of nucleic acid amplification and/or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of TMPRSS6 is determined by quantitative fluorogenic RT-PCR (i.e., the TaqMan™ System).

The expression levels of TMPRSS6 mRNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of TMPRSS6 expression level may also comprise using nucleic acid probes in solution.

In preferred embodiments, the level of mRNA expression is assessed using branched DNA (bDNA) assays or real time PCR (qPCR). The use of these methods is described and exemplified in the Examples presented herein.

The level of TMPRSS6 protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, Western blotting, radioimmunoas say (RIA), enzyme-linked immunosorbent assays (ELISAs), immunofluorescent assays, electrochemiluminescence assays, and the like.

The term "sample" as used herein refers to a collection of similar fluids, cells, or tissues isolated from a subject, as well as fluids, cells, or tissues present within a subject. Examples of biological fluids include blood, serum and serosal fluids, plasma, lymph, urine, cerebrospinal fluid, saliva, ocular fluids, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In preferred embodiments, a "sample derived from a subject" refers to blood or plasma drawn from the subject. In further embodiments, a "sample derived from a subject" refers to liver tissue derived from the subject.

In some embodiments of the methods of the invention, the RNAi agent is administered to a subject such that the RNAi agent is delivered to a specific site within the subject. The inhibition of expression of TMPRSS6 may be assessed using measurements of the level or change in the level of TMPRSS6 mRNA or TMPRSS6 protein in a sample derived from fluid or tissue from the specific site within the subject. In preferred embodiments, the site is the liver. The site may also be a subsection or subgroup of cells from any one of the aforementioned sites. The site may also include cells that express a particular type of receptor.

VI. Methods for Treating or Preventing a TMPRSS6 Associated Disorder

The present invention also provides methods for treating or preventing diseases and conditions that can be modulated by TMPRSS6 gene expression. For example, the compositions described herein can be used to treat any disorder associated with iron overload, e.g., a thalassemia (e.g., β-thalassemia or α-thalassemia), primary hemochromatosis, secondary hemochromatosis, severe juvenile hemochromatosis, erythropoietic *porphyria*, sideroblastic anemia, hemolytic anemia, dyserythropoietic anemia, or sickle-cell anemia. In one embodiment, a TMPRSS6 iRNA is used to treat a hemoglobinopathy. The TMPRSS6 iRNAs of the invention can also be used to treat elevated levels of iron due to other conditions, such as chronic alcoholism.

In thalassemias, the bone marrow synthesizes insufficient amounts of a hemoglobin chain; this in turn reduces the production of red blood cells and causes anemia. Either the α or the β chain may be affected, but β thalassemias are more common. Newborn babies are healthy because their bodies still produce HbF, which does not have β chains; during the first few months of life, the bone marrow switches to producing HbA, and symptoms start to appear.

β-thalassemias result from mutation with either non-expressing (β°) or low expressing (β+) alleles of the HBB gene, β-thalassemias vary in severity depending on the genotype, and include minor/trait β-thalassemia (β/β° or β/β+), intermedia β-thalassemia (β/β+), and major β-thalassemia (β°/β° or β"7 β+).

Thalassemia intermedia (TI) typically presents with little hemolysis, while major β-Thalassemia™ is typically accompanied by abundant hemolysis which causes, e.g., anemia and splenomegaly; and highly ineffective erythropoiesis, which causes bone marrow drive (skeletal changes, oteopenia), increased erythropoietin synthesis, hepato-splenomegaly, consumption of haematinics (megablastic anemia), and high uric acid in blood. The iRNAs of the invention, e.g., TMPRSS6 iRNAs, are better suited for treating the iron overload that typically accompanies thalassemia's that are more TI like (e.g., for treating individuals having a β°/β+, β/β° or β/β+ genotype).

Symptoms of β-thalassemias also include, e.g., complication due to therapy, e.g., iron overload, which causes endocrinopathy, liver fibrosis and cardiac fibrosis. Administration of an iRNA agent that targets TMPRSS6 can be effective to treat one or more of these symptoms. P α-thalassemias result from mutation with either non-expressing (α°) or low expressing (α+) alleles of the HBA1 or HBA2 genes, orthalassemias vary in severity depending on the genotype, and include trait thalassemia (-α/αα), Hb Bart and Hydrops fetalis)(α°/α°, a-Thalaseemia minor (-/αα), (-α/-α), and HbH disease (-/-α). Lower a-globin chains are produced, resulting in an excess of β chains in adults and excess γ chains in newborns. The excess β chains form unstable tetramers (called Hemoglobin H or HbH of 4 beta chains), which have abnormal oxygen dissociation curves. Administration of an iRNA agent that targets TMPRSS6 can be effective to treat iron overload in a subject who has an a-thalassemias.

Symptoms of hemochromatosis include, e.g., abdominal pain, joint pain, fatigue, lack of energy, weakness, darkening of the skin (often referred to as "bronzing"), and loss of body hair. Administration of an iRNA agent that targets TMPRSS6 can be effective to treat one or more of these symptoms.

Other symptoms associated with iron overload include increased risk for liver disease (cirrhosis, cancer), heart attack or heart failure, diabetes mellitus, osteoarthritis, osteoporosis, metabolic syndrome, hypothyroidism, hypogonadism, and in some cases premature death. Iron mismanagement resulting in overload can also accelerate such neurodegenerative diseases as Alzheimer's, early-onset Parkinson's, Huntington's, epilepsy and multiple sclerosis. Administration of an iRNA agent that targets TMPRSS6, e.g., an iRNA described in Tables 1 or 2 can treat one or more of these symptoms, or prevent the development or progression of a disease or disorder that is aggravated by increased iron levels.

The methods of the invention further relate to the use of an iRNA agent or a pharmaceutical composition thereof, e.g., for treating a disorder associated with iron overload, in combination with other pharmaceuticals and/or other therapeutic methods, e.g., with known pharmaceuticals and/or known therapeutic methods, such as, for example, those which are currently employed for treating these disorders. For example, in certain embodiments, an iRNA agent targeting TMPRSS6 is administered in combination with, e.g., iron chelators (e.g., desferoxamine), folic acid, a blood transfusion, a phlebotomy, agents to manage ulcers, agents to increase fetal hemoglobin levels (e.g., hydroxyurea), agents to control infection (e.g., antibiotics and antivirals), agents to treat thrombotic state, or a stem cell or bone marrow transplant. A stem cell transplant can utilize stem cells from an umbilical cord, such as from a relative, e.g., a sibling. Exemplary iron chelators include desferoxamine, Deferasirox (Exjade), deferiprone, vitamin E, wheat germ oil, tocophersolan, and indicaxanthin.

The iRNA agent and an additional therapeutic agent can be administered in the same composition, e.g., parenterally, or the additional therapeutic agent can be administered as part of a separate composition or by another method described herein. Administration of the iRNA agent and the additional therapeutic agent can be at the same time, or at different times and, in any order.

Administration of the iRNA agent of the invention can lower iron levels, lower ferritin levels, and/or lower transferrin saturation levels. For example, administration of the dsRNA can lower serum iron levels and/or lower serum ferritin levels. Transferrin saturation levels can be lowered by 5%, 10%, 15%, 20%, 25%, 30%, 35%, 40%, 45%, 50%, 55%, 60%, 65%, 70%, 75%, 80%, 85%, or more. In another embodiment, the transferrin saturation levels remain lower for 7 days, 10 days, 20 days, 30 days, or more following administration.

Transferrin saturation levels can be lowered to below 50%, below 45%, below 40%, below 35%, below 35%, below 30%, below 25%, below 20%, below 15%, or lower. In another embodiment, the lower transferrin saturation levels are maintained for 7 days, 10 days, 20 days, 30 days, or more following administration. Transferrin saturation is a measure of the amount of iron bound to serum transferrin, and corresponds to the ratio of serum iron and total iron-binding capacity.

Serum iron levels can be lowered by 20%, 30%, 40%, 50%, 60%, 70%, 80%, 90%, or more. In another embodiment, the serum iron levels remain lower for 7 days, 10 days, 20 days, 30 days, or more following administration.

Administration of the iRNA agent of the invention preferably results in lowered iron levels in the blood, and more particularly in the serum, or in one or more tissues of the mammal. In some embodiments, iron levels are decreased by at least 10%, 15%, 20%, 25%, 30%, 40%, 50%, 60%, 70%, 80%, 90% or more, as compared to pretreatment levels.

By "lower" in this context is meant a statistically significant decrease in such level. The decrease can be, for example, at least 10%, at least 20%, at least 30%, at least 40% or more, and is preferably down to a level accepted as within the range of normal for an individual without such disorder.

Administration of the iRNA agent of the invention can increase serum hepcidin levels, and/or increase hepcidin gene expression. For example, administration of the dsRNA can increase serum hepcidin by at least about 10%, 25%, 50%, 100%, 150%, 200%, 250%, 300%, or more. In a further example, administration of the dsRNA can increase hepcidin mRNA levels by at least about 1.5-fold, 2-fold, 3-fold, 4-fold, 5-fold, or greater.

Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, the levels of transferrin saturation or serum ferritin can be monitored for efficacy of a given treatment regime.

Iron level tests are typically performed on a sample of a patient's blood. An iron level test measure the amount of iron in the blood serum that is being carried by the proteins transferrin. A TIBC (Total iron-binding capacity) test measures the amount of iron that the blood would carry if the transferrin were fully saturated. Since transferrin is produced by the liver, the TIBC can be used to monitor liver function and nutrition. The transferrin test is a direct measure of transferrin (also called siderophilin) levels in the blood. The saturation level of transferrin can be calculated by dividing the serum iron level by the TIBC. The ferritin test measures the level of a protein in the blood that stores iron for later use by the body.

The iRNA treatments described herein can be used to treat individuals afflicted with a TMPRSS6 associated disorder, e.g., elevated iron levels, as may be indicated by iron levels in serum e.g., iron levels measuring greater than 350 µg/dL, greater than 500 µg/dL, greater than 1000 µg/dL, or more. In an embodiment, elevated levels of iron in serum, e.g., greater than 15, 20, 25, or 30 mg/g dry weight.

The iRNA treatments described herein can also be used to treat individuals having elevated iron levels, as may be indicated by elevated ferritin levels in serum, e.g., ferritin levels measuring greater than 300 µg/L, greater than 500 µg/L, greater than 1000 µg/L, greater than 1500 µg/L, greater than 2000 µg/L, greater than 2500 µg/L, or 3000 µg/L, or more.

The iRNA treatments described herein can further be used to treat individuals having elevated iron levels, as may be indicated by elevated transferrin levels in serum, e.g., transferrin levels measuring greater than 400 mg/dL, greater than 500 mg/L, greater than 1000 mg/dL, or more.

The iRNA treatments described herein can also be used to treat individuals having moderately elevated iron levels, as may be indicated by moderately elevated transferrin saturation levels, e.g., saturation levels of 40%, 45%, or 50% or more. In addition, the treatment described herein may also be used to prevent elevated iron levels in individuals with only minor elevations in transferrin saturation. One of skill in the art can easily monitor the transferrin saturation levels in subjects receiving treatment with iRNA as described herein and assay for a reduction in transferrin saturation levels of at least 5% or 10%.

The iRNA treatments described herein can be used to treat individuals having elevated iron levels, as may be indicated by a TIBC value greater than 400 µg/dL, greater than 500 µg/dL, or greater than 1000 µg/dL, or more.

In some embodiments, individuals in need of treatment with an iRNA agent of the invention have decreased hematocrit levels, decreased hemoglobin levels, increased red blood cell distribution width, increased number of reticulocytes, decreased number of mature red blood cells, increased unsaturated iron binding capacity, decreased ineffective erythropoiesis, decreased extradedullary hematopoiesis, and/or decreased HAMP1 expression levels.

A patient can be further monitored by assay of blood sugar (glucose) level or a fetoprotein level, by echocardiogram (e.g., to examine the heart's function), electrocardiogram (ECG) (e.g., to look at the electrical activity of the heart), imaging tests (such as CT scans, MRI and ultrasound), and liver function tests. Excess iron staining or iron concentrations can be measured on liver biopsy samples, or to confirm the extent of liver damage, e.g., the stage of liver disease.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given iRNA drug or formulation of that drug can also be judged using an experimental animal model for the given disease as known in the art. When using an experimental animal model, efficacy of treatment is evidenced when a statistically significant reduction in a marker or symptom is observed.

Alternatively, the efficacy can be measured by a reduction in the severity of disease as determined by one skilled in the art of diagnosis based on a clinically accepted disease severity grading scale.

As used herein, a "subject" includes a human or non-human animal, preferably a vertebrate, and more preferably a mammal. A subject may include a transgenic organism. Most preferably, the subject is a human, such as a human suffering from or predisposed to developing a TMPRSS6 associated disorder.

In some embodiments of the methods of the invention, TMPRSS6 expression is decreased for an extended duration, e.g., at least one week, two weeks, three weeks, or four weeks or longer. For example, in certain instances, expression of the TMPRSS6 gene is suppressed by at least about 5%, 10%, 15%, 20%, 25%, 30%, 35%, 40%, 45%, 50%, 55%, 60%, 65%, 70%, 75%, 80%, 85%, 90%, 95%, 98%, or 100% by administration of an iRNA agent described herein. In some embodiments, the TMPRSS6 gene is suppressed by at least about 60%, 70%, or 80% by administration of the iRNA agent. In some embodiments, the TMPRSS6 gene is suppressed by at least about 85%, 90%, or 95% by administration of the double-stranded oligonucleotide. In another embodiment, the TMPRSS6 gene remains suppressed for 7 days, 10 days, 20 days, 30 days, or more following administration.

The RNAi agents of the invention may be administered to a subject using any mode of administration known in the art, including, but not limited to subcutaneous, intravenous, intramuscular, intraocular, intrabronchial, intrapleural, intraperitoneal, intraarterial, lymphatic, cerebrospinal, and any combinations thereof. In preferred embodiments, the agents are administered subcutaneously.

In some embodiments, the administration is via a depot injection. A depot injection may release the RNAi agent in a consistent way over a prolonged time period. Thus, a depot injection may reduce the frequency of dosing needed to obtain a desired effect, e.g., a desired inhibition of TMPRSS6, or a therapeutic or prophylactic effect. A depot injection may also provide more consistent serum concentrations. Depot injections may include subcutaneous injections or intramuscular injections. In preferred embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intravenous, subcutaneous, arterial, or epidural infusions. In preferred embodiments, the infusion pump is a subcutaneous infusion pump. In other embodiments, the pump is a surgically implanted pump that delivers the RNAi agent to the liver.

Other modes of administration include epidural, intracerebral, intracerebroventricular, nasal administration, intraarterial, intracardiac, intraosseous infusion, intrathecal, and intravitreal, and pulmonary. The mode of administration may be chosen based upon whether local or systemic treatment is desired and based upon the area to be treated. The route and site of administration may be chosen to enhance targeting.

The method includes administering an iRNA agent, e.g., a dose sufficient to depress levels of TMPRSS6 mRNA for at least 5, more preferably 7, 10, 14, 21, 25, 30 or 40 days; and optionally, administering a second single dose of dsRNA, wherein the second single dose is administered at least 5, more preferably 7, 10, 14, 21, 25, 30 or 40 days after the first single dose is administered, thereby inhibiting the expression of the TMPRSS6 gene in a subject.

In one embodiment, doses of iRNA agent of the invention are administered not more than once every four weeks, not more than once every three weeks, not more than once every two weeks, or not more than once every week. In another embodiment, the administrations can be maintained for one, two, three, or six months, or one year or longer. In another embodiment, doses of iRNA agent of the invention are administered once a week for three weeks.

In general, the iRNA agent does not activate the immune system, e.g., it does not increase cytokine levels, such as TNF-alpha or IFN-alpha levels. For example, when measured by an assay, such as an in vitro PBMC assay, such as described herein, the increase in levels of TNF-alpha or IFN-alpha, is less than 30%, 20%, or 10% of control cells treated with a control dsRNA, such as a dsRNA that does not target TMPRSS6.

For example, a subject can be administered a therapeutic amount of an iRNA agent, such as 0.3 mg/kg, 0.5 mg/kg, 1.0 mg/kg, 1.5 mg/kg, 2.0 mg/kg, 2.5 mg/kg, or 3 mg/kg of dsRNA. The iRNA agent can be administered by intravenous infusion over a period of time, such as over a 5 minute, 10 minute, 15 minute, 20 minute, or 25 minute period. The administration is repeated, for example, on a regular basis, such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Administration of the iRNA agent can reduce TMPRSS6 levels, e.g., in a cell, tissue, blood, urine or other compartment of the patient by at least 10%, at least 15%, at least 20%, at least 25%, at least 30%, at least 40%, at least 50%, at least 60%, at least 70%, at least 80% or at least 90% or more.

Before administration of a full dose of the iRNA agent, patients can be administered a smaller dose, such as a dose resulting in less than 5% infusion reaction, and monitored for adverse effects, such as an allergic reaction, or for elevated lipid levels or blood pressure. In another example, the patient can be monitored for unwanted immunostimulatory effects, such as increased cytokine (e.g., TNF-alpha or INF-alpha) levels.

Many disorders associated with elevated iron levels are hereditary. Therefore, a patient in need of a TMPRSS6 iRNA may be identified by taking a family history. A healthcare provider, such as a doctor, nurse, or family member, can take a family history before prescribing or administering a TMPRSS6 dsRNA. A DNA test may also be performed on the patient to identify a mutation in the TMPRSS6 gene, before a TMPRSS6 dsRNA is administered to the patient. For example, diagnosis of hereditary hemochromatosis can be confirmed by identifying the two HFE (Hemochromatosis) gene mutations C282Y and H63D, according to GenBank Accession No. CAB07442.1 (GI: 1890180, record dated Oct. 23, 2008).

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given iRNA agent of the invention or formulation of that iRNA agent can also be judged using an experimental animal model for the given disease as known in the art. When using an experimental animal model, efficacy of treatment is evidenced when a statistically significant reduction in a marker or symptom is observed.

In one embodiment, the RNAi agent is administered at a dose of between about 0.25 mg/kg to about 50 mg/kg, e.g., between about 0.25 mg/kg to about 0.5 mg/kg, between about 0.25 mg/kg to about 1 mg/kg, between about 0.25 mg/kg to about 5 mg/kg, between about 0.25 mg/kg to about 10 mg/kg, between about 1 mg/kg to about 10 mg/kg, between about 5 mg/kg to about 15 mg/kg, between about 10 mg/kg to about 20 mg/kg, between about 15 mg/kg to about 25 mg/kg, between about 20 mg/kg to about 30 mg/kg, between about 25 mg/kg to about 35 mg/kg, or between about 40 mg/kg to about 50 mg/kg.

In some embodiments, the RNAi agent is administered at a dose of about 0.25 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21 mg/kg, about 22 mg/kg, about 23 mg/kg, about 24 mg/kg, about 25 mg/kg, about 26 mg/kg, about 27 mg/kg, about 28 mg/kg, about 29 mg/kg, 30 mg/kg, about 31 mg/kg, about 32 mg/kg, about 33 mg/kg, about 34 mg/kg, about 35 mg/kg, about 36 mg/kg, about 37 mg/kg, about 38 mg/kg, about 39 mg/kg, about 40 mg/kg, about 41 mg/kg, about 42 mg/kg, about 43 mg/kg, about 44 mg/kg, about 45 mg/kg, about 46 mg/kg, about 47 mg/kg, about 48 mg/kg, about 49 mg/kg or about 50 mg/kg.

In certain embodiments, for example, when a composition of the invention comprises a dsRNA as described herein and a lipid, subjects can be administered a therapeutic amount of iRNA, such as about 0.01 mg/kg to about 5 mg/kg, about 0.01 mg/kg to about 10 mg/kg, about 0.05 mg/kg to about 5 mg/kg, about 0.05 mg/kg to about 10 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 1 mg/kg to about 5 mg/kg, about 1 mg/kg to about 10 mg/kg, about 1.5 mg/kg to about 5 mg/kg, about 1.5 mg/kg to about 10 mg/kg, about 2 mg/kg to about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg. Values and ranges intermediate to the recited values are also intended to be part of this invention. For example, the dsRNA may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In certain embodiments of the invention, for example, when a double-stranded RNAi agent includes one or more modifications (e.g., motifs of three identical modifications on three consecutive nucleotides, including one such motif at or near the cleavage site of the agent), six phosphorothioate linkages, and a ligand, such an agent is administered at a dose of about 0.01 to about 0.5 mg/kg, about 0.01 to about 0.4 mg/kg, about 0.01 to about 0.3 mg/kg, about 0.01 to about 0.2 mg/kg, about 0.01 to about 0.1 mg/kg, about 0.01 mg/kg to about 0.09 mg/kg, about 0.01 mg/kg to about 0.08 mg/kg, about 0.01 mg/kg to about 0.07 mg/kg, about 0.01 mg/kg to about 0.06 mg/kg, about 0.01 mg/kg to about 0.05 mg/kg, about 0.02 to about 0.5 mg/kg, about 0.02 to about 0.4 mg/kg, about 0.02 to about 0.3 mg/kg, about 0.02 to about 0.2 mg/kg, about 0.02 to about 0.1 mg/kg, about 0.02 mg/kg to about 0.09 mg/kg, about 0.02 mg/kg to about 0.08 mg/kg, about 0.02 mg/kg to about 0.07 mg/kg, about 0.02 mg/kg to about 0.06 mg/kg, about 0.02 mg/kg to about 0.05 mg/kg, about 0.03 to about 0.5 mg/kg, about 0.03 to about 0.4 mg/kg, about 0.03 to about 0.3 mg/kg, about 0.03 to about 0.2 mg/kg, about 0.03 to about 0.1 mg/kg, about 0.03 mg/kg to about 0.09 mg/kg, about 0.03 mg/kg to about 0.08 mg/kg, about 0.03 mg/kg to about 0.07 mg/kg, about 0.03 mg/kg to about 0.06 mg/kg, about 0.03 mg/kg to about 0.05 mg/kg, about 0.04 to about 0.5 mg/kg, about 0.04 to about 0.4 mg/kg, about 0.04 to about 0.3 mg/kg, about 0.04 to about 0.2 mg/kg, about 0.04 to about 0.1 mg/kg, about 0.04 mg/kg to about 0.09 mg/kg, about 0.04 mg/kg to about 0.08 mg/kg, about 0.04 mg/kg to about 0.07 mg/kg, about 0.04 mg/kg to about 0.06 mg/kg, about 0.05 to about 0.5 mg/kg, about 0.05 to about 0.4 mg/kg, about 0.05 to about 0.3 mg/kg, about 0.05 to about 0.2 mg/kg, about 0.05 to about 0.1 mg/kg, about 0.05 mg/kg to about 0.09 mg/kg, about 0.05 mg/kg to about 0.08 mg/kg, or about 0.05 mg/kg to about 0.07 mg/kg. Values and ranges intermediate to the foregoing recited values are also intended to be part of this invention, e.g., the RNAi agent may be administered to the subject at a dose of about 0.015 mg/kg to about 0.45 mg/mg.

For example, the RNAi agent, e.g., RNAi agent in a pharmaceutical composition, may be administered at a dose of about 0.01 mg/kg, 0.0125 mg/kg, 0.015 mg/kg, 0.0175 mg/kg, 0.02 mg/kg, 0.0225 mg/kg, 0.025 mg/kg, 0.0275 mg/kg, 0.03 mg/kg, 0.0325 mg/kg, 0.035 mg/kg, 0.0375 mg/kg, 0.04 mg/kg, 0.0425 mg/kg, 0.045 mg/kg, 0.0475 mg/kg, 0.05 mg/kg, 0.0525 mg/kg, 0.055 mg/kg, 0.0575 mg/kg, 0.06 mg/kg, 0.0625 mg/kg, 0.065 mg/kg, 0.0675 mg/kg, 0.07 mg/kg, 0.0725 mg/kg, 0.075 mg/kg, 0.0775 mg/kg, 0.08 mg/kg, 0.0825 mg/kg, 0.085 mg/kg, 0.0875 mg/kg, 0.09 mg/kg, 0.0925 mg/kg, 0.095 mg/kg, 0.0975 mg/kg, 0.1 mg/kg, 0.125 mg/kg, 0.15 mg/kg, 0.175 mg/kg, 0.2 mg/kg, 0.225 mg/kg, 0.25 mg/kg, 0.275 mg/kg, 0.3 mg/kg, 0.325 mg/kg, 0.35 mg/kg, 0.375 mg/kg, 0.4 mg/kg, 0.425 mg/kg, 0.45 mg/kg, 0.475 mg/kg, or about 0.5 mg/kg. Values intermediate to the foregoing recited values are also intended to be part of this invention.

The dose of an RNAi agent that is administered to a subject may be tailored to balance the risks and benefits of a particular dose, for example, to achieve a desired level of TMPRSS6 gene suppression (as assessed, e.g., based on TMPRSS6 mRNA suppression, TMPRSS6 protein expression, or a reduction in lipid levels) or a desired therapeutic or prophylactic effect, while at the same time avoiding undesirable side effects.

In some embodiments, the RNAi agent is administered in two or more doses. If desired to facilitate repeated or frequent infusions, implantation of a delivery device, e.g., a pump, semi-permanent stent (e.g., intravenous, intraperitoneal, intracisternal or intracapsular), or reservoir may be advisable. In some embodiments, the number or amount of subsequent doses is dependent on the achievement of a desired effect, e.g., the suppression of a TMPRSS6 gene, or the achievement of a therapeutic or prophylactic effect, e.g., reducing iron overload. In some embodiments, the RNAi agent is administered according to a schedule. For example, the RNAi agent may be administered once per week, twice per week, three times per week, four times per week, or five times per week. In some embodiments, the schedule involves regularly spaced administrations, e.g., hourly, every four hours, every six hours, every eight hours, every twelve hours, daily, every 2 days, every 3 days, every 4 days, every 5 days, weekly, biweekly, or monthly. In other embodiments, the schedule involves closely spaced administrations followed by a longer period of time during which the agent is not administered. For example, the schedule may involve an initial set of doses that are administered in a relatively short period of time (e.g., about every 6 hours, about every 12 hours, about every 24 hours, about every 48 hours, or about every 72 hours) followed by a longer time period (e.g., about 1 week, about 2 weeks, about 3 weeks, about 4 weeks, about 5 weeks, about 6 weeks, about 7 weeks, or about 8 weeks) during which the RNAi agent is not administered. In one embodiment, the RNAi agent is initially administered hourly and is later administered at a longer interval (e.g., daily, weekly, biweekly, or monthly). In another embodiment, the RNAi agent is initially administered daily and is later administered at a longer interval (e.g., weekly, biweekly, or monthly). In certain embodiments, the longer interval increases over time or is determined based on the achievement of a desired effect. In a specific embodiment, the RNAi agent is administered once daily during a first week, followed by weekly dosing starting on the eighth day of administration. In another specific embodiment, the RNAi agent is administered every other day during a first week followed by weekly dosing starting on the eighth day of administration.

In some embodiments, the RNAi agent is administered in a dosing regimen that includes a "loading phase" of closely spaced administrations that may be followed by a "maintenance phase", in which the RNAi agent is administered at longer spaced intervals. In one embodiment, the loading phase comprises five daily administrations of the RNAi agent during the first week. In another embodiment, the maintenance phase comprises one or two weekly administrations of the RNAi agent. In a further embodiment, the maintenance phase lasts for 5 weeks.

Any of these schedules may optionally be repeated for one or more iterations. The number of iterations may depend on the achievement of a desired effect, e.g., the suppression of a TMPRSS6 gene, and/or the achievement of a therapeutic or prophylactic effect, e.g., reducing iron levels or reducing a symptom of thalassemia, e.g., β-thalassemia, or hemotochromatosis.

In another aspect, the invention features, a method of instructing an end user, e.g., a caregiver or a subject, on how to administer an iRNA agent described herein. The method includes, optionally, providing the end user with one or more doses of the iRNA agent, and instructing the end user to administer the iRNA agent on a regimen described herein, thereby instructing the end user.

VII. Kits

The present invention also provides kits for using any of the iRNA agents and/or performing any of the methods of the invention. Such kits include one or more RNAi agent(s) and instructions for use, e.g., instructions for inhibiting expression of a TMPRSS6 in a cell by contacting the cell with the RNAi agent(s) in an amount effective to inhibit expression of the TMPRSS6. The kits may optionally further comprise means for contacting the cell with the RNAi agent (e.g., an injection device), or means for measuring the inhibition of TMPRSS6 (e.g., means for measuring the inhibition of TMPRSS6 mRNA or TTR protein). Such means for measuring the inhibition of TMPRSS6 may comprise a means for obtaining a sample from a subject, such as, e.g., a plasma sample. The kits of the invention may optionally further comprise means for administering the RNAi agent(s) to a subject or means for determining the therapeutically effective or prophylactically effective amount.

Unless otherwise defined, all technical and scientific terms used herein have the same meaning as commonly understood by one of ordinary skill in the art to which this invention belongs. Although methods and materials similar or equivalent to those described herein can be used in the practice or testing of the iRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Materials and Methods

The following materials and methods were used in the Examples.

cDNA Synthesis Using ABI High Capacity cDNA Reverse Transcription Kit (*Applied Biosystems*, Foster City, Calif., Cat #4368813)

A master mix of 2 μl 10× Buffer, 0.8 μl 25× dNTPs, 2 μl Random primers, 1 μl Reverse Transcriptase, 1 μl RNase inhibitor and 3.2 μl of H$_2$O per reaction was added into 10 μl total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.

Cell Culture and Transfections

Hep3B cells (ATCC, Manassas, Va.) were grown to near confluence at 37° C. in an atmosphere of 5% CO2 in EMEM (ATCC) supplemented with 10% FBS, streptomycin, and glutamine (ATCC) before being released from the plate by trypsinization. Transfection was carried out by adding 14.8 μl of Opti-MEM plus 0.2 μl of Lipofectamine RNAiMax per well (Invitrogen, Carlsbad Calif. cat #13778-150) to 5 μl of siRNA duplexes per well into a 96-well plate and incubated at room temperature for 15 minutes. Subsequently, 80 μl of complete growth media without antibiotic containing ~2×10$^4$ Hep3B cells were then added to the siRNA mixture. Cells were incubated for 24 hours prior to RNA purification. Single dose experiments were performed at 10 nM and 0.1 nM final duplex concentration.

Total RNA Isolation Using DYNABEADS mRNA Isolation Kit (Invitrogen, Part #: 610-12)

Cells were harvested and lysed in 150 μl of Lysis/Binding Buffer then mixed for 5 minute at 850 rpm using a platform shaker (the mixing speed was the same throughout the process). Ten microliters of magnetic beads and 80 μl Lysis/Binding Buffer mixture were added to a round bottom plate and mixed for 1 minute. Magnetic beads were captured using magnetic stand and the supernatant was removed without disturbing the beads. After the supernatant was removed, the lysed cells were added to the remaining beads and mixed for 5 minutes. After the supernatant was removed, magnetic beads were washed 2 times with 150 μl Wash Buffer A and mixed for 1 minute. Beads were capture again and supernatant removed. Beads were then washed with 150 μl Wash Buffer B, captured and supernatant was removed. Beads were next washed with 150 μl Elution Buffer, captured and supernatant removed. Beads were allowed to dry for 2 minutes. After drying, 50 μl of Elution Buffer was added and mixed for 5 minutes at 75° C. Beads were captured on magnet for 5 minutes, and 50 μl of supernatant containing the purified RNA was removed and added to a new 96 well plate.

Real Time PCR

Two μl of cDNA was added to a master mix containing 0.5 μl human GAPDH TaqMan Probe (Applied Biosystems Cat #4326317E), 0.5 μl human TMPRSS6 TaqMan probe (Applied Biosystems cat # Hs00542184_m1) and 5 μl Lightcycler 480 probe master mix (Roche Cat #04887301001) per well in a 384 well plate (Roche cat #04887301001). Real time PCR was performed in a Roche LC480 Real Time PCR system (Roche) using the ΔΔCt(RQ) assay. Each duplex was tested in two independent transfections and each transfection was assayed in duplicate, unless otherwise noted.

To calculate relative fold change, real time data were analyzed using the ΔΔCt method and normalized to assays performed with cells transfected with 10 nM AD-1955, or mock transfected cells.

The sense and antisense sequences of AD-1955 are: SENSE: 5'-cuuAcGcuGAGuAcuucGAdTsdT-3' (SEQ ID NO: 15); and ANTISENSE: 5'-UCGAAGuACUcA-GCGuAAGdTsdT-3' (SEQ ID NO: 16).

TABLE B

Abbreviations of nucleotide monomers used in nucleic acid sequence representation.

| Abbreviation | Nucleotide(s) |
|---|---|
| A | Adenosine-3'-phosphate |
| Ab | beta-L-adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cb | beta-L-cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gb | beta-L-guanosine-3'-phosphate |
| Gbs | beta-L-guanosine-3'-phosphorothioate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine -3'-phosphorothioate |
| Us | uridine -3'-phosphorothioate |
| N | any nucleotide (G, A, C, T or U) |
| a | 2'-O-methyladenosine-3'-phosphate |
| as | 2'-O-methyladenosine-3'- phosphorothioate |
| c | 2'-O-methylcytidine-3'-phosphate |
| cs | 2'-O-methylcytidine-3'- phosphorothioate |
| g | 2'-O-methylguanosine-3'-phosphate |
| gs | 2'-O-methylguanosine-3'- phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| dT | 2'-deoxythymidine |
| dTs | 2'-deoxythymidine-3'-phosphorothioate |
| dU | 2'-deoxyuridine |
| s | phosphorothioate linkage |
| L96 | N-[tris(GalNAc-alkyl)-amidodecanoyl)]-4-hydroxyprolinol Hyp-(GalNAc-alkyl)3 |
| (Aeo) | 2'-O-methoxyethyladenosine-3'-phosphate |
| (Aeos) | 2'-O-methoxyethyladenosine-3'-phosphorothioate |
| (Geo) | 2'-O-methoxyethylguanosine-3'-phosphate |
| (Geos) | 2'-O-methoxyethylguanosine-3'- phosphorothioate |
| (Teo) | 2'-O-methoxyethyl-5-methyluridine-3'-phosphate |
| (Teos) | 2'-O-methoxyethyl-5-methyluridine-3'- phosphorothioate |
| (m5Ceo) | 2'-O-methoxyethyl-5-methylcytidine-3'-phosphate |
| (m5Ceos) | 2'-O-methoxyethyl-5-methylcytidine-3'- phosphorothioate |
| (A3m) | 3'-O-methyladenosine-2'-phosphate |
| (A3mx) | 3'-O-methyl-xylofuranosyladenosine-2'-phosphate |
| (G3m) | 3'-O-methylguanosine-2'-phosphate |
| (G3mx) | 3'-O-methyl-xylofuranosylguanosine-2'-phosphate |
| (C3m) | 3'-O-methylcytidine-2'-phosphate |
| (C3mx) | 3'-O-methyl-xylofuranosylcytidine-2'-phosphate |
| (U3m) | 3'-O-methyluridine-2'-phosphate |
| (U3mx) | 3'-O-methylxylouridine-2'-phosphate |
| (Chd) | 2'-O-hexadecyl-cytidine-3'-phosphate |
| (pshe) | Hydroxyethylphosphorothioate |
| (Uhd) | 2'-O-hexadecyl-uridine-3'-phosphate |

TABLE B-continued

Abbreviations of nucleotide monomers used
in nucleic acid sequence representation.

| Abbreviation | Nucleotide(s) |
|---|---|
| (Tgn) | Thymidine-glycol nucleic acid (GNA) S-Isomer |
| (Cgn) | Cytidine-glycol nucleic acid (GNA) |
| (Chd) | 2'-O-hexadecyl-cytidine-3'-phosphate |
| (Ggn) | 2'-O-hexadecyl-cytidine-3'-phosphate |
| (Agn) | Adenosine-glycol nucleic acid (GNA) |
| P | 5'-phosphate |
| (m5Cam) | 2'-O-(N-methylacetamide)-5-methylcytidine-3'-phosphate |
| (m5Cams) | 2'-O-(N-methylacetamide)-5-methylcytidine-3'-phosphorothioate |
| (Tam) | 2'-O-(N-methylacetamide)thymidine-3'-phosphate |
| (Tams) | 2'-O-(N-methylacetamide)thymidine-3'-phosphorothioate |
| (Aam) | 2'-O-(N-methylacetamide)adenosine-3'-phosphate |
| (Aams) | 2'-O-(N-methylacetamide)adenosine-3'-phosphorothioate |
| (Gam) | 2'-O-(N-methylacetamide)guanosine-3'-phosphate |
| (Gams) | 2'-O-(N-methylacetamide)guanosine-3'-phosphorothioate |
| Y44 | 2-hydroxymethyl-tetrahydrofurane-5-phosphate |

Example 1. Design, Specificity and Efficacy Prediction of Oligonucleotides

Transcripts siRNA design was carried out to identify siRNAs targeting human, rhesus (*Macaca mulatta*), mouse, and rat TMPRSS6 transcripts annotated in the NCBI Gene database (http://www.ncbi.nlm.nih.gov/gene/). Design used the following transcripts from the NCBI RefSeq collection: Human—NM_153609.2; Rhesus—XM_001085203.2 and XM_001085319.1; Mouse—NM_027902.2; Rat—NM_001130556.1. Due to high primate/rodent sequence divergence, siRNA duplexes were designed in several separate batches, including but not limited to batches containing duplexes matching human and rhesus transcripts only; human, rhesus, and mouse transcripts only; human, rhesus, mouse, and rat transcripts only; and mouse and rat transcripts only. All siRNA duplexes were designed that shared 100% identity with the listed human transcript and other species transcripts considered in each design batch (above).

The specificity of all possible 19mers was predicted from each sequence. Candidate 19mers that lacked repeats longer than 7 nucleotides were then selected. These 1259 candidate human/rhesus, 91 human/rhesus/mouse, 37 human/rhesus/mouse/rat, and 810 mouse/rat siRNAs were used in comprehensive searches against the appropriate transcriptomes (defined as the set of NM_ and XM_ records within the human, rhesus, mouse, or rat NCBI Refseq sets) using an exhaustive "brute-force" algorithm implemented in the python script 'BruteForce.py'. The script next parsed the transcript-oligo alignments to generate a score based on the position and number of mismatches between the siRNA and any potential 'off-target' transcript. The off-target score is weighted to emphasize differences in the 'seed' region of siRNAs, in positions 2-9 from the 5' end of the molecule. Each oligo-transcript pair from the brute-force search was given a mismatch score by summing the individual mismatch scores; mismatches in the position 2-9 were counted as 2.8, mismatches in the cleavage site positions 10-11 were counted as 1.2, and mismatches in region 12-19 counted as 1.0. An additional off-target prediction was carried out by comparing the frequency of heptamers and octomers derived from 3 distinct, seed-derived hexamers of each oligo. The hexamers from positions 2-7 relative to the 5' start were used to create 2 heptamers and one octomer. Heptamer1 was created by adding a 3' A to the hexamer; heptamer2 was created by adding a 5' A to the hexamer; the octomer was created by adding an A to both 5' and 3' ends of the hexamer. The frequency of octomers and heptamers in the human, rhesus, mouse, or rat 3'UTRome (defined as the subsequence of the transcriptome from NCBI's Refseq database where the end of the coding region, the 'CDS', is clearly defined) was pre-calculated. The octomer frequency was normalized to the heptamer frequency using the median value from the range of octomer frequencies. A 'mirSeedScore' was then calculated by calculating the sum of ((3× normalized octomer count)+(2× heptamer2 count)+(1× heptamer1 count)).

Both siRNA strands were assigned to a category of specificity according to the calculated scores: a score above 3 qualified as highly specific, equal to 3 as specific and between 2.2 and 2.8 qualified as moderately specific. The siRNAs were sorted by the specificity of the antisense strand. Duplexes from the human/rhesus and mouse/rat sets whose antisense oligos lacked GC at the first position, lacked G at both positions 13 and 14, and had 3 or more Us or As in the seed region (characteristics of duplexes with high predicted efficacy) were then selected. Similarly, duplexes from the human/rhesus/mouse and human/rhesus/mouse/rat sets that had had 3 or more Us or As in the seed region were selected.

Candidate GalNAc-conjugated duplexes, 21 and 23 nucleotides long on the sense and antisense strands respectively, were designed by extending antisense 19mers 4 additional nucleotides in the 3' direction (preserving perfect complementarity with the target transcript). The sense strand was specified as the reverse complement of the first 21 nucleotides of the antisense 23mer. Duplexes were selected that maintained perfect matches to all selected species transcripts across all 23 nucleotides.

siRNA Sequence Selection

A total of 39 sense and 39 antisense derived human/rhesus, 6 sense and 6 antisense derived human/rhesus/mouse, 3 sense and 3 antisense derived human/rhesus/mouse/rat, and 16 sense and 16 antisense derived mouse/rat siRNA 21/23mer oligos were synthesized and formed into GalNAc-conjugated duplexes.

The sequences of the sense and antisense strands of the modified duplexes are shown in Table 1, and the sequences of the sense and antisense strands of the unmodified duplexes are shown in Table 2.

TABLE 1

TMPRSS6 modified sequences

| Duplex ID | Sense sequence ID | Sense sequence | SEQ ID NO: |
|---|---|---|---|
| AD-58686.1 | A-119159.1 | UfsgsGfcCfuGfgAfGfAfgGfuGfuCfcUfuCfL96 | 17 |

TABLE 1-continued

TMPRSS6 modified sequences

| AD-58687.1 | A-119175.1 | GfsgsGfgUfgCfuAfCfUfcUfgGfuAfuUfuCfL96 | 18 |
| --- | --- | --- | --- |
| AD-58688.1 | A-119191.1 | CfsasAfcGfgCfcUfGfGfaUfgAfgAfgAfaAfL96 | 19 |
| AD-58689.1 | A-119207.1 | AfsusCfgCfcAfcUfUfCfuCfcCfaGfgAfuCfL96 | 20 |
| AD-58690.1 | A-119223.1 | GfsgsUfgGfcAfgGfAfGfgUfgGfcAfuCfuUfL96 | 21 |
| AD-58692.1 | A-119161.1 | GfsasCfcGfaCfuGfGfCfcAfuGfuAfuGfaCfL96 | 22 |
| AD-58693.1 | A-119177.1 | GfsgsUfgUfgCfgGfGfUfgCfaCfuAfuGfgCfL96 | 23 |
| AD-58694.1 | A-119193.1 | GfsgsCfcUfgGfaUfGfAfgAfgAfaAfcUfgCfL96 | 24 |
| AD-58695.1 | A-119209.1 | CfsusCfuGfgUfaUfUfUfcCfuAfgGfgUfaCfL96 | 25 |
| AD-58696.1 | A-119225.1 | GfscsCfcCfuGfgUfCfUfaAfcUfgGfgAfaUfL96 | 26 |
| AD-58698.1 | A-119163.1 | GfsasGfgCfaGfaAfGfUfaUfgAfuUfuGfcCfL96 | 27 |
| AD-58699.1 | A-119179.1 | AfsasGfcCfaGfuGfUfGfaAfaGfaCfaUfaGfL96 | 28 |
| AD-58700.1 | A-119195.1 | GfscsCfgGfgAfcCfGfAfcUfgGfcCfaUfgUfL96 | 29 |
| AD-58701.1 | A-119211.1 | CfsusCfcAfgGfuUfCfGfgGfgUfcGfaCfaCfL96 | 30 |
| AD-58702.1 | A-119227.1 | AfsgsCfcCfcUfgGfUfCfuAfaCfuGfgGfaAfL96 | 31 |
| AD-58704.1 | A-119165.1 | UfscsGfcCfaCfuUfCfUfcCfcAfgGfaUfcUfL96 | 32 |
| AD-58705.1 | A-119181.1 | AfscsUfcUfgGfuAfUfUfuCfuAfgGfgUfaUfL96 | 33 |
| AD-58706.1 | A-119197.1 | UfscsGfcUfgAfcCfGfCfuGfgGfuGfaUfaAfL96 | 34 |
| AD-58707.1 | A-119213.1 | GfscsCfcCfaAfcGfGfCfcUfgGfaUfgAfgAfL96 | 35 |
| AD-58708.1 | A-119229.1 | GfscsCfaAfgCfaGfGfGfgGfaCfaAfgUfaUfL96 | 36 |
| AD-58710.1 | A-119167.1 | UfscsCfcCfuAfcAfGfGfgCfcGfaGfuAfcGfL96 | 37 |
| AD-58711.1 | A-119183.1 | CfsusGfgGfuUfgUfUfAfcCfgCfuAfcAfgCfL96 | 38 |
| AD-58712.1 | A-119199.1 | CfsusGfgCfcUfgGfAfGfaGfgUfgUfcCfuUfL96 | 39 |
| AD-58713.1 | A-119215.1 | GfsusGfcGfgGfuGfCfAfcUfaUfgGfcUfuGfL96 | 40 |
| AD-58714.1 | A-119231.1 | UfsgsGfcAfgGfaGfGfUfgGfcAfuCfuUfgUfL96 | 41 |
| AD-58716.1 | A-119169.1 | CfscsCfuAfcAfgGfGfCfcGfaGfuAfcGfaAfL96 | 42 |
| AD-58717.1 | A-119185.1 | AfscsCfuGfcUfuCfUfUfcUfgGfuUfcAfuUfL96 | 43 |

TABLE 1-continued

TMPRSS6 modified sequences

| | | | |
|---|---|---|---|
| AD-58718.1 | A-119201.1 | UfsgsCfcUfgUfgAfUfGfgGfgUfcAfaGfgAfL96 | 44 |
| AD-58719.1 | A-119217.1 | CfsasGfcUfuCfgGfAfAfgCfcCfcUfgGfuCfL96 | 45 |
| AD-58720.1 | A-119233.1 | CfscsCfcUfgGfuCfUfAfaCfuUfgGfgAfuCfL96 | 46 |
| AD-58721.1 | A-119171.1 | UfsgsCfuUfcUfuCfUfGfgUfuCfaUfuCfuCfL96 | 47 |
| AD-58722.1 | A-119187.1 | CfscsCfaAfcGfgCfCfUfgGfaUfgAfgAfgAfL96 | 48 |
| AD-58723.1 | A-119203.1 | AfsasGfgGfcCfuGfCfAfcAfgCfuAfcUfaCfL96 | 49 |
| AD-58724.1 | A-119219.1 | GfsusCfuAfaCfuUfGfGfgAfuCfuGfgGfaAfL96 | 50 |
| AD-58725.1 | A-119235.1 | AfsgsCfuUfcGfgAfAfGfcCfcCfuGfgUfcUfL96 | 51 |
| AD-58726.1 | A-119173.1 | CfscsAfgUfgUfgAfAfAfgAfcAfuAfgCfuGfL96 | 52 |
| AD-58727.1 | A-119189.1 | CfscsAfgGfuUfcGfGfGfgUfcGfaCfaCfaUfL96 | 53 |
| AD-58728.1 | A-119205.1 | UfscsCfaCfgCfuGfGfGfuUfgUfuAfcCfgCfL96 | 54 |
| AD-58729.1 | A-119221.1 | UfsgsCfcAfaGfcAfGfGfgGfgAfcAfaGfuAfL96 | 55 |
| AD-58697.1 | A-119241.1 | AfsusCfcAfgAfaCfAfGfgAfgGfcUfgUfgUfL96 | 56 |
| AD-58703.1 | A-119243.1 | UfsusCfaCfcUfcCfCfAfgAfuCfuCfcCfuCfL96 | 57 |
| AD-58709.1 | A-119245.1 | CfscsUfcCfgAfgGfGfUfgAfgUfgGfcCfaUfL96 | 58 |
| AD-58715.1 | A-119247.1 | UfscsCfaGfaAfcAfGfGfaGfcUfgUfgUfgGfL96 | 59 |
| AD-58730.1 | A-119237.1 | GfsusGfuCfcUfcCfGfAfgGfgUfgAfgUfgGfL96 | 60 |
| AD-58731.1 | A-119249.1 | UfsusCfgGfgUfCfGfAfcAfcAfuCfuGfuGfL96 | 61 |
| AD-58734.1 | A-119251.1 | UfscsGfgGfgUfcGfAfCfaCfaUfcUfgUfgGfL96 | 62 |
| AD-58737.1 | A-119253.1 | UfsgsCfuUfcCfaGfGfAfgGfaCfaGfcAfuGfL96 | 63 |
| AD-59743.1 | A-120243.1 | UfscsUfgGfuAfuUfUfCfcUfaGfgGfuAfcAfL96 | 64 |

| Duplex ID | Antisense sequence | Antisense sequence | SEQ ID NO: |
|---|---|---|---|
| AD-58686.1 | A-119160.1 | usUfsgAfaGfgAfccuCfuCfcAfgGfcsCfsa | 65 |
| AD-58687.1 | A-119176.1 | asGfsgAfaAfuAfcCfagaGfuAfgCfaCfcsCfsc | 66 |
| AD-58688.1 | A-119192.1 | asGfsuUfuCfuCfuCfaucCfaGfgCfcGfusUfsg | 67 |
| AD-58689.1 | A-119208.1 | asAfsgAfuCfcUfgGfgagAfaGfuGfgCfgsAfsu | 68 |

TABLE 1-continued

| | TMPRSS6 modified sequences | | |
|---|---|---|---|
| AD-58690.1 | A-119224.1 | asCfsaAfgAfuGfcCfaccUfcCfuGfcCfasCfsc | 69 |
| AD-58692.1 | A-119162.1 | asCfsgUfcAfuAfcAfuggCfcAfgUfcGfgsUfsC | 70 |
| AD-58693.1 | A-119178.1 | asAfsgCfcAfuAfgUfgcaCfcCfgCfaCfasCfsc | 71 |
| AD-58694.1 | A-119194.1 | asCfsgCfaGfuUfuCfucuCfaUfcCfaGfgsCfsc | 72 |
| AD-58695.1 | A-119210.1 | usUfsgUfaCfcCfuAfggaAfaUfaCfcAfgsAfsg | 73 |
| AD-58696.1 | A-119226.1 | asGfsaUfcCfcAfaGfuuaGfaCfcAfgGfgsGfsc | 74 |
| AD-58698.1 | A-119164.1 | asCfsgGfcAfaAfuCfauaCfuUfcUfgCfcsUfsc | 75 |
| AD-58699.1 | A-119180.1 | asGfscUfaUfgUfcUfuucAfcAfcUfgGfcsUfsu | 76 |
| AD-58700.1 | A-119196.1 | asUfsaCfaUfgGfcCfaguCfgGfuCfcCfgsGfsc | 77 |
| AD-58701.1 | A-119212.1 | asUfsgUfgUfcGfaCfcccGfaAfcCfuGfgsAfsg | 78 |
| AD-58702.1 | A-119228.1 | gsAfsuCfcCfaAfgUfuagAfcCfaGfgGfgsCfsu | 79 |
| AD-58704.1 | A-119166.1 | usAfsaGfaUfcCfuGfggaGfaAfgUfgGfcsGfsa | 80 |
| AD-58705.1 | A-119182.1 | usGfsuAfcCfcUfaGfgaaAfuAfcCfaGfasGfsu | 81 |
| AD-58706.1 | A-119198.1 | usGfsuUfaUfcAfcCfcagCfgGfuCfaGfcsGfsa | 82 |
| AD-58707.1 | A-119214.1 | usCfsuCfuCfaUfcCfaggCfcGfuUfgGfgsGfsc | 83 |
| AD-58708.1 | A-119230.1 | gsAfsaUfaCfuUfgUfcccCfcUfgCfuUfgsGfsc | 84 |
| AD-58710.1 | A-119168.1 | usUfscGfuAfcUfcGfgccCfuGfuAfgGfgsGfsa | 85 |
| AD-58711.1 | A-119184.1 | usAfsgCfuGfuAfgCfgguAfaCfaAfcCfcsAfsg | 86 |
| AD-58712.1 | A-119200.1 | usGfsaAfgGfaCfaCfcucUfcCfaGfgCfcsAfsg | 87 |
| AD-58713.1 | A-119216.1 | usAfscAfaGfcCfaUfaguGfcAfcCfcGfcsAfsc | 88 |
| AD-58714.1 | A-119232.1 | asGfsaCfaAfgAfuGfccaCfcUfcCfuGfcsCfsa | 89 |
| AD-58716.1 | A-119170.1 | asCfsuUfcGfuAfcUfcggCfcCfuGfuAfgsGfsg | 90 |
| AD-58717.1 | A-119186.1 | asGfsaAfuGfaAfcCfagaAfgAfaGfcAfgsGfsu | 91 |
| AD-58718.1 | A-119202.1 | asGfsuCfcUfuGfaCfcccAfuCfaCfaGfgsCfsa | 92 |
| AD-58719.1 | A-119218.1 | usAfsgAfcCfaGfgGfgcuUfcCfgAfaGfcsUfsg | 93 |
| AD-58720.1 | A-119234.1 | csAfsgAfuCfcCfaAfguuAfgAfcCfaGfgsGfsg | 94 |

TABLE 1-continued

TMPRSS6 modified sequences

| | | | |
|---|---|---|---|
| AD-58721.1 | A-119172.1 | usGfsgAfgAfaUfgAfaccAfgAfaGfaAfgsCfsa | 95 |
| AD-58722.1 | A-119188.1 | usUfsuCfuCfuCfaUfccaGfgCfcGfuUfgsGfsg | 96 |
| AD-58723.1 | A-119204.1 | usCfsgUfaGfuAfgCfuguGfcAfgGfcCfcsUfsu | 97 |
| AD-58724.1 | A-119220.1 | csAfsuUfcCfcAfgAfuccCfaAfgUfuAfgsAfsc | 98 |
| AD-58725.1 | A-119236.1 | usUfsaGfaCfcAfgGfggcUfuCfcGfaAfgsCfsu | 99 |
| AD-58726.1 | A-119174.1 | usGfscAfgCfuAfuGfucuUfuCfaCfaCfusGfsg | 100 |
| AD-58727.1 | A-119190.1 | asGfsaUfgUfgUfcGfaccCfcGfaAfcCfusGfsg | 101 |
| AD-58728.1 | A-119206.1 | usAfsgCfgGfuAfaCfaacCfcAfgCfgUfgsGfsa | 102 |
| AD-58729.1 | A-119222.1 | asAfsuAfcUfuGfuCfcccCfuGfcUfuGfgsCfsa | 103 |
| AD-58697.1 | A-119242.1 | csCfsaCfaCfaGfcCfuccUfgUfcUfuGfgsAfsu | 104 |
| AD-58703.1 | A-119244.1 | gsUfsgAfgGfgAfgAfucuGfgGfaGfgUfgsAfsa | 105 |
| AD-58709.1 | A-119246.1 | csCfsaUfgGfcCfaCfucaCfcCfuCfgGfasGfsg | 106 |
| AD-58715.1 | A-119248.1 | gsCfscAfcAfcAfgCfcucCfuGfuUfcUfgsGfsa | 107 |
| AD-58730.1 | A-119238.1 | gsGfscCfaCfuCfaCfccuCfgGfaGfgAfcsAfsc | 108 |
| AD-58731.1 | A-119250.1 | csCfscAfcAfgAfuGfuguCfgAfcCfcCfgsAfsa | 109 |
| AD-58734.1 | A-119252.1 | csCfscCfaCfaGfaUfgugUfcGfaCfcCfcsGfsa | 110 |
| AD-58737.1 | A-119254.1 | gsCfscAfuGfcUfgUfccuCfcUfgGfaAfgsCfsa | 111 |
| AD-59743.1 | A-120244.1 | usGfsuAfcCfcUfaGfgaaAfuAfcCfaGfasgsu | 112 |

TABLE 2

TMPRSS6 unmodified sequences

| Duplex ID | Sense sequence ID | Sense sequence | SEQ ID NO: | Position in NM_153609.2 | Antisense sequence ID | Antisense sequence | SEQ ID NO: | Position in NM_153609.2 |
|---|---|---|---|---|---|---|---|---|
| AD-58686.1 | A-119159.1 | UGGCCUGGAGAGGUGUCCUUC | 113 | 2041-2063 | A-119160.1 | UUGAAGGACACCUCUCCAGGCCA | 161 | 2041-2063 |
| AD-58687.1 | A-119175.1 | GGGGUGCUACUCUGGUAUUUC | 114 | 319-341 | A-119176.1 | AGGAAAUACCAGAGUAGCACCCC | 162 | 319-341 |
| AD-58688.1 | A-119191.1 | CAACGGCCUGGAUGAGAGAAA | 115 | 1557-1579 | A-119192.1 | AGUUUCUCUCAUCCAGGCCGUUG | 163 | 1557-1579 |
| AD-58689.1 | A-119207.1 | AUCGCCACUUCUCCCAGGAUC | 116 | 401-423 | A-119208.1 | AAGAUCCUGGGAGAAGUGGCGAU | 164 | 401-423 |

TABLE 2-continued

TMPRSS6 unmodified sequences

| Duplex ID | Sense sequence ID | Sense sequence | SEQ ID NO: | Position in NM_153609.2 | Antisense sequence ID | Antisense sequence | SEQ ID NO: | Position in NM_153609.2 |
|---|---|---|---|---|---|---|---|---|
| AD-58690.1 | A-119223.1 | GGUGGCAGGAGGUGGCAUCUU | 117 | 2665-2688 | A-119224.1 | ACAAGAUGCCACCUCCUGCCACC | 165 | 2665-2688 |
| AD-58692.1 | A-119161.1 | GACCGACUGGCCAUGUAUGAC | 118 | 922-944 | A-119162.1 | ACGUCAUACAUGGCCAGUCGGUC | 166 | 922-944 |
| AD-58693.1 | A-119177.1 | GGUGUGCGGGUGCACUAUGGC | 119 | 1444-1466 | A-119178.1 | AAGCCAUAGUGCACCCGCACACC | 167 | 1444-1466 |
| AD-58694.1 | A-119193.1 | GGCCUGGAUGAGAGAAACUGC | 120 | 1561-1583 | A-119194.1 | ACGCAGUUUCUCUCAUCCAGGCC | 168 | 1561-1583 |
| AD-58695.1 | A-119209.1 | CUCUGGUAUUUCCUAGGGUAC | 121 | 328-350 | A-119210.1 | UUGUACCCUAGGAAAUACCAGAG | 169 | 328-350 |
| AD-58696.1 | A-119225.1 | GCCCCUGGUCUAACUUGGGAU | 122 | 2966-2989 | A-119226.1 | AGAUCCCAAGUUAGACCAGGGGC | 170 | 2966-2989 |
| AD-58698.1 | A-119163.1 | GAGGCAGAAGUAUGAUUUGCC | 123 | 1281-1303 | A-119164.1 | ACGGCAAAUCAUACUUCUGCCUC | 171 | 1281-1303 |
| AD-58699.1 | A-119179.1 | AAGCCAGUGUGAAAGACAUAG | 124 | 731-753 | A-119180.1 | AGCUAUGUCUUUCACACUGGCUU | 172 | 731-753 |
| AD-58700.1 | A-119195.1 | GCCGGACCGACUGGCCAUGU | 125 | 917-939 | A-119196.1 | AUACAUGGCCAGUCGGUCCCGGC | 173 | 917-939 |
| AD-58701.1 | A-119211.1 | CUCCAGGUUCGGGGUCGACAC | 126 | 1894-1916 | A-119212.1 | AUGUGUCGACCCCGAACCUGGAG | 174 | 1894-1916 |
| AD-58702.1 | A-119227.1 | AGCCCCUGGUCUAACUUGGGA | 127 | 2965-2988 | A-119228.1 | GAUCCCAAGUUAGACCAGGGGCU | 175 | 2965-2988 |
| AD-58704.1 | A-119165.1 | UCGCCACUUCUCCCAGGAUCU | 128 | 402-424 | A-119166.1 | UAAGAUCCUGGGAGAAGUGGCGA | 176 | 402-424 |
| AD-58705.1 | A-119181.1 | ACUCUGGUAUUUCCUAGGGUA | 129 | 327-349 | A-119182.1 | UGUACCCUAGGAAAUACCAGAGU | 177 | 327-349 |
| AD-58706.1 | A-119197.1 | UCGCUGACCGCUGGGUGAUAA | 130 | 1934-1956 | A-119198.1 | UGUUAUCACCCAGCGGUCAGCGA | 178 | 1934-1956 |
| AD-58707.1 | A-119213.1 | GCCCCAACGGCCUGGAUGAGA | 131 | 1553-1575 | A-119214.1 | UCUCUCAUCCAGGCCGUUGGGGC | 179 | 1553-1575 |
| AD-58708.1 | A-119229.1 | GCCAAGCAGGGGACAAGUAU | 132 | 2610-2633 | A-119230.1 | GAAUACUUGUCCCCUGCUUGGC | 180 | 2610-2633 |
| AD-58710.1 | A-119167.1 | UCCCCUACAGGGCCGAGUACG | 133 | 680-702 | A-119168.1 | UUCGUACUCGGCCCUGUAGGGA | 181 | 680-702 |
| AD-58711.1 | A-119183.1 | CUGGGUUGUUACCGCUACAGC | 134 | 769-791 | A-119184.1 | UAGCUGUAGCGGUAACAACCCAG | 182 | 769-791 |
| AD-58712.1 | A-119199.1 | CUGGCCUGGAGAGGUGUCCUU | 135 | 2040-2062 | A-119200.1 | UGAAGGACACCUCUCCAGGCCAG | 183 | 2040-2062 |
| AD-58713.1 | A-119215.1 | GUGCGGGUGCACUAUGGCUUG | 136 | 1447-1469 | A-119216.1 | UACAAGCCAUAGUGCACCCGCAC | 184 | 1447-1469 |
| AD-58714.1 | A-119231.1 | UGGCAGGAGGUGGCAUCUUGU | 137 | 2667-2690 | A-119232.1 | AGACAAGAUGCCACCUCCUGCCA | 185 | 2667-2690 |
| AD-58716.1 | A-119169.1 | CCCUACAGGGCCGAGUACGAA | 138 | 682-704 | A-119170.1 | ACUUCGUACUCGGCCCUGUAGGG | 186 | 682-704 |
| AD-58717.1 | A-119185.1 | ACCUGCUUCUUCUGGUUCAUU | 139 | 559-581 | A-119186.1 | AGAAUGAACCAGAAGAAGCAGGU | 187 | 559-581 |
| AD-58718.1 | A-119201.1 | UGCCUGUGAUGGGGUCAAGGA | 140 | 1530-1552 | A-119202.1 | AGUCCUUGACCCCAUCACAGGCA | 188 | 1530-1552 |
| AD-58719.1 | A-119217.1 | CAGCUUCGGAAGCCCCUGGUC | 141 | 2955-2978 | A-119218.1 | UAGACCAGGGGCUUCCGAAGCUG | 189 | 2955-2978 |

TABLE 2-continued

TMPRSS6 unmodified sequences

| Duplex ID | Sense sequence ID | Sense sequence | SEQ ID NO: | Position in NM_153609.2 | Antisense ID | Antisense sequence | SEQ ID NO: | Position in NM_153609.2 |
|---|---|---|---|---|---|---|---|---|
| AD-58720.1 | A-119233.1 | CCCCUGGUCUAACUUGGGAUC | 142 | 2967-2990 | A-119234.1 | CAGAUCCCAAGUUAGACCAGGGG | 190 | 2967-2990 |
| AD-58721.1 | A-119171.1 | UGCUUCUUCUGGUUCAUUCUC | 143 | 562-584 | A-119172.1 | UGGAGAAUGAACCAGAAGAAGCA | 191 | 562-584 |
| AD-58722.1 | A-119187.1 | CCCAACGGCCUGGAUGAGAGA | 144 | 1555-1577 | A-119188.1 | UUUCUCUCAUCCAGGCCGUUGGG | 192 | 1555-1577 |
| AD-58723.1 | A-119203.1 | AAGGGCCUGCACAGCUACUAC | 145 | 1054-1076 | A-119204.1 | UCGUAGUAGCUGUGCAGGCCCUU | 193 | 1054-1076 |
| AD-58724.1 | A-119219.1 | GUCUAACUUGGGAUCUGGGAA | 146 | 2973-2996 | A-119220.1 | CAUUCCCAGAUCCCAAGUUAGAC | 194 | 2973-2996 |
| AD-58725.1 | A-119235.1 | AGCUUCGGAAGCCCCUGGUCU | 147 | 2956-2979 | A-119236.1 | UUAGACCAGGGGCUUCCGAAGCU | 195 | 2956-2979 |
| AD-58726.1 | A-119173.1 | CCAGUGUGAAAGACAUAGCUG | 148 | 734-756 | A-119174.1 | UGCAGCUAUGUCUUUCACACUGG | 196 | 734-756 |
| AD-58727.1 | A-119189.1 | CCAGGUUCGGGGUCGACACAU | 149 | 1896-1918 | A-119190.1 | AGAUGUGUCGACCCCGAACCUGG | 197 | 1896-1918 |
| AD-58728.1 | A-119205.1 | UCCACGCUGGGUUGUUACCGC | 150 | 763-785 | A-119206.1 | UAGCGGUAACAACCCAGCGUGGA | 198 | 763-785 |
| AD-58729.1 | A-119221.1 | UGCCAAGCAGGGGACAAGUA | 151 | 2609-2632 | A-119222.1 | AAUACUUGUCCCCUGCUUGGCA | 199 | 2609-2632 |
| AD-58697.1 | A-119241.1 | AUCCAGAACAGGAGGCUGUGU | 152 | 1324-1346 | A-119242.1 | CCACACAGCCUCCUGUUCUGGAU | 200 | 1324-1346 |
| AD-58703.1 | A-119243.1 | UUCACCUCCCAGAUCUCCCUC | 153 | 1414-1436 | A-119244.1 | GUGAGGGAGAUCUGGGAGGUGAA | 201 | 1414-1436 |
| AD-58709.1 | A-119245.1 | CCUCCGAGGGUGAGUGGCCAU | 154 | 1862-1884 | A-119246.1 | CCAUGGCCACUCACCCUCGGAGG | 202 | 1862-1884 |
| AD-58715.1 | A-119247.1 | UCCAGAACAGGAGGCUGUGUG | 155 | 1325-1347 | A-119248.1 | GCCACACAGCCUCCUGUUCUGGA | 203 | 1325-1347 |
| AD-58730.1 | A-119237.1 | GUGUCCUCCGAGGGUGAGUGG | 156 | 1858-1880 | A-119238.1 | GGCCACUCACCCUCGGAGGACAC | 204 | 1858-1880 |
| AD-58731.1 | A-119249.1 | UUCGGGGUCGACACAUCUGUG | 157 | 1901-1923 | A-119250.1 | CCCACAGAUGUGUCGACCCCGAA | 205 | 1901-1923 |
| AD-58734.1 | A-119251.1 | UCGGGGUCGACACAUCUGUGG | 158 | 1902-1924 | A-119252.1 | CCCCACAGAUGUGUCGACCCCGA | 206 | 1902-1924 |
| AD-58737.1 | A-119253.1 | UGCUUCCAGGAGGACAGCAUG | 159 | 1966-1988 | A-119254.1 | GCCAUGCUGUCCUCCUGGAAGCA | 207 | 1966-1988 |
| AD-59743.1 | A-120243.1 | UCUGGUAUUUCCUAGGGUACA | 160 | | A-120244.1 | UGUACCCUAGGAAAUACCAGAGU | 208 | |

Example 2. In Vitro Single Dose Screen

The modified and conjugated TMPRSS6 siRNA duplexes were also evaluated for efficacy by transfection assays in human cell line Hep3B. TMPRSS6 siRNAs were transfected at two doses, 10 nM and 0.1 nM. The results of these assays are shown in Table 3 and the data are expressed as a fraction of the message remaining in cells transfected with siRNAs targeting TMPRSS6, relative to cells transfected with a negative control siRNA, AD-1955±the standard deviation (SD).

TABLE 3

TMPRSS6 single dose screen.

| Duplex ID | Avg 10 nM | SD 10 nM | Avg 0.1 nM | SD 0.1 nM |
|---|---|---|---|---|
| AD-58686.1 | 71.58 | 18.94 | 103.29 | 32.00 |
| AD-58687.1 | 89.33 | 13.14 | 104.94 | 20.06 |
| AD-58688.1 | 34.16 | 11.36 | 87.18 | 8.43 |
| AD-58689.1 | 79.82 | 7.28 | 110.37 | 6.08 |
| AD-58690.1 | 69.10 | 9.83 | 99.92 | 24.84 |
| AD-58692.1 | 79.21 | 5.67 | 136.49 | 0.84 |
| AD-58693.1 | 77.29 | 12.12 | 106.01 | 17.97 |

TABLE 3-continued

TMPRSS6 single dose screen.

| Duplex ID | Avg 10 nM | SD 10 nM | Avg 0.1 nM | SD 0.1 nM |
|---|---|---|---|---|
| AD-58694.1 | 50.51 | 10.36 | 89.47 | 3.84 |
| AD-58695.1 | 54.37 | 5.75 | 87.66 | 13.59 |
| AD-58696.1 | 93.26 | 0.06 | 84.79 | 3.84 |
| AD-58697.1 | 72.95 | 23.41 | 98.98 | 10.29 |
| AD-58698.1 | 42.61 | 7.81 | 109.98 | 16.78 |
| AD-58699.1 | 24.93 | 8.58 | 79.71 | 12.55 |
| AD-58700.1 | 74.10 | 15.37 | 89.75 | 7.80 |
| AD-58701.1 | 79.18 | 8.18 | 89.70 | 9.98 |
| AD-58702.1 | 96.43 | 18.38 | 113.05 | 10.65 |
| AD-58703.1 | 79.15 | 28.50 | 97.30 | 6.79 |
| AD-58704.1 | 67.92 | 0.87 | 92.26 | 1.24 |
| AD-58705.1 | 59.50 | 20.47 | 99.25 | 3.28 |
| AD-58706.1 | 71.67 | 0.75 | 102.38 | 14.88 |
| AD-58707.1 | 77.89 | 22.26 | 97.52 | 1.31 |
| AD-58708.1 | 73.87 | 9.61 | 98.38 | 1.81 |
| AD-58709.1 | 94.62 | 4.69 | 100.73 | 16.10 |
| AD-58710.1 | 59.19 | 10.57 | 95.23 | 11.99 |
| AD-58711.1 | 63.62 | 16.83 | 103.11 | 3.66 |
| AD-58712.1 | 65.79 | 6.96 | 81.58 | 1.50 |
| AD-58713.1 | 84.14 | 26.41 | 101.56 | 5.60 |
| AD-58714.1 | 64.73 | 6.06 | 102.37 | 1.63 |
| AD-58715.1 | 91.05 | 18.67 | 101.08 | 11.00 |
| AD-58716.1 | 70.07 | 13.02 | 97.20 | 2.98 |
| AD-58717.1 | 11.27 | 6.91 | 66.56 | 4.32 |
| AD-58718.1 | 62.10 | 18.62 | 89.01 | 15.30 |
| AD-58719.1 | 72.94 | 18.26 | 91.58 | 9.97 |
| AD-58720.1 | 60.51 | 14.43 | 90.92 | 5.68 |
| AD-58721.1 | 17.72 | 7.70 | 56.72 | 2.57 |
| AD-58722.1 | 51.65 | 11.33 | 81.44 | 0.50 |
| AD-58723.1 | 53.27 | 21.60 | 94.25 | 16.20 |
| AD-58724.1 | 58.03 | 49.89 | 77.11 | 4.63 |
| AD-58725.1 | 54.58 | 40.10 | 76.12 | 1.59 |
| AD-58726.1 | 10.33 | 9.88 | 42.75 | 7.97 |
| AD-58727.1 | 62.80 | 26.45 | 83.23 | 13.10 |
| AD-58728.1 | 49.36 | 36.27 | 83.30 | 1.74 |
| AD-58729.1 | 43.83 | 61.99 | 73.54 | 19.33 |
| AD-58730.1 | 59.60 | 41.85 | 76.12 | 1.03 |
| AD-58731.1 | 85.29 | 24.78 | 128.06 | 32.14 |
| AD-58734.1 | 85.71 | 10.74 | 101.75 | 6.11 |
| AD-58737.1 | 79.87 | 10.59 | 114.89 | 7.46 |

Example 3. In Vivo Single Dose Screen Using AD-59743

The ability of AD-59743 to suppress expression of TMPRSS6 protein was assessed by measuring levels of TMPRSS6 and hepcidin mRNA in the liver of wild-type C57BL/6 mice following administration of AD-59743. A single dose of 1, 3 or 10 mg/kg of AD-59743 was administered subcutaneously, and the mice were sacrificed on day 3 or day 7. Levels of TMPRSS6 and hepcidin mRNA in the liver were measured by qPCR using the methods described above. A control group received injections with PBS.

Figure 2:
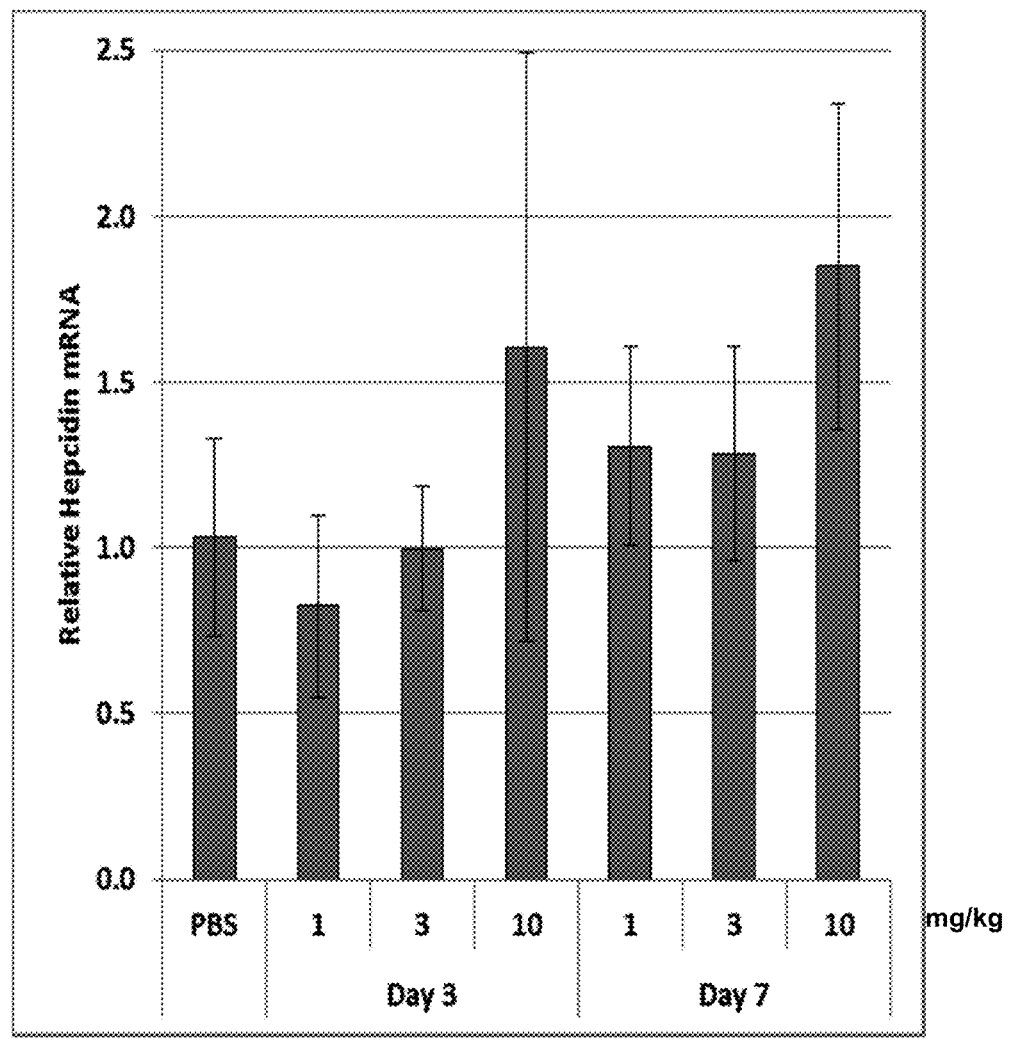
FIG. 2 is a graph showing relative levels of hepcidin mRNA in the liver of wild-type mice following administration of a single dose of 1 mg/kg, 3 mg/kg or 10 mg/kg of the iRNA agent AD-59743.

The levels of TMPRSS6 mRNA following administration of AD-59743 are shown in FIG. 1, and the levels of hepcidin mRNA following administration of AD-59743 are shown in FIG. 2. The results demonstrate a dose-dependent decrease in the levels of TMPRSS6 transcripts that is sustained through day 7.

Example 4. In Vivo Effect of TMPRSS6 iRNA Agents in Combination with an Iron Chelator The purpose of this study was to test the effect of co-administered TMPRSS6 specific siRNA and iron chelators on iron levels. In the study, 6-week old wild-type C57BL/6 and thalassemic Th3/+ mice (Douet et al., *Am. J. Pathol.* (2011), 178(2):774-83) were fed low-iron diets containing 3-5 ppm iron. The mice were administered intravenously the formulation AF-011-46273 containing deferiprone, an iron chelator at a dose of 250 mg/kg/day and an iRNA agent with the following structure: oligoSeq-sense—uGGuAuuuccuAGGGuAcAdTsdT (SEQ ID NO: 209); oligoSeq-antisense—UGuACCCuAGGAAAuACcAdTsdT (SEQ ID NO: 210). The formulation also contained MC-3/DSPC/Cholesterol/PEG-DMG 50/10/38.5/1.5. Liver and spleen tissues were collected and tissue nonheme iron concentrations were determined as described previously (see, e.g., Schmidt et al. (2013) *Blood* 121(7):1200-8; Cook, J D, et al. *Tissue iron stores.* In: Cook J D, editor. *Methods in Hematology.* Vol 1. New York, N.Y.: Churchill Livingstone Press; 1980. p. 104-109).

The results of these experiments demonstrate an additive effect of AD-46273 and deferiprone in Th3/+ mice, with the decreased iron levels relative to the negative controls.

Example 5. Design, Specificity and Efficacy Prediction of Oligonucleotides

Transcripts siRNA design was carried out to identify siRNAs targeting human, cynomolgus monkey (*Macaca fascicularis*; henceforth "cyno"), mouse, and rat TMPRSS6 transcripts annotated in the NCBI Gene database (http://www.ncbi.nlm.nih.gov/gene/). Design used the following transcripts from the NCBI RefSeq collection: Human—NM_153609.2; Mouse—NM_027902.2; Rat—NM_001130556.1. For cyno, a transcript sequence was obtained via alignment with human TMPRSS6 of sequence assembled from two accessions: "ENSP00000384964 [mRNA] locus=chr10: 82446450:82485403:-" and FR874253.1, available from the *M. fascicularis* genome project and NCBI Nucleotide databases, respectively (http://macaque.genomics.org.cn/page/species/download.jsp and http://www.ncbi.nlm.nih.gov/nucleotide/). Due to high primate/rodent sequence divergence, siRNA duplexes were designed in several separate batches, including but not limited to batches containing duplexes matching human and cyno transcripts only; human, cyno, and mouse transcripts only; and human, cyno, mouse, and rat transcripts only. Most siRNA duplexes were designed that shared 100% identity in the designated region with the listed human transcript and other species transcripts considered in each design batch (above). In some instances, mismatches between duplex and mRNA target were allowed at the first antisense (last sense) position when the antisense strand: target mRNA complementary basepair was a GC or CG pair. In these cases, duplexes were designed with UA or AU pairs at the first antisense:last sense pair. Thus the duplexes maintained complementarity but were mismatched with respect to target (U:C, U:G, A:C, or A:G).

The specificity of all possible 19mers was predicted from each sequence. Candidate 19mers that lacked repeats longer than 7 nucleotides were then selected. These 1128 candidate human/cyno, 69 human/cyno/mouse, and 23 human/cyno/mouse/rat siRNAs were used in comprehensive searches against the appropriate transcriptomes (defined as the set of NM_ and XM_ records within the human, mouse, or rat NCBI Refseq sets, and the cyno transcriptome set in NCBI nucleotide) using an exhaustive "brute-force" algorithm implemented in the python script 'BruteForce.py'. The script next parsed the transcript-oligo alignments to generate a score based on the position and number of mismatches between the siRNA and any potential 'off-target' transcript. The off-target score is weighted to emphasize differences in the 'seed' region of siRNAs, in positions 2-9 from the 5' end of the molecule. Each oligo-transcript pair from the brute-force search was given a mismatch score by summing the individual mismatch scores; mismatches in the position 2-9 were counted as 2.8, mismatches in the cleavage site positions 10-11 were counted as 1.2, and mismatches in region 12-19 counted as 1.0. An additional off-target prediction was carried out by comparing the frequency of heptamers and octomers derived from 3 distinct, seed-derived hexamers of each oligo. The hexamers from positions 2-7 relative to the 5' start were used to create 2 heptamers and one octomer. Heptamer1 was created by adding a 3' A to the hexamer; heptamer2 was created by adding a 5' A to the hexamer; the octomer was created by adding an A to both 5' and 3' ends of the hexamer. The frequency of octomers and heptamers in the human, cyno, mouse, or rat 3'UTRome (defined as the subsequence of the transcriptome from NCBI's Refseq database where the end of the coding region, the 'CDS', is clearly defined) was pre-calculated. The octomer frequency was normalized to the heptamer frequency using the median value from the range of octomer frequencies. A 'mirSeed-Score' was then calculated by calculating the sum of ((3× normalized octomer count)+(2× heptamer2 count)+(1× heptamer1 count)).

Both siRNAs strands were assigned to a category of specificity according to the calculated scores: a score above 3 qualifies as highly specific, equal to 3 as specific and between 2 and 2.8 as moderately specific. We sorted by the specificity of the antisense strand. We then selected moderately (or higher) specific duplexes whose antisense oligos possessed characteristics of duplexes with high predicted efficacy, including maximal UA content in the seed region and low overall GC content.

For GalNaC-conjugated duplexes, sense 21mer and antisense 23mer oligos were designed by extending antisense 19mers (described above) to 23 nucleotides of target-complementary sequence. All species transcripts included in the design batch were checked for complementarity. For each duplex, the sense 21mer was specified as the reverse complement of the first 21 nucleotides of the antisense strand.

siRNA Sequence Selection

A total of 5 sense and 5 antisense human, 32 sense and 32 antisense derived human/cyno, 4 sense and 4 antisense derived human/cyno/mouse, 8 sense and 8 antisense derived human/cyno/mouse/rat, 19 sense and 19 antisense derived human/cyno/rat, 2 sense and 2 antisense derived human/mouse, and 1 sense and 1 antisense derived human/mouse/rat siRNA 21/23mer oligos were synthesized and formed into GalNAc-conjugated duplexes.

The sequences of the sense and antisense strands of the unmodified duplexes are shown in Table 4, and the sequences of the sense and antisense strands of the modified duplexes are shown in Table 5.

TABLE 4

TMPRSS6- unmodified seqeunces

| Duplex ID | Sense sequence ID | Sense sequence | SEQ ID NO: | Antisense sequence ID | Antisense sequence | SEQ ID NO: | Position in NM_153609.2 |
|---|---|---|---|---|---|---|---|
| AD-60944.1 | A-122732.1 | GGUGCUACUCUGGUAUUCCU | 211 | A-122733.1 | AGGAAAUACCAGAGUAGCACCCC | 280 | 318 |
| AD-59743.1 | A-120243.1 | UCUGGUAUUUCCUAGGGUACA | 212 | A-120244.1 | UGUACCCUAGGAAAUACCAGAGU | 281 | 326 |
| AD-60940.1 | A-122745.1 | CUGGUAUUUCCUAGGGUACAA | 213 | A-122746.1 | UUGUACCCUAGGAAAUACCAGAG | 282 | 327 |
| AD-61002.2 | A-122838.1 | UGGUAUUUCCUAGGGUACAAA | 214 | A-122839.1 | UUUGUACCCUAGGAAAUACCAGA | 283 | 328 |
| AD-61000.1 | A-122852.1 | GGUAUUUCCUAGGGUACAAGA | 215 | A-122853.1 | UCUUGUACCCUAGGAAAUACCAG | 284 | 329 |
| AD-46273.1 | A-96908.1 | UGGUAUUUCCUAGGGUACA | 216 | A-96909.1 | UGUACCCUAGGAAAUACCA | 285 | 330 |
| AD-61003.1 | A-122854.1 | GUAUUUCCUAGGGUACAAGGA | 217 | A-122855.1 | UCCUUGUACCCUAGGAAAUACCA | 286 | 330 |
| AD-60994.1 | A-122848.1 | AUUUCCUAGGGUACAAGGCGA | 218 | A-122849.1 | UCGCCUUGUACCCUAGGAAAUAC | 287 | 332 |
| AD-60990.1 | A-122830.1 | UUUCCUAGGGUACAAGGCGGA | 219 | A-122831.1 | UCCGCCUUGUACCCUAGGAAAUA | 288 | 333 |
| AD-60956.1 | A-122736.1 | CGCCACUUCUCCCAGGAUCUU | 220 | A-122737.1 | AAGAUCCUGGGAGAAGUGGCGAU | 289 | 400 |
| AD-60981.1 | A-122757.1 | GCCACUUCUCCCAGGAUCUUA | 221 | A-122758.1 | UAAGAUCCUGGGAGAAGUGGCGA | 290 | 401 |
| AD-60953.1 | A-122775.1 | CUGCUUCUUCUGGUUCAUUCU | 222 | A-122776.1 | AGAAUGAACCAGAAGAAGCAGGU | 291 | 558 |
| AD-60977.1 | A-122783.1 | CUUCUUCUGGUUCAUUCUCCA | 223 | A-122784.1 | UGGAGAAUGAACCAGAAGAAGCA | 292 | 561 |
| AD-60964.1 | A-119169.2 | CCCUACAGGGCCGAGUACGAA | 224 | A-122764.1 | UUCGUACUCGGCCCUGUAGGGA | 293 | 679 |
| AD-60947.1 | A-122773.1 | CUACAGGGCCGAGUACGAAGU | 225 | A-122774.1 | ACUUCGUACUCGGCCCUGUAGGG | 294 | 681 |
| AD-60957.1 | A-122751.1 | GCCAGUGUGAAAGACAUAGCU | 226 | A-122752.1 | AGCUAUGUCUUUCACACUGGCUU | 295 | 730 |
| AD-60960.1 | A-122792.1 | AGUGUGAAAGACAUAGCUGCA | 227 | A-122793.1 | UGCAGCUAUGUCUUUCACACUGG | 296 | 733 |
| AD-60972.1 | A-122796.1 | CACGCUGGGUUGUUACCGCUA | 228 | A-122797.1 | UAGCGGUAACAACCCAGCGUGGA | 297 | 762 |
| AD-60970.1 | A-122765.1 | GGGUUGUUACCGCUACAGCUA | 229 | A-122766.1 | UAGCUGUAGCGGUAACAACCCAG | 298 | 768 |
| AD-60963.1 | A-122753.1 | CGGGACCGACUGGCCAUGUAU | 230 | A-122754.1 | AUACAUGGCCAGUCGGUCCCGGC | 299 | 916 |

TABLE 4-continued

TMPRSS6- unmodified seqeunces

| Duplex ID | Sense sequence ID | Sense sequence | SEQ ID NO: | Antisense sequence ID | Antisense sequence | SEQ ID NO: | Position in NM_153609.2 |
|---|---|---|---|---|---|---|---|
| AD-60968.1 | A-122739.1 | CCGACUGGCCAUGUAUGACGU | 231 | A-122740.1 | ACGUCAUACAUGGCCAGUCGGUC | 300 | 921 |
| AD-60942.1 | A-122786.1 | GGGCCUGCACAGCUACUACGA | 232 | A-122787.1 | UCGUAGUAGCUGUGCAGGCCCUU | 301 | 1053 |
| AD-60951.1 | A-122749.1 | GGCAGAAGUAUGAUUUGCCGU | 233 | A-122750.1 | ACGGCAAAUCAUACUUCUGCCUC | 302 | 1280 |
| AD-60984.1 | A-122800.1 | CCAGAACAGGAGGCUGUGUGG | 234 | A-122801.1 | CCACACAGCCUCCUGUUCUGGAU | 303 | 1323 |
| AD-60955.1 | A-122806.1 | CAGAACAGGAGGCUGUGUGGC | 235 | A-122807.1 | GCCACACAGCCUCCUGUUCUGGA | 304 | 1324 |
| AD-60943.1 | A-122802.1 | CACCUCCCAGAUCUCCCUCAC | 236 | A-122803.1 | GUGAGGGAGAUCUGGGAGGUGAA | 305 | 1413 |
| AD-61001.1 | A-122823.1 | CACCUCCCAGAUCUCCCUCAA | 237 | A-122824.1 | UUGAGGGAGAUCUGGGAGGUGAA | 306 | 1413 |
| AD-60974.1 | A-122741.1 | UGUGCGGGUGCACUAUGGCUU | 238 | A-122742.1 | AAGCCAUAGUGCACCCGCACACC | 307 | 1443 |
| AD-60982.1 | A-122769.1 | GCGGGUGCACUAUGGCUUGUA | 239 | A-122770.1 | UACAAGCCAUAGUGCACCCGCAC | 308 | 1446 |
| AD-60996.1 | A-122834.1 | CCCCUGCCCUGGAGAGUUCCU | 240 | A-122835.1 | AGGAACUCUCCAGGGCAGGGGUC | 309 | 1479 |
| AD-60997.1 | A-122850.1 | CCCUGCCCUGGAGAGUUCCUA | 241 | A-122851.1 | UAGGAACUCUCCAGGGCAGGGGU | 310 | 1480 |
| AD-61006.1 | A-122856.1 | CCUGCCCUGGAGAGUUCCUCU | 242 | A-122857.1 | AGAGGAACUCUCCAGGGCAGGGG | 311 | 1481 |
| AD-60988.1 | A-122844.1 | CUGCCCUGGAGAGUUCCUCUA | 243 | A-122845.1 | UAGAGGAACUCUCCAGGGCAGGG | 312 | 1482 |
| AD-60959.1 | A-122777.1 | CCUGUGAUGGGGUCAAGGACU | 244 | A-122778.1 | AGUCCUUGACCCCAUCACAGGCA | 313 | 1529 |
| AD-60999.1 | A-122836.1 | GGACUGCCCAACGGCCUGGA | 245 | A-122837.1 | UCCAGGCCGUUGGGGCAGUCCUU | 314 | 1545 |
| AD-60991.1 | A-122846.1 | ACUGCCCCAACGGCCUGGAUA | 246 | A-122847.1 | UAUCCAGGCCGUUGGGGCAGUCC | 315 | 1547 |
| AD-60993.1 | A-122832.1 | CUGCCCCAACGGCCUGGAUGA | 247 | A-122833.1 | UCAUCCAGGCCGUUGGGGCAGUC | 316 | 1548 |
| AD-61005.1 | A-122840.1 | UGCCCCAACGGCCUGGAUGAA | 248 | A-122841.1 | UUCAUCCAGGCCGUUGGGGCAGU | 317 | 1549 |
| AD-60987.1 | A-119213.2 | GCCCCAACGGCCUGGAUGAGA | 249 | A-122829.1 | UCUCAUCCAGGCCGUUGGGGCAG | 318 | 1550 |
| AD-60986.1 | A-122842.1 | CCCCAACGGCCUGGAUGAGAA | 250 | A-122843.1 | UUCUCAUCCAGGCCGUUGGGGCA | 319 | 1551 |
| AD-60952.1 | A-119187.2 | CCCAACGGCCUGGAUGAGAGA | 251 | A-122761.1 | UCUCUCAUCCAGGCCGUUGGGGC | 320 | 1552 |
| AD-60983.1 | A-119191.2 | CAACGGCCUGGAUGAGAGAAA | 252 | A-122785.1 | UUUCUCUCAUCCAGGCCGUUGGG | 321 | 1554 |
| AD-60950.1 | A-122734.1 | ACGGCCUGGAUGAGAGAAACU | 253 | A-122735.1 | AGUUUCUCUCAUCCAGGCCGUUG | 322 | 1556 |
| AD-60980.1 | A-122743.1 | CCUGGAUGAGAGAAACUGCGU | 254 | A-122744.1 | ACGCAGUUUCUCUCAUCCAGGCC | 323 | 1560 |
| AD-60998.1 | A-122821.1 | CACUGUGACUGUGGCCUCCAA | 255 | A-122822.1 | UUGGAGGCCACAGUCACAGUGCU | 324 | 1804 |
| AD-60961.1 | A-122808.1 | GUCCUCCGAGGGUGAGUGGCC | 256 | A-122809.1 | GGCCACUCACCCUCGGAGGACAC | 325 | 1857 |
| AD-61004.1 | A-122825.1 | CUCCGAGGGUGAGUGGCCAUA | 257 | A-122826.1 | UAUGGCCACUCACCCUCGGAGGA | 326 | 1860 |
| AD-60949.1 | A-122804.1 | UCCGAGGGUGAGUGGCCAUGG | 258 | A-122805.1 | CCAUGGCCACUCACCCUCGGAGG | 327 | 1861 |
| AD-60969.1 | A-119189.2 | CCAGGUUCGGGGUCGACACAU | 259 | A-122755.1 | AUGUGUCGACCCCGAACCUGGAG | 328 | 1893 |
| AD-60966.1 | A-122794.1 | AGGUUCGGGGUCGACACAUCU | 260 | A-122795.1 | AGAUGUGUCGACCCCGAACCUGG | 329 | 1895 |
| AD-60967.1 | A-122810.1 | CGGGGUCGACACAUCUGUGGG | 261 | A-122811.1 | CCCACAGAUGUGUCGACCCCGAA | 330 | 1900 |
| AD-60989.1 | A-122816.1 | CGGGGUCGACACAUCUGUGGA | 262 | A-122817.1 | UCCACAGAUGUGUCGACCCCGAA | 331 | 1900 |
| AD-60973.1 | A-122812.1 | GGGGUCGACACAUCUGUGGGG | 263 | A-122813.1 | CCCCACAGAUGUGUCGACCCCGA | 332 | 1901 |
| AD-60992.1 | A-122818.1 | GGGGUCGACACAUCUGUGGGA | 264 | A-122819.1 | UCCCACAGAUGUGUCGACCCCGA | 333 | 1901 |
| AD-60985.1 | A-122827.1 | GGGUCGACACAUCUGUGGGGA | 265 | A-122828.1 | UCCCCACAGAUGUGUCGACCCCG | 334 | 1902 |
| AD-60946.1 | A-122759.1 | GCUGACCGCUGGGUGAUAACA | 266 | A-122760.1 | UGUUAUCACCCAGCGGUCAGCGA | 335 | 1933 |
| AD-60979.1 | A-122814.1 | CUUCCAGGAGGACAGCAUGGC | 267 | A-122815.1 | GCCAUGCUGUCCUCCUGGAAGCA | 336 | 1965 |

TABLE 4-continued

TMPRSS6- unmodified seqeunces

| Duplex ID | Sense sequence ID | Sense sequence | SEQ ID NO: | Antisense sequence ID | Antisense sequence | SEQ ID NO: | Position in NM_153609.2 |
|---|---|---|---|---|---|---|---|
| AD-60976.1 | A-122767.1 | GGCCUGGAGAGGUGUCCUUCA | 268 | A-122768.1 | UGAAGGACACCUCUCCAGGCCAG | 337 | 2039 |
| AD-60939.1 | A-122730.1 | GCCUGGAGAGGUGUCCUUCAA | 269 | A-122731.1 | UUGAAGGACACCUCUCCAGGCCA | 338 | 2040 |
| AD-60978.1 | A-122798.1 | CCAAGCAGGGGACAAGUAUU | 270 | A-122799.1 | AAUACUUGUCCCCCUGCUUGGCA | 339 | 2608 |
| AD-60958.1 | A-122762.1 | CAAGCAGGGGACAAGUAUUC | 271 | A-122763.1 | GAAUACUUGUCCCCCUGCUUGGC | 340 | 2609 |
| AD-60962.1 | A-119231.2 | UGGCAGGAGGUGGCAUCUUGU | 272 | A-122738.1 | ACAAGAUGCCACCUCCUGCCACC | 341 | 2664 |
| AD-60941.1 | A-122771.1 | GCAGGAGGUGGCAUCUUGUCU | 273 | A-122772.1 | AGACAAGAUGCCACCUCCUGCCA | 342 | 2666 |
| AD-60965.1 | A-122779.1 | GCUUCGGAAGCCCCUGGUCUA | 274 | A-122780.1 | UAGACCAGGGGCUUCCGAAGCUG | 343 | 2954 |
| AD-60954.1 | A-122790.1 | CUUCGGAAGCCCCUGGUCUAA | 275 | A-122791.1 | UUAGACCAGGGGCUUCCGAAGCU | 344 | 2955 |
| AD-60975.1 | A-119233.2 | CCCCUGGUCUAACUUGGGAUC | 276 | A-122756.1 | GAUCCCAAGUUAGACCAGGGGCU | 345 | 2964 |
| AD-60945.1 | A-122747.1 | CCCUGGUCUAACUUGGGAUCU | 277 | A-122748.1 | AGAUCCCAAGUUAGACCAGGGGC | 346 | 2965 |
| AD-60971.1 | A-122781.1 | CCUGGUCUAACUUGGGAUCUG | 278 | A-122782.1 | CAGAUCCCAAGUUAGACCAGGGG | 347 | 2966 |
| AD-60948.1 | A-122788.1 | CUAACUUGGGAUCUGGGAAUG | 279 | A-122789.1 | CAUUCCCAGAUCCCAAGUUAGAC | 348 | 2972 |

TABLE 5

TMPRSS6 modified sequences

| Duplex ID | Sense sequence ID | Sense sequence | SEQ ID NO: |
|---|---|---|---|
| AD-46273.1 | A-96908.1 | uGGuAuuuccuAGGGuAcAdTsdT | 349 |
| AD-59743.1 | A-120243.1 | UfscsUfgGfuAfuUfUfCfcUfaGfgGfuAfcAfL96 | 350 |
| AD-60939.1 | A-122730.1 | GfscsCfuGfgAfgAfGfGfuGfuCfcUfUfCfaAfL96 | 351 |
| AD-60940.1 | A-122745.1 | CfsusGfgUfaUfuUfCfCfuAfgGfgUfaCfaAfL96 | 352 |
| AD-60941.1 | A-122771.1 | GfscsAfgGfaGfgUfGfGfcAfuCfuUfgUfcUfL96 | 353 |
| AD-60942.1 | A-122786.1 | GfsgsGfcCfuGfcAfCfAfgCfuAfcUfaCfgAfL96 | 354 |
| AD-60943.1 | A-122802.1 | CfsasCfcUfcCfcAfGfAfuCfuCfcCfuCfaCfL96 | 355 |
| AD-60944.1 | A-122732.1 | GfsgsUfgCfuAfcUfCfUfgGfuAfuUfuCfcUfL96 | 356 |
| AD-60945.1 | A-122747.1 | CfscsCfuGfgUfcUfAfAfcUfuGfgGfaUfcUfL96 | 357 |
| AD-60946.1 | A-122759.1 | GfscsUfgAfcCfgCfUfGfgGfuGfaUfaAfcAfL96 | 358 |
| AD-60947.1 | A-122773.1 | CfsusAfcAfgGfcCfCfGfaGfuAfcGfaAfgUfL96 | 359 |
| AD-60948.1 | A-122788.1 | CfsusAfaCfuUfgGfgAfuCfuGfgGfaAfuGfL96 | 360 |
| AD-60949.1 | A-122804.1 | UfscsCfgAfgGfgUfGfAfgUfgGfcCfaUfgGfL96 | 361 |
| AD-60950.1 | A-122734.1 | AfscsGfgCfcUfgGfAfUfgAfgAfgAfaAfcUfL96 | 362 |
| AD-60951.1 | A-122749.1 | GfsgsCfaGfaAfgUfAfUfgAfuUfuGfcCfgUfL96 | 363 |
| AD-60952.1 | A-119187.2 | CfscsCfaAfcGfgCfCfUfgGfaUfgAfgAfgAfL96 | 364 |
| AD-60953.1 | A-122775.1 | CfsusGfcUfuCfuUfCfUfgGfuUfcAfuUfcUfL96 | 365 |
| AD-60954.1 | A-122790.1 | CfsusUfcGfgAfaGfCfCfcCfuGfgUfcUfaAfL96 | 366 |
| AD-60955.1 | A-122806.1 | CfsasGfaAfcAfgGfAfGfgCfuGfuGfuGfgCfL96 | 367 |

TABLE 5-continued

| TMPRSS6 modified sequences | | | |
|---|---|---|---|
| AD-60956.1 | A-122736.1 | CfsgsCfcAfcUfuCfUfCfcCfaGfgAfuCfuUfL96 | 368 |
| AD-60957.1 | A-122751.1 | GfscsCfaGfuGfuGfAfAfaGfaCfaUfaGfcUfL96 | 369 |
| AD-60958.1 | A-122762.1 | CfsasAfgCfaGfgGfGfGfacCfaAfgUfaUfuCfL96 | 370 |
| AD-60959.1 | A-122777.1 | CfscsUfgUfgAfuGfGfGfgUfcAfaGfgAfcUfL96 | 371 |
| AD-60960.1 | A-122792.1 | AfsgsUfgUfgAfaAfGfAfcAfuAfgCfuGfcAfL96 | 372 |
| AD-60961.1 | A-122808.1 | GfsusCfcUfcCfgAfGfGfgUfgAfgUfgGfcCfL96 | 373 |
| AD-60962.1 | A-119231.2 | UfsgsGfcAfgGfaGfGfUfgGfcAfuCfuUfgUfL96 | 374 |
| AD-60963.1 | A-122753.1 | CfsgsGfgAfcCfgAfCfUfgGfcCfaUfgUfaUfL96 | 375 |
| AD-60964.1 | A-119169.2 | CfscsCfuAfcAfgGfGfCfcGfaGfuAfcGfaAfL96 | 376 |
| AD-60965.1 | A-122779.1 | GfscsUfuCfgGfaAfGfCfcCfcUfgGfuCfuAfL96 | 377 |
| AD-60966.1 | A-122794.1 | AfsgsGfuUfcGfgGfGfUfcGfaCfaCfaUfcUfL96 | 378 |
| AD-60967.1 | A-122810.1 | CfsgsGfgGfuCfgAfCfAfcAfuCfuGfuGfgGfL96 | 379 |
| AD-60968.1 | A-122739.1 | CfscsGfaCfuGfgCfCfAfuGfuAfuGfaCfgUfL96 | 380 |
| AD-60969.1 | A-119189.2 | CfscsAfgGfuUfcGfGfGfgUfcGfaCfaCfaUfL96 | 381 |
| AD-60970.1 | A-122765.1 | GfsgsGfuUfgUfuAfCfCfgCfuAfcAfgCfuAfL96 | 382 |
| AD-60971.1 | A-122781.1 | CfscsUfgGfuCfuAfAfCfuUfgGfgAfuCfuGfL96 | 383 |
| AD-60972.1 | A-122796.1 | CfsasCfgCfuGfgGfUfUfgUfuAfcCfgCfuAfL96 | 384 |
| AD-60973.1 | A-122812.1 | GfsgsGfgUfcGfaCfAfCfaUfcUfgUfgGfgGfL96 | 385 |
| AD-60974.1 | A-122741.1 | UfsgsUfgCfgGfgUfGfCfaCfuAfuGfgCfuUfL96 | 386 |
| AD-60975.1 | A-119233.2 | CfscsCfcUfgGfuCfUfAfaCfuUfgGfgAfuCfL96 | 387 |
| AD-60976.1 | A-122767.1 | GfsgsCfcUfgGfaGfAfGfgUfgUfcCfuUfcAfL96 | 388 |
| AD-60977.1 | A-122783.1 | CfsusUfcUfuCfuGfGfUfcCfaUfcUfcCfcAfL96 | 389 |
| AD-60978.1 | A-122798.1 | CfscsAfaGfcAfgGfGfGfgAfcAfaGfuAfuUfL96 | 390 |
| AD-60979.1 | A-122814.1 | CfsusUfcCfaGfgAfGfGfaCfaGfcAfuGfgCfL96 | 391 |
| AD-60980.1 | A-122743.1 | CfscsUfgGfaUfgAfGfAfgAfaAfcUfgCfgUfL96 | 392 |
| AD-60981.1 | A-122757.1 | GfscsCfaCfuUfcUfCfCfcAfgGfaUfcUfaAfL96 | 393 |
| AD-60982.1 | A-122769.1 | GfscsGfgGfuGfcAfCfUfaUfgGfcUfuGfuAfL96 | 394 |
| AD-60983.1 | A-119191.2 | CfsasAfcGfgCfcUfGfGfaUfgAfgAfgAfaAfL96 | 395 |
| AD-60984.1 | A-122800.1 | CfscsAfgAfaCfaGfGfAfgGfcUfgUfgUfgGfL96 | 396 |
| AD-60985.1 | A-122827.1 | GfsgsGfuCfgAfcAfCfAfuCfuGfuGfgGfaAfL96 | 397 |
| AD-60986.1 | A-122842.1 | CfscsCfcAfaCfgGfCfCfuGfgAfuGfaGfaAfL96 | 398 |
| AD-60987.1 | A-119213.2 | GfscsCfcCfaAfcGfGfCfcUfgGfaUfgAfgAfL96 | 399 |
| AD-60988.1 | A-122844.1 | CfsusGfcCfcUfgGfAfGfaGfuUfcCfuCfuAfL96 | 400 |
| AD-60989.1 | A-122816.1 | CfsgsGfgGfuCfgAfCfAfcAfuCfuGfuGfgAfL96 | 401 |
| AD-60990.1 | A-122830.1 | UfsusUfcCfuAfgGfGfUfaCfaAfgGfcGfgAfL96 | 402 |
| AD-60991.1 | A-122846.1 | AfscsUfgCfcCfcAfAfCfgGfcCfuGfgAfuAfL96 | 403 |
| AD-60992.1 | A-122818.1 | GfsgsGfgUfcGfaCfAfCfaUfcUfgUfgGfgAfL96 | 404 |
| AD-60993.1 | A-122832.1 | CfsusGfcCfcCfaAfCfgGfcCfcUfgGfaUfgAfL96 | 405 |
| AD-60994.1 | A-122848.1 | AfsusUfuCfcCfUfaGfGfGfuAfcAfaGfCfgAfL96 | 406 |

TABLE 5-continued

TMPRSS6 modified sequences

| | | | |
|---|---|---|---|
| AD-60996.1 | A-122834.1 | CfscsCfcUfgCfcCfUfGfgAfgAfgUfuCfcUfL96 | 407 |
| AD-60997.1 | A-122850.1 | CfscsCfuGfcCfcUfGfGfaGfaGfuUfcCfuAfL96 | 408 |
| AD-60998.1 | A-122821.1 | CfsasCfuGfuGfaCfUfGfuGfgCfcUfcCfaAfL96 | 409 |
| AD-60999.1 | A-122836.1 | GfsgsAfcUfgCfcCfCfAfaCfgGfcCfuGfgAfL96 | 410 |
| AD-61000.1 | A-122852.1 | GfsgsUfaUfuUfcCfUfAfgGfgUfaCfaAfgAfL96 | 411 |
| AD-61001.1 | A-122823.1 | CfsasCfcUfcCfcAfGfAfuCfuCfcCfuCfaAfL96 | 412 |
| AD-61002.1 | A-122838.1 | UfsgsGfuAfuUfuCfCfUfaGfgGfuAfcAfaAfL96 | 413 |
| AD-61003.1 | A-122854.1 | GfsusAfuUfuCfcUfAfGfgGfuAfcAfaGfaAfL96 | 414 |
| AD-61004.1 | A-122825.1 | CfsusCfcGfaGfgGfUfGfaGfuGfgCfcAfuAfL96 | 415 |
| AD-61005.1 | A-122840.1 | UfsgsCfcCfcAfaCfGfGfcCfuGfgAfuGfaAfL96 | 416 |
| AD-61006.1 | A-122856.1 | CfscsUfgCfcCfuGfGfAfgAfgUfuCfcUfcUfL96 | 417 |

| Duplex ID | Antisense sequence ID | Antisense sequence | SEQ ID NO: |
|---|---|---|---|
| AD-46273.1 | A-96909.1 | UGuACCCuAGGAAAuACcAdTsdT | 418 |
| AD-59743.1 | A-120244.1 | usGfsuAfcCfcUfaGfgaaAfuAfcCfaGfasgsu | 419 |
| AD-60939.1 | A-122731.1 | usUfsgAfaGfgAfcAfccuCfuCfcAfgGfcscsa | 420 |
| AD-60940.1 | A-122746.1 | usUfsgUfaCfcCfuAfggaAfaUfaCfcAfgsasg | 421 |
| AD-60941.1 | A-122772.1 | asGfsaCfaAfgAfuGfccaCfcUfcCfuGfcscsa | 422 |
| AD-60942.1 | A-122787.1 | usCfsgUfaGfuAfgCfuguGfcAfgGfcCfcsusu | 423 |
| AD-60943.1 | A-122803.1 | gsUfsgAfgGfgAfgAfucuGfgGfaGfgUfgsasa | 424 |
| AD-60944.1 | A-122733.1 | asGfsgAfaAfuAfcCfagaGfuAfgCfaCfcscsc | 425 |
| AD-60945.1 | A-122748.1 | asGfsaUfcCfcAfaGfuuaGfaCfcAfgGfgsgsc | 426 |
| AD-60946.1 | A-122760.1 | usGfsuUfaUfcAfcCfcagCfgGfuCfaGfcsgsa | 427 |
| AD-60947.1 | A-122774.1 | asCfsuUfcGfuAfcUfcggCfcCfuGfuAfgsgsg | 428 |
| AD-60948.1 | A-122789.1 | csAfsuUfcCfcAfgAfuccCfaAfgUfuAfgsasc | 429 |
| AD-60949.1 | A-122805.1 | csCfsaUfgGfcCfaCfucaCfcCfuCfgGfasgsg | 430 |
| AD-60950.1 | A-122735.1 | asGfsuUfcUfuCfuCfaucCfaGfgCfcGfususg | 431 |
| AD-60951.1 | A-122750.1 | asCfsgGfcAfaAfuCfauaCfuUfcCfuGfcscsc | 432 |
| AD-60952.1 | A-122761.1 | usCfsuCfuCfaUfcCfaggCfcGfuUfgGfgsgsc | 433 |
| AD-60953.1 | A-122776.1 | asGfsaAfuGfaAfcCfagaAfgAfaGfcAfgsgsu | 434 |
| AD-60954.1 | A-122791.1 | usUfsaGfaCfcAfgGfggcUfuCfcGfaAfgscsu | 435 |
| AD-60955.1 | A-122807.1 | gsCfscAfcAfcAfgCfcucCfuGfuUfcUfgsgsa | 436 |
| AD-60956.1 | A-122737.1 | asAfsgAfuCfcUfgGfgagAfaGfuGfgCfgsasu | 437 |
| AD-60957.1 | A-122752.1 | asGfscUfaUfgUfcUfuucAfcAfcUfgGfcsusu | 438 |
| AD-60958.1 | A-122763.1 | gsAfsaUfaCfuUfgUfcccCfcUfgCfuUfgsgsc | 439 |
| AD-60959.1 | A-122778.1 | asGfsuCfcUfuGfaCfcccAfuCfaCfaGfgscsa | 440 |
| AD-60960.1 | A-122793.1 | usGfscAfgCfuAfuGfucuUfuCfaCfaCfusgsg | 441 |
| AD-60961.1 | A-122809.1 | gsGfscCfaCfuCfaCfccuCfgGfaGfgAfcsasc | 442 |
| AD-60962.1 | A-122738.1 | asCfsaAfgAfuGfcCfaccUfcCfuGfcCfascsc | 443 |

TABLE 5-continued

| | TMPRSS6 modified sequences | | |
|---|---|---|---|
| AD-60963.1 | A-122754.1 | asUfsaCfaUfgGfcCfaguCfgGfuCfcCfgsgsc | 444 |
| AD-60964.1 | A-122764.1 | usUfscGfuAfcUfcGfgccCfuGfuAfgGfgsgsa | 445 |
| AD-60965.1 | A-122780.1 | usAfsgAfcCfaGfgGfgcuUfcCfgAfaGfcsusg | 446 |
| AD-60966.1 | A-122795.1 | asGfsaUfgUfgUfcGfaccCfcGfaAfcCfusgsg | 447 |
| AD-60967.1 | A-122811.1 | csCfscAfcAfgAfuGfuguCfgAfcCfcCfgsasa | 448 |
| AD-60968.1 | A-122740.1 | asCfsgUfcAfuAfcAfuggCfcAfgUfcGfgsusc | 449 |
| AD-60969.1 | A-122755.1 | asUfsgUfgUfcGfaCfcccGfaAfcCfuGfgsasg | 450 |
| AD-60970.1 | A-122766.1 | usAfsgCfuGfuAfgCfgguAfaCfaAfcCfcsasg | 451 |
| AD-60971.1 | A-122782.1 | csAfsgAfuCfcCfaAfguuAfgAfcCfaGfgsgsg | 452 |
| AD-60972.1 | A-122797.1 | usAfsgCfgGfuAfaCfaacCfcAfgCfgUfgsgsa | 453 |
| AD-60973.1 | A-122813.1 | csCfscCfaCfaGfaUfgugUfcGfaCfcCfcsgsa | 454 |
| AD-60974.1 | A-122742.1 | asAfsgCfcAfuAfgUfgcaCfcCfgCfaCfascsc | 455 |
| AD-60975.1 | A-122756.1 | gsAfsuCfcCfaAfgUfuagAfcCfaGfgGfgscsu | 456 |
| AD-60976.1 | A-122768.1 | usGfsaAfgGfaCfaCfcucUfcCfaGfgCfcsasg | 457 |
| AD-60977.1 | A-122784.1 | usGfsgAfgAfaUfgAfaccAfgAfaGfaAfgscsa | 458 |
| AD-60978.1 | A-122799.1 | asAfsuAfcUfuGfuCfcccCfuGfcUfuGfgscsa | 459 |
| AD-60979.1 | A-122815.1 | gsCfscAfuGfcUfgUfccuCfcUfgGfaAfgscsa | 460 |
| AD-60980.1 | A-122744.1 | asCfsgCfaGfuUfuCfucuCfaUfcCfaGfgscsc | 461 |
| AD-60981.1 | A-122758.1 | usAfsaGfaUfcCfuGfggaGfaAfgUfgGfcsgsa | 462 |
| AD-60982.1 | A-122770.1 | usAfscAfaGfcCfaUfaguGfcAfcCfcGfcsasc | 463 |
| AD-60983.1 | A-122785.1 | usUfsuCfuCfuCfaUfccaGfgCfcGfuUfgsgsg | 464 |
| AD-60984.1 | A-122801.1 | csCfsaCfaCfaGfcCfuccUfgUfuCfuGfgsasu | 465 |
| AD-60985.1 | A-122828.1 | usCfscCfcAfcAfgAfuguGfuCfgAfcCfcscsg | 466 |
| AD-60986.1 | A-122843.1 | usUfscUfcAfuCfcAfggcCfgUfuGfgGfgscsa | 467 |
| AD-60987.1 | A-122829.1 | usCfsuCfaUfcCfaGfgccGfuUfgGfgGfcsasg | 468 |
| AD-60988.1 | A-122845.1 | usAfsgAfgGfaAfcUfcucCfaGfgGfcAfgsgsg | 469 |
| AD-60989.1 | A-122817.1 | usCfscAfcAfgAfuGfuguCfgAfcCfcCfgsasa | 470 |
| AD-60990.1 | A-122831.1 | usCfscGfcCfuUfgUfaccCfuAfgGfaAfasusa | 471 |
| AD-60991.1 | A-122847.1 | usAfsuCfcAfgGfcCfguuGfgGfgCfaGfuscsc | 472 |
| AD-60992.1 | A-122819.1 | usCfscCfaCfaGfaUfgugUfcGfaCfcCfcsgsa | 473 |
| AD-60993.1 | A-122833.1 | usCfsaUfcCfaGfgCfcguUfgGfgGfcAfgsusc | 474 |
| AD-60994.1 | A-122849.1 | usCfsgCfcUfuGfuAfcccUfaGfgAfaAfusasc | 475 |
| AD-60996.1 | A-122835.1 | asGfsgAfaCfuCfuCfcagGfgCfaGfgGfgsusc | 476 |
| AD-60997.1 | A-122851.1 | usAfsgGfaAfcUfcUfccaGfgGfcAfgGfgsgsu | 477 |
| AD-60998.1 | A-122822.1 | usUfsgGfaGfgCfcAfcagUfcAfcAfgUfgscsu | 478 |
| AD-60999.1 | A-122837.1 | usCfscAfgGfcCfgUfuggGfgCfaGfuCfcsusu | 479 |
| AD-61000.1 | A-122853.1 | usCfsuUfgUfaCfcCfuagGfaAfaUfaCfcsasg | 480 |
| AD-61001.1 | A-122824.1 | usUfsgAfgGfaGfaAfucuGfgGfaGfgUfgsasa | 481 |
| AD-61002.1 | A-122839.1 | usUfsuGfuAfcCfcCfuaggAfaAfuAfcCfasgsa | 482 |

TABLE 5-continued

TMPRSS6 modified sequences

| | | | |
|---|---|---|---|
| AD-61003.1 | A-122855.1 | usCfscUfuGfuAfcCfcuaGfgAfaAfuAfcscsa | 483 |
| AD-61004.1 | A-122826.1 | usAfsuGfgCfcAfcUfcacCfcUfcGfgAfgsgsa | 484 |
| AD-61005.1 | A-122841.1 | usUfscAfuCfcAfgGfccgUfuGfgGfgCfasgsu | 485 |
| AD-61006.1 | A-122857.1 | asGfsaGfgAfaCfuCfuccAfgGfgCfaGfgsgsg | 486 |

Example 6. In Vitro Single Dose Screen

Cell Culture and Transfections for Single Dose and Dose Response Studies

Hep3B cells (ATCC, Manassas, Va.) were grown to near confluence at 37° C. in an atmosphere of 5% $CO_2$ in DMEM (ATCC) supplemented with 10% FBS, streptomycin, and glutamine (ATCC) before being released from the plate by trypsinization. Transfection was carried out by adding 14.8 µl of Opti-MEM plus 0.2 µl of Lipofectamine RNAiMax per well (Invitrogen, Carlsbad Calif. cat #13778-150) to 5 µl of siRNA duplexes per well into a 96-well plate and incubated at room temperature for 15 minutes. 80 µl of complete growth media without antibiotic containing ~$2 \times 10^4$ Hep3B cells were then added to the siRNA mixture. Cells were incubated for 24 hours prior to RNA purification. Experiments were performed at 10 nM and 0.1 nM final duplex concentration.

Total RNA Isolation Using DYNABEADS mRNA Isolation Kit (Invitrogen, Part #: 610-12)

Cells were harvested and lysed in 150 µl of Lysis/Binding Buffer then mixed for 5 minutes at 850 rpm using an Eppendorf Thermomixer (the mixing speed was the same throughout the process). Ten microliters of magnetic beads and 80 µl Lysis/Binding Buffer mixture were added to a round bottom plate and mixed for 1 minute. Magnetic beads were captured using magnetic stand and the supernatant was removed without disturbing the beads. After removing supernatant, the lysed cells were added to the remaining beads and mixed for 5 minutes. After removing supernatant, magnetic beads were washed 2 times with 150 µl Wash Buffer A and mixed for 1 minute. Beads were capture again and supernatant removed. Beads were then washed with 150 µl Wash Buffer B, captured and supernatant was removed. Beads were next washed with 150 µl Elution Buffer, captured and supernatant removed. Beads were allowed to dry for 2 minutes. After drying, 50 µl of Elution Buffer was added and mixed for 5 minutes at 70° C. Beads were captured on magnet for 5 minutes. 40 µl of supernatant was removed and added to another 96 well plate.

cDNA Synthesis Using ABI High Capacity cDNA Reverse Transcription Kit (*Applied Biosystems*, Foster City, Calif., Cat #4368813)

A master mix of 2 µl 10× Buffer, 0.8 µl 25× dNTPs, 2 µl Random primers, 1 µl Reverse Transcriptase, 1 µl RNase inhibitor and 3.2 µl of $H_2O$ per reaction were added into 10 µl total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.

Real Time PCR

2 µl of cDNA were added to a master mix containing 0.5 µl GAPDH TaqMan Probe (*Applied Biosystems* Cat #4326317E), 0.5 µl TMPRSS6 TaqMan probe (*Applied Biosystems* cat # Hs00542184_m1) and 5 µl Lightcycler 480 probe master mix (Roche Cat #04887301001) per well in a 384 well 50 plates (Roche cat #04887301001). Real time PCR was done in an Roche Lightcycler Real Time PCR system (Roche) using the ΔΔCt(RQ) assay. Each duplex was tested in two independent transfections and each transfection was assayed in duplicate, unless otherwise noted in the summary tables.

To calculate relative fold change, real time data were analyzed using the ΔΔCt method and normalized to assays performed with cells transfected with 10 nM AD-1955, or mock transfected cells.

Data are expressed as a fraction of TMPRSS6 message remaining in cells transfected with siRNAs targeting TMPRSS6, relative to naïve cells. All siRNAs were transfected at least two times and qPCR reactions were performed in duplicate. Data are show in Table 6.

TABLE 6

TMPRSS6 single dose screen.

| Duplex ID | Avg 10 nM | Avg 0.1 nM | SD 10 nM | SD 0.1 nM |
|---|---|---|---|---|
| AD-46273 | 76.5 | 112.1 | 14.3 | 18.6 |
| AD-59743 | 61.4 | 108.2 | 8.7 | 4.4 |
| AD-60939 | 38.0 | 85.7 | 19.3 | 25.2 |
| AD-60940 | 24.2 | 22.6 | 10.1 | 9.7 |
| AD-60941 | 48.5 | 84.7 | 11.7 | 29.7 |
| AD-60942 | 102.9 | 111.2 | 4.3 | 44.8 |
| AD-60943 | 86.2 | 96.5 | 2.3 | 28.8 |
| AD-60944 | 24.6 | 78.5 | 1.1 | 36.5 |
| AD-60945 | 65.8 | 140.9 | 0.5 | 59.2 |
| AD-60946 | 50.3 | 105.9 | 4.1 | 31.2 |
| AD-60947 | 79.1 | 147.2 | 12.3 | 51.2 |
| AD-60948 | 81.0 | 113.9 | 0.6 | 32.7 |
| AD-60949 | 111.3 | 96.2 | 8.2 | 28.1 |
| AD-60950 | 53.8 | 93.2 | 7.6 | 42.3 |
| AD-60951 | 74.1 | 121.6 | 6.4 | 56.2 |
| AD-60952 | 47.6 | 118.3 | 8.1 | 52.4 |
| AD-60953 | 22.0 | 56.7 | 8.3 | 18.0 |
| AD-60954 | 23.3 | 55.8 | 5.3 | 31.7 |
| AD-60955 | 110.8 | 117.5 | 1.6 | 38.7 |
| AD-60956 | 15.8 | 29.6 | 1.7 | 10.2 |
| AD-60957 | 22.3 | 58.3 | 1.5 | 6.1 |
| AD-60958 | 106.4 | 136.0 | 24.1 | 61.7 |
| AD-60959 | 79.6 | 123.3 | 0.6 | 49.9 |
| AD-60960 | 17.4 | 49.4 | 8.6 | 10.2 |
| AD-60961 | 107.7 | 129.0 | 6.6 | 50.5 |
| AD-60962 | 90.2 | 113.3 | 8.0 | 67.2 |
| AD-60963 | 117.4 | 138.1 | 2.6 | 16.8 |
| AD-60964 | 80.7 | 123.2 | 24.2 | 18.9 |
| AD-60965 | 30.1 | 80.2 | 9.0 | 20.8 |
| AD-60966 | 54.1 | 133.6 | 4.6 | 44.0 |
| AD-60967 | 122.2 | 147.4 | 11.7 | 42.0 |
| AD-60968 | 86.9 | 142.0 | 39.9 | 49.7 |
| AD-60969 | 106.2 | 116.3 | 16.6 | 39.1 |
| AD-60970 | 54.6 | 112.6 | 7.3 | 11.8 |
| AD-60971 | 50.5 | 118.8 | 6.9 | 47.0 |
| AD-60972 | 55.6 | 94.2 | 6.5 | 3.4 |
| AD-60973 | 126.1 | 133.6 | 8.0 | 36.8 |
| AD-60974 | 82.6 | 115.0 | 8.7 | 43.7 |
| AD-60975 | 88.2 | 114.3 | 13.6 | 43.9 |
| AD-60976 | 46.3 | 71.0 | 11.6 | 30.2 |

TABLE 6-continued

TMPRSS6 single dose screen.

| Duplex ID | Avg 10 nM | Avg 0.1 nM | SD 10 nM | SD 0.1 nM |
|---|---|---|---|---|
| AD-60977 | 13.5 | 26.4 | 3.4 | 9.2 |
| AD-60978 | 72.7 | 92.9 | 6.4 | 31.7 |
| AD-60979 | 103.8 | 97.0 | 13.7 | 29.2 |
| AD-60980 | 28.4 | 58.0 | 12.3 | 21.1 |
| AD-60981 | 56.0 | 80.6 | 18.3 | 4.5 |
| AD-60982 | 102.4 | 137.4 | 15.2 | 16.4 |
| AD-60983 | 60.8 | 87.1 | 10.1 | 20.3 |
| AD-60984 | 53.6 | 116.7 | 1.2 | 47.8 |
| AD-60985 | 72.6 | 99.2 | 0.7 | 21.7 |
| AD-60986 | 90.1 | 96.4 | 6.6 | 29.5 |
| AD-60987 | 83.1 | 90.7 | 1.6 | 13.7 |
| AD-60988 | 69.4 | 102.3 | 2.4 | 55.4 |
| AD-60989 | 112.4 | 105.7 | 0.6 | 14.7 |
| AD-60990 | 90.4 | 93.4 | 6.2 | 4.1 |
| AD-60991 | 97.6 | 95.6 | 15.5 | 23.4 |
| AD-60992 | 104.0 | 131.4 | 6.9 | 33.7 |
| AD-60993 | 118.6 | 129.2 | 10.5 | 30.1 |
| AD-60994 | 25.9 | 57.2 | 6.8 | 0.3 |
| AD-60996 | 77.3 | 94.2 | 7.8 | 12.6 |
| AD-60997 | 60.1 | 80.9 | 18.8 | 7.5 |
| AD-60998 | 32.6 | 61.4 | 5.7 | 24.6 |
| AD-60999 | 133.6 | 110.9 | 39.7 | 15.4 |
| AD-61000 | 55.8 | 117.6 | 14.2 | 24.9 |
| AD-61001 | 57.9 | 85.2 | 8.1 | 42.0 |
| AD-61002 | 15.4 | 31.4 | 1.5 | 10.1 |
| AD-61003 | 82.3 | 98.1 | 4.0 | 11.8 |
| AD-61004 | 106.4 | 97.7 | 38.5 | 18.8 |
| AD-61005 | 138.0 | 141.2 | 65.7 | 20.0 |
| AD-61006 | 31.7 | 70.9 | 7.8 | 6.6 |

Example 7. In Vivo Effect of Single Dose Administration of TMPRSS6 iRNA Agent

Female C57BL/6 mice were administered a single subcutaneous injection of AD-60940 at a dose of 0.3 mg/kg, 1.0 mg/kg or 3.0 mg/kg, or PBS alone as a control. Three mice were evaluated per dose for hepatic TMPRSS6 mRNA, hepatic hepcidin mRNA, serum hepcidin, total serum iron, and percent transferrin saturation at various time points. Mice receiving 1.0 mg/kg or 3.0 mg/kg of AD-60940 or PBS were evaluated at day 0 (pre-treatment) and 7, 11, 14 and 21 days after treatment. Mice receiving 0.3 mg/kg AD-60940 were evaluated at day 0 (pre-treatment) and at 7 and 11 days after treatment. Hepatic TMPRSS6 mRNA and hepatic hepcidin mRNA levels were determined by qPCR, normalized to GAPDH mRNA levels and expressed relative to the mRNA levels in mice administered PBS alone. Serum hepcidin was measured by ELISA (Intrinsic Life Sciences). Total serum iron and percent transferrin saturation (% TfSat) were measured using an Olympus AU400 Serum Chemistry Analyzer. Each data point represents the mean value from three mice. The standard deviation of the mean is represented by error bars.

Figure 3A:
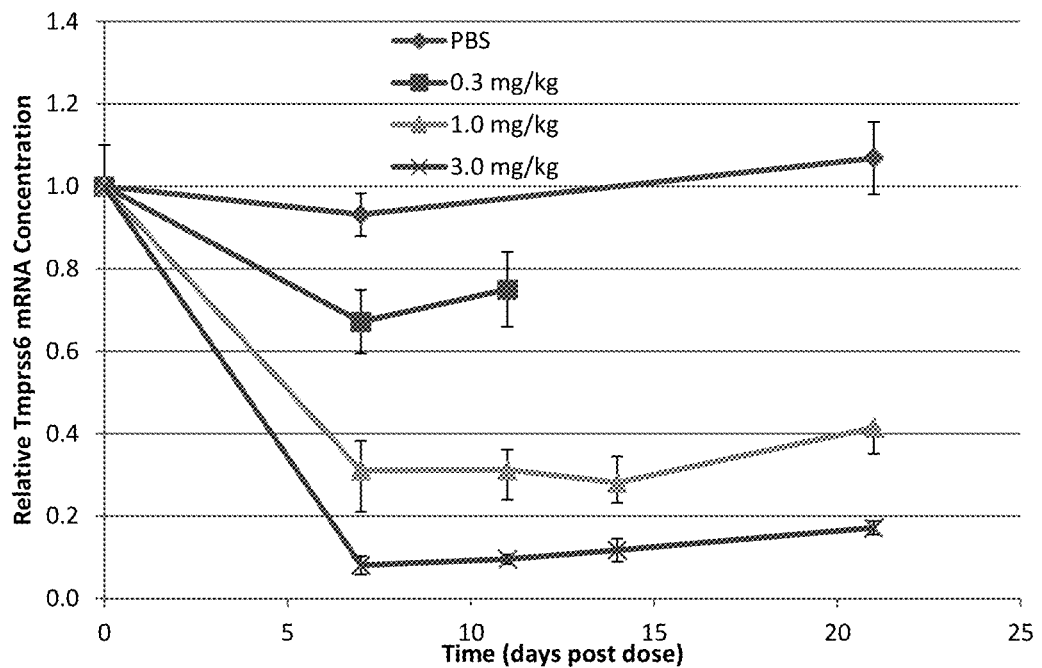
FIG. 3A is a graph showing the levels of hepatic TMPRSS6 mRNA in C57BL/6 mice at various time points following a single subcutaneous injection of AD-60940 at a dose of 0.3 mg/kg, 1.0 mg/kg or 3.0 mg/kg, or PBS alone (control). Each data point represents the mean value from three mice. The standard deviation of the mean is represented by error bars.
Figure 3B:
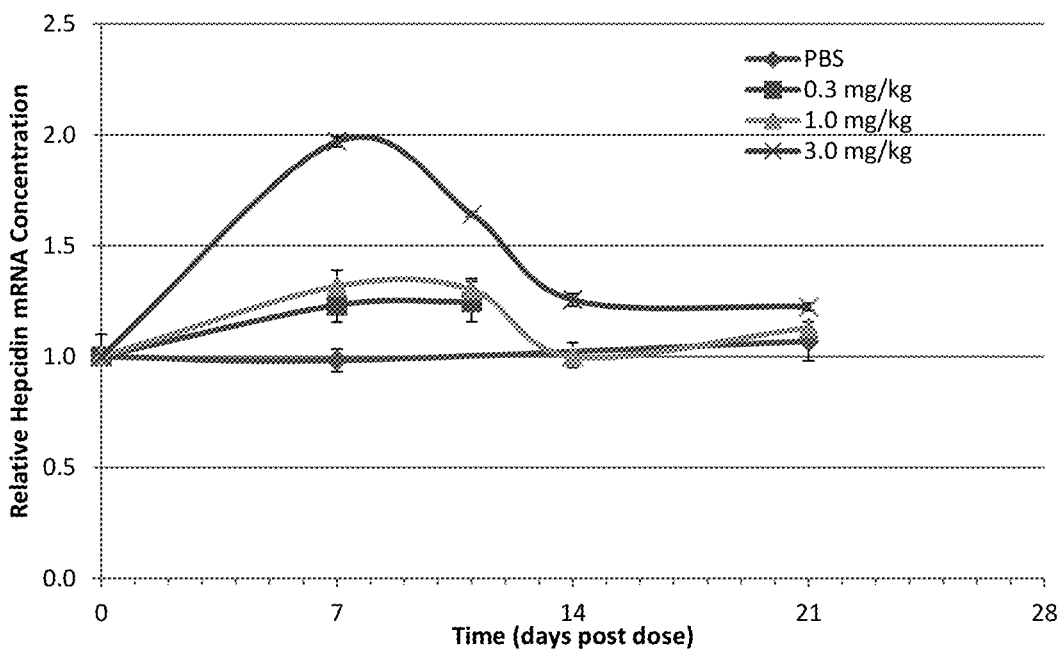
FIG. 3B is a graph showing the levels of hepatic hepcidin mRNA in C57BL/6 mice at various time points following a single subcutaneous injection of AD-60940 at a dose of 0.3 mg/kg, 1.0 mg/kg or 3.0 mg/kg, or PBS alone (control). Each data point represents the mean value from three mice. The standard deviation of the mean is represented by error bars.
Figure 3C:
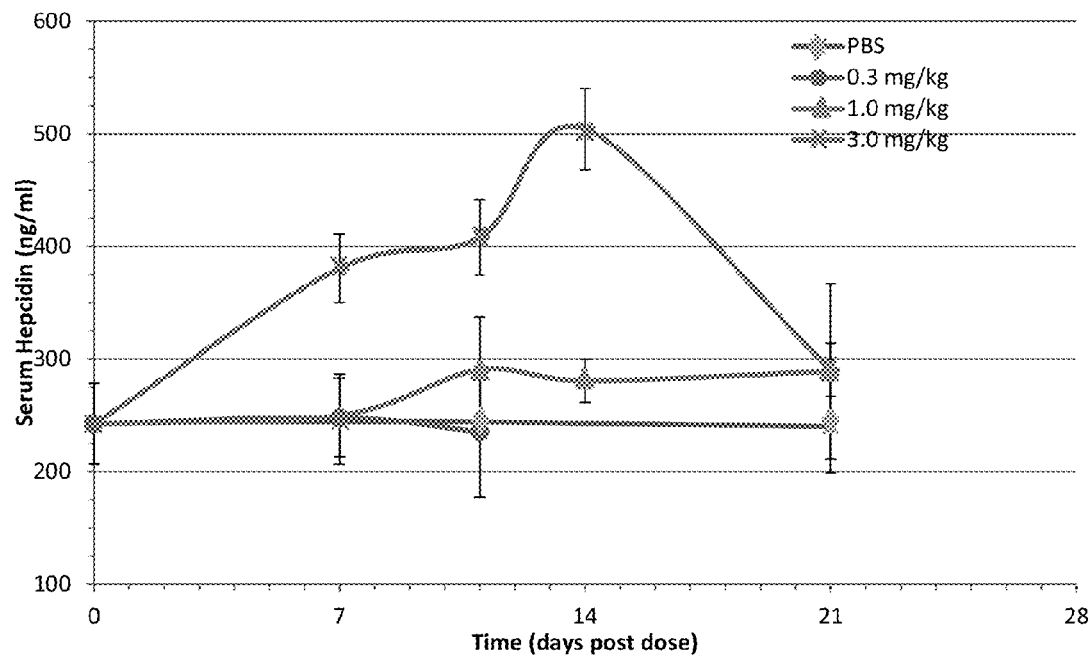
FIG. 3C is a graph showing the levels of serum hepcidin in C57BL/6 mice at various time points following a single subcutaneous injection of AD-60940 at a dose of 0.3 mg/kg, 1.0 mg/kg or 3.0 mg/kg, or PBS alone (control). Each data point represents the mean value from three mice. The standard deviation of the mean is represented by error bars.
Figure 3D:
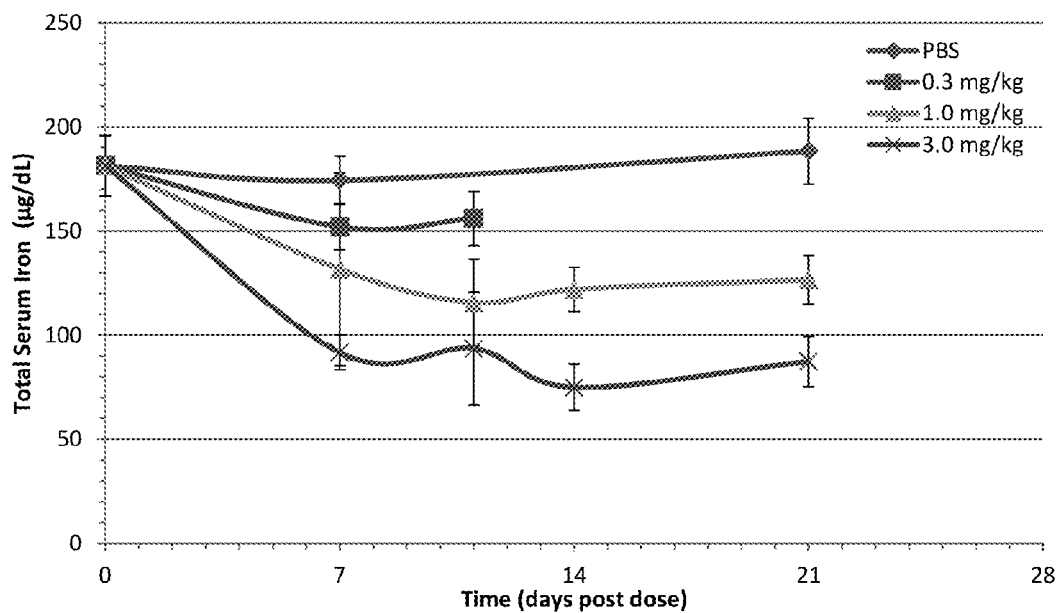
FIG. 3D is a graph showing the levels of total serum iron in C57BL/6 mice at various time points following a single subcutaneous injection of AD-60940 at a dose of 0.3 mg/kg, 1.0 mg/kg or 3.0 mg/kg, or PBS alone (control). Each data point represents the mean value from three mice. The standard deviation of the mean is represented by error bars.
Figure 3E:
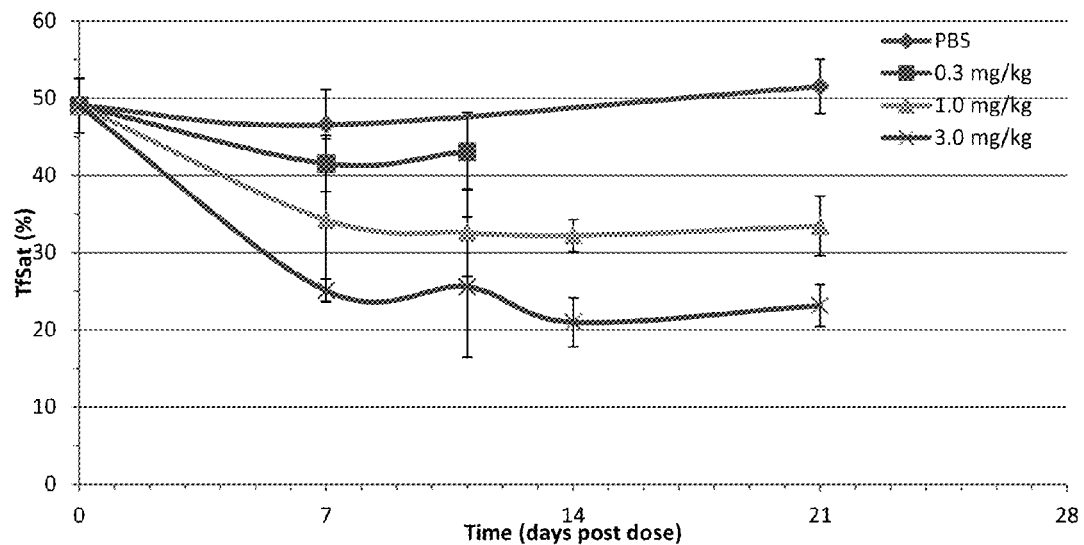
FIG. 3E is a graph showing the percent transferrin saturation (FIG. 3E) in C57BL/6 mice at various time points following a single subcutaneous injection of AD-60940 at a dose of 0.3 mg/kg, 1.0 mg/kg or 3.0 mg/kg, or PBS alone (control). Each data point represents the mean value from three mice. The standard deviation of the mean is represented by error bars.
Figure 3F:
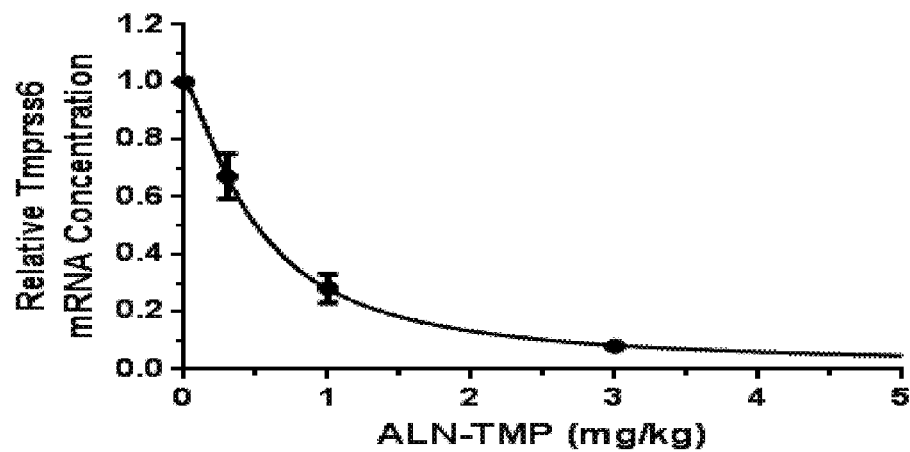
FIG. 3F is a graph demonstrating the relative hepatic TMPRSS6 mRNA concentration as a function of AD-60940 dose at 11 days following administration. Each data point represents the maximum suppression of TMPRSS6 mRNA concentration observed at each dose level. The data were fit to the Hill equation.

Single dose administration of AD-60940 resulted in robust and durable suppression of hepatic TMPRSS6 mRNA relative to the control. TMPRSS6 mRNA concentration was suppressed by greater than 90% for up to three weeks following administration of the 3.0 mg/kg dose (FIG. 3A). As a result of the suppression of hepatic TMPRSS6 mRNA concentration, hepcidin mRNA levels, increased two-fold relative to the control (FIG. 3B), and serum hepcidin concentration increased greater than 2-fold relative to the control (FIG. 3C). In addition, total serum iron (FIG. 3D) decreased and percent transferrin saturation decreased by greater than 50% relative to the control (FIG. 3E). The decreases in total serum iron and percent transferrin saturation were durable for up to three weeks following administration of AD-60940. FIG. 3F demonstrates the relative hepatic TMPRSS6 mRNA concentration as a function of AD-60940 dose at 11 days following administration. Each data point represents the maximum suppression of TMPRSS6 mRNA concentration observed at each dose level. The data were fit to the Hill equation.

The degree to which AD-60940 modulates hepcidin and serum iron mobilization is nearly identical to that observed in the previous Hbb$^{th3/+}$ mouse studies (Schmidt et al., *Blood* (2013), 121(7), 1200-1208) and indicates that AD-60940 is a potent RNAi therapeutic for producing disease modifying effects in β-Thalassemia.

Example 8. In Vivo Effect of Multi-Dose Administration of TMPRSS6 iRNA Agent

Figure 4A:
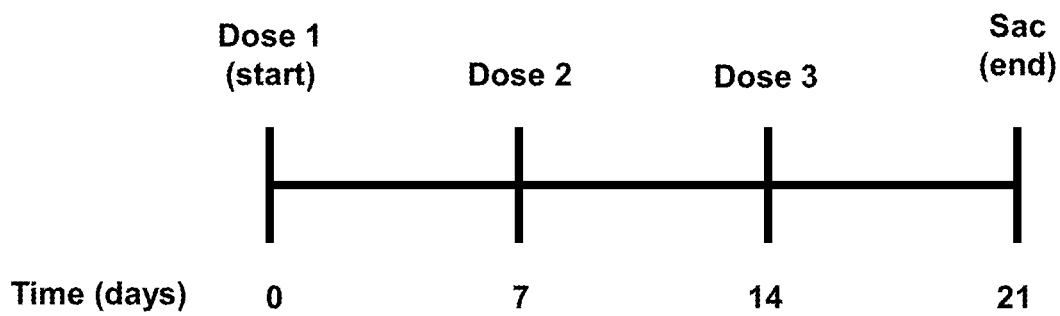
FIG. 4A is a schematic depicting the administration regimen of one dose per week for three weeks followed by sacrifice of the mice at day 21.

Female C57BL/6 mice were administered a subcutaneous injection of AD-60940 at a dose of 0.3 mg/kg, 1.0 mg/kg, or PBS alone (as a control) once per week for three weeks then sacrificed 7 days after the final dose (FIG. 4A). Three mice per dose were evaluated for hepatic TMPRSS6 mRNA, hepatic hepcidin mRNA, and percent transferrin saturation. Hepatic TMPRSS6 mRNA and hepatic hepcidin mRNA levels were determined by qPCR, normalized to GAPDH mRNA levels and expressed relative to the mRNA levels in mice administered PBS alone. Percent transferrin saturation (% TfSat) was measured using an Olympus AU400 Serum Chemistry Analyzer. Each data point represents the mean value from three mice. The standard deviation of the mean is represented by error bars.

Figure 4B:
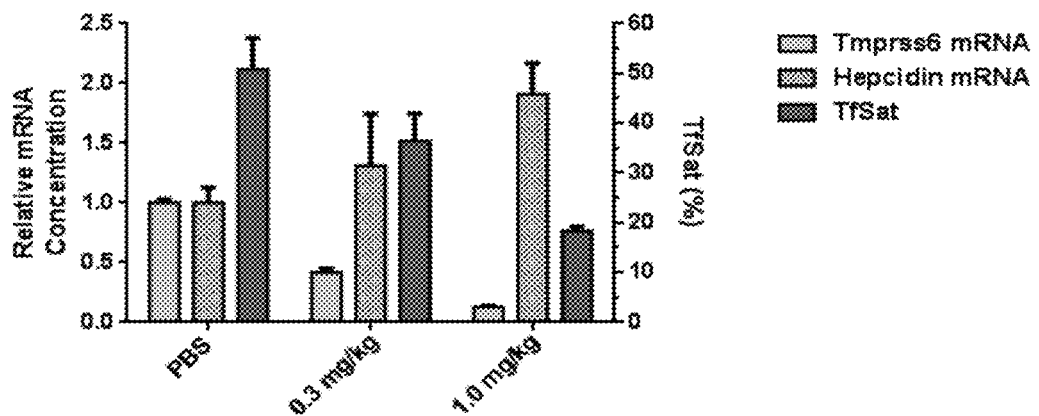
FIG. 4B is a graph showing the levels of hepatic TMPRSS6 mRNA, hepatic hepcidin mRNA, and percent transferrin saturation in C57BL/6 mice administered a subcutaneous injection of AD-60940 at a dose of 0.3 mg/kg, 1.0 mg/kg, or PBS (control) according to the regimen shown in FIG. 4A. Each bar represents the mean value from three mice. The standard deviation of the mean is represented by error bars.
Figure 4C:
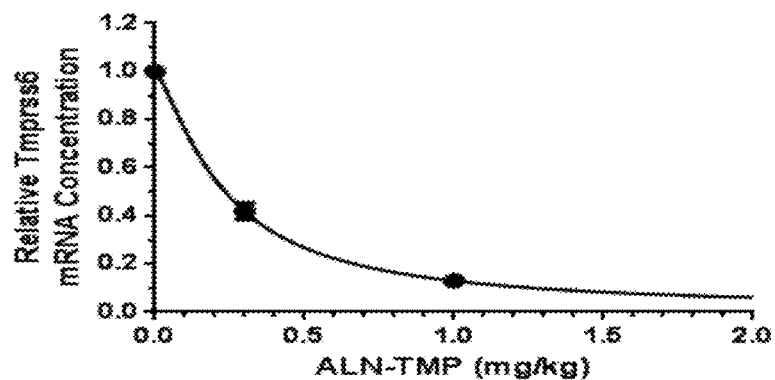
FIG. 4C demonstrates the relative hepatic TMPRSS6 mRNA concentration as a function of AD-60940 dose. The data were fit to the Hill equation.

Multi-dose administration of 1.0 mg/kg AD-60940 resulted in greater than 90% suppression of TMPRSS6 mRNA concentration (FIG. 4B). Hepcidin mRNA concentration increased two-fold and percent transferrin saturation decreased by greater than 50% relative to the control (FIG. 4B). FIG. 4C demonstrates the relative hepatic TMPRSS6 mRNA concentration as a function of AD-60940 dose. The data were fit to the Hill equation. These data indicate that the multi-dose ED80 is less than 1.0 mg/kg.

This study demonstrates that AD-60940 exhibits robust and durable suppression of TMPRSS6, resulting in hepcidin induction and systemic iron restriction and indicates that AD-60940 is a potent RNAi therapeutic for producing disease modifying effects in β-Thalassemia.

Figure 5A:
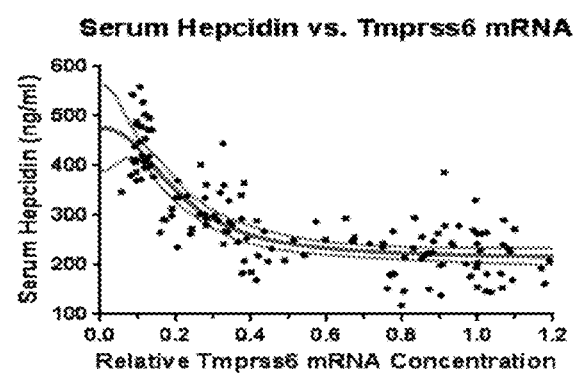
FIG. 5A is a graph showing the relationship between serum hepcidin concentration and relative TMPRSS6 mRNA levels.
Figure 5B:
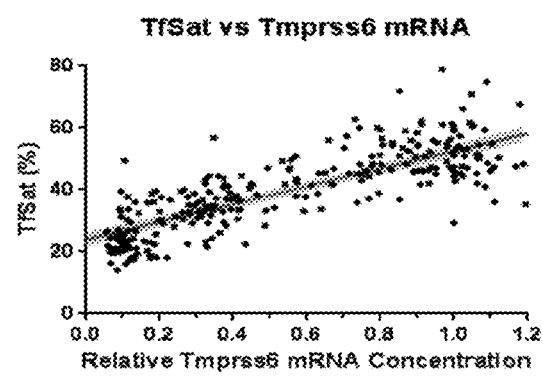
FIG. 5B is a graph showing the relationship between percent transferrin saturation and relative TMPRSS6 mRNA levels.
Figure 5C:
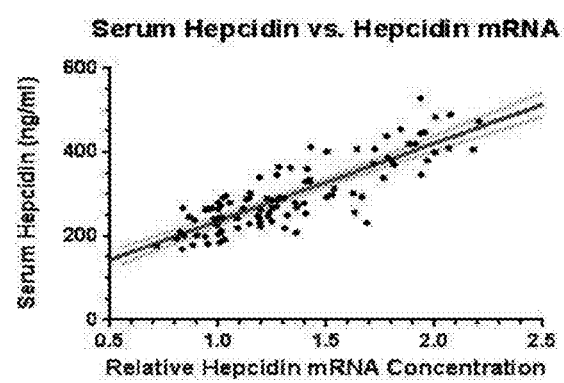
FIG. 5C is a graph showing the relationship between serum hepcidin concentration and relative hepcidin mRNA levels.
Figure 5D:
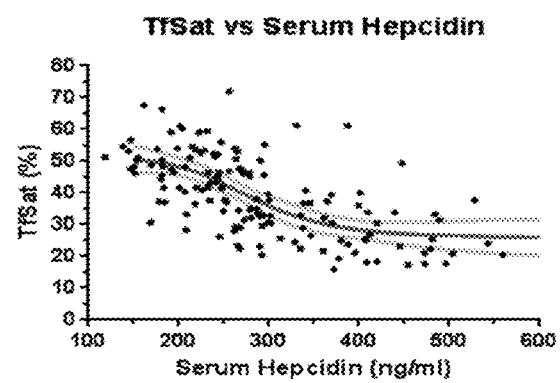
FIG. 5D is a graph showing the relationship between percent transferrin saturation and serum hepcidin concentration.

Example 9. Relationship Between Liver TMPRSS6 mRNA Levels and Serum Hepcidin Concentration and Percent Transferrin Saturation Data generated using AD-59743, AD-61002, AD-60940, and other TMPRSS6 iRNA agents were further analyzed to evaluate the relationship between liver TMPRSS6 mRNA levels and serum hepcidin levels and percent transferrin saturation. Serum hepcidin concentration demonstrated a non-linear relationship to TMPRSS6 mRNA levels using the Hill equation (FIG. 5A). The percent transferrin saturation demonstrated a linear relationship to TMPRSS6 mRNA levels when fit to a simple linear regression equation (FIG. 5B). The linear relationship between TMPRSS6 mRNA levels and percent transferrin saturation indicate that iron restriction can be precisely and predictably modulated by AD-60940. Serum hepcidin concentration and relative hepcidin mRNA levels also demonstrated a linear relationship when fit to a simple linear regression equation (FIG. 5C). In contrast, the relationship between percent transferrin saturation and serum hepcidin concentration was non-linear and fit to the Hill equation (FIG. 5D).

Example 10. In Vivo Single Dose Screen

Figure 6:
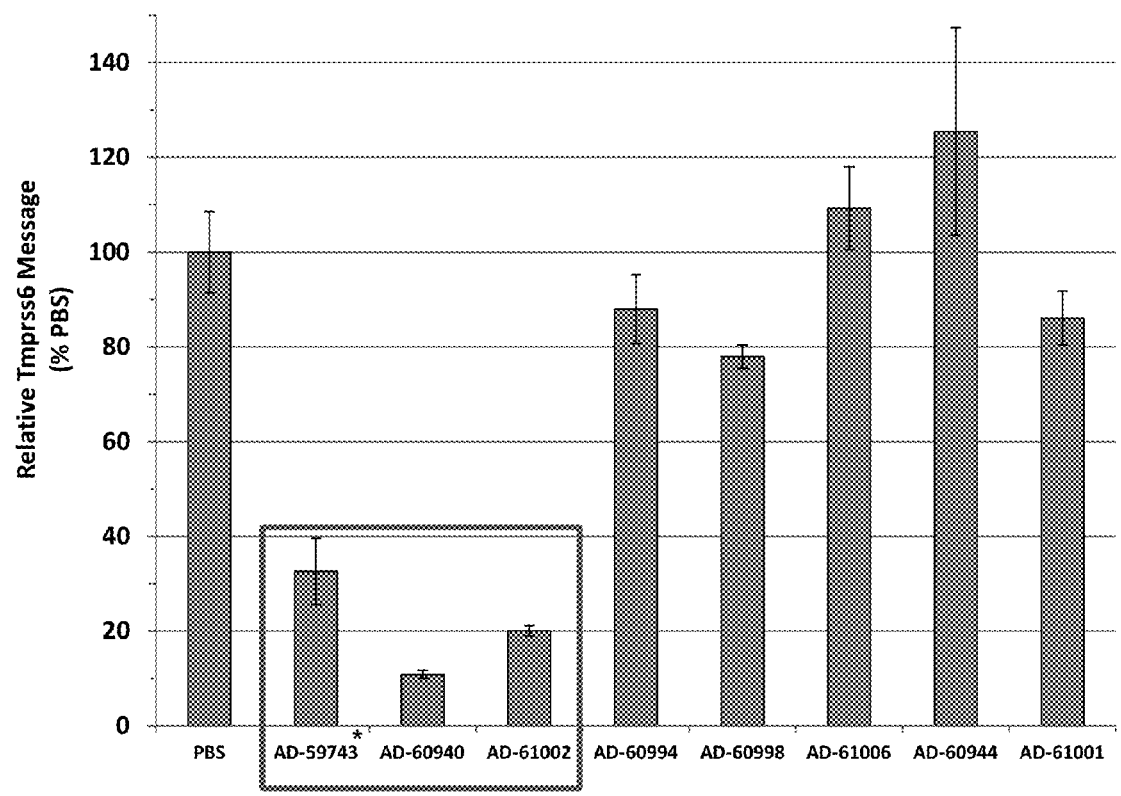
FIG. 6 is a graph showing relative levels of TMPRSS6 mRNA in the liver of C57BL/6 mice following administration of a single subcutaneous dose of 3 mg/kg of the indicated iRNA agent or PBS (control). The bars represent the mean from three mice and the error bars represent the standard deviation of the mean.

TMPRSS6 siRNA duplexes as indicated in FIG. 6 were evaluated for efficacy by their ability to suppress levels of TMPRSS6 mRNA in the liver of female C57BL/6 mice following administration of the siRNA duplex. A single subcutaneous dose of 3 mg/kg of TMPRSS6 siRNA duplex was administered, and the mice were sacrificed 7 days later. The level of TMPRSS6 mRNA in the liver was measured by qPCR using the methods described above. Mice in a control group received an injection of PBS.

The levels of TMPRSS6 mRNA following administration of a TMPRSS6 siRNA duplex are shown in FIG. 6. The results demonstrate that administration of AD-60940, AD-59743 and AD-61002 resulted in substantial suppression of liver TMPRSS6 mRNA with AD60940 producing the greatest silencing. Specifically, TMPRSS6 siRNA duplex AD-60940 reduced TMPRSS6 mRNA by greater than 80% relative to the control. The data also demonstrate that treatment with AD-59743, AD-60940, AD-61002, AD-60994, AD-60998 and AD-61001 result in a decrease in the level of TMPRSS6 transcript that is maintained through day 7.

Example 11. In Vivo Multi-Dose Screen

Figure 7:
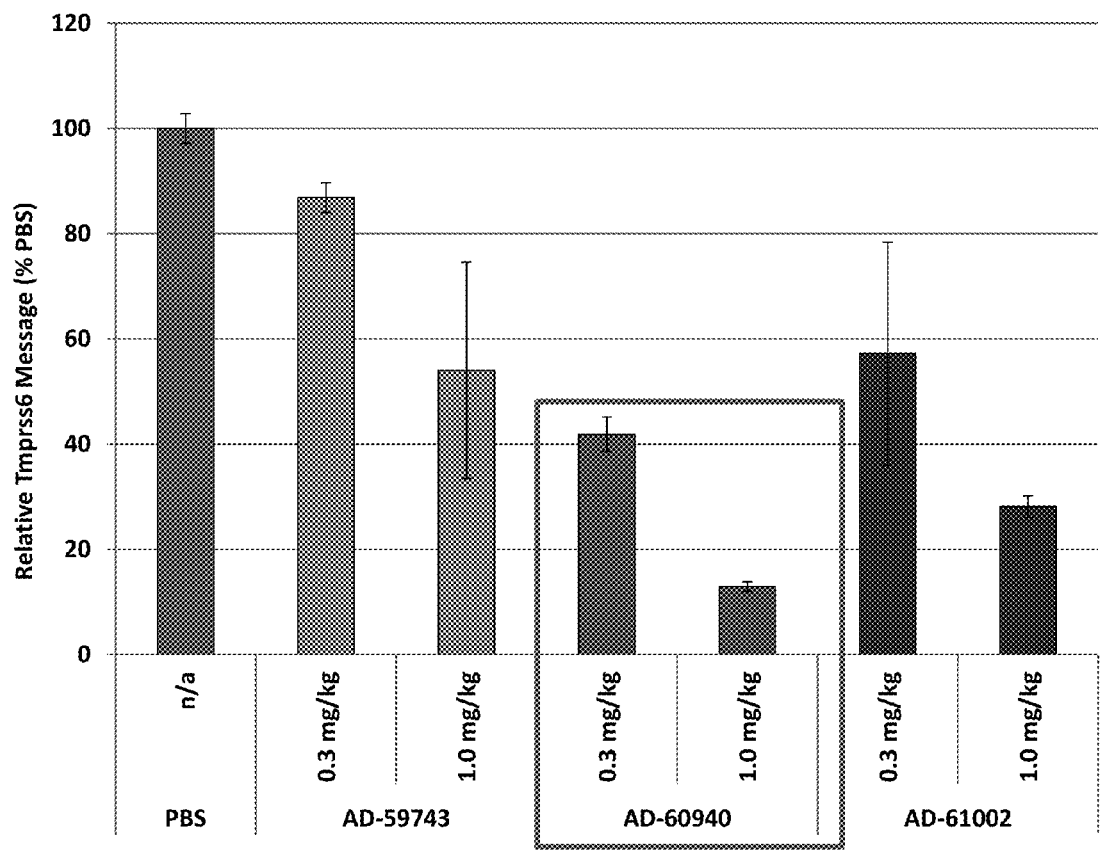
FIG. 7 is a graph showing relative levels of TMPRSS6 mRNA in the liver of C57BL/6 mice following a subcutaneous dose of 0.3 mg/kg or 1.0 mg/kg of the indicated iRNA agent, or PBS (control), once a week for three weeks. The bars represent the mean from three mice and the error bars represent the standard deviation of the mean.

TMPRSS6 siRNA duplexes as indicated in FIG. 7 were evaluated for efficacy by their ability to suppress levels of TMPRSS6 mRNA in the liver of wild-type C57BL/6 mice following administration of the siRNA duplex. A subcutaneous dose of either 0.3 mg/kg or 1.0 mg/kg of TMPRSS6 siRNA duplex was administered once a week for three weeks. The mice were sacrificed 7 days after the last dose. The level of TMPRSS6 mRNA in the liver was measured by qPCR using the methods described above. Mice in a control group received an injection of PBS.

The levels of TMPRSS6 mRNA following administration of a TMPRSS6 siRNA duplex are shown in FIG. 7. The results demonstrate that the 1.0 mg/kg dosing regimen of TMPRSS6 siRNA duplex AD-60940 reduces TMPRSS6 mRNA by greater than 80% relative to the control.

Example 12. Optimization of AD-60940

Based on the observation that administration of AD-60940 durably reduced TMPRSS6 mRNA by greater than 80% relative to the control, additional siRNAs based on the parent sequence of AD-60940 with a variety of chemical modifications were evaluated for efficacy in single dose screens at 10 nM and 0.1 nM by transfection in Hep3B cells. The sequences of the sense and antisense strands of these agents are shown in Table 8 and the results of this screen are shown in Table 9. The data in Table 9 are expressed as the average fraction message remaining relative to control.

In addition, a subset of siRNA described in Tables 4 and 5, above, were modified to replace a 2'F with a 2'OMe modification at the 5'-end of the sense strand and to add a 5'-phosphate on the antisense strand. These siRNA agents were also evaluated for in vitro efficacy in single dose screens at 10 nM and 0.1 nM by transfection in Hep3B cells. The sequences of the sense and antisense strands of these agents are shown in Table 10 and the results of this screen are shown in Table 11. The data in Table 11 are expressed as the average fraction message remaining relative to control.

TABLE 8

TMPRSS6 Modified Sequences

| Duplex ID | Sense ID | Sense Sequence | SEQ ID NO: |
|---|---|---|---|
| AD-63214 | A-126586.2 | Y44CfsusGfgUfaUfuUfCfCfuAfgGfgUfaCfaAfL96 | 487 |
| AD-63240 | A-122745.11 | CfsusGfgUfaUfuUfCfCfuAfgGfgUfaCfaAfL96 | 488 |
| AD-63209 | A-126594.1 | csusgguaUfuUfCfCfuaggGfdTacaaL96 | 489 |
| AD-63208 | A-122745.6 | CfsusGfgUfaUfuUfCfCfuAfgGfgUfaCfaAfL96 | 490 |
| AD-63202 | A-126586.1 | Y44CfsusGfgUfaUfuUfCfCfuAfgGfgUfaCfaAfL96 | 491 |
| AD-63216 | A-122745.7 | CfsusGfgUfaUfuUfCfCfuAfgGfgUfaCfaAfL96 | 492 |
| AD-63219 | A-126617.1 | gsgsUfaUfuUfCfCfuAfgGfgUfaCfaAfL96 | 493 |
| AD-63228 | A-122745.9 | CfsusGfgUfaUfuUfCfCfuAfgGfgUfaCfaAfL96 | 494 |
| AD-63205 | A-122745.13 | CfsusGfgUfaUfuUfCfCfuAfgGfgUfaCfaAfL96 | 495 |
| AD-63241 | A-126589.2 | csusgguaUfuUfCfCfuaggGfuacaaL96 | 496 |
| AD-63243 | A-126621.3 | csusGfguaUfuUfCfCfuAfgGfguAfcaaL96 | 497 |
| AD-63203 | A-126593.1 | csusgguaUfuUfCfCfuaggGfuadCaaL96 | 498 |
| AD-63223 | A-122745.16 | CfsusGfgUfaUfuUfCfCfuAfgGfgUfaCfaAfL96 | 499 |
| AD-63231 | A-126621.1 | csusGfguaUfuUfCfCfuAfgGfguAfcaaL96 | 500 |
| AD-63199 | A-122745.12 | CfsusGfgUfaUfuUfCfCfuAfgGfgUfaCfaAfL96 | 501 |
| AD-63217 | A-122745.15 | CfsusGfgUfaUfuUfCfCfuAfgGfgUfaCfaAfL96 | 502 |

TABLE 8-continued

| | | TMPRSS6 Modified Sequences | |
|---|---|---|---|
| AD-63229 | A-122745.17 | CfsusGfgUfaUfuUfCfCfuAfgGfgUfaCfaAfL96 | 503 |
| AD-63255 | A-126621.5 | csusGfguaUfuUfCfCfuAfgGfguAfcaaL96 | 504 |
| AD-63226 | A-126589.1 | csusgguaUfuUfCfCfuaggGfuacaaL96 | 505 |
| AD-63211 | A-122745.14 | CfsusGfgUfaUfuUfCfCfuAfgGfgUfaCfaAfL96 | 506 |
| AD-63273 | A-126621.8 | csusGfguaUfuUfCfCfuAfgGfguAfcaaL96 | 507 |
| AD-60940 | A-122745.1 | CfsusGfgUfaUfuUfCfCfuAfgGfgUfaCfaAfL96 | 508 |
| AD-63249 | A-126621.4 | csusGfguaUfuUfCfCfuAfgGfguAfcaaL96 | 509 |
| AD-63256 | A-122745.19 | CfsusGfgUfaUfuUfCfCfuAfgGfgUfaCfaAfL96 | 510 |
| AD-63280 | A-126639.1 | csusGfgUfaUfuUfCfCfuAfgGfgUfaCfaAfL96 | 511 |
| AD-63237 | A-126621.2 | csusGfguaUfuUfCfCfuAfgGfguAfcaaL96 | 512 |
| AD-63285 | A-126621.10 | csusGfguaUfuUfCfCfuAfgGfguAfcaaL96 | 513 |
| AD-63215 | A-126595.1 | csusgguaUfuUfCfdCuaggGfuacaaL96 | 514 |
| AD-63222 | A-122745.8 | CfsusGfgUfaUfuUfCfCfuAfgGfgUfaCfaAfL96 | 515 |
| AD-63232 | A-126590.1 | csusgguAfuuUfcCfUfagGfGfuacaaL96 | 516 |
| AD-63218 | A-126594.2 | csusgguaUfuUfCfCfuaggGfdTacaaL96 | 517 |
| AD-63261 | A-126621.6 | csusGfguaUfuUfCfCfuAfgGfguAfcaaL96 | 518 |
| AD-63267 | A-126621.7 | csusGfguaUfuUfCfCfuAfgGfguAfcaaL96 | 519 |
| AD-63234 | A-122745.10 | CfsusGfgUfaUfuUfCfCfuAfgGfgUfaCfaAfL96 | 520 |
| AD-63250 | A-122745.18 | CfsusGfgUfaUfuUfCfCfuAfgGfgUfaCfaAfL96 | 521 |
| AD-63212 | A-126593.2 | csusgguaUfuUfCfCfuaggGfuadCaaL96 | 522 |
| AD-63210 | A-126602.1 | csusgguauuucdCuaggg(Tgn)acaaL96 | 523 |
| AD-63244 | A-126621.11 | csusGfguaUfuUfCfCfuAfgGfguAfcaaL96 | 524 |
| AD-63235 | A-126588.2 | csusgguAfuuuCfCfuAfggGfuacaaL96 | 525 |
| AD-63279 | A-126621.9 | csusGfguaUfuUfCfCfuAfgGfguAfcaaL96 | 526 |
| AD-63227 | A-126597.1 | csusgguAfuuucCfuagggdTacaaL96 | 527 |
| AD-63220 | A-126588.1 | csusgguAfuuuCfCfuAfggGfuacaaL96 | 528 |
| AD-63238 | A-126591.1 | csusgguAfuuucCfuagggguacaaL96 | 529 |
| AD-63242 | A-126598.2 | csusgguAfuuucCfdTagggguacaaL96 | 530 |
| AD-63239 | A-126599.1 | csusgguauuucCfdTagggguacaaL96 | 531 |
| AD-63233 | A-126598.1 | csusgguAfuuucCfdTagggguacaaL96 | 532 |
| AD-63268 | A-126636.1 | CfsusGfgUfaUfuUfCfcuAfgGfgUfaCfaAfL96 | 533 |
| AD-63221 | A-126596.1 | csusgguAfuuucCfuaggguadCaaL96 | 534 |
| AD-63236 | A-126597.2 | csusgguAfuuucCfuagggdTacaaL96 | 535 |
| AD-63197 | A-126592.1 | csusgguauuucCfUfagggguacaaL96 | 536 |
| AD-63224 | A-126595.2 | csusgguaUfuUfCfdCuaggGfuacaaL96 | 537 |
| AD-63200 | A-126590.2 | csusgguAfuuUfcCfUfagGfGfuacaaL96 | 538 |
| AD-63262 | A-122745.20 | CfsusGfgUfaUfuUfCfCfuAfgGfgUfaCfaAfL96 | 539 |
| AD-63204 | A-126601.1 | csusgguauuucdCuaggguacaaL96 | 540 |
| AD-63230 | A-126596.2 | csusgguAfuuucCfuaggguadCaaL96 | 541 |

TABLE 8-continued

TMPRSS6 Modified Sequences

| | | | |
|---|---|---|---|
| AD-63198 | A-126600.1 | csusgguauuucdCdTagggguacaaL96 | 542 |
| AD-63206 | A-126591.2 | csusgguAfuuucCfuagggguacaaL96 | 543 |

| Duplex ID | Antisense ID | Antisense Sequence | SEQ ID NO: |
|---|---|---|---|
| AD-63214 | A-126587.2 | PusUfsgUfaCfcCfuAfggaAfaUfaCfcAfgsasg | 544 |
| AD-63240 | A-126607.1 | usUfsguaCfcCfuAfggaAfaUfaccagsasg | 545 |
| AD-63209 | A-122746.13 | usUfsgUfaCfcCfuAfggaAfaUfaCfcAfgsasg | 546 |
| AD-63208 | A-126587.1 | PusUfsgUfaCfcCfuAfggaAfaUfaCfcAfgsasg | 547 |
| AD-63202 | A-122746.6 | usUfsgUfaCfcCfuAfggaAfaUfaCfcAfgsasg | 548 |
| AD-63216 | A-126603.1 | usUfsgUfaCfccuAfggaAfaUfaCfcAfgsasg | 549 |
| AD-63219 | A-126618.1 | PusUfsgUfaCfcCfuAfggaAfaUfaCfcsasg | 550 |
| AD-63228 | A-126605.1 | usUfsgUfaCfcCfuAfggaAfaUfaccagsasg | 551 |
| AD-63205 | A-126609.1 | usUfsgUfaccCfuaggaAfaUfaccAfgsasg | 552 |
| AD-63241 | A-126611.3 | usUfsguaCfccUfaggaAfaUfaccagsasg | 553 |
| AD-63243 | A-126624.1 | usUfsGfuaCfcCfuAfggaAfAfuaCfcAfgsasg | 554 |
| AD-63203 | A-122746.12 | usUfsgUfaCfcCfuAfggaAfaUfaCfcAfgsasg | 555 |
| AD-63223 | A-126612.1 | usUfsguaCfccuaggaAfaUfaccagsasg | 556 |
| AD-63231 | A-126622.1 | usUfsGfuaCfcCfuAfggaAfaUfaCfcAfgsasg | 557 |
| AD-63199 | A-126608.1 | usUfsgUfaccCfuAfggaAfaUfaccAfgsasg | 558 |
| AD-63217 | A-126611.1 | usUfsguaCfccUfaggaAfaUfaccagsasg | 559 |
| AD-63229 | A-126613.1 | usUfsguaCfcCfUfaggaAfaUfaccagsasg | 560 |
| AD-63255 | A-126626.1 | usUfsGfuAfCfcCfuAfggaAfAfuaCfcAfgsasg | 561 |
| AD-63226 | A-122746.8 | usUfsgUfaCfcCfuAfggaAfaUfaCfcAfgsasg | 562 |
| AD-63211 | A-126610.1 | usUfsgUfaccCfuAfggaAfaUfaccAfgsasg | 563 |
| AD-63273 | A-126629.1 | usUfsGfuaCfcCfuAfggaAfAfuAfccagsasg | 564 |
| AD-60940 | A-122746.1 | usUfsgUfaCfcCfuAfggaAfaUfaCfcAfgsasg | 565 |
| AD-63249 | A-126625.1 | usUfsGfuAfCfcCfuAfggaAfAfuAfCfcAfgsasg | 566 |
| AD-63256 | A-126634.1 | usUfsgUfaccCfuAfggaAfaUfaCfcAfgsasg | 567 |
| AD-63280 | A-126587.3 | PusUfsgUfaCfcCfuAfggaAfaUfaCfcAfgsasg | 568 |
| AD-63237 | A-126623.1 | usUfsGfuAfCfcCfuAfggaAfaUfaCfcAfgsasg | 569 |
| AD-63285 | A-126631.1 | usUfsGfuaCfcCfuAfggaAfAfuAfccAfgsasg | 570 |
| AD-63215 | A-122746.14 | usUfsgUfaCfcCfuAfggaAfaUfaCfcAfgsasg | 571 |
| AD-63222 | A-126604.1 | usUfsguaCfcCfuAfggaAfaUfaccAfgsasg | 572 |
| AD-63232 | A-122746.9 | usUfsgUfaCfcCfuAfggaAfaUfaCfcAfgsasg | 573 |
| AD-63218 | A-126611.7 | usUfsguaCfccUfaggaAfaUfaccagsasg | 574 |
| AD-63261 | A-126627.1 | usUfsGfuaCfcCfuAfggaAfAfuAfCfcagsasg | 575 |
| AD-63267 | A-126628.1 | usUfsGfuAfCfcCfuAfggaAfAfuAfCfcagsasg | 576 |
| AD-63234 | A-126606.1 | usUfsguaCfccuAfggaAfaUfaccAfgsasg | 577 |
| AD-63250 | A-126633.1 | ususgUfaCfcCfuAfggaAfaUfaCfcAfgsasg | 578 |

TABLE 8-continued

TMPRSS6 Modified Sequences

| | | | |
|---|---|---|---|
| AD-63212 | A-126611.6 | usUfsguaCfccUfaggaAfaUfaccagsasg | 579 |
| AD-63210 | A-122746.21 | usUfsgUfaCfcCfuAfggaAfaUfaCfcAfgsasg | 580 |
| AD-63244 | A-126632.1 | usUfsGfuAfCfcCfuAfggaAfAfuAfccAfgsasg | 581 |
| AD-63235 | A-126611.2 | usUfsguaCfccUfaggaAfaUfaccagsasg | 582 |
| AD-63279 | A-126630.1 | usUfsGfuAfCfcCfuAfggaAfAfuAfccagsasg | 583 |
| AD-63227 | A-122746.16 | usUfsgUfaCfcCfuAfggaAfaUfaCfcAfgsasg | 584 |
| AD-63220 | A-122746.7 | usUfsgUfaCfcCfuAfggaAfaUfaCfcAfgsasg | 585 |
| AD-63238 | A-122746.10 | usUfsgUfaCfcCfuAfggaAfaUfaCfcAfgsasg | 586 |
| AD-63242 | A-126611.11 | usUfsguaCfccUfaggaAfaUfaccagsasg | 587 |
| AD-63239 | A-122746.18 | usUfsgUfaCfcCfuAfggaAfaUfaCfcAfgsasg | 588 |
| AD-63233 | A-122746.17 | usUfsgUfaCfcCfuAfggaAfaUfaCfcAfgsasg | 589 |
| AD-63268 | A-122746.22 | usUfsgUfaCfcCfuAfggaAfaUfaCfcAfgsasg | 590 |
| AD-63221 | A-122746.15 | usUfsgUfaCfcCfuAfggaAfaUfaCfcAfgsasg | 591 |
| AD-63236 | A-126611.10 | usUfsguaCfccUfaggaAfaUfaccagsasg | 592 |
| AD-63197 | A-122746.11 | usUfsgUfaCfcCfuAfggaAfaUfaCfcAfgsasg | 593 |
| AD-63224 | A-126611.8 | usUfsguaCfccUfaggaAfaUfaccagsasg | 594 |
| AD-63200 | A-126611.4 | usUfsguaCfccUfaggaAfaUfaccagsasg | 595 |
| AD-63262 | A-126635.1 | usUfsgUfaCfcCfuAfggaaaUfaCfcAfgsasg | 596 |
| AD-63204 | A-122746.20 | usUfsgUfaCfcCfuAfggaAfaUfaCfcAfgsasg | 597 |
| AD-63230 | A-126611.9 | usUfsguaCfccUfaggaAfaUfaccagsasg | 598 |
| AD-63198 | A-122746.19 | usUfsgUfaCfcCfuAfggaAfaUfaCfcAfgsasg | 599 |
| AD-63206 | A-126611.5 | usUfsguaCfccUfaggaAfaUfaccagsasg | 600 |

TABLE 9

TMPRSS6 Single Dose Screen

| DuplexID | 10 nM Avg | 0.1 nM Avg |
|---|---|---|
| AD-63214 | 12.40 | 19.46 |
| AD-63240 | 12.29 | 27.03 |
| AD-63209 | 17.11 | 23.38 |
| AD-63208 | 14.77 | 23.31 |
| AD-63202 | 14.87 | 27.08 |
| AD-63216 | 15.97 | 34.05 |
| AD-63219 | 18.47 | 27.82 |
| AD-63228 | 19.44 | 34.52 |
| AD-63205 | 15.44 | 38.23 |
| AD-63241 | 18.81 | 41.42 |
| AD-63243 | 19.15 | 30.87 |
| AD-63203 | 17.06 | 42.12 |
| AD-63223 | 21.98 | 27.52 |
| AD-63231 | 22.42 | 30.68 |
| AD-63199 | 17.74 | 39.50 |
| AD-63217 | 18.81 | 38.99 |
| AD-63229 | 22.33 | 33.42 |
| AD-63255 | 21.06 | 34.31 |
| AD-63226 | 18.36 | 41.65 |
| AD-63211 | 26.00 | 32.07 |
| AD-63273 | 23.11 | 34.96 |
| AD-60940 | 22.99 | 34.34 |
| AD-63249 | 30.83 | 28.35 |
| AD-63256 | 23.18 | 35.19 |
| AD-63280 | 25.10 | 32.42 |
| AD-63237 | 23.95 | 35.43 |
| AD-63285 | 21.53 | 39.60 |
| AD-63215 | 29.27 | 42.54 |
| AD-63222 | 23.88 | 38.24 |
| AD-63232 | 30.29 | 35.04 |
| AD-63218 | 27.02 | 37.31 |
| AD-63261 | 24.22 | 46.61 |
| AD-63267 | 28.32 | 38.90 |
| AD-63234 | 24.42 | 55.83 |
| AD-63250 | 26.77 | 47.92 |
| AD-63212 | 28.43 | 46.01 |
| AD-63210 | 27.91 | 44.35 |
| AD-63244 | 30.66 | 45.65 |
| AD-63235 | 32.75 | 51.82 |
| AD-63279 | 38.00 | 48.80 |
| AD-63227 | 33.15 | 58.12 |
| AD-63220 | 38.31 | 54.08 |
| AD-63238 | 45.56 | 51.50 |
| AD-63242 | 47.96 | 54.26 |
| AD-63239 | 51.98 | 49.22 |
| AD-63233 | 51.37 | 65.83 |

TABLE 9-continued

TMPRSS6 Single Dose Screen

| DuplexID | 10 nM Avg | 0.1 nM Avg |
|---|---|---|
| AD-63268 | 41.22 | 82.16 |
| AD-63221 | 57.02 | 65.11 |
| AD-63236 | 49.86 | 71.66 |
| AD-63197 | 47.67 | 78.29 |
| AD-63224 | 67.73 | 60.88 |
| AD-63200 | 62.89 | 67.68 |
| AD-63262 | 64.25 | 79.72 |
| AD-63204 | 68.01 | 80.99 |
| AD-63230 | 66.88 | 81.04 |
| AD-63198 | 65.67 | 78.28 |
| AD-63206 | 65.10 | 82.71 |

TABLE 10

TMPRSS6 Modified Sequences

| Duplex ID | Sense ID | Sense Sequence | SEQ ID NO: |
|---|---|---|---|
| AD-63214 | A-126586.2 | Y44CfsusGfgUfaUfuUfCfCfuAfgGfgUfaCfaAfL96 | 601 |
| AD-63240 | A-122745.11 | CfsusGfgUfaUfuUfCfCfuAfgGfgUfaCfaAfL96 | 602 |
| AD-63209 | A-126594.1 | csusgguaUfuUfCfCfuaggGfdTacaaL96 | 603 |
| AD-63208 | A-122745.6 | CfsusGfgUfaUfuUfCfCfuAfgGfgUfaCfaAfL96 | 604 |
| AD-63202 | A-126586.1 | Y44CfsusGfgUfaUfuUfCfCfuAfgGfgUfaCfaAfL96 | 605 |
| AD-63216 | A-122745.7 | CfsusGfgUfaUfuUfCfCfuAfgGfgUfaCfaAfL96 | 606 |
| AD-63219 | A-126617.1 | gsgsUfaUfuUfCfCfuAfgGfgUfaCfaAfL96 | 607 |
| AD-63228 | A-122745.9 | CfsusGfgUfaUfuUfCfCfuAfgGfgUfaCfaAfL96 | 608 |
| AD-63205 | A-122745.13 | CfsusGfgUfaUfuUfCfCfuAfgGfgUfaCfaAfL96 | 609 |
| AD-63241 | A-126589.2 | csusgguaUfuUfCfCfuaggGfuacaaL96 | 610 |
| AD-63243 | A-126621.3 | csusGfguaUfuUfCfCfuAfgGfguAfcaaL96 | 611 |
| AD-63203 | A-126593.1 | csusgguaUfuUfCfCfuaggGfuadCaaL96 | 612 |
| AD-63223 | A-122745.16 | CfsusGfgUfaUfuUfCfCfuAfgGfgUfaCfaAfL96 | 613 |
| AD-63231 | A-126621.1 | csusGfguaUfuUfCfCfuAfgGfguAfcaaL96 | 614 |
| AD-63199 | A-122745.12 | CfsusGfgUfaUfuUfCfCfuAfgGfgUfaCfaAfL96 | 615 |
| AD-63217 | A-122745.15 | CfsusGfgUfaUfuUfCfCfuAfgGfgUfaCfaAfL96 | 616 |
| AD-63229 | A-122745.17 | CfsusGfgUfaUfuUfCfCfuAfgGfgUfaCfaAfL96 | 617 |
| AD-63255 | A-126621.5 | csusGfguaUfuUfCfCfuAfgGfguAfcaaL96 | 618 |
| AD-63226 | A-126589.1 | csusgguaUfuUfCfCfuaggGfuacaaL96 | 619 |
| AD-63211 | A-122745.14 | CfsusGfgUfaUfuUfCfCfuAfgGfgUfaCfaAfL96 | 620 |
| AD-63273 | A-126621.8 | csusGfguaUfuUfCfCfuAfgGfguAfcaaL96 | 621 |
| AD-60940 | A-122745.1 | CfsusGfgUfaUfuUfCfCfuAfgGfgUfaCfaAfL96 | 622 |
| AD-63249 | A-126621.4 | csusGfguaUfuUfCfCfuAfgGfguAfcaaL96 | 623 |
| AD-63256 | A-122745.19 | CfsusGfgUfaUfuUfCfCfuAfgGfgUfaCfaAfL96 | 624 |
| AD-63280 | A-126639.1 | csusGfgUfaUfuUfCfCfuAfgGfgUfaCfaAfL96 | 625 |
| AD-63237 | A-126621.2 | csusGfguaUfuUfCfCfuAfgGfguAfcaaL96 | 626 |
| AD-63285 | A-126621.10 | csusGfguaUfuUfCfCfuAfgGfguAfcaaL96 | 627 |
| AD-63215 | A-126595.1 | csusgguaUfuUfCfdCuaggGfuacaaL96 | 628 |
| AD-63222 | A-122745.8 | CfsusGfgUfaUfuUfCfCfuAfgGfgUfaCfaAfL96 | 629 |

TABLE 10-continued

TMPRSS6 Modified Sequences

| AD-63232 | A-126590.1 | csusgguAfuuUfcCfUfagGfGfuacaaL96 | 630 |
|---|---|---|---|
| AD-63218 | A-126594.2 | csusgguaUfuUfCfCfuaggGfdTacaaL96 | 631 |
| AD-63261 | A-126621.6 | csusGfguaUfuUfCfCfuAfgGfguAfcaaL96 | 632 |
| AD-63267 | A-126621.7 | csusGfguaUfuUfCfCfuAfgGfguAfcaaL96 | 633 |
| AD-63234 | A-122745.10 | CfsusGfgUfaUfuUfCfCfuAfgGfgUfaCfaAfL96 | 634 |
| AD-63250 | A-122745.18 | CfsusGfgUfaUfuUfCfCfuAfgGfgUfaCfaAfL96 | 635 |
| AD-63212 | A-126593.2 | csusgguaUfuUfCfCfuaggGfuadCaaL96 | 636 |
| AD-63210 | A-126602.1 | csusgguauuucdCuaggg(Tgn)acaaL96 | 637 |
| AD-63244 | A-126621.11 | csusGfguaUfuUfCfCfuAfgGfguAfcaaL96 | 638 |
| AD-63235 | A-126588.2 | csusgguAfuuuCfCfuAfggGfuacaaL96 | 639 |
| AD-63279 | A-126621.9 | csusGfguaUfuUfCfCfuAfgGfguAfcaaL96 | 640 |
| AD-63227 | A-126597.1 | csusgguAfuuucCfuagggdTacaaL96 | 641 |
| AD-63220 | A-126588.1 | csusgguAfuuuCfCfuAfggGfuacaaL96 | 642 |
| AD-63238 | A-126591.1 | csusgguAfuuucCfuaggguacaaL96 | 643 |
| AD-63242 | A-126598.2 | csusgguAfuuucCfdTagggguacaaL96 | 644 |
| AD-63239 | A-126599.1 | csusgguauuucCfdTagggguacaaL96 | 645 |
| AD-63233 | A-126598.1 | csusgguAfuuucCfdTagggguacaaL96 | 646 |
| AD-63268 | A-126636.1 | CfsusGfgUfaUfuUfCfcuAfgGfgUfaCfaAfL96 | 647 |
| AD-63221 | A-126596.1 | csusgguAfuuucCfuagggguadCaaL96 | 648 |
| AD-63236 | A-126597.2 | csusgguAfuuucCfuagggdTacaaL96 | 649 |
| AD-63197 | A-126592.1 | csusgguauuucCfUfaggguacaaL96 | 650 |
| AD-63224 | A-126595.2 | csusgguaUfuUfCfdCuaggGfuacaaL96 | 651 |
| AD-63200 | A-126590.2 | csusgguAfuuUfcCfUfagGfGfuacaaL96 | 652 |
| AD-63262 | A-122745.20 | CfsusGfgUfaUfuUfCfCfuAfgGfgUfaCfaAfL96 | 653 |
| AD-63204 | A-126601.1 | csusgguauuucdCuaggguacaaL96 | 654 |
| AD-63230 | A-126596.2 | csusgguAfuuucCfuagggguadCaaL96 | 655 |
| AD-63198 | A-126600.1 | csusgguauuucdCdTagggguacaaL96 | 656 |
| AD-63206 | A-126591.2 | csusgguAfuuucCfuagggguacaaL96 | 657 |

| Duplex ID | Antisense ID | Antisense Sequence | SEQ ID NO: |
|---|---|---|---|
| AD-63214 | A-126587.2 | PusUfsgUfaCfcCfuAfggaAfaUfaCfcAfgsasg | 658 |
| AD-63240 | A-126607.1 | usUfsguaCfcCfuAfggaAfaUfaccagsasg | 659 |
| AD-63209 | A-122746.13 | usUfsgUfaCfcCfuAfggaAfaUfaCfcAfgsasg | 660 |
| AD-63208 | A-126587.1 | PusUfsgUfaCfcCfuAfggaAfaUfaCfcAfgsasg | 661 |
| AD-63202 | A-122746.6 | usUfsgUfaCfcCfuAfggaAfaUfaCfcAfgsasg | 662 |
| AD-63216 | A-126603.1 | usUfsgUfaCfccuAfggaAfaUfaCfcAfgsasg | 663 |
| AD-63219 | A-126618.1 | PusUfsgUfaCfcCfuAfggaAfaUfaCfcsasg | 664 |
| AD-63228 | A-126605.1 | usUfsgUfaCfcCfuAfggaAfaUfaccagsasg | 665 |
| AD-63205 | A-126609.1 | usUfsgUfaccCfuaggaAfaUfaccAfgsasg | 666 |

TABLE 10-continued

TMPRSS6 Modified Sequences

| | | | |
|---|---|---|---|
| AD-63241 | A-126611.3 | usUfsguaCfccUfaggaAfaUfaccagsasg | 667 |
| AD-63243 | A-126624.1 | usUfsGfuaCfcCfuAfggaAfAfuaCfcAfgsasg | 668 |
| AD-63203 | A-122746.12 | usUfsgUfaCfcCfuAfggaAfaUfaCfcAfgsasg | 669 |
| AD-63223 | A-126612.1 | usUfsguaCfccuaggaAfaUfaccagsasg | 670 |
| AD-63231 | A-126622.1 | usUfsGfuaCfcCfuAfggaAfaUfaCfcAfgsasg | 671 |
| AD-63199 | A-126608.1 | usUfsgUfaccCfuAfggaAfaUfaccAfgsasg | 672 |
| AD-63217 | A-126611.1 | usUfsguaCfccUfaggaAfaUfaccagsasg | 673 |
| AD-63229 | A-126613.1 | usUfsguaCfcCfUfaggaAfaUfaccagsasg | 674 |
| AD-63255 | A-126626.1 | usUfsGfuAfCfcCfuAfggaAfAfuaCfcAfgsasg | 675 |
| AD-63226 | A-122746.8 | usUfsgUfaCfcCfuAfggaAfaUfaCfcAfgsasg | 676 |
| AD-63211 | A-126610.1 | usUfsgUfacccuAfggaAfaUfaccAfgsasg | 677 |
| AD-63273 | A-126629.1 | usUfsGfuaCfcCfuAfggaAfAfuAfccagsasg | 678 |
| AD-60940 | A-122746.1 | usUfsgUfaCfcCfuAfggaAfaUfaCfcAfgsasg | 679 |
| AD-63249 | A-126625.1 | usUfsGfuAfCfcCfuAfggaAfAfuAfCfcAfgsasg | 680 |
| AD-63256 | A-126634.1 | usUfsgUfaccCfuAfggaAfaUfaCfcAfgsasg | 681 |
| AD-63280 | A-126587.3 | PusUfsgUfaCfcCfuAfggaAfAfuAfcAfgsasg | 682 |
| AD-63237 | A-126623.1 | usUfsGfuAfCfcCfuAfggaAfaUfaCfcAfgsasg | 683 |
| AD-63285 | A-126631.1 | usUfsGfuaCfcCfuAfggaAfAfuAfccAfgsasg | 684 |
| AD-63215 | A-122746.14 | usUfsgUfaCfcCfuAfggaAfaUfaCfcAfgsasg | 685 |
| AD-63222 | A-126604.1 | usUfsguaCfcCfuAfggaAfaUfaccAfgsasg | 686 |
| AD-63232 | A-122746.9 | usUfsgUfaCfcCfuAfggaAfaUfaCfcAfgsasg | 687 |
| AD-63218 | A-126611.7 | usUfsguaCfccUfaggaAfaUfaccagsasg | 688 |
| AD-63261 | A-126627.1 | usUfsGfuaCfcCfuAfggaAfAfuAfCfcagsasg | 689 |
| AD-63267 | A-126628.1 | usUfsGfuAfCfcCfuAfggaAfAfuAfCfcagsasg | 690 |
| AD-63234 | A-126606.1 | usUfsguaCfccuAfggaAfaUfaccAfgsasg | 691 |
| AD-63250 | A-126633.1 | ususgUfaCfcCfuAfggaAfaUfaCfcAfgsasg | 692 |
| AD-63212 | A-126611.6 | usUfsguaCfccUfaggaAfaUfaccagsasg | 693 |
| AD-63210 | A-122746.21 | usUfsgUfaCfcCfuAfggaAfaUfaCfcAfgsasg | 694 |
| AD-63244 | A-126632.1 | usUfsGfuAfCfcCfuAfggaAfAfuAfccAfgsasg | 695 |
| AD-63235 | A-126611.2 | usUfsguaCfccUfaggaAfaUfaccagsasg | 696 |
| AD-63279 | A-126630.1 | usUfsGfuAfCfcCfuAfggaAfAfuAfccagsasg | 697 |
| AD-63227 | A-122746.16 | usUfsgUfaCfcCfuAfggaAfaUfaCfcAfgsasg | 698 |
| AD-63220 | A-122746.7 | usUfsgUfaCfcCfuAfggaAfaUfaCfcAfgsasg | 699 |
| AD-63238 | A-122746.10 | usUfsgUfaCfcCfuAfggaAfaUfaCfcAfgsasg | 700 |
| AD-63242 | A-126611.11 | usUfsguaCfccUfaggaAfaUfaccagsasg | 701 |
| AD-63239 | A-122746.18 | usUfsgUfaCfcCfuAfggaAfaUfaCfcAfgsasg | 702 |
| AD-63233 | A-122746.17 | usUfsgUfaCfcCfuAfggaAfaUfaCfcAfgsasg | 703 |
| AD-63268 | A-122746.22 | usUfsgUfaCfcCfuAfggaAfaUfaCfcAfgsasg | 704 |
| AD-63221 | A-122746.15 | usUfsgUfaCfcCfuAfggaAfaUfaCfcAfgsasg | 705 |

TABLE 10-continued

TMPRSS6 Modified Sequences

| AD-63236 | A-126611.10 | usUfsguaCfccUfaggaAfaUfaccagsasg | 706 |
| AD-63197 | A-122746.11 | usUfsgUfaCfcCfuAfggaAfaUfaCfcAfgsasg | 707 |
| AD-63224 | A-126611.8 | usUfsguaCfccUfaggaAfaUfaccagsasg | 708 |
| AD-63200 | A-126611.4 | usUfsguaCfccUfaggaAfaUfaccagsasg | 709 |
| AD-63262 | A-126635.1 | usUfsgUfaCfcCfuAfggaaaUfaCfcAfgsasg | 710 |
| AD-63204 | A-122746.20 | usUfsgUfaCfcCfuAfggaAfaUfaCfcAfgsasg | 711 |
| AD-63230 | A-126611.9 | usUfsguaCfccUfaggaAfaUfaccagsasg | 712 |
| AD-63198 | A-122746.19 | usUfsgUfaCfcCfuAfggaAfaUfaCfcAfgsasg | 713 |
| AD-63206 | A-126611.5 | usUfsguaCfccUfaggaAfaUfaccagsasg | 714 |

TABLE 11

TMPRSS6 Single Dose Screen

| DuplexID | 10 nM Avg | 10 nM SD | 0.1 nM Avg | 0.1 nM SD |
| --- | --- | --- | --- | --- |
| AD-60998 | 26.1 | 3.1 | 42.9 | 13.3 |
| AD-60970 | 24.3 | 9.3 | 39.0 | 24.2 |
| AD-61002 | 27.5 | 8.5 | 32.1 | 9.8 |
| AD-60994 | 19.9 | 5.8 | 28.2 | 9.3 |
| AD-60992 | 57.9 | 15.4 | 67.5 | 13.6 |
| AD-61006 | 25.8 | 2.5 | 33.4 | 8.7 |
| AD-59743 | 21.1 | 3.2 | 31.7 | 8.1 |
| AD-60966 | 64.6 | 15.6 | 76.0 | 18.2 |
| AD-60952 | 44.1 | 10.7 | 76.9 | 16.5 |
| AD-61000 | 37.2 | 5.8 | 43.3 | 12.7 |
| AD-60949 | 94.9 | 22.3 | 91.3 | 13.2 |
| AD-60969 | 100.7 | 18.5 | 124.5 | 43.0 |
| AD-60967 | 93.7 | 6.4 | 112.1 | 31.5 |
| AD-60984 | 44.7 | 21.4 | 58.2 | 9.6 |
| AD-60943 | 65.6 | 11.0 | 61.7 | 9.8 |
| AD-61001 | 69.2 | 8.3 | 100.8 | 8.4 |
| AD-60986 | 38.9 | 13.9 | 58.9 | 4.8 |
| AD-60988 | 61.7 | 12.0 | 68.6 | 15.2 |
| AD-60993 | 92.1 | 13.1 | 86.5 | 10.0 |
| AD-60987 | 113.9 | 15.3 | 97.9 | 21.0 |
| AD-60997 | 54.8 | 7.2 | 75.8 | 16.4 |
| AD-60973 | 61.5 | 15.7 | 80.8 | 9.3 |
| AD-61005 | 116.8 | 23.4 | 128.1 | 10.8 |
| AD-60985 | 71.2 | 15.1 | 78.7 | 14.6 |
| AD-61003 | 101.0 | 15.2 | 97.5 | 15.8 |
| AD-60989 | 75.8 | 9.8 | 97.2 | 20.8 |
| AD-60955 | 108.6 | 23.4 | 102.0 | 16.6 |
| AD-60991 | 96.6 | 19.4 | 95.6 | 12.4 |
| AD-61004 | 111.1 | 6.4 | 110.9 | 18.3 |
| AD-60961 | 96.9 | 36.0 | 84.1 | 28.2 |
| AD-60999 | 106.7 | 12.7 | 92.3 | 24.6 |
| AD-60990 | 92.9 | 38.4 | 97.6 | 16.8 |
| AD-60996 | 71.2 | 7.5 | 101.5 | 8.9 |

Example 13. Optimization of AD-60940

Additional duplexes targeting TMPRSS6 were produced and screened in vitro for efficacy using the materials and methods below.
Design, Synthesis, and In Vitro Screening of Additional siRNAs
siRNA Design TMPRSS6 duplexes, 19 nucleotides long for both the sense and antisense strand, were designed using the human TMPRSS6 mRNA sequence set forth in GenBank Accession No. NM_153609.3. Three thousand one hundred and eighty duplexes were initially identified that did not contain repeats longer than 7 nucleotides, spanning substantially the entire 3209 nucleotide transcript. All 3180 duplexes were then scored for predicted efficacy according to a linear model that evaluates the nucleotide pair at each duplex position, and the dose and cell line used for screening. The duplexes were also matched against all transcripts in the human RefSeq collection using a custom brute force algorithm, and scored for lowest numbers of mismatches (per strand) to transcripts other than TMPRSS6. Duplexes to be synthesized and screened were then selected from the 3180, according to the following scheme: Beginning at the 5' end of the transcript, a duplex was selected within a "window" of every 10±2 nucleotides that had the highest predicted efficacy, had at least one mismatch in both strands to all transcripts other than TMPRSS6, and had not already been synthesized and screened as part of other duplex sets. If no duplex is identified within a given window that satisfied all criteria, that window was skipped. Three hundred and three duplexes were selected according to the above criteria. An additional 31 duplexes were also selected.

A detailed list of the 334 TMPRSS6 sense and antisense strand sequences is shown in Table 12.

Cell Culture and Transfections

Hep3B2.1-7 cells were obtained from American Type Culture Collection (Rockville, Md., cat. No. HB-8064) and cultured in EMEM (ATCC #30-2003), supplemented to contain 10% fetal calf serum (FCS) (Biochrom AG, Berlin, Germany, cat. No. S0115) and Penicillin 100 U/ml, Streptomycin 100 mg/ml (Biochrom AG, Berlin, Germany, cat. No. A2213), at 37° C. in an atmosphere with 5% $CO_2$ in a humidified incubator (Heraeus HERAcell, Kendro Laboratory Products, Langenselbold, Germany).

Transfection of dsRNA was performed directly after seeding 15,000 cells/well on a 96-well plate, and was carried out with Lipofectamine 2000 (Invitrogen GmbH, Karlsruhe, Germany, cat. No. 11668-019) as described by the manufacturer. Transfections were performed in quadruplicates and dsRNAs were transfected at a concentration of 10 nM.
Branched DNA Assays—QunatiGene 2.0 (Panomics Cat #: QS0011)

For measurement of TMPRSS6 mRNA cells were harvested 24 hours after transfection and lysed at 53° C. following procedures recommended by the manufacturer of the Quantigene II Kit for TMPRSS6 and Quantigene I Explore Kit for bDNA (Panomics, Fremont, Calif., USA, cat. No. 15735 or QG0004, respectively). Subsequently, 50

µl of the lysates were incubated with probesets specific to human TMPRSS6 and 10 µl of the lysates for human GAPDH and processed according to the manufacturer's protocol for QuantiGene. Chemoluminescence was measured in a Victor2-Light (Perkin Elmer, Wiesbaden, Germany) as RLUs (relative light units) and values obtained with the human TMPRSS6 probeset were normalized to the respective human GAPDH values for each well and then related to the mean of three unrelated control dsRNAs.

The in vitro efficacy of the compounds is shown in Table 13.

TABLE 12

Additional modified TMPRSS6 siRNAs

| Duplex ID | Sense Sequence | SEQ ID NO: | Sense ID | Position in NM_153609.3 |
| --- | --- | --- | --- | --- |
| AD-63290.1 | UGAGCCAGACCCAGUCCAGdTdT | 715 | A-126858.1 | 3-21 |
| AD-63296.1 | GACCCAGUCCAGCUCUGGUdTdT | 716 | A-126860.1 | 10-28 |
| AD-63302.1 | CUCUGGUGCCUGCCCUCUGdTdT | 717 | A-126862.1 | 22-40 |
| AD-63308.1 | GCCCUCUGGUGCGAGCUGAdTdT | 718 | A-126864.1 | 33-51 |
| AD-63314.1 | GGUGCGAGCUGACCUGAGAdTdT | 719 | A-126866.1 | 40-58 |
| AD-63320.1 | UGACCUGAGAUGCACUUCCdTdT | 720 | A-126868.1 | 49-67 |
| AD-63326.1 | UGCACUUCCCUCCUCUGUGdTdT | 721 | A-126870.1 | 59-77 |
| AD-63332.1 | CUGUGAGCUGUCUCGGCACdTdT | 722 | A-126872.1 | 73-91 |
| AD-63291.1 | GUCUCGGCACCCACUUGCAdTdT | 723 | A-126874.1 | 82-100 |
| AD-63297.1 | CCACUUGCAGUCACUGCCGdTdT | 724 | A-126876.1 | 92-110 |
| AD-63303.1 | GUCACUGCCGCCUGAUGUUdTdT | 725 | A-126878.1 | 101-119 |
| AD-63309.1 | GCCUGAUGUUGUUACUCUUdTdT | 726 | A-126880.1 | 110-128 |
| AD-63315.1 | UUACUCUUCCACUCCAAAAdTdT | 727 | A-126882.1 | 121-139 |
| AD-63321.1 | ACUCCAAAAGGAUGCCCGUdTdT | 728 | A-126884.1 | 131-149 |
| AD-63327.1 | UGCCCGUGGCCGAGGCCCCdTdT | 729 | A-126886.1 | 143-161 |
| AD-63333.1 | UGGCCGAGGCCCCCCAGGUdTdT | 730 | A-126888.1 | 149-167 |
| AD-63292.1 | CCAGGUGGCUGGCGGGCAGdTdT | 731 | A-126890.1 | 162-180 |
| AD-63298.1 | GCGGGCAGGGGGACGGAGGdTdT | 732 | A-126892.1 | 173-191 |
| AD-63304.1 | GGACGGAGGUGAUGGCGAGdTdT | 733 | A-126894.1 | 183-201 |
| AD-63310.1 | GUGAUGGCGAGGAAGCGGAdTdT | 734 | A-126896.1 | 191-209 |
| AD-63316.1 | GAAGCGGAGCCGGAGGGGAdTdT | 735 | A-126898.1 | 202-220 |
| AD-63322.1 | GCCGGAGGGGAUGUUCAAGdTdT | 736 | A-126900.1 | 210-228 |
| AD-63328.1 | UGUUCAAGGCCUGUGAGGAdTdT | 737 | A-126902.1 | 221-239 |
| AD-63334.1 | CUGUGAGGACUCCAAGAGAdTdT | 738 | A-126904.1 | 231-249 |
| AD-63293.1 | ACUCCAAGAGAAAAGCCCGdTdT | 739 | A-126906.1 | 239-257 |
| AD-63299.1 | GCCCGGGGCUACCUCCGCCdTdT | 740 | A-126908.1 | 253-271 |
| AD-63305.1 | ACCUCCGCCUGGUGCCCCUdTdT | 741 | A-126910.1 | 263-281 |
| AD-63311.1 | GCCUGGUGCCCCUGUUUGUdTdT | 742 | A-126912.1 | 269-287 |
| AD-63317.1 | UGUUUGUGCUGCUGGCCCUdTdT | 743 | A-126914.1 | 281-299 |
| AD-63323.1 | UGCUGGCCCUGCUCGUGCUdTdT | 744 | A-126916.1 | 290-308 |
| AD-63329.1 | GCUCGUGCUGGCUUCGGCGdTdT | 745 | A-126918.1 | 300-318 |
| AD-63335.1 | UCGGCGGGGUGCUACUCUdTdT | 746 | A-126920.1 | 313-331 |
| AD-63294.1 | CGGCGGGGUGCUACUCUGdTdT | 747 | A-126922.1 | 314-332 |
| AD-63300.1 | GGCGGGGUGCUACUCUGGdTdT | 748 | A-126924.1 | 315-333 |

TABLE 12-continued

Additional modified TMPRSS6 siRNAs

| | | | | |
|---|---|---|---|---|
| AD-63306.1 | GCGGGGGUGCUACUCUGGUdTdT | 749 | A-126926.1 | 316-334 |
| AD-63312.1 | CGGGGGUGCUACUCUGGUAdTdT | 750 | A-126928.1 | 317-335 |
| AD-63318.1 | GGGGGUGCUACUCUGGUAUdTdT | 751 | A-126930.1 | 318-336 |
| AD-63324.1 | GGGUGCUACUCUGGUAUUUdTdT | 752 | A-126932.1 | 320-338 |
| AD-63330.1 | GGUGCUACUCUGGUAUUUCdTdT | 753 | A-126934.1 | 321-339 |
| AD-63336.1 | GUGCUACUCUGGUAUUUCCdTdT | 754 | A-126936.1 | 322-340 |
| AD-63295.1 | GCUACUCUGGUAUUUCCUAdTdT | 755 | A-126938.1 | 324-342 |
| AD-63301.1 | CUACUCUGGUAUUUCCUAGdTdT | 756 | A-126940.1 | 325-343 |
| AD-63307.1 | UACUCUGGUAUUUCCUAGGdTdT | 757 | A-126942.1 | 326-344 |
| AD-63313.1 | ACUCUGGUAUUUCCUAGGGdTdT | 758 | A-126944.1 | 327-345 |
| AD-63319.1 | CUCUGGUAUUUCCUAGGGUdTdT | 759 | A-126946.1 | 328-346 |
| AD-63325.1 | CUGGUAUUUCCUAGGGUACdTdT | 760 | A-126948.1 | 330-348 |
| AD-63331.1 | GUAUUUCCUAGGGUACAAdTdT | 761 | A-126950.1 | 333-351 |
| AD-63337.1 | UAUUUCCUAGGGUACAAGdTdT | 762 | A-126952.1 | 334-352 |
| AD-63343.1 | AUUUCCUAGGGUACAAGGCdTdT | 763 | A-126954.1 | 335-353 |
| AD-63349.1 | UUUCCUAGGGUACAAGGCGdTdT | 764 | A-126956.1 | 336-354 |
| AD-63355.1 | UUCCUAGGGUACAAGGCGGdTdT | 765 | A-126958.1 | 337-355 |
| AD-63361.1 | CCUAGGGUACAAGGCGGAGdTdT | 766 | A-126960.1 | 339-357 |
| AD-63367.1 | CUAGGGUACAAGGCGGAGGdTdT | 767 | A-126962.1 | 340-358 |
| AD-63373.1 | UAGGGUACAAGGCGGAGGUdTdT | 768 | A-126964.1 | 341-359 |
| AD-63379.1 | AGGGUACAAGGCGGAGGUGdTdT | 769 | A-126966.1 | 342-360 |
| AD-63338.1 | GGGUACAAGGCGGAGGUGAdTdT | 770 | A-126968.1 | 343-361 |
| AD-63344.1 | GGUACAAGGCGGAGGUGAUdTdT | 771 | A-126970.1 | 344-362 |
| AD-63350.1 | GUACAAGGCGGAGGUGAUGdTdT | 772 | A-126972.1 | 345-363 |
| AD-63356.1 | UACAAGGCGGAGGUGAUGGdTdT | 773 | A-126974.1 | 346-364 |
| AD-63362.1 | ACAAGGCGGAGGUGAUGGUdTdT | 774 | A-126976.1 | 347-365 |
| AD-63368.1 | CAAGGCGGAGGUGAUGGUCdTdT | 775 | A-126978.1 | 348-366 |
| AD-63374.1 | AAGGCGGAGGUGAUGGUCAdTdT | 776 | A-126980.1 | 349-367 |
| AD-63380.1 | AGGCGGAGGUGAUGGUCAGdTdT | 777 | A-126982.1 | 350-368 |
| AD-63339.1 | UGAUGGUCAGCCAGGUGUAdTdT | 778 | A-126984.1 | 359-377 |
| AD-63345.1 | CCAGGUGUACUCAGGCAGdTdT | 779 | A-126986.1 | 369-387 |
| AD-63351.1 | GCAGUCUGCGUGUACUCAAdTdT | 780 | A-126988.1 | 383-401 |
| AD-63357.1 | GCGUGUACUCAAUCGCCACdTdT | 781 | A-126990.1 | 390-408 |
| AD-63363.1 | UCGCCACUUCUCCCAGGAUdTdT | 782 | A-126992.1 | 402-420 |
| AD-63369.1 | CUCCCAGGAUCUUACCCGCdTdT | 783 | A-126994.1 | 411-429 |
| AD-63375.1 | UACCCGCCGGGAAUCUAGUdTdT | 784 | A-126996.1 | 423-441 |
| AD-63381.1 | CCGGGAAUCUAGUGCCUUCdTdT | 785 | A-126998.1 | 429-447 |
| AD-63340.1 | AGUGCCUUCCGCAGUGAAAdTdT | 786 | A-127000.1 | 439-457 |
| AD-63346.1 | GUGAAACCGCCAAAGCCCAdTdT | 787 | A-127002.1 | 452-470 |

TABLE 12-continued

Additional modified TMPRSS6 siRNAs

| | | | | |
|---|---|---|---|---|
| AD-63352.1 | CGCCAAAGCCCAGAAGAUGdTdT | 788 | A-127004.1 | 459-477 |
| AD-63358.1 | CAGAAGAUGCUCAAGGAGCdTdT | 789 | A-127006.1 | 469-487 |
| AD-63364.1 | UCAAGGAGCUCAUCACCAGdTdT | 790 | A-127008.1 | 479-497 |
| AD-63370.1 | ACCAGCACCCGCCUGGGAAdTdT | 791 | A-127010.1 | 493-511 |
| AD-63376.1 | GCCUGGGAACUUACUACAAdTdT | 792 | A-127012.1 | 503-521 |
| AD-63382.1 | GAACUUACUACAACUCCAGdTdT | 793 | A-127014.1 | 509-527 |
| AD-63341.1 | AACUCCAGCUCCGUCUAUUdTdT | 794 | A-127016.1 | 520-538 |
| AD-63347.1 | CCGUCUAUUCCUUUGGGAdTdT | 795 | A-127018.1 | 530-548 |
| AD-63353.1 | UUGGGGAGGGACCCCUCACdTdT | 796 | A-127020.1 | 542-560 |
| AD-63359.1 | CCCCUCACCUGCUUCUUCUdTdT | 797 | A-127022.1 | 553-571 |
| AD-63365.1 | CUGCUUCUUCUGGUUCAUUdTdT | 798 | A-127024.1 | 561-579 |
| AD-63371.1 | CUGGUUCAUUCUCCAAAUCdTdT | 799 | A-127026.1 | 570-588 |
| AD-63377.1 | UCUCCAAAUCCCCGAGCACdTdT | 800 | A-127028.1 | 579-597 |
| AD-63383.1 | CCGAGCACCGCCGGCUGAUdTdT | 801 | A-127030.1 | 590-608 |
| AD-63342.1 | GGCUGAUGCUGAGCCCCGAdTdT | 802 | A-127032.1 | 602-620 |
| AD-63348.1 | UGAGCCCCGAGGUGGUGCAdTdT | 803 | A-127034.1 | 611-629 |
| AD-63354.1 | UGGUGCAGGCACUGCUGGUdTdT | 804 | A-127036.1 | 623-641 |
| AD-63360.1 | AGGCACUGCUGGUGGAGGAdTdT | 805 | A-127038.1 | 629-647 |
| AD-63366.1 | GUGGAGGAGCUGCUGUCCAdTdT | 806 | A-127040.1 | 640-658 |
| AD-63372.1 | UGUCCACAGUCAACAGCUCdTdT | 807 | A-127042.1 | 653-671 |
| AD-63378.1 | UCAACAGCUCGGCUGCCGUdTdT | 808 | A-127044.1 | 662-680 |
| AD-63384.1 | UCGGCUGCCGUCCCCUACAdTdT | 809 | A-127046.1 | 670-688 |
| AD-63390.1 | AGUGGACCCCGAGGGCCUAdTdT | 810 | A-127048.1 | 702-720 |
| AD-63396.1 | AGGGCCUAGUGAUCCUGGAdTdT | 811 | A-127050.1 | 713-731 |
| AD-63402.1 | UAGUGAUCCUGGAAGCCAGdTdT | 812 | A-127052.1 | 719-737 |
| AD-63408.1 | AAGCCAGUGUGAAAGACAUdTdT | 813 | A-127054.1 | 731-749 |
| AD-63414.1 | UGAAAGACAUAGCUGCAUUdTdT | 814 | A-127056.1 | 740-758 |
| AD-63420.1 | UGCAUUGAAUUCCACGCUGdTdT | 815 | A-127058.1 | 753-771 |
| AD-63426.1 | CUACAGCUACGUGGGCCAGdTdT | 816 | A-127060.1 | 783-801 |
| AD-63385.1 | CUACGUGGGCCAGGGCCAGdTdT | 817 | A-127062.1 | 789-807 |
| AD-63391.1 | AGGGCCAGGUCCUCCGGCUdTdT | 818 | A-127064.1 | 800-818 |
| AD-63397.1 | CCGGCUGAAGGGGCCUGACdTdT | 819 | A-127066.1 | 813-831 |
| AD-63403.1 | GGGCCUGACCACCUGGCCUdTdT | 820 | A-127068.1 | 823-841 |
| AD-63409.1 | CCACCUGGCCUCCAGCUGCdTdT | 821 | A-127070.1 | 831-849 |
| AD-63415.1 | CCAGCUGCCUGUGGGCACCUdTdT | 822 | A-127072.1 | 842-860 |
| AD-63421.1 | CUGUGGCACCUGCAGGGCCdTdT | 823 | A-127074.1 | 850-868 |
| AD-63427.1 | CUGCAGGGCCCCAAGGACCdTdT | 824 | A-127076.1 | 859-877 |
| AD-63386.1 | CCAAGGACCUCAUGCUCAAdTdT | 825 | A-127078.1 | 869-887 |
| AD-63392.1 | UGCUCAAACUCCGGCUGGAdTdT | 826 | A-127080.1 | 881-899 |

TABLE 12-continued

Additional modified TMPRSS6 siRNAs

| | | | | |
|---|---|---|---|---|
| AD-63398.1 | CCGGCUGGAGUGGACGCUGdTdT | 827 | A-127082.1 | 891-909 |
| AD-63404.1 | GACGCUGGCAGAGUGCCGGdTdT | 828 | A-127084.1 | 903-921 |
| AD-63410.1 | GGCAGAGUGCCGGGACCGAdTdT | 829 | A-127086.1 | 909-927 |
| AD-63416.1 | ACCGACUGGCCAUGUAUGAdTdT | 830 | A-127088.1 | 923-941 |
| AD-63422.1 | CCAUGUAUGACGUGGCCGGdTdT | 831 | A-127090.1 | 932-950 |
| AD-63428.1 | GUGGCCGGGCCCCUGGAGAdTdT | 832 | A-127092.1 | 943-961 |
| AD-63387.1 | CCCUGGAGAAGAGGCUCAUdTdT | 833 | A-127094.1 | 953-971 |
| AD-63393.1 | AGAAGAGGCUCAUCACCUCdTdT | 834 | A-127096.1 | 959-977 |
| AD-63399.1 | ACCUCGGUGUACGGCUGCAdTdT | 835 | A-127098.1 | 973-991 |
| AD-63405.1 | ACGGCUGCAGCCGCCAGGAdTdT | 836 | A-127100.1 | 983-1001 |
| AD-63411.1 | GCCGCCAGGAGCCCGUGGUdTdT | 837 | A-127102.1 | 992-1010 |
| AD-63417.1 | AGCCCGUGGUGGAGGUUCUdTdT | 838 | A-127104.1 | 1001-1019 |
| AD-63423.1 | GUGGAGGUUCUGGCGUCGGdTdT | 839 | A-127106.1 | 1009-1027 |
| AD-63429.1 | UGGCGUCGGGGGCCAUCAUdTdT | 840 | A-127108.1 | 1019-1037 |
| AD-63388.1 | CCAUCAUGGCGGUCGUCUGdTdT | 841 | A-127110.1 | 1031-1049 |
| AD-63394.1 | GCGGUCGUCUGGAAGAAGGdTdT | 842 | A-127112.1 | 1039-1057 |
| AD-63400.1 | GGAAGAAGGGCCUGCACAGdTdT | 843 | A-127114.1 | 1049-1067 |
| AD-63406.1 | CCUGCACAGCUACUACGACdTdT | 844 | A-127116.1 | 1059-1077 |
| AD-63412.1 | ACUACGACCCCUUCGUGCUdTdT | 845 | A-127118.1 | 1070-1088 |
| AD-63418.1 | CCUUCGUGCUCUCCGUGCAdTdT | 846 | A-127120.1 | 1079-1097 |
| AD-63424.1 | CCGUGCAGCCGGUGGUCUUdTdT | 847 | A-127122.1 | 1091-1109 |
| AD-63430.1 | CGGUGGUCUUCCAGGCCUGdTdT | 848 | A-127124.1 | 1100-1118 |
| AD-63389.1 | AGGCCUGUGAAGUGAACCUdTdT | 849 | A-127126.1 | 1112-1130 |
| AD-63395.1 | AAGUGAACCUGACGCUGGAdTdT | 850 | A-127128.1 | 1121-1139 |
| AD-63401.1 | GACGCUGGACAACAGGCUCdTdT | 851 | A-127130.1 | 1131-1149 |
| AD-63407.1 | ACAACAGGCUCGACUCCCAdTdT | 852 | A-127132.1 | 1139-1157 |
| AD-63413.1 | ACUCCCAGGGCGUCCUCAGdTdT | 853 | A-127134.1 | 1151-1169 |
| AD-63419.1 | CCCCGUACUUCCCCAGCUAdTdT | 854 | A-127136.1 | 1172-1190 |
| AD-63425.1 | UUCCCCAGCUACUACUCGCdTdT | 855 | A-127138.1 | 1180-1198 |
| AD-63431.1 | ACUACUCGCCCCAAACCCAdTdT | 856 | A-127140.1 | 1190-1208 |
| AD-63437.1 | CCCAAACCCACUGCUCCUGdTdT | 857 | A-127142.1 | 1199-1217 |
| AD-63443.1 | GCUCCUGGCACCUCACGGUdTdT | 858 | A-127144.1 | 1211-1229 |
| AD-63449.1 | ACCUCACGGUGCCCUCUCUdTdT | 859 | A-127146.1 | 1220-1238 |
| AD-63455.1 | CUCUCUGGACUACGGCUUGdTdT | 860 | A-127148.1 | 1233-1251 |
| AD-63461.1 | GACUACGGCUUGGCCCUCUdTdT | 861 | A-127150.1 | 1240-1258 |
| AD-63467.1 | CCCUCUGGUUUGAUGCCUAdTdT | 862 | A-127152.1 | 1253-1271 |
| AD-63473.1 | GUUUGAUGCCUAUGCACUGdTdT | 863 | A-127154.1 | 1260-1278 |
| AD-63432.1 | GCACUGAGGAGGCAGAAGUdTdT | 864 | A-127156.1 | 1273-1291 |
| AD-63438.1 | GGAGGCAGAAGUAUGAUUUdTdT | 865 | A-127158.1 | 1280-1298 |

TABLE 12-continued

Additional modified TMPRSS6 siRNAs

| | | | | |
|---|---|---|---|---|
| AD-63444.1 | AUGAUUUGCCGUGCACCCAdTdT | 866 | A-127160.1 | 1292-1310 |
| AD-63450.1 | UGCACCCAGGGCCAGUGGAdTdT | 867 | A-127162.1 | 1303-1321 |
| AD-63456.1 | GCCAGUGGACGAUCCAGAAdTdT | 868 | A-127164.1 | 1313-1331 |
| AD-63462.1 | GGACGAUCCAGAACAGGAGdTdT | 869 | A-127166.1 | 1319-1337 |
| AD-63468.1 | ACAGGAGGCUGUGUGGCUUdTdT | 870 | A-127168.1 | 1331-1349 |
| AD-63474.1 | CUGUGUGGCUUGCGCAUCCdTdT | 871 | A-127170.1 | 1339-1357 |
| AD-63433.1 | UGCGCAUCCUGCAGCCCUAdTdT | 872 | A-127172.1 | 1349-1367 |
| AD-63439.1 | AGCCCUACGCCGAGAGGAUdTdT | 873 | A-127174.1 | 1361-1379 |
| AD-63445.1 | CCGAGAGGAUCCCCGUGGUdTdT | 874 | A-127176.1 | 1370-1388 |
| AD-63451.1 | CCGUGGUGGCCACGGCCGGdTdT | 875 | A-127178.1 | 1382-1400 |
| AD-63457.1 | CCACGGCCGGGAUCACCAUdTdT | 876 | A-127180.1 | 1391-1409 |
| AD-63463.1 | GGAUCACCAUCAACUUCACdTdT | 877 | A-127182.1 | 1400-1418 |
| AD-63469.1 | UCAACUUCACCUCCCAGAUdTdT | 878 | A-127184.1 | 1409-1427 |
| AD-63475.1 | CCCAGAUCUCCCUCACCGGdTdT | 879 | A-127186.1 | 1421-1439 |
| AD-63434.1 | CCCUCACCGGGCCCGGUGUdTdT | 880 | A-127188.1 | 1430-1448 |
| AD-63440.1 | CCCGGUGUGCGGGUGCACUdTdT | 881 | A-127190.1 | 1441-1459 |
| AD-63446.1 | GCUUGUACAACCAGUCGGAdTdT | 882 | A-127192.1 | 1463-1481 |
| AD-63452.1 | ACAACCAGUCGGACCCCUGdTdT | 883 | A-127194.1 | 1469-1487 |
| AD-63458.1 | ACCCCUGCCCUGGAGAGUUdTdT | 884 | A-127196.1 | 1481-1499 |
| AD-63464.1 | CCUGGAGAGUUCCUCUGUUdTdT | 885 | A-127198.1 | 1489-1507 |
| AD-63470.1 | UCUGUUCUGUGAAUGGACUdTdT | 886 | A-127200.1 | 1502-1520 |
| AD-63476.1 | GAAUGGACUCUGUGUCCCUdTdT | 887 | A-127202.1 | 1512-1530 |
| AD-63435.1 | CUGUGUCCCUGCCUGUGAUdTdT | 888 | A-127204.1 | 1521-1539 |
| AD-63441.1 | CUGCCUGUGAUGGGGUCAAdTdT | 889 | A-127206.1 | 1529-1547 |
| AD-63447.1 | GGUCAAGGACUGCCCCAACdTdT | 890 | A-127208.1 | 1542-1560 |
| AD-63453.1 | UGCCCCAACGGCCUGGAUGdTdT | 891 | A-127210.1 | 1552-1570 |
| AD-63459.1 | CGGCCUGGAUGAGAGAAACdTdT | 892 | A-127212.1 | 1560-1578 |
| AD-63465.1 | GAGAGAAACUGCGUUUGCAdTdT | 893 | A-127214.1 | 1570-1588 |
| AD-63471.1 | UUUGCAGAGCCACAUUCCAdTdT | 894 | A-127216.1 | 1583-1601 |
| AD-63477.1 | GCCACAUUCCAGUGCAAAGdTdT | 895 | A-127218.1 | 1591-1609 |
| AD-63436.1 | GUGCAAAGAGGACAGCACAdTdT | 896 | A-127220.1 | 1602-1620 |
| AD-63442.1 | GAGGACAGCACAUGCAUCUdTdT | 897 | A-127222.1 | 1609-1627 |
| AD-63448.1 | GCAUCUCACUGCCCAAGGUdTdT | 898 | A-127224.1 | 1622-1640 |
| AD-63454.1 | GCCCAAGGUCUGUGAUGGGdTdT | 899 | A-127226.1 | 1632-1650 |
| AD-63460.1 | UGUGAUGGGCAGCCUGAUUdTdT | 900 | A-127228.1 | 1642-1660 |
| AD-63466.1 | GCAGCCUGAUUGUCUCAACdTdT | 901 | A-127230.1 | 1650-1668 |
| AD-63472.1 | GUCUCAACGGCAGCGACGAdTdT | 902 | A-127232.1 | 1661-1679 |
| AD-63478.1 | GCGACGAAGAGCAGUGCCAdTdT | 903 | A-127234.1 | 1673-1691 |
| AD-63484.1 | AGCAGUGCCAGGAAGGGGUdTdT | 904 | A-127236.1 | 1682-1700 |

TABLE 12-continued

Additional modified TMPRSS6 siRNAs

| | | | | |
|---|---|---|---|---|
| AD-63490.1 | GAAGGGGUGCCAUGUGGGAdTdT | 905 | A-127238.1 | 1693-1711 |
| AD-63496.1 | CCAUGUGGGACAUUCACCUdTdT | 906 | A-127240.1 | 1702-1720 |
| AD-63502.1 | CAUUCACCUUCCAGUGUGAdTdT | 907 | A-127242.1 | 1712-1730 |
| AD-63508.1 | CAGUGUGAGGACCGGAGCUdTdT | 908 | A-127244.1 | 1723-1741 |
| AD-63514.1 | GACCGGAGCUGCGUGAAGAdTdT | 909 | A-127246.1 | 1732-1750 |
| AD-63520.1 | CUGCGUGAAGAAGCCCAACdTdT | 910 | A-127248.1 | 1740-1758 |
| AD-63479.1 | AGCCCAACCCGCAGUGUGAdTdT | 911 | A-127250.1 | 1751-1769 |
| AD-63485.1 | CAGUGUGAUGGGCGGCCCGdTdT | 912 | A-127252.1 | 1762-1780 |
| AD-63491.1 | GCGGCCCGACUGCAGGGACdTdT | 913 | A-127254.1 | 1773-1791 |
| AD-63497.1 | CUGCAGGGACGGCUCGGAUdTdT | 914 | A-127256.1 | 1782-1800 |
| AD-63503.1 | ACGGCUCGGAUGAGGAGCAdTdT | 915 | A-127258.1 | 1790-1808 |
| AD-63509.1 | UGAGGAGCACUGUGACUGUdTdT | 916 | A-127260.1 | 1800-1818 |
| AD-63515.1 | CUGUGACUGUGGCCUCCAGdTdT | 917 | A-127262.1 | 1809-1827 |
| AD-63521.1 | GCCUCCAGGGCCCCUCCAGdTdT | 918 | A-127264.1 | 1820-1838 |
| AD-63480.1 | CCCCUCCAGCCGCAUUGUUdTdT | 919 | A-127266.1 | 1830-1848 |
| AD-63486.1 | CCGCAUUGUUGGUGGAGCUdTdT | 920 | A-127268.1 | 1839-1857 |
| AD-63492.1 | GUGGAGCUGUGUCCUCCGAdTdT | 921 | A-127270.1 | 1850-1868 |
| AD-63498.1 | CUCCGAGGGUGAGUGGCCAdTdT | 922 | A-127272.1 | 1863-1881 |
| AD-63504.1 | GGGUGAGUGGCCAUGGCAGdTdT | 923 | A-127274.1 | 1869-1887 |
| AD-63510.1 | AUGGCAGGCCAGCCUCCAGdTdT | 924 | A-127276.1 | 1881-1899 |
| AD-63516.1 | CCUCCAGGUUCGGGGUCGAdTdT | 925 | A-127278.1 | 1893-1911 |
| AD-63522.1 | GGUUCGGGGUCGACACAUCdTdT | 926 | A-127280.1 | 1899-1917 |
| AD-63481.1 | ACAUCUGUGGGGGGGCCCUdTdT | 927 | A-127282.1 | 1913-1931 |
| AD-63487.1 | GUGGGGGGGCCCUCAUCGCdTdT | 928 | A-127284.1 | 1919-1937 |
| AD-63493.1 | AUCGCUGACCGCUGGGUGAdTdT | 929 | A-127286.1 | 1933-1951 |
| AD-63499.1 | ACCGCUGGGUGAUAACAGCdTdT | 930 | A-127288.1 | 1940-1958 |
| AD-63505.1 | UGAUAACAGCUGCCCACUGdTdT | 931 | A-127290.1 | 1949-1967 |
| AD-63511.1 | CCCACUGCUUCCAGGAGGAdTdT | 932 | A-127292.1 | 1961-1979 |
| AD-63517.1 | CCAGGAGGACAGCAUGGCCdTdT | 933 | A-127294.1 | 1971-1989 |
| AD-63523.1 | ACAGCAUGGCCUCCACGGUdTdT | 934 | A-127296.1 | 1979-1997 |
| AD-63482.1 | CCACGGUGCUGUGGACCGUdTdT | 935 | A-127298.1 | 1991-2009 |
| AD-63488.1 | GGACCGUGUUCCUGGGCAAdTdT | 936 | A-127300.1 | 2003-2021 |
| AD-63494.1 | UCCUGGGCAAGGUGUGGCAdTdT | 937 | A-127302.1 | 2012-2030 |
| AD-63500.1 | GUGUGGCAGAACUCGCGCUdTdT | 938 | A-127304.1 | 2023-2041 |
| AD-63506.1 | GAACUCGCGCUGGCCUGGAdTdT | 939 | A-127306.1 | 2031-2049 |
| AD-63512.1 | GGCCUGGAGAGGUGUCCUUdTdT | 940 | A-127308.1 | 2042-2060 |
| AD-63518.1 | AGGUGUCCUUCAAGGUGAGdTdT | 941 | A-127310.1 | 2051-2069 |
| AD-63524.1 | CAAGGUGAGCCGCCUGCUCdTdT | 942 | A-127312.1 | 2061-2079 |
| AD-63483.1 | GCCUGCUCCUGCACCCGUAdTdT | 943 | A-127314.1 | 2072-2090 |

TABLE 12-continued

Additional modified TMPRSS6 siRNAs

| | | | | |
|---|---|---|---|---|
| AD-63489.1 | GCACCCGUACCACGAAGAGdTdT | 944 | A-127316.1 | 2082-2100 |
| AD-63495.1 | CCACGAAGAGGACAGCCAUdTdT | 945 | A-127318.1 | 2091-2109 |
| AD-63501.1 | AGGACAGCCAUGACUACGAdTdT | 946 | A-127320.1 | 2099-2117 |
| AD-63507.1 | ACUACGACGUGGCGCUGCUdTdT | 947 | A-127322.1 | 2111-2129 |
| AD-63513.1 | UGGCGCUGCUGCAGCUCGAdTdT | 948 | A-127324.1 | 2120-2138 |
| AD-63519.1 | AGCUCGACCACCCGGUGGUdTdT | 949 | A-127326.1 | 2132-2150 |
| AD-63525.1 | CCGGUGGUGCGCUCGGCCGdTdT | 950 | A-127328.1 | 2143-2161 |
| AD-63531.1 | UGCGCUCGGCCGCCGUGCGdTdT | 951 | A-127330.1 | 2150-2168 |
| AD-63537.1 | CCGUGCGCCCCGUCUGCCUdTdT | 952 | A-127332.1 | 2162-2180 |
| AD-63543.1 | CCGUCUGCCUGCCCGCGCGdTdT | 953 | A-127334.1 | 2171-2189 |
| AD-63549.1 | CCGCGCGCUCCCACUUCUUdTdT | 954 | A-127336.1 | 2183-2201 |
| AD-63555.1 | CCCACUUCUUCGAGCCCGGdTdT | 955 | A-127338.1 | 2192-2210 |
| AD-63561.1 | GAGCCCGGCCUGCACUGCUdTdT | 956 | A-127340.1 | 2203-2221 |
| AD-63567.1 | GGCCUGCACUGCUGGAUUAdTdT | 957 | A-127342.1 | 2209-2227 |
| AD-63526.1 | UGGAUUACGGGCUGGGGCGdTdT | 958 | A-127344.1 | 2221-2239 |
| AD-63532.1 | GCUGGGGCGCCUUGCGCGAdTdT | 959 | A-127346.1 | 2231-2249 |
| AD-63538.1 | UGCGCGAGGGCGGCCCCAUdTdT | 960 | A-127348.1 | 2243-2261 |
| AD-63544.1 | AGGGCGGCCCCAUCAGCAAdTdT | 961 | A-127350.1 | 2249-2267 |
| AD-63550.1 | UCAGCAACGCUCUGCAGAAdTdT | 962 | A-127352.1 | 2261-2279 |
| AD-63556.1 | UGCAGAAAGUGGAUGUGCAdTdT | 963 | A-127354.1 | 2273-2291 |
| AD-63562.1 | AAGUGGAUGUGCAGUUGAUdTdT | 964 | A-127356.1 | 2279-2297 |
| AD-63568.1 | GCAGUUGAUCCCACAGGACdTdT | 965 | A-127358.1 | 2289-2307 |
| AD-63527.1 | CACAGGACCUGUGCAGCGAdTdT | 966 | A-127360.1 | 2300-2318 |
| AD-63533.1 | GCAGCGAGGUCUAUCGCUAdTdT | 967 | A-127362.1 | 2312-2330 |
| AD-63539.1 | GUCUAUCGCUACCAGGUGAdTdT | 968 | A-127364.1 | 2320-2338 |
| AD-63545.1 | CCAGGUGACGCCACGCAUGdTdT | 969 | A-127366.1 | 2331-2349 |
| AD-63551.1 | CCACGCAUGCUGUGUGCCGdTdT | 970 | A-127368.1 | 2341-2359 |
| AD-63557.1 | CUGUGUGCCGGCUACCGCAdTdT | 971 | A-127370.1 | 2350-2368 |
| AD-63563.1 | ACCGCAAGGGCAAGAAGGAdTdT | 972 | A-127372.1 | 2363-2381 |
| AD-63569.1 | GCAAGAAGGAUGCCUGUCAdTdT | 973 | A-127374.1 | 2372-2390 |
| AD-63528.1 | GCCUGUCAGGGUGACUCAGdTdT | 974 | A-127376.1 | 2383-2401 |
| AD-63534.1 | GUGACUCAGGUGGUCCGCUdTdT | 975 | A-127378.1 | 2393-2411 |
| AD-63540.1 | GUGGUCCGCUGGUGUGCAAdTdT | 976 | A-127380.1 | 2402-2420 |
| AD-63546.1 | UGGUGUGCAAGGCACUCAGdTdT | 977 | A-127382.1 | 2411-2429 |
| AD-63552.1 | GCACUCAGUGGCCGCUGGUdTdT | 978 | A-127384.1 | 2422-2440 |
| AD-63558.1 | GCCGCUGGUUCCUGGCGGGdTdT | 979 | A-127386.1 | 2432-2450 |
| AD-63564.1 | UCCUGGCGGGGCUGGUCAGdTdT | 980 | A-127388.1 | 2441-2459 |
| AD-63570.1 | GCUGGUCAGCUGGGGCCUGdTdT | 981 | A-127390.1 | 2451-2469 |
| AD-63529.1 | GGGCCUGGGCUGUGGCCGGdTdT | 982 | A-127392.1 | 2463-2481 |

TABLE 12-continued

Additional modified TMPRSS6 siRNAs

| | | | | |
|---|---|---|---|---|
| AD-63535.1 | GGCUGUGGCCGGCCUAACUdTdT | 983 | A-127394.1 | 2470-2488 |
| AD-63541.1 | CUAACUACUUCGGCGUCUAdTdT | 984 | A-127396.1 | 2483-2501 |
| AD-63547.1 | CGGCGUCUACACCCGCAUCdTdT | 985 | A-127398.1 | 2493-2511 |
| AD-63553.1 | ACACCCGCAUCACAGGUGUdTdT | 986 | A-127400.1 | 2501-2519 |
| AD-63559.1 | ACAGGUGUGAUCAGCUGGAdTdT | 987 | A-127402.1 | 2512-2530 |
| AD-63565.1 | UCAGCUGGAUCCAGCAAGUdTdT | 988 | A-127404.1 | 2522-2540 |
| AD-63571.1 | CAGCAAGUGGUGACCUGAGdTdT | 989 | A-127406.1 | 2533-2551 |
| AD-63530.1 | UGACCUGAGGAACUGCCCCdTdT | 990 | A-127408.1 | 2543-2561 |
| AD-63536.1 | GGAACUGCCCCCUGCAAAdTdT | 991 | A-127410.1 | 2551-2569 |
| AD-63542.1 | CUGCAAAGCAGGGCCCACCdTdT | 992 | A-127412.1 | 2563-2581 |
| AD-63548.1 | GCAGGGCCCACCUCCUGGAdTdT | 993 | A-127414.1 | 2570-2588 |
| AD-63554.1 | CCUCCUGGACUCAGAGAGCdTdT | 994 | A-127416.1 | 2580-2598 |
| AD-63560.1 | CUCAGAGAGCCCAGGGCAAdTdT | 995 | A-127418.1 | 2589-2607 |
| AD-63566.1 | CCAGGGCAACUGCCAAGCAdTdT | 996 | A-127420.1 | 2599-2617 |
| AD-63572.1 | GGACAAGUAUUCUGGCGGGdTdT | 997 | A-127422.1 | 2621-2639 |
| AD-63578.1 | CUGGCGGGGGUGGGGAGdTdT | 998 | A-127424.1 | 2632-2650 |
| AD-63584.1 | GGGUGGGGAGAGAGCAGGdTdT | 999 | A-127426.1 | 2640-2658 |
| AD-63590.1 | AGAGAGCAGGCCCUGUGGUdTdT | 1000 | A-127428.1 | 2649-2667 |
| AD-63596.1 | CCCUGUGGUGGCAGGAGGUdTdT | 1001 | A-127430.1 | 2659-2677 |
| AD-63602.1 | GGAGGUGGCAUCUUGUCUCdTdT | 1002 | A-127432.1 | 2672-2690 |
| AD-63608.1 | CAUCUUGUCUCGUCCCUGAdTdT | 1003 | A-127434.1 | 2680-2698 |
| AD-63614.1 | CCCUGAUGUCUGCUCCAGUdTdT | 1004 | A-127436.1 | 2693-2711 |
| AD-63573.1 | CUGCUCCAGUGAUGGCAGGdTdT | 1005 | A-127438.1 | 2702-2720 |
| AD-63579.1 | AUGGCAGGAGGAUGGAGAAdTdT | 1006 | A-127440.1 | 2713-2731 |
| AD-63585.1 | GGAUGGAGAAGUGCCAGCAdTdT | 1007 | A-127442.1 | 2722-2740 |
| AD-63591.1 | UGCCAGCAGCUGGGGGUCAdTdT | 1008 | A-127444.1 | 2733-2751 |
| AD-63597.1 | AGCUGGGGGUCAAGACGUCdTdT | 1009 | A-127446.1 | 2740-2758 |
| AD-63603.1 | UCAAGACGUCCCCUGAGGAdTdT | 1010 | A-127448.1 | 2749-2767 |
| AD-63609.1 | CCCUGAGGACCCAGGCCCAdTdT | 1011 | A-127450.1 | 2759-2777 |
| AD-63615.1 | GCCCACACCCAGCCCUUCUdTdT | 1012 | A-127452.1 | 2773-2791 |
| AD-63574.1 | AGCCCUUCUGCCUCCCAAUdTdT | 1013 | A-127454.1 | 2783-2801 |
| AD-63580.1 | CCUCCCAAUUCUCUCUCCUdTdT | 1014 | A-127456.1 | 2793-2811 |
| AD-63586.1 | CUCUCUCCUCCGUCCCCUUdTdT | 1015 | A-127458.1 | 2803-2821 |
| AD-63592.1 | UCCGUCCCCUUCCUCCACUdTdT | 1016 | A-127460.1 | 2811-2829 |
| AD-63598.1 | CUUCCUCCACUGCUGCCUAdTdT | 1017 | A-127462.1 | 2819-2837 |
| AD-63604.1 | CUGCCUAAUGCAAGGCAGUdTdT | 1018 | A-127464.1 | 2831-2849 |
| AD-63610.1 | GCAAGGCAGUGGCUCAGCAdTdT | 1019 | A-127466.1 | 2840-2858 |
| AD-63616.1 | UGGCUCAGCAGCAAGAAUGdTdT | 1020 | A-127468.1 | 2849-2867 |
| AD-63575.1 | CAAGAAUGCUGGUUCUACAdTdT | 1021 | A-127470.1 | 2860-2878 |

TABLE 12-continued

Additional modified TMPRSS6 siRNAs

| Duplex ID | Antisense Sequence | SEQ ID NO: | Antisense ID | |
|---|---|---|---|---|
| AD-63581.1 | UGGUUCUACAUCCCGAGGAdTdT | 1022 | A-127472.1 | 2869-2887 |
| AD-63587.1 | CCCGAGGAGUGUCUGAGGUdTdT | 1023 | A-127474.1 | 2880-2898 |
| AD-63593.1 | GUCUGAGGUGCGCCCCACUdTdT | 1024 | A-127476.1 | 2890-2908 |
| AD-63599.1 | GCCCCACUCUGUACAGAGGdTdT | 1025 | A-127478.1 | 2901-2919 |
| AD-63605.1 | CUGUACAGAGGCUGUUUGGdTdT | 1026 | A-127480.1 | 2909-2927 |
| AD-63611.1 | CUGUUUGGGCAGCCUUGCCdTdT | 1027 | A-127482.1 | 2920-2938 |
| AD-63617.1 | CUUGCCUCCAGAGAGCAGAdTdT | 1028 | A-127484.1 | 2933-2951 |
| AD-63576.1 | UCCAGAGAGCAGAUUCCAGdTdT | 1029 | A-127486.1 | 2939-2957 |
| AD-63582.1 | GAUUCCAGCUUCGGAAGCCdTdT | 1030 | A-127488.1 | 2950-2968 |
| AD-63588.1 | GAAUGGAAGGUGCUCCCAUdTdT | 1031 | A-127490.1 | 2991-3009 |
| AD-63594.1 | GUGCUCCCAUCGGAGGGGAdTdT | 1032 | A-127492.1 | 3000-3018 |
| AD-63600.1 | UCGGAGGGGACCCUCAGAGdTdT | 1033 | A-127494.1 | 3009-3027 |
| AD-63606.1 | CCCUCAGAGCCCUGGAGAdTdT | 1034 | A-127496.1 | 3019-3037 |
| AD-63612.1 | GAGACUGCCAGGUGGGCCUdTdT | 1035 | A-127498.1 | 3033-3051 |
| AD-63618.1 | AGGUGGGCCUGCUGCCACUdTdT | 1036 | A-127500.1 | 3042-3060 |
| AD-63577.1 | CUGCCACUGUAAGCCAAAAdTdT | 1037 | A-127502.1 | 3053-3071 |
| AD-63583.1 | CUGUAAGCCAAAAGGUGGGdTdT | 1038 | A-127504.1 | 3059-3077 |
| AD-63589.1 | GUGGGGAAGUCCUGACUCCdTdT | 1039 | A-127506.1 | 3073-3091 |
| AD-63595.1 | CCUGACUCCAGGGUCCUUGdTdT | 1040 | A-127508.1 | 3083-3101 |
| AD-63601.1 | GGGUCCUUGCCCCACCCCUdTdT | 1041 | A-127510.1 | 3093-3111 |
| AD-63607.1 | GCCCCACCCCUGCCUGCCAdTdT | 1042 | A-127512.1 | 3101-3119 |
| AD-63613.1 | CCUGCCACCUGGGCCCUCAdTdT | 1043 | A-127514.1 | 3113-3131 |
| AD-63619.1 | CUGGGCCCUCACAGCCCAGdTdT | 1044 | A-127516.1 | 3121-3139 |
| AD-63620.1 | UCACAGCCCAGACCCUCACdTdT | 1045 | A-127518.1 | 3129-3147 |
| AD-63621.1 | CUCACUGGGAGGUGAGCUCdTdT | 1046 | A-127520.1 | 3143-3161 |
| AD-63622.1 | GGUGAGCUCAGCUGCCCUUdTdT | 1047 | A-127522.1 | 3153-3171 |
| AD-63623.1 | UGGAAUAAAGCUGCCUGAUdTdT | 1048 | A-127524.1 | 3172-3190 |

| Duplex ID | Antisense Sequence | SEQ ID NO: | Antisense ID |
|---|---|---|---|
| AD-63290.1 | CUGGACUGGGUCUGGCUCAdTdT | 1049 | A-126859.1 |
| AD-63296.1 | ACCAGAGCUGGACUGGGUCdTdT | 1050 | A-126861.1 |
| AD-63302.1 | CAGAGGGCAGGCACCAGAGdTdT | 1051 | A-126863.1 |
| AD-63308.1 | UCAGCUCGCACCAGAGGGCdTdT | 1052 | A-126865.1 |
| AD-63314.1 | UCUCAGGUCAGCUCGCACCdTdT | 1053 | A-126867.1 |
| AD-63320.1 | GGAAGUGCAUCUCAGGUCAdTdT | 1054 | A-126869.1 |
| AD-63326.1 | CACAGAGGAGGGAAGUGCAdTdT | 1055 | A-126871.1 |
| AD-63332.1 | GUGCCGAGACAGCUCACAGdTdT | 1056 | A-126873.1 |
| AD-63291.1 | UGCAAGUGGGUGCCGAGACdTdT | 1057 | A-126875.1 |
| AD-63297.1 | CGGCAGUGACUGCAAGUGGdTdT | 1058 | A-126877.1 |

TABLE 12-continued

Additional modified TMPRSS6 siRNAs

| | | | |
|---|---|---|---|
| AD-63303.1 | AACAUCAGGCGGCAGUGACdTdT | 1059 | A-126879.1 |
| AD-63309.1 | AAGAGUAACAACAUCAGGCdTdT | 1060 | A-126881.1 |
| AD-63315.1 | UUUUGGAGUGGAAGAGUAAdTdT | 1061 | A-126883.1 |
| AD-63321.1 | ACGGGCAUCCUUUUGGAGUdTdT | 1062 | A-126885.1 |
| AD-63327.1 | GGGGCCUCGGCCACGGGCAdTdT | 1063 | A-126887.1 |
| AD-63333.1 | ACCUGGGGGCCUCGGCCAdTdT | 1064 | A-126889.1 |
| AD-63292.1 | CUGCCCGCCAGCCACCUGGdTdT | 1065 | A-126891.1 |
| AD-63298.1 | CCUCCGUCCCCUGCCCGCdTdT | 1066 | A-126893.1 |
| AD-63304.1 | CUCGCCAUCACCUCCGUCCdTdT | 1067 | A-126895.1 |
| AD-63310.1 | UCCGCUUCCUCGCCAUCACdTdT | 1068 | A-126897.1 |
| AD-63316.1 | UCCCCUCCGGCUCCGCUUCdTdT | 1069 | A-126899.1 |
| AD-63322.1 | CUUGAACAUCCCCUCCGGCdTdT | 1070 | A-126901.1 |
| AD-63328.1 | UCCUCACAGGCCUUGAACAdTdT | 1071 | A-126903.1 |
| AD-63334.1 | UCUCUUGGAGUCCUCACAGdTdT | 1072 | A-126905.1 |
| AD-63293.1 | CGGGCUUUUCUCUUGGAGUdTdT | 1073 | A-126907.1 |
| AD-63299.1 | GGCGGAGGUAGCCCCGGGCdTdT | 1074 | A-126909.1 |
| AD-63305.1 | AGGGGCACCAGGCGGAGGUdTdT | 1075 | A-126911.1 |
| AD-63311.1 | ACAAACAGGGGCACCAGGCdTdT | 1076 | A-126913.1 |
| AD-63317.1 | AGGGCCAGCAGCACAAACAdTdT | 1077 | A-126915.1 |
| AD-63323.1 | AGCACGAGCAGGGCCAGCAdTdT | 1078 | A-126917.1 |
| AD-63329.1 | CGCCGAAGCCAGCACGAGCdTdT | 1079 | A-126919.1 |
| AD-63335.1 | AGAGUAGCACCCCCGCCGAdTdT | 1080 | A-126921.1 |
| AD-63294.1 | CAGAGUAGCACCCCCGCCGdTdT | 1081 | A-126923.1 |
| AD-63300.1 | CCAGAGUAGCACCCCCGCCdTdT | 1082 | A-126925.1 |
| AD-63306.1 | ACCAGAGUAGCACCCCCGCdTdT | 1083 | A-126927.1 |
| AD-63312.1 | UACCAGAGUAGCACCCCCGdTdT | 1084 | A-126929.1 |
| AD-63318.1 | AUACCAGAGUAGCACCCCCdTdT | 1085 | A-126931.1 |
| AD-63324.1 | AAAUACCAGAGUAGCACCCdTdT | 1086 | A-126933.1 |
| AD-63330.1 | GAAAUACCAGAGUAGCACCdTdT | 1087 | A-126935.1 |
| AD-63336.1 | GGAAAUACCAGAGUAGCACdTdT | 1088 | A-126937.1 |
| AD-63295.1 | UAGGAAAUACCAGAGUAGCdTdT | 1089 | A-126939.1 |
| AD-63301.1 | CUAGGAAAUACCAGAGUAGdTdT | 1090 | A-126941.1 |
| AD-63307.1 | CCUAGGAAAUACCAGAGUAdTdT | 1091 | A-126943.1 |
| AD-63313.1 | CCCUAGGAAAUACCAGAGUdTdT | 1092 | A-126945.1 |
| AD-63319.1 | ACCCUAGGAAAUACCAGAGdTdT | 1093 | A-126947.1 |
| AD-63325.1 | GUACCCUAGGAAAUACCAGdTdT | 1094 | A-126949.1 |
| AD-63331.1 | CUUGUACCCUAGGAAAUACdTdT | 1095 | A-126951.1 |
| AD-63337.1 | CCUUGUACCCUAGGAAAUAdTdT | 1096 | A-126953.1 |
| AD-63343.1 | GCCUUGUACCCUAGGAAAUdTdT | 1097 | A-126955.1 |

TABLE 12-continued

Additional modified TMPRSS6 siRNAs

| | | | |
|---|---|---|---|
| AD-63349.1 | CGCCUUGUACCCUAGGAAAdTdT | 1098 | A-126957.1 |
| AD-63355.1 | CCGCCUUGUACCCUAGGAAdTdT | 1099 | A-126959.1 |
| AD-63361.1 | CUCCGCCUUGUACCCUAGGdTdT | 1100 | A-126961.1 |
| AD-63367.1 | CCUCCGCCUUGUACCCUAGdTdT | 1101 | A-126963.1 |
| AD-63373.1 | ACCUCCGCCUUGUACCCUAdTdT | 1102 | A-126965.1 |
| AD-63379.1 | CACCUCCGCCUUGUACCCUdTdT | 1103 | A-126967.1 |
| AD-63338.1 | UCACCUCCGCCUUGUACCCdTdT | 1104 | A-126969.1 |
| AD-63344.1 | AUCACCUCCGCCUUGUACCdTdT | 1105 | A-126971.1 |
| AD-63350.1 | CAUCACCUCCGCCUUGUACdTdT | 1106 | A-126973.1 |
| AD-63356.1 | CCAUCACCUCCGCCUUGUAdTdT | 1107 | A-126975.1 |
| AD-63362.1 | ACCAUCACCUCCGCCUUGUdTdT | 1108 | A-126977.1 |
| AD-63368.1 | GACCAUCACCUCCGCCUUGdTdT | 1109 | A-126979.1 |
| AD-63374.1 | UGACCAUCACCUCCGCCUUdTdT | 1110 | A-126981.1 |
| AD-63380.1 | CUGACCAUCACCUCCGCCUdTdT | 1111 | A-126983.1 |
| AD-63339.1 | UACACCUGGCUGACCAUCAdTdT | 1112 | A-126985.1 |
| AD-63345.1 | ACUGCCUGAGUACACCUGGdTdT | 1113 | A-126987.1 |
| AD-63351.1 | UUGAGUACACGCAGACUGCdTdT | 1114 | A-126989.1 |
| AD-63357.1 | GUGGCGAUUGAGUACACGCdTdT | 1115 | A-126991.1 |
| AD-63363.1 | AUCCUGGGAGAAGUGGCGAdTdT | 1116 | A-126993.1 |
| AD-63369.1 | GCGGGUAAGAUCCUGGGAGdTdT | 1117 | A-126995.1 |
| AD-63375.1 | ACUAGAUUCCCGGCGGGUAdTdT | 1118 | A-126997.1 |
| AD-63381.1 | GAAGGCACUAGAUUCCCGGdTdT | 1119 | A-126999.1 |
| AD-63340.1 | UUUCACUGCGGAAGGCACUdTdT | 1120 | A-127001.1 |
| AD-63346.1 | UGGGCUUUGGCGGUUUCACdTdT | 1121 | A-127003.1 |
| AD-63352.1 | CAUCUUCUGGGCUUUGGCGdTdT | 1122 | A-127005.1 |
| AD-63358.1 | GCUCCUUGAGCAUCUUCUGdTdT | 1123 | A-127007.1 |
| AD-63364.1 | CUGGUGAUGAGCUCCUUGAdTdT | 1124 | A-127009.1 |
| AD-63370.1 | UUCCCAGGCGGGUGCUGGUdTdT | 1125 | A-127011.1 |
| AD-63376.1 | UUGUAGUAAGUUCCCAGGCdTdT | 1126 | A-127013.1 |
| AD-63382.1 | CUGGAGUUGUAGUAAGUUCdTdT | 1127 | A-127015.1 |
| AD-63341.1 | AAUAGACGGAGCUGGAGUUdTdT | 1128 | A-127017.1 |
| AD-63347.1 | UCCCAAAGGAAUAGACGGdTdT | 1129 | A-127019.1 |
| AD-63353.1 | GUGAGGGGUCCCUCCCCAAdTdT | 1130 | A-127021.1 |
| AD-63359.1 | AGAAGAAGCAGGUGAGGGGdTdT | 1131 | A-127023.1 |
| AD-63365.1 | AAUGAACCAGAAGAAGCAGdTdT | 1132 | A-127025.1 |
| AD-63371.1 | GAUUUGGAGAAUGAACCAGdTdT | 1133 | A-127027.1 |
| AD-63377.1 | GUGCUCGGGGAUUUGGAGAdTdT | 1134 | A-127029.1 |
| AD-63383.1 | AUCAGCCGGCGGUGCUCGGdTdT | 1135 | A-127031.1 |
| AD-63342.1 | UCGGGGCUCAGCAUCAGCCdTdT | 1136 | A-127033.1 |

TABLE 12-continued

Additional modified TMPRSS6 siRNAs

| | | | |
|---|---|---|---|
| AD-63348.1 | UGCACCACCUCGGGGCUCAdTdT | 1137 | A-127035.1 |
| AD-63354.1 | ACCAGCAGUGCCUGCACCAdTdT | 1138 | A-127037.1 |
| AD-63360.1 | UCCUCCACCAGCAGUGCCUdTdT | 1139 | A-127039.1 |
| AD-63366.1 | UGGACAGCAGCUCCUCCACdTdT | 1140 | A-127041.1 |
| AD-63372.1 | GAGCUGUUGACUGUGGACAdTdT | 1141 | A-127043.1 |
| AD-63378.1 | ACGGCAGCCGAGCUGUUGAdTdT | 1142 | A-127045.1 |
| AD-63384.1 | UGUAGGGGACGGCAGCCGAdTdT | 1143 | A-127047.1 |
| AD-63390.1 | UAGGCCCUCGGGGUCCACUdTdT | 1144 | A-127049.1 |
| AD-63396.1 | UCCAGGAUCACUAGGCCCUdTdT | 1145 | A-127051.1 |
| AD-63402.1 | CUGGCUUCCAGGAUCACUAdTdT | 1146 | A-127053.1 |
| AD-63408.1 | AUGUCUUUCACACUGGCUUdTdT | 1147 | A-127055.1 |
| AD-63414.1 | AAUGCAGCUAUGUCUUUCAdTdT | 1148 | A-127057.1 |
| AD-63420.1 | CAGCGUGGAAUUCAAUGCAdTdT | 1149 | A-127059.1 |
| AD-63426.1 | CUGGCCCACGUAGCUGUAGdTdT | 1150 | A-127061.1 |
| AD-63385.1 | CUGGCCCUGGCCCACGUAGdTdT | 1151 | A-127063.1 |
| AD-63391.1 | AGCCGGAGGACCUGGCCCUdTdT | 1152 | A-127065.1 |
| AD-63397.1 | GUCAGGCCCCUUCAGCCGGdTdT | 1153 | A-127067.1 |
| AD-63403.1 | AGGCCAGGUGGUCAGGCCCdTdT | 1154 | A-127069.1 |
| AD-63409.1 | GCAGCUGGAGGCCAGGUGGdTdT | 1155 | A-127071.1 |
| AD-63415.1 | AGGUGCCACAGGCAGCUGGdTdT | 1156 | A-127073.1 |
| AD-63421.1 | GGCCCUGCAGGUGCCACAGdTdT | 1157 | A-127075.1 |
| AD-63427.1 | GGUCCUUGGGGCCCUGCAGdTdT | 1158 | A-127077.1 |
| AD-63386.1 | UUGAGCAUGAGGUCCUUGGdTdT | 1159 | A-127079.1 |
| AD-63392.1 | UCCAGCCGGAGUUUGAGCAdTdT | 1160 | A-127081.1 |
| AD-63398.1 | CAGCGUCCACUCCAGCCGGdTdT | 1161 | A-127083.1 |
| AD-63404.1 | CCGGCACUCUGCCAGCGUCdTdT | 1162 | A-127085.1 |
| AD-63410.1 | UCGGUCCCGGCACUCUGCCdTdT | 1163 | A-127087.1 |
| AD-63416.1 | UCAUACAUGGCCAGUCGGUdTdT | 1164 | A-127089.1 |
| AD-63422.1 | CCGGCCACGUCAUACAUGGdTdT | 1165 | A-127091.1 |
| AD-63428.1 | UCUCCAGGGGCCCGGCCACdTdT | 1166 | A-127093.1 |
| AD-63387.1 | AUGAGCCUCUUCUCCAGGGdTdT | 1167 | A-127095.1 |
| AD-63393.1 | GAGGUGAUGAGCCUCUUCUdTdT | 1168 | A-127097.1 |
| AD-63399.1 | UGCAGCCGUACACCGAGGUdTdT | 1169 | A-127099.1 |
| AD-63405.1 | UCCUGGCGGCUGCAGCCGUdTdT | 1170 | A-127101.1 |
| AD-63411.1 | ACCACGGGCUCCUGGCGGCdTdT | 1171 | A-127103.1 |
| AD-63417.1 | AGAACCUCCACCACGGGCUdTdT | 1172 | A-127105.1 |
| AD-63423.1 | CCGACGCCAGAACCUCCACdTdT | 1173 | A-127107.1 |
| AD-63429.1 | AUGAUGGCCCCCGACGCCAdTdT | 1174 | A-127109.1 |
| AD-63388.1 | CAGACGACCGCCAUGAUGGdTdT | 1175 | A-127111.1 |

TABLE 12-continued

Additional modified TMPRSS6 siRNAs

| | | | |
|---|---|---|---|
| AD-63394.1 | CCUUCUUCCAGACGACCGCdTdT | 1176 | A-127113.1 |
| AD-63400.1 | CUGUGCAGGCCCUUCUUCCdTdT | 1177 | A-127115.1 |
| AD-63406.1 | GUCGUAGUAGCUGUGCAGGdTdT | 1178 | A-127117.1 |
| AD-63412.1 | AGCACGAAGGGGUCGUAGUdTdT | 1179 | A-127119.1 |
| AD-63418.1 | UGCACGGAGAGCACGAAGGdTdT | 1180 | A-127121.1 |
| AD-63424.1 | AAGACCACCGGCUGCACGGdTdT | 1181 | A-127123.1 |
| AD-63430.1 | CAGGCCUGGAAGACCACCGdTdT | 1182 | A-127125.1 |
| AD-63389.1 | AGGUUCACUUCACAGGCCUdTdT | 1183 | A-127127.1 |
| AD-63395.1 | UCCAGCGUCAGGUUCACUUdTdT | 1184 | A-127129.1 |
| AD-63401.1 | GAGCCUGUUGUCCAGCGUCdTdT | 1185 | A-127131.1 |
| AD-63407.1 | UGGGAGUCGAGCCUGUUGUdTdT | 1186 | A-127133.1 |
| AD-63413.1 | CUGAGGACGCCCUGGGAGUdTdT | 1187 | A-127135.1 |
| AD-63419.1 | UAGCUGGGGAAGUACGGGGdTdT | 1188 | A-127137.1 |
| AD-63425.1 | GCGAGUAGUAGCUGGGGAAdTdT | 1189 | A-127139.1 |
| AD-63431.1 | UGGGUUUGGGGCGAGUAGUdTdT | 1190 | A-127141.1 |
| AD-63437.1 | CAGGAGCAGUGGGUUUGGGdTdT | 1191 | A-127143.1 |
| AD-63443.1 | ACCGUGAGGUGCCAGGAGCdTdT | 1192 | A-127145.1 |
| AD-63449.1 | AGAGAGGGCACCGUGAGGUdTdT | 1193 | A-127147.1 |
| AD-63455.1 | CAAGCCGUAGUCCAGAGAGdTdT | 1194 | A-127149.1 |
| AD-63461.1 | AGAGGGCCAAGCCGUAGUCdTdT | 1195 | A-127151.1 |
| AD-63467.1 | UAGGCAUCAAACCAGAGGGdTdT | 1196 | A-127153.1 |
| AD-63473.1 | CAGUGCAUAGGCAUCAAACdTdT | 1197 | A-127155.1 |
| AD-63432.1 | ACUUCUGCCUCCUCAGUGCdTdT | 1198 | A-127157.1 |
| AD-63438.1 | AAAUCAUACUUCUGCCUCCdTdT | 1199 | A-127159.1 |
| AD-63444.1 | UGGGUGCACGGCAAAUCAUdTdT | 1200 | A-127161.1 |
| AD-63450.1 | UCCACUGGCCCUGGGUGCAdTdT | 1201 | A-127163.1 |
| AD-63456.1 | UUCUGGAUCGUCCACUGGCdTdT | 1202 | A-127165.1 |
| AD-63462.1 | CUCCUGUUCUGGAUCGUCCdTdT | 1203 | A-127167.1 |
| AD-63468.1 | AAGCCACACAGCCUCCUGUdTdT | 1204 | A-127169.1 |
| AD-63474.1 | GGAUGCGCAAGCCACACAGdTdT | 1205 | A-127171.1 |
| AD-63433.1 | UAGGGCUGCAGGAUGCGCAdTdT | 1206 | A-127173.1 |
| AD-63439.1 | AUCCUCUCGGCGUAGGGCUdTdT | 1207 | A-127175.1 |
| AD-63445.1 | ACCACGGGGAUCCUCUCGGdTdT | 1208 | A-127177.1 |
| AD-63451.1 | CCGGCCGUGGCCACCACGGdTdT | 1209 | A-127179.1 |
| AD-63457.1 | AUGGUGAUCCCGGCCGUGGdTdT | 1210 | A-127181.1 |
| AD-63463.1 | GUGAAGUUGAUGGUGAUCCdTdT | 1211 | A-127183.1 |
| AD-63469.1 | AUCUGGGAGGUGAAGUUGAdTdT | 1212 | A-127185.1 |
| AD-63475.1 | CCGGUGAGGGAGAUCUGGGdTdT | 1213 | A-127187.1 |
| AD-63434.1 | ACACCGGGCCCGGUGAGGGdTdT | 1214 | A-127189.1 |

TABLE 12-continued

Additional modified TMPRSS6 siRNAs

| | | | |
|---|---|---|---|
| AD-63440.1 | AGUGCACCCGCACACCGGGdTdT | 1215 | A-127191.1 |
| AD-63446.1 | UCCGACUGGUUGUACAAGCdTdT | 1216 | A-127193.1 |
| AD-63452.1 | CAGGGGUCCGACUGGUUGUdTdT | 1217 | A-127195.1 |
| AD-63458.1 | AACUCUCCAGGGCAGGGGUdTdT | 1218 | A-127197.1 |
| AD-63464.1 | AACAGAGGAACUCUCCAGGdTdT | 1219 | A-127199.1 |
| AD-63470.1 | AGUCCAUUCACAGAACAGAdTdT | 1220 | A-127201.1 |
| AD-63476.1 | AGGGACACAGAGUCCAUUCdTdT | 1221 | A-127203.1 |
| AD-63435.1 | AUCACAGGCAGGGACACAGdTdT | 1222 | A-127205.1 |
| AD-63441.1 | UUGACCCCAUCACAGGCAGdTdT | 1223 | A-127207.1 |
| AD-63447.1 | GUUGGGGCAGUCCUUGACCdTdT | 1224 | A-127209.1 |
| AD-63453.1 | CAUCCAGGCCGUUGGGGCAdTdT | 1225 | A-127211.1 |
| AD-63459.1 | GUUUCUCUCAUCCAGGCCGdTdT | 1226 | A-127213.1 |
| AD-63465.1 | UGCAAACGCAGUUUCUCUCdTdT | 1227 | A-127215.1 |
| AD-63471.1 | UGGAAUGUGGCUCUGCAAAdTdT | 1228 | A-127217.1 |
| AD-63477.1 | CUUUGCACUGGAAUGUGGCdTdT | 1229 | A-127219.1 |
| AD-63436.1 | UGUGCUGUCCUCUUUGCACdTdT | 1230 | A-127221.1 |
| AD-63442.1 | AGAUGCAUGUGCUGUCCUCdTdT | 1231 | A-127223.1 |
| AD-63448.1 | ACCUUGGGCAGUGAGAUGCdTdT | 1232 | A-127225.1 |
| AD-63454.1 | CCCAUCACAGACCUUGGGCdTdT | 1233 | A-127227.1 |
| AD-63460.1 | AAUCAGGCUGCCCAUCACAdTdT | 1234 | A-127229.1 |
| AD-63466.1 | GUUGAGACAAUCAGGCUGCdTdT | 1235 | A-127231.1 |
| AD-63472.1 | UCGUCGCUGCCGUUGAGACdTdT | 1236 | A-127233.1 |
| AD-63478.1 | UGGCACUGCUCUUCGUCGCdTdT | 1237 | A-127235.1 |
| AD-63484.1 | ACCCCUUCCUGGCACUGCUdTdT | 1238 | A-127237.1 |
| AD-63490.1 | UCCCACAUGGCACCCCUUCdTdT | 1239 | A-127239.1 |
| AD-63496.1 | AGGUGAAUGUCCCACAUGGdTdT | 1240 | A-127241.1 |
| AD-63502.1 | UCACACUGGAAGGUGAAUGdTdT | 1241 | A-127243.1 |
| AD-63508.1 | AGCUCCGGUCCUCACACUGdTdT | 1242 | A-127245.1 |
| AD-63514.1 | UCUUCACGCAGCUCCGGUCdTdT | 1243 | A-127247.1 |
| AD-63520.1 | GUUGGGCUUCUUCACGCAGdTdT | 1244 | A-127249.1 |
| AD-63479.1 | UCACACUGCGGGUUGGGCUdTdT | 1245 | A-127251.1 |
| AD-63485.1 | CGGGCCGCCCAUCACACUGdTdT | 1246 | A-127253.1 |
| AD-63491.1 | GUCCCUGCAGUCGGGCCGCdTdT | 1247 | A-127255.1 |
| AD-63497.1 | AUCCGAGCCGUCCCUGCAGdTdT | 1248 | A-127257.1 |
| AD-63503.1 | UGCUCCUCAUCCGAGCCGUdTdT | 1249 | A-127259.1 |
| AD-63509.1 | ACAGUCACAGUGCUCCUCAdTdT | 1250 | A-127261.1 |
| AD-63515.1 | CUGGAGGCCACAGUCACAGdTdT | 1251 | A-127263.1 |
| AD-63521.1 | CUGGAGGGGCCCUGGAGGCdTdT | 1252 | A-127265.1 |
| AD-63480.1 | AACAAUGCGGCUGGAGGGGdTdT | 1253 | A-127267.1 |

TABLE 12-continued

Additional modified TMPRSS6 siRNAs

| | | | |
|---|---|---|---|
| AD-63486.1 | AGCUCCACCAACAAUGCGGdTdT | 1254 | A-127269.1 |
| AD-63492.1 | UCGGAGGACACAGCUCCACdTdT | 1255 | A-127271.1 |
| AD-63498.1 | UGGCCACUCACCCUCGGAGdTdT | 1256 | A-127273.1 |
| AD-63504.1 | CUGCCAUGGCCACUCACCCdTdT | 1257 | A-127275.1 |
| AD-63510.1 | CUGGAGGCUGGCCUGCCAUdTdT | 1258 | A-127277.1 |
| AD-63516.1 | UCGACCCCGAACCUGGAGGdTdT | 1259 | A-127279.1 |
| AD-63522.1 | GAUGUGUCGACCCCGAACCdTdT | 1260 | A-127281.1 |
| AD-63481.1 | AGGGCCCCCCCACAGAUGUdTdT | 1261 | A-127283.1 |
| AD-63487.1 | GCGAUGAGGGCCCCCCCACdTdT | 1262 | A-127285.1 |
| AD-63493.1 | UCACCCAGCGGUCAGCGAUdTdT | 1263 | A-127287.1 |
| AD-63499.1 | GCUGUUAUCACCCAGCGGUdTdT | 1264 | A-127289.1 |
| AD-63505.1 | CAGUGGGCAGCUGUUAUCAdTdT | 1265 | A-127291.1 |
| AD-63511.1 | UCCUCCUGGAAGCAGUGGGdTdT | 1266 | A-127293.1 |
| AD-63517.1 | GGCCAUGCUGUCCUCCUGGdTdT | 1267 | A-127295.1 |
| AD-63523.1 | ACCGUGGAGGCCAUGCUGUdTdT | 1268 | A-127297.1 |
| AD-63482.1 | ACGGUCCACAGCACCGUGGdTdT | 1269 | A-127299.1 |
| AD-63488.1 | UUGCCCAGGAACACGGUCCdTdT | 1270 | A-127301.1 |
| AD-63494.1 | UGCCACACCUUGCCCAGGAdTdT | 1271 | A-127303.1 |
| AD-63500.1 | AGCGCGAGUUCUGCCACACdTdT | 1272 | A-127305.1 |
| AD-63506.1 | UCCAGGCCAGCGCGAGUUCdTdT | 1273 | A-127307.1 |
| AD-63512.1 | AAGGACACCUCUCCAGGCCdTdT | 1274 | A-127309.1 |
| AD-63518.1 | CUCACCUUGAAGGACACCUdTdT | 1275 | A-127311.1 |
| AD-63524.1 | GAGCAGGCGGCUCACCUUGdTdT | 1276 | A-127313.1 |
| AD-63483.1 | UACGGGUGCAGGAGCAGGCdTdT | 1277 | A-127315.1 |
| AD-63489.1 | CUCUUCGUGGUACGGGUGCdTdT | 1278 | A-127317.1 |
| AD-63495.1 | AUGGCUGUCCUCUUCGUGGdTdT | 1279 | A-127319.1 |
| AD-63501.1 | UCGUAGUCAUGGCUGUCCUdTdT | 1280 | A-127321.1 |
| AD-63507.1 | AGCAGCGCCACGUCGUAGUdTdT | 1281 | A-127323.1 |
| AD-63513.1 | UCGAGCUGCAGCAGCGCCAdTdT | 1282 | A-127325.1 |
| AD-63519.1 | ACCACCGGGUGGUCGAGCUdTdT | 1283 | A-127327.1 |
| AD-63525.1 | CGGCCGAGCGCACCACCGGdTdT | 1284 | A-127329.1 |
| AD-63531.1 | CGCACGGCGGCCGAGCGCAdTdT | 1285 | A-127331.1 |
| AD-63537.1 | AGGCAGACGGGGCGCACGGdTdT | 1286 | A-127333.1 |
| AD-63543.1 | CGCGCGGGCAGGCAGACGGdTdT | 1287 | A-127335.1 |
| AD-63549.1 | AAGAAGUGGGAGCGCGCGGdTdT | 1288 | A-127337.1 |
| AD-63555.1 | CCGGGCUCGAAGAAGUGGGdTdT | 1289 | A-127339.1 |
| AD-63561.1 | AGCAGUGCAGGCCGGGCUCdTdT | 1290 | A-127341.1 |
| AD-63567.1 | UAAUCCAGCAGUGCAGGCCdTdT | 1291 | A-127343.1 |
| AD-63526.1 | CGCCCCAGCCCGUAAUCCAdTdT | 1292 | A-127345.1 |

TABLE 12-continued

Additional modified TMPRSS6 siRNAs

| | | | |
|---|---|---|---|
| AD-63532.1 | UCGCGCAAGGCGCCCCAGCdTdT | 1293 | A-127347.1 |
| AD-63538.1 | AUGGGGCCGCCCUCGCGCAdTdT | 1294 | A-127349.1 |
| AD-63544.1 | UUGCUGAUGGGGCCGCCCUdTdT | 1295 | A-127351.1 |
| AD-63550.1 | UUCUGCAGAGCGUUGCUGAdTdT | 1296 | A-127353.1 |
| AD-63556.1 | UGCACAUCCACUUUCUGCAdTdT | 1297 | A-127355.1 |
| AD-63562.1 | AUCAACUGCACAUCCACUUdTdT | 1298 | A-127357.1 |
| AD-63568.1 | GUCCUGUGGGAUCAACUGCdTdT | 1299 | A-127359.1 |
| AD-63527.1 | UCGCUGCACAGGUCCUGUGdTdT | 1300 | A-127361.1 |
| AD-63533.1 | UAGCGAUAGACCUCGCUGCdTdT | 1301 | A-127363.1 |
| AD-63539.1 | UCACCUGGUAGCGAUAGACdTdT | 1302 | A-127365.1 |
| AD-63545.1 | CAUGCGUGGCGUCACCUGGdTdT | 1303 | A-127367.1 |
| AD-63551.1 | CGGCACACAGCAUGCGUGGdTdT | 1304 | A-127369.1 |
| AD-63557.1 | UGCGGUAGCCGGCACACAGdTdT | 1305 | A-127371.1 |
| AD-63563.1 | UCCUUCUUGCCCUUGCGGUdTdT | 1306 | A-127373.1 |
| AD-63569.1 | UGACAGGCAUCCUUCUUGCdTdT | 1307 | A-127375.1 |
| AD-63528.1 | CUGAGUCACCCUGACAGGCdTdT | 1308 | A-127377.1 |
| AD-63534.1 | AGCGGACCACCUGAGUCACdTdT | 1309 | A-127379.1 |
| AD-63540.1 | UUGCACACCAGCGGACCACdTdT | 1310 | A-127381.1 |
| AD-63546.1 | CUGAGUGCCUUGCACACCAdTdT | 1311 | A-127383.1 |
| AD-63552.1 | ACCAGCGGCCACUGAGUGCdTdT | 1312 | A-127385.1 |
| AD-63558.1 | CCCGCCAGGAACCAGCGGCdTdT | 1313 | A-127387.1 |
| AD-63564.1 | CUGACCAGCCCCGCCAGGAdTdT | 1314 | A-127389.1 |
| AD-63570.1 | CAGGCCCCAGCUGACCAGCdTdT | 1315 | A-127391.1 |
| AD-63529.1 | CCGGCCACAGCCCAGGCCCdTdT | 1316 | A-127393.1 |
| AD-63535.1 | AGUUAGGCCGGCCACAGCCdTdT | 1317 | A-127395.1 |
| AD-63541.1 | UAGACGCCGAAGUAGUUAGdTdT | 1318 | A-127397.1 |
| AD-63547.1 | GAUGCGGGUGUAGACGCCGdTdT | 1319 | A-127399.1 |
| AD-63553.1 | ACACCUGUGAUGCGGGUGUdTdT | 1320 | A-127401.1 |
| AD-63559.1 | UCCAGCUGAUCACACCUGUdTdT | 1321 | A-127403.1 |
| AD-63565.1 | ACUUGCUGGAUCCAGCUGAdTdT | 1322 | A-127405.1 |
| AD-63571.1 | CUCAGGUCACCACUUGCUGdTdT | 1323 | A-127407.1 |
| AD-63530.1 | GGGGCAGUUCCUCAGGUCAdTdT | 1324 | A-127409.1 |
| AD-63536.1 | UUUGCAGGGGGGCAGUUCCdTdT | 1325 | A-127411.1 |
| AD-63542.1 | GGUGGGCCCUGCUUUGCAGdTdT | 1326 | A-127413.1 |
| AD-63548.1 | UCCAGGAGGUGGGCCCUGCdTdT | 1327 | A-127415.1 |
| AD-63554.1 | GCUCUCUGAGUCCAGGAGGdTdT | 1328 | A-127417.1 |
| AD-63560.1 | UUGCCCUGGGCUCUCUGAGdTdT | 1329 | A-127419.1 |
| AD-63566.1 | UGCUUGGCAGUUGCCCUGGdTdT | 1330 | A-127421.1 |
| AD-63572.1 | CCCGCCAGAAUACUUGUCCdTdT | 1331 | A-127423.1 |

TABLE 12-continued

Additional modified TMPRSS6 siRNAs

| | | | |
|---|---|---|---|
| AD-63578.1 | CUCCCCCACCCCCCGCCAGdTdT | 1332 | A-127425.1 |
| AD-63584.1 | CCUGCUCUCUCCCCCACCCdTdT | 1333 | A-127427.1 |
| AD-63590.1 | ACCACAGGGCCUGCUCUCUdTdT | 1334 | A-127429.1 |
| AD-63596.1 | ACCUCCUGCCACCACAGGGdTdT | 1335 | A-127431.1 |
| AD-63602.1 | GAGACAAGAUGCCACCUCCdTdT | 1336 | A-127433.1 |
| AD-63608.1 | UCAGGGACGAGACAAGAUGdTdT | 1337 | A-127435.1 |
| AD-63614.1 | ACUGGAGCAGACAUCAGGGdTdT | 1338 | A-127437.1 |
| AD-63573.1 | CCUGCCAUCACUGGAGCAGdTdT | 1339 | A-127439.1 |
| AD-63579.1 | UUCUCCAUCCUCCUGCCAUdTdT | 1340 | A-127441.1 |
| AD-63585.1 | UGCUGGCACUUCUCCAUCCdTdT | 1341 | A-127443.1 |
| AD-63591.1 | UGACCCCCAGCUGCUGGCAdTdT | 1342 | A-127445.1 |
| AD-63597.1 | GACGUCUUGACCCCCAGCUdTdT | 1343 | A-127447.1 |
| AD-63603.1 | UCCUCAGGGGACGUCUUGAdTdT | 1344 | A-127449.1 |
| AD-63609.1 | UGGGCCUGGGUCCUCAGGGdTdT | 1345 | A-127451.1 |
| AD-63615.1 | AGAAGGGCUGGGUGUGGGCdTdT | 1346 | A-127453.1 |
| AD-63574.1 | AUUGGGAGGCAGAAGGGCUdTdT | 1347 | A-127455.1 |
| AD-63580.1 | AGGAGAGAGAAUUGGGAGGdTdT | 1348 | A-127457.1 |
| AD-63586.1 | AAGGGGACGGAGGAGAGAGdTdT | 1349 | A-127459.1 |
| AD-63592.1 | AGUGGAGGAAGGGGACGGAdTdT | 1350 | A-127461.1 |
| AD-63598.1 | UAGGCAGCAGUGGAGGAAGdTdT | 1351 | A-127463.1 |
| AD-63604.1 | ACUGCCUUGCAUUAGGCAGdTdT | 1352 | A-127465.1 |
| AD-63610.1 | UGCUGAGCCACUGCCUUGCdTdT | 1353 | A-127467.1 |
| AD-63616.1 | CAUUCUUGCUGCUGAGCCAdTdT | 1354 | A-127469.1 |
| AD-63575.1 | UGUAGAACCAGCAUUCUUGdTdT | 1355 | A-127471.1 |
| AD-63581.1 | UCCUCGGGAUGUAGAACCAdTdT | 1356 | A-127473.1 |
| AD-63587.1 | ACCUCAGACACUCCUCGGGdTdT | 1357 | A-127475.1 |
| AD-63593.1 | AGUGGGGCGCACCUCAGACdTdT | 1358 | A-127477.1 |
| AD-63599.1 | CCUCUGUACAGAGUGGGGCdTdT | 1359 | A-127479.1 |
| AD-63605.1 | CCAAACAGCCUCUGUACAGdTdT | 1360 | A-127481.1 |
| AD-63611.1 | GGCAAGGCUGCCCAAACAGdTdT | 1361 | A-127483.1 |
| AD-63617.1 | UCUGCUCUCUGGAGGCAAGdTdT | 1362 | A-127485.1 |
| AD-63576.1 | CUGGAAUCUGCUCUCUGGAdTdT | 1363 | A-127487.1 |
| AD-63582.1 | GGCUUCCGAAGCUGGAAUCdTdT | 1364 | A-127489.1 |
| AD-63588.1 | AUGGGAGCACCUUCCAUUCdTdT | 1365 | A-127491.1 |
| AD-63594.1 | UCCCCUCCGAUGGGAGCACdTdT | 1366 | A-127493.1 |
| AD-63600.1 | CUCUGAGGGUCCCCUCCGAdTdT | 1367 | A-127495.1 |
| AD-63606.1 | GUCUCCAGGGCUCUGAGGGdTdT | 1368 | A-127497.1 |
| AD-63612.1 | AGGCCCACCUGGCAGUCUCdTdT | 1369 | A-127499.1 |
| AD-63618.1 | AGUGGCAGCAGGCCCACCUdTdT | 1370 | A-127501.1 |

TABLE 12-continued

Additional modified TMPRSS6 siRNAs

| | | | |
|---|---|---|---|
| AD-63577.1 | UUUUGGCUUACAGUGGCAGdTdT | 1371 | A-127503.1 |
| AD-63583.1 | CCCACCUUUUGGCUUACAGdTdT | 1372 | A-127505.1 |
| AD-63589.1 | GGAGUCAGGACUUCCCCACdTdT | 1373 | A-127507.1 |
| AD-63595.1 | CAAGGACCCUGGAGUCAGGdTdT | 1374 | A-127509.1 |
| AD-63601.1 | AGGGGUGGGGCAAGGACCCdTdT | 1375 | A-127511.1 |
| AD-63607.1 | UGGCAGGCAGGGGUGGGGCdTdT | 1376 | A-127513.1 |
| AD-63613.1 | UGAGGGCCCAGGUGGCAGGdTdT | 1377 | A-127515.1 |
| AD-63619.1 | CUGGGCUGUGAGGGCCCAGdTdT | 1378 | A-127517.1 |
| AD-63620.1 | GUGAGGGUCUGGGCUGUGAdTdT | 1379 | A-127519.1 |
| AD-63621.1 | GAGCUCACCUCCCAGUGAGdTdT | 1380 | A-127521.1 |
| AD-63622.1 | AAGGGCAGCUGAGCUCACCdTdT | 1381 | A-127523.1 |
| AD-63623.1 | AUCAGGCAGCUUUAUUCCAdTdT | 1382 | A-127525.1 |

TABLE 13

TMPRSS6 single dose screen (10 nM) in Hep3B cells with dT modified siRNAs

| Duplex ID | Avg % message remaining | SD |
|---|---|---|
| AD-63290.1 | 122.8 | 18.0 |
| AD-63296.1 | 87.4 | 6.0 |
| AD-63302.1 | 71.4 | 16.9 |
| AD-63308.1 | 82.1 | 10.3 |
| AD-63314.1 | 59.1 | 5.3 |
| AD-63320.1 | 90.7 | 4.5 |
| AD-63326.1 | 121.0 | 18.2 |
| AD-63332.1 | 114.4 | 11.6 |
| AD-63291.1 | 84.7 | 15.0 |
| AD-63297.1 | 82.8 | 3.9 |
| AD-63303.1 | 67.6 | 5.5 |
| AD-63309.1 | 55.8 | 6.5 |
| AD-63315.1 | 64.2 | 7.4 |
| AD-63321.1 | 85.8 | 6.4 |
| AD-63327.1 | 91.9 | 14.9 |
| AD-63333.1 | 76.4 | 5.2 |
| AD-63292.1 | 54.4 | 22.9 |
| AD-63298.1 | 54.6 | 5.0 |
| AD-63304.1 | 24.6 | 7.3 |
| AD-63310.1 | 23.3 | 0.6 |
| AD-63316.1 | 50.9 | 7.2 |
| AD-63322.1 | 53.7 | 10.5 |
| AD-63328.1 | 29.2 | 2.3 |
| AD-63334.1 | 28.5 | 1.2 |
| AD-63293.1 | 50.9 | 6.8 |
| AD-63299.1 | 85.5 | 2.3 |
| AD-63305.1 | 43.0 | 7.2 |
| AD-63311.1 | 28.9 | 2.6 |
| AD-63317.1 | 40.9 | 2.7 |
| AD-63323.1 | 40.2 | 7.3 |
| AD-63329.1 | 27.9 | 12.0 |
| AD-63335.1 | 82.0 | 4.2 |
| AD-63294.1 | 21.8 | 1.0 |
| AD-63300.1 | 32.3 | 8.0 |
| AD-63306.1 | 32.9 | 8.3 |
| AD-63312.1 | 26.5 | 4.6 |
| AD-63318.1 | 31.3 | 2.4 |
| AD-63324.1 | 25.7 | 1.9 |
| AD-63330.1 | 24.5 | 2.0 |
| AD-63336.1 | 36.1 | 8.6 |
| AD-63295.1 | 29.2 | 1.8 |
| AD-63301.1 | 28.9 | 5.2 |
| AD-63307.1 | 68.8 | 10.6 |
| AD-63313.1 | 90.2 | 8.2 |
| AD-63319.1 | 21.9 | 3.3 |
| AD-63325.1 | 26.1 | 4.8 |
| AD-63331.1 | 36.7 | 4.5 |
| AD-63337.1 | 67.7 | 9.3 |
| AD-63343.1 | 83.9 | 15.0 |
| AD-63349.1 | 71.6 | 3.5 |
| AD-63355.1 | 62.8 | 10.4 |
| AD-63361.1 | 56.0 | 3.3 |
| AD-63367.1 | 49.3 | 8.7 |
| AD-63373.1 | 54.1 | 8.2 |
| AD-63379.1 | 47.5 | 6.3 |
| AD-63338.1 | 28.0 | 2.8 |
| AD-63344.1 | 29.7 | 5.7 |
| AD-63350.1 | 23.0 | 2.3 |
| AD-63356.1 | 81.5 | 13.7 |
| AD-63362.1 | 19.7 | 2.9 |
| AD-63368.1 | 42.2 | 4.7 |
| AD-63374.1 | 24.5 | 2.0 |
| AD-63380.1 | 24.9 | 4.9 |
| AD-63339.1 | 28.9 | 10.1 |
| AD-63345.1 | 29.9 | 5.6 |
| AD-63351.1 | 20.4 | 3.7 |
| AD-63357.1 | 35.8 | 6.8 |
| AD-63363.1 | 30.4 | 2.5 |
| AD-63369.1 | 29.0 | 3.1 |
| AD-63375.1 | 36.6 | 2.4 |
| AD-63381.1 | 29.1 | 4.3 |
| AD-63340.1 | 40.4 | 18.8 |
| AD-63346.1 | 36.4 | 3.5 |
| AD-63352.1 | 25.8 | 3.9 |
| AD-63358.1 | 42.6 | 8.1 |
| AD-63364.1 | 48.1 | 6.6 |
| AD-63370.1 | 24.6 | 2.8 |
| AD-63376.1 | 22.1 | 4.2 |
| AD-63382.1 | 31.0 | 7.5 |
| AD-63341.1 | 37.6 | 13.7 |
| AD-63347.1 | 27.6 | 2.0 |
| AD-63353.1 | 76.4 | 14.5 |
| AD-63359.1 | 25.3 | 1.1 |
| AD-63365.1 | 27.3 | 3.4 |
| AD-63371.1 | 16.3 | 1.3 |
| AD-63377.1 | 65.4 | 7.1 |
| AD-63383.1 | 72.2 | 7.0 |
| AD-63342.1 | 30.8 | 7.3 |

TABLE 13-continued

TMPRSS6 single dose screen (10 nM) in Hep3B cells with dT modified siRNAs

| Duplex ID | Avg % message remaining | SD |
|---|---|---|
| AD-63348.1 | 72.7 | 9.2 |
| AD-63354.1 | 38.7 | 5.0 |
| AD-63360.1 | 28.7 | 3.0 |
| AD-63366.1 | 30.9 | 6.8 |
| AD-63372.1 | 84.0 | 9.0 |
| AD-63378.1 | 64.1 | 8.6 |
| AD-63384.1 | 38.0 | 2.6 |
| AD-63390.1 | 48.3 | 10.6 |
| AD-63396.1 | 45.6 | 7.0 |
| AD-63402.1 | 42.0 | 9.9 |
| AD-63408.1 | 40.4 | 9.1 |
| AD-63414.1 | 23.8 | 6.2 |
| AD-63420.1 | 55.3 | 5.2 |
| AD-63426.1 | 61.6 | 8.5 |
| AD-63385.1 | 61.6 | 10.2 |
| AD-63391.1 | 38.0 | 3.1 |
| AD-63397.1 | 66.7 | 16.8 |
| AD-63403.1 | 77.2 | 15.4 |
| AD-63409.1 | 60.3 | 10.7 |
| AD-63415.1 | 35.0 | 5.4 |
| AD-63421.1 | 60.6 | 2.9 |
| AD-63427.1 | 40.5 | 7.2 |
| AD-63386.1 | 42.0 | 7.4 |
| AD-63392.1 | 34.2 | 3.1 |
| AD-63398.1 | 62.6 | 18.5 |
| AD-63404.1 | 65.9 | 8.1 |
| AD-63410.1 | 19.7 | 4.0 |
| AD-63416.1 | 51.3 | 9.0 |
| AD-63422.1 | 59.3 | 2.7 |
| AD-63428.1 | 58.2 | 9.7 |
| AD-63387.1 | 42.2 | 4.8 |
| AD-63393.1 | 27.9 | 4.4 |
| AD-63399.1 | 49.6 | 8.4 |
| AD-63405.1 | 72.5 | 9.3 |
| AD-63411.1 | 45.4 | 14.9 |
| AD-63417.1 | 36.7 | 9.4 |
| AD-63423.1 | 76.8 | 4.9 |
| AD-63429.1 | 77.8 | 14.4 |
| AD-63388.1 | 37.4 | 4.4 |
| AD-63394.1 | 31.5 | 4.6 |
| AD-63400.1 | 60.9 | 28.6 |
| AD-63406.1 | 40.7 | 14.3 |
| AD-63412.1 | 22.0 | 7.0 |
| AD-63418.1 | 22.8 | 4.3 |
| AD-63424.1 | 25.5 | 2.8 |
| AD-63430.1 | 21.5 | 3.2 |
| AD-63389.1 | 34.4 | 5.3 |
| AD-63395.1 | 31.1 | 0.7 |
| AD-63401.1 | 44.3 | 9.5 |
| AD-63407.1 | 41.5 | 4.9 |
| AD-63413.1 | 52.4 | 6.4 |
| AD-63419.1 | 26.3 | 5.6 |
| AD-63425.1 | 78.8 | 4.6 |
| AD-63431.1 | 32.8 | 6.6 |
| AD-63437.1 | 42.3 | 1.4 |
| AD-63443.1 | 56.4 | 8.9 |
| AD-63449.1 | 26.0 | 5.9 |
| AD-63455.1 | 28.0 | 9.7 |
| AD-63461.1 | 32.1 | 11.1 |
| AD-63467.1 | 33.8 | 19.8 |
| AD-63473.1 | 28.9 | 3.4 |
| AD-63432.1 | 36.5 | 7.4 |
| AD-63438.1 | 27.3 | 4.3 |
| AD-63444.1 | 54.6 | 36.0 |
| AD-63450.1 | 42.0 | 6.1 |
| AD-63456.1 | 36.6 | 10.2 |
| AD-63462.1 | 23.3 | 3.0 |
| AD-63468.1 | 48.8 | 27.3 |
| AD-63474.1 | 23.8 | 3.2 |
| AD-63433.1 | 51.8 | 13.8 |
| AD-63439.1 | 41.7 | 5.5 |
| AD-63445.1 | 74.6 | 6.1 |
| AD-63451.1 | 49.6 | 9.0 |
| AD-63457.1 | 26.7 | 4.9 |
| AD-63463.1 | 27.8 | 3.8 |
| AD-63469.1 | 48.4 | 14.0 |
| AD-63475.1 | 40.3 | 1.4 |
| AD-63434.1 | 93.3 | 9.9 |
| AD-63440.1 | 37.6 | 4.7 |
| AD-63446.1 | 38.1 | 15.4 |
| AD-63452.1 | 42.3 | 4.0 |
| AD-63458.1 | 29.7 | 7.9 |
| AD-63464.1 | 25.7 | 3.4 |
| AD-63470.1 | 44.8 | 7.8 |
| AD-63476.1 | 33.9 | 4.7 |
| AD-63435.1 | 23.4 | 5.2 |
| AD-63441.1 | 37.1 | 4.5 |
| AD-63447.1 | 46.5 | 9.0 |
| AD-63453.1 | 73.1 | 16.8 |
| AD-63459.1 | 31.8 | 4.6 |
| AD-63465.1 | 27.3 | 6.6 |
| AD-63471.1 | 19.5 | 3.1 |
| AD-63477.1 | 35.2 | 4.7 |
| AD-63436.1 | 21.8 | 4.7 |
| AD-63442.1 | 44.1 | 11.2 |
| AD-63448.1 | 33.6 | 6.0 |
| AD-63454.1 | 58.2 | 16.8 |
| AD-63460.1 | 27.7 | 2.4 |
| AD-63466.1 | 27.1 | 4.4 |
| AD-63472.1 | 20.5 | 4.1 |
| AD-63478.1 | 36.3 | 7.3 |
| AD-63484.1 | 48.4 | 31.3 |
| AD-63490.1 | 44.0 | 6.1 |
| AD-63496.1 | 45.5 | 19.9 |
| AD-63502.1 | 49.0 | 18.3 |
| AD-63508.1 | 41.4 | 2.7 |
| AD-63514.1 | 36.0 | 5.1 |
| AD-63520.1 | 40.9 | 4.2 |
| AD-63479.1 | 35.1 | 6.5 |
| AD-63485.1 | 45.5 | 24.0 |
| AD-63491.1 | 69.0 | 14.5 |
| AD-63497.1 | 57.1 | 25.1 |
| AD-63503.1 | 36.0 | 15.3 |
| AD-63509.1 | 29.7 | 6.4 |
| AD-63515.1 | 33.9 | 5.7 |
| AD-63521.1 | 117.2 | 10.2 |
| AD-63480.1 | 38.6 | 0.7 |
| AD-63486.1 | 48.5 | 12.1 |
| AD-63492.1 | 38.7 | 3.7 |
| AD-63498.1 | 64.6 | 20.3 |
| AD-63504.1 | 41.7 | 1.9 |
| AD-63510.1 | 39.6 | 4.0 |
| AD-63516.1 | 30.9 | 4.8 |
| AD-63522.1 | 56.4 | 15.6 |
| AD-63481.1 | 72.0 | 7.3 |
| AD-63487.1 | 128.8 | 48.9 |
| AD-63493.1 | 31.7 | 6.7 |
| AD-63499.1 | 44.2 | 17.7 |
| AD-63505.1 | 69.4 | 7.6 |
| AD-63511.1 | 43.8 | 5.3 |
| AD-63517.1 | 75.3 | 2.2 |
| AD-63523.1 | 82.1 | 10.6 |
| AD-63482.1 | 40.1 | 12.2 |
| AD-63488.1 | 42.3 | 12.7 |
| AD-63494.1 | 19.0 | 1.1 |
| AD-63500.1 | 30.2 | 11.2 |
| AD-63506.1 | 30.5 | 7.6 |
| AD-63512.1 | 38.1 | 15.2 |
| AD-63518.1 | 35.0 | 7.3 |
| AD-63524.1 | 60.5 | 3.7 |
| AD-63483.1 | 22.7 | 3.6 |
| AD-63489.1 | 47.6 | 13.7 |
| AD-63495.1 | 31.0 | 12.7 |
| AD-63501.1 | 24.3 | 2.1 |
| AD-63507.1 | 37.4 | 7.0 |
| AD-63513.1 | 32.3 | 5.1 |
| AD-63519.1 | 46.0 | 6.6 |
| AD-63525.1 | 66.5 | 14.5 |
| AD-63531.1 | 104.0 | 24.1 |
| AD-63537.1 | 32.1 | 3.4 |

TABLE 13-continued

TMPRSS6 single dose screen (10 nM) in Hep3B cells with dT modified siRNAs

| Duplex ID | Avg % message remaining | SD |
|---|---|---|
| AD-63543.1 | 31.2 | 3.8 |
| AD-63549.1 | 35.2 | 5.2 |
| AD-63555.1 | 41.7 | 9.3 |
| AD-63561.1 | 44.2 | 7.0 |
| AD-63567.1 | 39.2 | 4.9 |
| AD-63526.1 | 66.9 | 15.7 |
| AD-63532.1 | 90.3 | 17.8 |
| AD-63538.1 | 50.8 | 11.5 |
| AD-63544.1 | 31.9 | 2.4 |
| AD-63550.1 | 35.0 | 8.8 |
| AD-63556.1 | 31.0 | 6.0 |
| AD-63562.1 | 20.2 | 2.4 |
| AD-63568.1 | 30.6 | 2.7 |
| AD-63527.1 | 28.8 | 2.4 |
| AD-63533.1 | 63.3 | 6.9 |
| AD-63539.1 | 28.4 | 3.5 |
| AD-63545.1 | 26.9 | 8.5 |
| AD-63551.1 | 52.5 | 4.7 |
| AD-63557.1 | 26.7 | 2.2 |
| AD-63563.1 | 28.1 | 2.7 |
| AD-63569.1 | 29.2 | 2.8 |
| AD-63528.1 | 52.9 | 9.0 |
| AD-63534.1 | 42.5 | 6.8 |
| AD-63540.1 | 50.5 | 10.9 |
| AD-63546.1 | 53.6 | 10.5 |
| AD-63552.1 | 38.8 | 5.0 |
| AD-63558.1 | 49.3 | 3.0 |
| AD-63564.1 | 69.2 | 3.1 |
| AD-63570.1 | 50.6 | 6.0 |
| AD-63529.1 | 59.5 | 6.5 |
| AD-63535.1 | 21.0 | 1.7 |
| AD-63541.1 | 40.1 | 23.4 |
| AD-63547.1 | 26.0 | 9.6 |
| AD-63553.1 | 31.5 | 6.0 |
| AD-63559.1 | 34.9 | 2.7 |
| AD-63565.1 | 43.3 | 5.3 |
| AD-63571.1 | 41.6 | 4.4 |
| AD-63530.1 | 127.6 | 15.0 |
| AD-63536.1 | 38.0 | 16.0 |
| AD-63542.1 | 48.3 | 8.4 |
| AD-63548.1 | 41.9 | 7.9 |
| AD-63554.1 | 88.2 | 15.2 |
| AD-63560.1 | 48.8 | 17.7 |
| AD-63566.1 | 33.6 | 6.8 |
| AD-63572.1 | 82.4 | 67.9 |
| AD-63578.1 | 78.5 | 11.5 |
| AD-63584.1 | 55.7 | 7.2 |
| AD-63590.1 | 53.4 | 2.9 |
| AD-63596.1 | 63.5 | 8.6 |
| AD-63602.1 | 49.3 | 3.6 |
| AD-63608.1 | 29.2 | 4.4 |
| AD-63614.1 | 30.0 | 7.4 |
| AD-63573.1 | 96.1 | 14.7 |
| AD-63579.1 | 38.1 | 4.5 |
| AD-63585.1 | 40.0 | 2.1 |
| AD-63591.1 | 30.5 | 2.5 |
| AD-63597.1 | 55.1 | 5.8 |
| AD-63603.1 | 43.6 | 4.0 |
| AD-63609.1 | 37.7 | 2.7 |
| AD-63615.1 | 44.4 | 9.7 |
| AD-63574.1 | 44.3 | 10.3 |
| AD-63580.1 | 33.1 | 3.5 |
| AD-63586.1 | 39.3 | 2.9 |
| AD-63592.1 | 73.7 | 1.6 |
| AD-63598.1 | 32.4 | 6.6 |
| AD-63604.1 | 98.7 | 7.1 |
| AD-63610.1 | 42.1 | 7.1 |
| AD-63616.1 | 55.2 | 10.4 |
| AD-63575.1 | 27.8 | 3.0 |
| AD-63581.1 | 36.3 | 3.2 |
| AD-63587.1 | 36.1 | 3.3 |
| AD-63593.1 | 39.2 | 4.7 |
| AD-63599.1 | 37.0 | 5.6 |
| AD-63605.1 | 49.3 | 3.7 |
| AD-63611.1 | 88.8 | 7.7 |
| AD-63617.1 | 45.6 | 6.6 |
| AD-63576.1 | 59.9 | 2.9 |
| AD-63582.1 | 82.9 | 8.3 |
| AD-63588.1 | 33.5 | 6.7 |
| AD-63594.1 | 64.7 | 18.0 |
| AD-63600.1 | 99.5 | 11.9 |
| AD-63606.1 | 40.8 | 2.7 |
| AD-63612.1 | 44.5 | 5.3 |
| AD-63618.1 | 41.7 | 4.6 |
| AD-63577.1 | 31.1 | 0.3 |
| AD-63583.1 | 57.3 | 8.6 |
| AD-63589.1 | 61.9 | 5.9 |
| AD-63595.1 | 51.2 | 8.5 |
| AD-63601.1 | 70.7 | 15.4 |
| AD-63607.1 | 39.4 | 1.9 |
| AD-63613.1 | 36.8 | 2.7 |
| AD-63619.1 | 83.8 | 13.8 |
| AD-63620.1 | 69.4 | 7.3 |
| AD-63621.1 | 30.6 | 3.1 |
| AD-63622.1 | 51.8 | 8.4 |
| AD-63623.1 | 37.3 | 8.6 |

We claim:

1. A double stranded ribonucleic acid (dsRNA) agent for inhibiting expression of a TMPRSS6 (matriptase-2) gene in a cell, wherein said dsRNA agent comprises a sense strand and an antisense strand forming a double-stranded region, wherein said sense strand comprises at least 15 contiguous nucleotides differing by no more than 3 nucleotides from the nucleotide sequence of 5'-CUUCUUCUGGUUCAUU-CUCCA-3' (SEQ ID NO:223), and said antisense strand comprises at least 15 contiguous nucleotides differing by no more than 3 nucleotides from the nucleotide sequence of 5'-UGGAGAAUGAACCAGAAGAAGCA-3' (SEQ ID NO:292),
wherein the sense strand and the antisense strand are each independently about 14 to about 30 nucleotides in length,
wherein substantially all of the nucleotides of said sense strand and substantially all of the nucleotides of said antisense strand are modified nucleotides, and
wherein said sense strand is conjugated to a ligand attached at the 3'-terminus.

2. The dsRNA agent of claim 1, wherein all of the nucleotides of said sense strand and all of the nucleotides of said antisense strand are modified nucleotides.

3. The dsRNA agent of claim 1, wherein at least one strand comprises a 3' overhang of at least 1 nucleotide or at least 2 nucleotides.

4. A double stranded ribonucleic acid (dsRNA) agent for inhibiting expression of a TMPRSS6 (matriptase-2) gene in a cell, wherein said dsRNA agent comprises a sense strand and an antisense strand forming a double stranded region, wherein said antisense strand comprises a region of complementary to part of an mRNA encoding a TMPRSS6 gene, wherein the region of complementarity comprises at least 15 contiguous nucleotides differing by no more than 3 nucleotides from the nucleotide sequence of 5'-UGGA-GAAUGAACCAGAAGAAGCA-3' (SEQ ID NO:292), wherein the sense strand and the antisense strand are each independently about 14 to about 30 nucleotides in length, wherein said dsRNA agent is represented by formula (III):

sense:
5' $n_p$-$N_a$-(XXX)$_i$-$N_b$-YYY-$N_b$-(ZZZ)$_j$-$N_a$-$n_q$ 3' antisense:
3' $n_p'$-$N_a'$-(X'X'X')$_k$-$N_b'$-Y'Y'Y'-$N_b'$-(Z'Z'Z')$_l$-$N_a'$-$n_q'$ 5' (III)

wherein:
j, k, and l are each independently 0 or 1;
p, p', q, and q' are each independently 0-6;
each $N_a$ and $N_a'$ independently represents an oligonucleotide sequence comprising 0-25 nucleotides which are either modified or unmodified or combinations thereof, each sequence comprising at least two differently modified nucleotides;
each $N_b$ and $N_b'$ independently represents an oligonucleotide sequence comprising 0-10 nucleotides which are either modified or unmodified or combinations thereof;
each $n_p$, $n_p'$, $n_q$, and $n_q'$, each of which may or may not be present, independently represents an overhang nucleotide;
XXX, YYY, ZZZ, X'X'X', Y'Y'Y', and Z'Z'Z' each independently represent one motif of three identical modifications on three consecutive nucleotides;
modifications on $N_b$ differ from the modification on Y and modifications on $N_b'$ differ from the modification on Y'; and
wherein the sense strand is conjugated to at least one ligand.

5. The dsRNA agent of claim 4, wherein the YYY motif occurs at or near the cleavage site of the sense strand.

6. The dsRNA agent of claim 4, wherein the double-stranded region is 15-30 nucleotide pairs in length.

7. The dsRNA agent of claim 4, wherein each strand independently has 17-25 nucleotides.

8. The dsRNA agent of claim 4, wherein the modifications on the nucleotides are selected from the group consisting of LNA, HNA, CeNA, 2'-methoxyethyl, 2'-O-alkyl, 2'-O-allyl, 2'-C-allyl, 2'-fluoro, 2'-deoxy, 2'-hydroxyl, and combinations thereof.

9. The dsRNA agent of claim 1 or 4, wherein the ligand is one or more GalNAc derivatives attached through a bivalent or trivalent branched linker.

10. The dsRNA agent of claim 1 or 4, wherein the ligand is

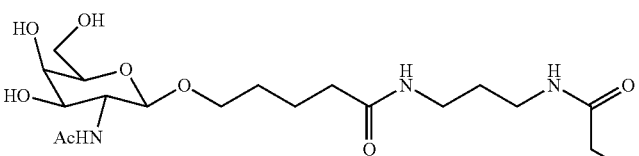
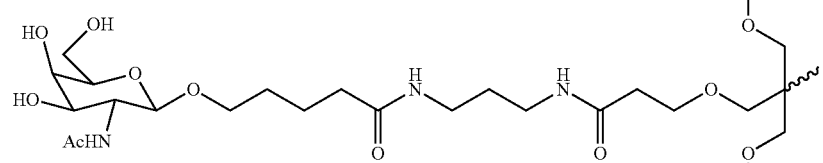
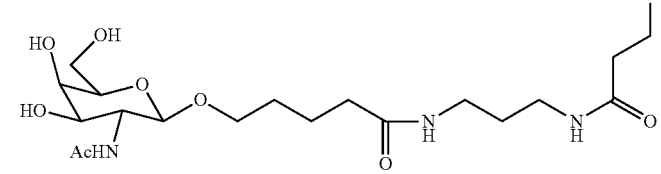

11. The dsRNA agent of claim 1 or 4, wherein said agent further comprises at least one phosphorothioate or methylphosphonate internucleotide linkage.

12. The dsRNA agent of claim 11, wherein said dsRNA agent comprises 6-8 phosphorothioate internucleotide linkages.

13. A double stranded ribonucleic acid (dsRNA) agent for inhibiting expression of a TMPRSS6 (matriptase-2) gene in a cell,
   wherein said dsRNA agent comprises a sense strand and an antisense strand forming a double stranded region,
   wherein said sense strand comprises at least 15 contiguous nucleotides differing by no more than 3 nucleotides from the nucleotide sequence of 5'-CUUCUUCUG-GUUCAUUCUCCA-3' (SEQ ID NO:223), and said antisense strand comprises at least 15 contiguous nucleotides differing by no more than 3 nucleotides from the nucleotide sequence of 5'-UGGA-GAAUGAACCAGAAGAAGCA-3' (SEQ ID NO:292),
   wherein the sense strand and the antisense strand are each independently about 14 to about 30 nucleotides in length,
   wherein substantially all of the nucleotides of said sense strand comprise a modification selected from the group consisting of a 2'-O-methyl modification and a 2'-fluoro modification,
   wherein said sense strand comprises two phosphorothioate internucleotide linkages at the 5'-terminus,
   wherein substantially all of the nucleotides of said antisense strand comprise a modification selected from the group consisting of a 2'-O-methyl modification and a 2'-fluoro modification,
   wherein said antisense strand comprises two phosphorothioate internucleotide linkages at the 5'-terminus and two phosphorothioate internucleotide linkages at the 3'-terminus, and
   wherein said sense strand is conjugated to one or more GalNAc derivatives attached through a branched bivalent or trivalent linker at the 3'-terminus.

14. A cell containing the dsRNA agent of claim 1.

15. A pharmaceutical composition comprising the dsRNA agent of claim 1.

16. A method of inhibiting TMPRSS6 expression in a cell, the method comprising:
   (a) contacting the cell with the dsRNA agent of claim 1, or a pharmaceutical composition of claim 15: and
   (b) maintaining the cell produced in step (a) for a time sufficient to obtain degradation of the mRNA transcript of a TMPRSS6 gene, thereby inhibiting expression of the TMPRSS6 gene in the cell.

17. A method of treating a subject having hereditary hemochromatosis, B-thalassemia, or erythropoietic *porphyria*, comprising administering to the subject a therapeutically effective amount of the dsRNA agent of claim 1, or a pharmaceutical composition of claim 15, thereby treating said subject.

18. The double stranded RNAi agent of claim 1, wherein at least one of said modified nucleotides is selected from the group consisting of a 3'-terminal deoxy-thymine (dT) nucleotide, a 2'-O-methyl modified nucleotide, a 2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, a non-natural base comprising nucleotide, a nucleotide comprising a 5'-phosphorothioate group, a nucleotide comprising a 5' phosphate or 5' phosphate mimic, and a terminal nucleotide linked to a cholesteryl derivative or a dodecanoic acid bisdecylamide group.

19. The double stranded RNAi agent of claim 1, wherein each strand independently has 17-25 nucleotides.

20. The dsRNA agent of claim 1, wherein the sense strand comprises 5'-CfsusUfcUfuCfuGfGfUfuCfaUfuCfuCfcA-3' (SEQ ID NO:389) and the antisense strand comprises 5'-usGfsgAfgAfaUfgAfaccAfgAfaGfaAfgscsa-3' (SEQ ID NO:458),
   wherein a, g, c, and u are 2'-O-methyl (2'-OMe) A, G, C, and U, respectively; Af, Gf, Cf and Uf are 2'-fluoro A, G, C and U, respectively; and s is a phosphorothioate linkage.

21. The method of claim 17, wherein the subject is a human.

22. A pharmaceutical composition comprising the dsRNA agent of claim 4.

23. The method of claim 16, wherein the cell is in a subject.

24. The method of claim 23, wherein the subject is human.

25. A method of treating a subject having a disorder associated with iron overload selected from the group consisting of Parkinson's Disease, Alzheimer's Disease or Friedreich's Ataxia, comprising administering to the subject a therapeutically effective amount of the dsRNA agent of claim 1, or a pharmaceutical composition of claim 15, thereby treating said subject.

26. A method of treating a subject having a disorder associated with iron overload selected from the group consisting of Parkinson's Disease, Alzheimer's Disease or Friedreich's Ataxia, comprising administering to the subject a therapeutically effective amount of the dsRNA agent of claim 4, or a pharmaceutical composition of claim 22, thereby treating said subject.

27. The method of claim 24, wherein the subject has hereditary hemochromatosis, β-thalassemia, or erythropoietic *porphyria*.

28. The method of claim 24, wherein the subject has a disorder associated with iron overload selected from the group consisting of Parkinson's Disease, Alzheimer's Disease or Friedreich's Ataxia.

29. A method of inhibiting TMPRSS6 expression in a cell, the method comprising:
   (a) contacting the cell with the dsRNA agent of claim 4, or a pharmaceutical composition of claim 22: and
   (b) maintaining the cell produced in step (a) for a time sufficient to obtain degradation of the mRNA transcript of a TMPRSS6 gene, thereby inhibiting expression of the TMPRSS6 gene in the cell.

30. A method of treating a subject having hereditary hemochromatosis, B-thalassemia, or erythropoietic *porphyria*, comprising administering to the subject a therapeutically effective amount of the dsRNA agent of claim 4, or a pharmaceutical composition of claim 22, thereby treating said subject.

* * * * *

SEQUENCE LISTING

<160> NUMBER OF SEQ ID NOS: 1382

<210> SEQ ID NO 1
<211> LENGTH: 3212
<212> TYPE: DNA
<213> ORGANISM: Homo sapiens

<400> SEQUENCE: 1

```
cttgagccag acccagtcca gctctggtgc ctgccctctg gtgcgagctg acctgagatg      60
cacttccctc tctgtgagc tgtctcggca cccacttgca gtcactgccg cctgatgttg     120
ttactcttcc actccaaaag gatgcccgtg gccgaggccc cccaggtggc tggcgggcag    180
ggggacggag gtgatggcga ggaagcggag ccggagggga tgttcaaggc ctgtgaggac   240
tccaagagaa aagcccgggg ctacctccgc ctggtgcccc tgtttgtgct gctggccctg    300
```

```
ctcgtgctgg cttcggcggg ggtgctactc tggtatttcc tagggtacaa ggcggaggtg      360
atggtcagcc aggtgtactc aggcagtctg cgtgtactca atcgccactt ctcccaggat      420
cttacccgcc gggaatctag tgccttccgc agtgaaaccg ccaaagccca agagatgctc      480
aaggagctca tcaccagcac ccgcctggga acttactaca actccagctc cgtctattcc      540
tttggggagg gacccctcac ctgcttcttc tggttcattc tccaaatccc cgagcaccgc      600
cggctgatgc tgagcccga ggtggtgcag gcactgctgg tggaggagct gctgtccaca       660
gtcaacagct cggctgccgt cccctacagg gccgagtacg aagtggaccc cgagggccta      720
gtgatcctgg aagccagtgt gaaagacata gctgcattga attccacgct gggttgttac      780
cgctacagct acgtgggcca gggccaggtc tccggctga agggcctga ccacctggcc        840 tccagctgcc tgtggcacct gcagggcccc aaggacctca tgctcaaact ccggctggag      900
tggacgctgg cagagtgccg ggaccgactg gccatgtatg acgtggccgg gcccctggag      960
aagaggctca tcacctcggt gtacggctgc agccgccagg agcccgtggt ggaggttctg     1020
gcgtcggggg ccatcatggc ggtcgtctgg aagaagggcc tgcacagcta ctacgacccc     1080
ttcgtgctct ccgtgcagcc ggtggtcttc caggcctgtg aagtgaacct gacgctggac     1140
aacaggctcg actcccaggg cgtcctcagc accccgtact ccccagcta ctactcgccc     1200 caaaccccact gctcctggca cctcacggtg ccctctctgg actacggctt ggccctctgg     1260
tttgatgcct atgcactgag gaggcagaag tatgatttgc cgtgcaccca gggccagtgg     1320
acgatccaga acaggaggct gtgtggcttg cgcatcctgc agccctacgc cgagaggatc     1380
cccgtggtgg ccacggccgg gatcaccatc aacttcacct cccagatctc cctcaccggg     1440
cccggtgtgc gggtgcacta tggcttgtac aaccagtcgg accctgccc tggagagttc     1500 ctctgttctg tgaatggact ctgtgtccct gcctgtgatg gggtcaagga ctgccccaac     1560
ggcctggatg agagaaactg cgtttgcaga gccacattcc agtgcaaaga ggacagcaca     1620
tgcatctcac tgcccaaggt ctgtgatggg cagcctgatt gtctcaacgg cagcgacgaa     1680
gagcagtgcc aggaaggggt gccatgtggg acattcacct ccagtgtga ggaccggagc      1740 tgcgtgaaga agcccaaccc gcagtgtgat gggcggcccg actgcaggga cggctcggat     1800
gaggagcact gtgactgtgg cctccagggc ccctccagcc gcattgttgg tggagctgtg     1860
tcctccgagg gtgagtggcc atggcaggcc agcctccagg ttcggggtcg acacatctgt     1920 ggggggccc tcatcgctga ccgctgggtg ataacagctg cccactgctt ccaggaggac      1980
agcatggcct ccacggtgct gtggaccgtg ttcctgggca aggtgtggca gaactcgcgc     2040
tggcctggag aggtgtcctt caaggtgagc cgcctgctcc tgcacccgta ccacgaagag     2100
gacagccatg actacgacgt ggcgctgctg cagctcgacc accggtggt gcgctcggcc      2160 gccgtgcgcc ccgtctgcct gcccgcgcgc tcccacttct tcgagcccgg cctgcactgc     2220
tggattacgg gctggggcgc cttcgcgag ggcggcccca tcagcaacgc tctgcagaaa      2280
gtggatgtgc agttgatccc acaggacctg tgcagcgagg tctatcgcta ccaggtgacg     2340
ccacgcatgc tgtgtgccgg ctaccgcaag ggcaagaagg atgcctgtca gggtgactca     2400
ggtggtccgc tggtgtgcaa ggcactcagt ggccgctggt tcctggcggg gctggtcagc     2460
tggggcctgg gctgtggccg gcctaactac ttcggcgtct acacccgcat cacaggtgtg     2520
atcagctgga tccagcaagt ggtgacctga ggaactgccc cctgcaaag cagggcccac      2580 ctcctggact cagagagccc agggcaactg ccaagcaggg ggacaagtat ctggcgggg      2640 ggtgggggag agagcaggcc ctgtggtggc aggaggtggc atcttgtctc gtccctgatg     2700
```

| | |
|---|---|
| tctgctccag tgatggcagg aggatggaga agtgccagca gctggggtc aagacgtccc | 2760 |
| ctgaggaccc aggcccacac ccagcccttc tgcctcccaa ttctctctcc tccgtcccct | 2820 |
| tcctccactg ctgcctaatg caaggcagtg gctcagcagc aagaatgctg gttctacatc | 2880 |
| ccgaggagtg tctgaggtgc gccccactct gtacagaggc tgtttgggca gccttgcctc | 2940 |
| cagagagcag attccagctt cggaagcccc tggtctaact tgggatctgg aatggaagg | 3000 |
| tgctcccatc ggaggggacc ctcagagccc tggagactgc caggtgggcc tgctgccact | 3060 |
| gtaagccaaa aggtggggaa gtcctgactc caggtccctt gccccacccc tgcctgccac | 3120 |
| ctgggcccct cacagcccaga ccctcactgg gaggtgagct cagctgccct ttggaataaa | 3180 |
| gctgcctgat caaaaaaaaa aaaaaaaaaa aa | 3212 |

<210> SEQ ID NO 2
<211> LENGTH: 3206
<212> TYPE: DNA
<213> ORGANISM: Mus musculus

<400> SEQUENCE: 2

| | |
|---|---|
| agtttcattg tcgccctgga cctgacagga gaggcccatg gaacttgggg ccacaggcca | 60 |
| caagggacaa gggccagaca ccccagccat ggctccaggc cattgatcca acctaagctg | 120 |
| gccagttggg ggtggaaaga ccttggcctg gataaacaga ggcctccagg cctgtgtgca | 180 |
| ggcccggcac ctaccttcca ctcttgaaga tgccgagatg tttccagctc ccctgttcta | 240 |
| ccaggatgcc caccaccgag gtcccccaag cggctgatgg tcagggcgat gcgggtgatg | 300 |
| gagaggaagc tgctgagcca gaggggaagt tcaagccccc aaaaaacacc aagagaaaaa | 360 |
| accgggacta cgtccgcttc acgccactgt tgctggtctt ggctgcgctg gtctcagcag | 420 |
| gggtcatgct ttggtatttc ctagggtaca aagcggaagt gaccgtaagc caggtgtact | 480 |
| ctggcagcct ccgggtgctc aaccgtcatt tctcccagga cctgggccga cgggagtcta | 540 |
| ttgctttccg cagtgaatct gccaaagccc agaagatgct ccaagaactg gttgccagca | 600 |
| cccgcctggg tacttactac aactctagtt ctgtctactc cttgtgggag gacccctca | 660 |
| cctgcttctt ctggtttatc cttgacatcc ctgagtacca gcgactgacc ctgagccctg | 720 |
| aagtagtgcg cgagctcctg gtggatgagc tactgtccaa cagctcaacc ctggcttcct | 780 |
| ataagaccga atatgaggtg gacccggaag gcctggtgat cctggaagcc agtgtgaacg | 840 |
| acatagtcgt actgaattcc acgctgggct gttatcgcta cagctatgtg aacccaggcc | 900 |
| aggtcctccc cattgaagggg cctgaccagc agaccacaag ctgcctgtgg catctgcaag | 960 |
| ggcccgaaga cctcatgatc aaagtgcggc tggagtggac ccgggtcgat tgcagagaca | 1020 |
| gggtggcgat gtacgacgca gctgggcccc tggagaagag acttatcacc tcggtctatg | 1080 |
| ggtgcagccg ccaggaacct gtgatggagg tgctggcatc gggctccgtc atggccgtgg | 1140 |
| tgtgaaaaaa gggcatgcat agctactatg accctttcct gctctcagtg aagtctgtgg | 1200 |
| ccttccagga ctgccaggtg aacctgacac tggagggccg gctggacaca cagggcttcc | 1260 |
| tccgtacacc ctactacccc agttactact ctcccagtac ccactgctcc tggcatctca | 1320 |
| cggtaccctc tctggactac ggcttggcgc tctggttcga tgcctacgca ctgaggaggc | 1380 |
| agaagtacaa ccgactgtgt actcagggcc agtggatgat ccagaacagg aggctgtgtg | 1440 |
| gcttccgtac cctgcagcca tatgctgaga ggatccccat ggtggcctca gatggtgtca | 1500 |
| ccatcaactt cacctcccag atctccctca caggcccggg tgtgcaagtg tactacagct | 1560 |

| | |
|---|---|
| tgtacaacca atcagacccc tgccctggtg agttcctctg ctctgtgaat ggactgtgtg | 1620 |
| tccctgcgtg tgacgggatc aaggactgcc ccaatggcct ggatgagaga aactgtgtct | 1680 |
| gcagagccat gttccagtgc aagaggaca gcacgtgcat ttcactgcct agagtctgtg | 1740 |
| accggcagcc cgactgtctc aatggcagtg acgaagaaca gtgccaagaa ggagtgccct | 1800 |
| gtgggacatt cactttccag tgtgaggacc ggagctgtgt gaagaagccc aacccagagt | 1860 |
| gtgacggcca gtcagattgc agagacggct cagatgagca acactgtgac tgtggcctcc | 1920 |
| agggcctctc cagccgtatt gtgggcggga ccgtgtcctc cgagggtgag tggccatggc | 1980 |
| aggccagcct ccagattcgg ggtcgacaca tctgtggggg ggctctcatc gctgaccgct | 2040 |
| gggtcataac ggccgcccac tgcttccagg aggacagcat ggcctccccg aagctgtgga | 2100 |
| ccgtgttcct gggaaagatg cggcagaact cgcgctggcc aggcgaggtg tccttcaagg | 2160 |
| tgagccgtct gttcctgcac ccgtaccacg aggaggacag ccatgactac gacgtggccc | 2220 |
| tgctgcagct cgaccacccc gtggtgtact cggccactgt gcgccccgtc tgcctgcctg | 2280 |
| cccgctccca cttctttgag ccaggccagc actgctggat cacaggctgg ggagcccagc | 2340 |
| gagagggtgg tccggtgagc aacaccctgc agaaggtgga cgtacagctg gtccctcagg | 2400 |
| acctctgcag tgaggcctac cgctaccagg tgtccccacg catgctctgt gctggctacc | 2460 |
| gcaagggcaa gaaagatgcc tgccaggtg actctggagg cccactggtt gcagggagc | 2520 |
| ccagtggccg ctggttcctg gcagggttgg ttagctgggg cctgggctgt ggccgaccca | 2580 |
| atttctttgg cgtctacacc cgtgtcacac gtgtgatcaa ctggatccag caggtgctga | 2640 |
| cctgagggct gttctacaga gctggacctg cctccaggcc aagttcaggg tgtccaccca | 2700 |
| gccaggacac aagtattctg gggcaagtga ccctgctaag gcctgttcc ctcaggccta | 2760 |
| ccccagtgac agtacagaga aggatgtcag ctggtggtta ggatgcctcc tgaggtccag | 2820 |
| gggccagcct cggctaggtt tcacttctaa ccctttctta ttctagtcct ttcccctccc | 2880 |
| tgctcctacc actgttttgg agtggggtct ggcggccatg accttggcct ccgggtctct | 2940 |
| gtaggaaaga aagaatcctt ccccttgcaa aagcctcttg ggggaactgc acagagaaag | 3000 |
| aaggtgcctc tatcaaggct ctatcagagc ccttgagtct gccaagtggg ctgtactcta | 3060 |
| agccaaatca ccgggcagcc tcagctgcag atgcctgctg aagctctgcc tgctacaggg | 3120 |
| gcctccctgc cattcactgg aggcccactg tctgttctgg aataaagca cttgaccaag | 3180 |
| ccctgacact gaaaaaaaaa aaaaaa | 3206 |

<210> SEQ ID NO 3
<211> LENGTH: 2999
<212> TYPE: DNA
<213> ORGANISM: Rattus norvegicus

<400> SEQUENCE: 3

| | |
|---|---|
| attgtccgtc ctggacctga caggaggccc atgaacttg gggccacagg ccacgaggga | 60 |
| caagggccag acaccccagt catggttcca ggctattgat ccaacctaag ctggccagtt | 120 |
| gtgggtggag agaccttggc ctggataaac agaggcctcc aggcctgtgt tcaggcccag | 180 |
| cacctacctt ccactcttga agatgccaag atgtttccag ctcccctgtt ctaccaggat | 240 |
| gcccaccgct gaggttcccc aagcagctgg tggtcagggt gatggaggtg atggagagga | 300 |
| agctgcagag ccagaggggg tgttcaaggc cccagaaac gccaagagaa agacaggga | 360 |
| ctacgtccgc ttcacaccac tgttgctggt cttggctgcg ttggcttcgg caggagtcat | 420 |
| gctctggtat ttcctagggt acaaggcgga agtgaccata agccaggtgt actctggcag | 480 |

```
cctccgggtg ctcaaccgcc attttcaca ggacttggcc cgacgggagt ctattgcttt    540
ccgcactgaa actgccaaag cccagaagat gttccaagag ctggttgcca gcacccgctt    600
gggtacttac tacaactcca gttccatcta cgcctttggg gagggacccc ttatctgctt    660
cttctggttc atccttgaca tccccgagta ccagcgactg accctgagcc ctgaggtggt    720
gcgcgagctc ctggtgggtg agctactgtc caacagctca gccttggctt cctataggac    780
cgaatatgag gtgacccgg aaggcctggt gatactagaa gccagcgtga acgacatagt    840
cgtactgaat tccacgctgg gctgttaccg ctacagctac gtgaacccgg gccaggtcct    900
ccggttgagg gggcccgacc agcagaccac tagctgcctg tggcacctgc aggggcccga    960
ggacctcatg ctcaaagtgc agctagagtg gactcgggtt gattgcagag acagggtggc   1020
gatgtacgac gcagctgggc ccctggagaa gagacttatc acctcggtct atgggtgcag   1080
ccgccaggaa cccgtgatgg aggtgctggc gtcgggctct gtcatggccg tggtgtggaa   1140
gaagggcttg catagcttct atgacccttt tctgctctca gtgaagtctg tggccttcca   1200
ggactgccag gtgaacctga ccctggaagg ccggctggat ccacagggct cctccgtac    1260 accctactac cccagttact actcgcccag tacccactgc tcctggcatc tcacggttcc   1320
ctctctggac tatggcttgg cactctggtt tgacgcctat gcactgagga ggcagaagta   1380
caacctacta tgtactcagg gccagtggat gatccagaac aggaggctat gtggcttccg   1440
taccctgcag ccatatgctg agaggatccc cgtggtggcc tcggatggta tcaccatcaa   1500
cttcacctcc cagatctccc tcacaggccc gggtgtgcaa gtgtactaca gcttgtacaa   1560
ccaatcagac ccctgccctg gagagttcct ctgctctgtg aatggattgt gtgtccctgc   1620
ttgtgacgga atcaaggact gccccaacgg cctggatgag aggaactgtg tctgcagagc   1680
catgttccag tgccaagagg acagcacgtg catctcactg ccgagagtct gtgaccggca   1740
gcccgactgt tcaatggta gcgacgaaga gcagtgccaa gaaggagtgc cctgtgggac   1800
attcactttc cagtgtgagg accggagctg tgtgaagaag cccaacccg agtgtgacgg   1860 gcaggcagac tgcagggatg gctcggatga ggagcactgt gactgtggcc tccagggccc   1920
ctccagccgc attgtgggcg gggccatgtc ctcggagggt gagtggccct ggcaggccag   1980
tctccagatt cggggtcgac acatctgtgg gggggctctc atcgctgacc gctgggtcat   2040
aacagccgct cactgcttcc aggaggacag catggcctcc ccgaggctgt ggaccgtgtt   2100
tctgggaaag atgcggcaga attcacgctg gccgggcgag gtgtccttca aggtgagccg   2160
cctgttcctg cacccgtatc atgaggagga cagccatgac tacgacgtgg ccctgctgca   2220
gctggaccac cctgtggtgt actcggccac cgtgcgcccc gtctgcctgc ccgcacgctc   2280
tcacttcttt gagccaggcc agcactgctg gatcacaggc tggggagccc agcgagaggg   2340
tggtcctggt agcagcaccc ttcagaaggt ggatgtgcaa ctgatccctc aggacctgtg   2400
caatgaggcc taccgttacc aggtgacccc acgcatgctc tgtgctggtt atcgcaaggg   2460
caagaaagat gcctgccagg gcgactctgg aggcccactg gtttgcaagg agcccaggtg   2520
accacccagc cagggcacaa gtattctggg gcgagcgacc ctgctaaggc ctgtcccctc   2580
atgcctaccc cagggacagt acagagaagg atgtcagctg gtggttagga tgcctccagg   2640
ggctagcctc agctcggctt cacttccaac cctttcttat tctagtcctt tccctctcc    2700 cctcctactg ctgttttggg gtggggtctg gtggcaatga tgctggttcc aaggtctgtg   2760
ggaaagtaag attccttccc cttgcaaaag cctctagggg gaactggatc cgagaaagaa   2820
```

-continued

| | | |
|---|---|---|
| ggtgcctcta tcaaggctct gtcagagccc ttgagactgc caagtagggc cataccgtaa | 2880 | |
| gccaaatcat ggggcagcct cagctgcggg tgcctgctgt gctctgcctg ctacagggcc | 2940 | |
| ctccctgcca ttcactggag gcccactgtc tgttccggaa ataaagcagt tggccaagc | 2999 | |

<210> SEQ ID NO 4
<211> LENGTH: 2440
<212> TYPE: DNA
<213> ORGANISM: Macaca mulatta

<400> SEQUENCE: 4

| | | |
|---|---|---|
| caggatgcct gtggccaagg ccccccaggt ggctggtggg caggggacg gaggtgatgg | 60 | |
| cgaggaagcg gagccagagg ggatgttcga ggcccgtgag gactccaaga gaaaagcccg | 120 | |
| gggctacctc cgcctggcgc ccctgtggct gaccctggtt gtgctgactt cagtgggggt | 180 | |
| gctactctgg tatttcctag ggtacaaggc ggaggtgacg gtcagccagg tgtactcagg | 240 | |
| cagcctgcgc gtgctcaatc gccacttctc ccaggatctt acccgccggg aatccagtgc | 300 | |
| cttccgcagt gaaaccgcca agcccagaa gatgctcaag gagctcatcg ccagcacccg | 360 | |
| cctgggaact tattacaact ccagctccgt ctattccttt ggggagggac cgctcacctg | 420 | |
| cttcttctgg ttcattctcc aaatccccga gcaccgccgg ctgatgctga gccccgaggt | 480 | |
| ggtgcaggca ctgctggtgg aggagctgct gtccacagtc aacagctcgg cggctgtccc | 540 | |
| ctacagggcc gagtacgaag tggacccccga gggcctagtg atcctagaag ccagtgtgaa | 600 | |
| agacatagct gcactgaatt ccacgctggg ttgttaccgc tacagctacg tgggccaggg | 660 | |
| tcaggtcctc cggctgaagg gacccgacca cctggcctcc agctgcctgt ggcacctgca | 720 | |
| gggccccgaa gacctcatgc tgaaactccg gctggagtgg acgctggccg agtgccggga | 780 | |
| ccgactggca atgtatgacg tggctgggcc cctggagaag aggctcatca cctcggtgta | 840 | |
| tggctgcagc cgccaggagc ctgtggtgga agtcctggca tcgggggcca tcatggcggt | 900 | |
| ggtctggaag aagggcctgc acagctacta cgaccccttt atgctctccg tgcagtcggt | 960 | |
| ggtcttccag gcctgcgagg taaacctgac gctggatgac aggctggact cccagggcgt | 1020 | |
| cctcagcacc ccgtacttcc ccagctacta ctcgccccga acccactgct cctggcacct | 1080 | |
| cacggtgccc tctctggact acggcttggc cctctggttt gacgcctacg cactgcggag | 1140 | |
| gcagaagtat gatttgccgt gcacccaggg ccagtggacg atccagaaca ggaggctgtg | 1200 | |
| tggcctgcgc atcctgcagc cttacgccga ggatccccc gtggtggcca cggccggcat | 1260 | |
| caccatcaat ttcacctccc agatctccct cacagggcct ggtgtgcggg tgcactatgg | 1320 | |
| cttgtacaac cagtcggacc cctgccctgg agagttcctc tgctctgtga cggactctg | 1380 | |
| cgtccctgcc tgtgatgggg tcaaggactg ccccaacggc ctggatgaga gaaactgcgt | 1440 | |
| tgcagagcc acattccagt gccaagagga cagcacgtgc atctcactgc ttaaggtctg | 1500 | |
| tgacgggcag cctgactgtc tcaacggcag cgatgaagag cggtgccagg aagggtgcc | 1560 | |
| ctgcgggaca ttcaccttcc agtgtgagga ccagagctgc gtgaagaagc ccaacccaca | 1620 | |
| gtgtgatggg cggcccgact gcagggacgg ctcagacgag cagcactgtg actgtggcct | 1680 | |
| ccagggcccc tccagtcgca ttgttggtgg ggccgtgtcc tccgagggtg agtggccatg | 1740 | |
| gcaggccagc ctccaggttc ggggtcgaca catctgtggg ggcgccctca tcgctgaccg | 1800 | |
| ctgggtgata acagctgccc attgcttcca ggaggacagc atggcctccc ggcgctgtg | 1860 | |
| gacggtgttc ctgggcaagg tgtggcagaa ctcgcgctgg cctggagagg tgtccttcaa | 1920 | |
| ggtgagccgc ctactcctgc atccgtatca cgaagaggac agccacgact acgacgtggc | 1980 | |

```
gctgttgcag ctcgaccacc cggtggtgcg ctcggccgcc gtgcgtccag tctgcctgcc      2040
cgcgcgctcc cacttcttcg aacccggcct gcactgctgg atcactggct ggggcgccct      2100
gcgcgaaggc ggccccacca gcaatgctct gcagaaagtg gacgtgcagt tgatcccaca      2160
ggacctgtgc agcgaggcct atcgctacca ggtgacgcca cgcatgctgt gtgccggcta      2220
ccgcaagggc aagaaggatg cctgccaggg tgactcgggt ggtccgctgg tatgcaaggc      2280
actcagtggc cgctggttcc tggcagggct ggtcagctgg ggcctgggct gtggccggcc      2340
taactacttc ggcgtctaca cccgcatcac aggtgtgatc ggctggatcc agcaagtggt      2400
gacctgagga actgcccccc tgcagagcag gtcccacctc                            2440

<210> SEQ ID NO 5
<211> LENGTH: 3188
<212> TYPE: DNA
<213> ORGANISM: Macaca mulatta

<400> SEQUENCE: 5
cttgagccac acccagtcca gctctggtgc ctgccctctg gggtgagctg ccttgagatg       60
cacttcgctc ctctgtgaac tgtctcggca cccacttccg gtcactgccg cctgatgttg      120
ttactcttcc actctgaaag gatgcctgtg gccaaggccc ccaggtggc tggtgggcag       180 ggggacggag gtgatggcga ggaagcggag ccagagggga tgttcgaggc ccgtgaggac      240
tccaagagaa aagcccgggg ctacctccgc ctggcgcccc tgtggctgac cctggttgtg      300
ctgacttcag tgggggtgct actctggtat ttcctagggt acaaggcgga ggtgacggtc      360
agccaggtgt actcaggcag cctgcgcgtg ctcaatcgcc acttctccca ggatcttacc      420
cgccgggaat ccagtgcctt ccgcagtgaa accgccaaag cccagaagat gctcaaggag      480
ctcatcgcca gcacccgcct gggaacttat tacaactcca gctccgtcta ttcctttggg      540
gagggaccgc tcacctgctt cttctggttc attctccaaa tccccgagca ccgccggctg      600
atgctgagcc ccgaggtggt gcaggcactg ctggtggagg agctgctgtc cacagtcaac      660
agctcggcgg ctgtccccta cagggccgag tacgaagtgg accccgaggg cctagtgatc      720
ctagaagcca gtgtgaaaga catagctgca ctgaattcca cgctgggttg ttaccgctac      780
agctacgtgg gccagggtca ggtcctccgg ctgaagggac ccgaccacct ggcctccagc      840
tgcctgtggc acctgcaggg ccccgaagac ctcatgctga actccggct ggagtggacg      900 ctggccgagt gccgggaccg actggccatg tatgacgtgg ctgggcccct ggagaagagg      960
ctcatcacct cggtgtatgg ctgcagccgc caggagcctg tggtgaagt cctgcatcg      1020 ggggccatca tggcggtggt ctggaagaag ggcctgcaca gctactacga cccctttatg      1080
ctctccgtgc agtcggtggt cttccaggcc tgcgaggtaa acctgacgct ggatgacagg      1140
ctggactccc agggcgtcct cagcaccccg tacttcccca gctactactc gccccgaacc      1200
cactgctcct ggcacctcac ggtgccctct ctggactacg cttggccct ctggtttgac      1260 gcctacgcac tgcggaggca gaagtatgat ttgccgtgca cccagggcca gtggacgatc      1320
cagaacagga ggctgtgtgg cctgcgcatc ctgcagcctt acgccgagag gatccccgtg      1380
gtggccacgg ccgcatcac catcaatttc acctcccaga tctccctcac agggcctggt      1440
gtgcgggtgc actatggctt gtacaaccag tcggacccct gcctggaga gttcctctgc      1500 tctgtgaacg gactctgcgt ccctgcctgt gatgggtca aggactgccc caacggcctg      1560
gatgagagaa actgcgtttg cagagccaca ttccagtgcc aagaggacag cacgtgcatc      1620
```

```
tcactgctta aggtctgtga cgggcagcct gactgtctca acggcagcga tgaagagcgg    1680
tgccaggaag gggtgccctg cgggacattc accttccagt gtgaggacca gagctgcgtg    1740
aagaagccca acccacagtg tgatgggcgg cccgactgca gggacggctc agacgagcag    1800
cactgtgact gtggcctcca gggcccctcc agtcgcattg ttggtggggc cgtgtcctcc    1860
gagggtgagt ggccatggca ggccagcctc caggttcggg gtcgacacat ctgtgggggc    1920
gccctcatcg ctgaccgctg ggtgataaca gctgcccatt gcttccagga ggacagcatg    1980
gcctccccgg cgctgtggac ggtgttcctg ggcaaggtgt ggcagaactc cgcctggcct    2040
ggagaggtgt ccttcaaggt gagccgccta ctcctgcatc cgtatcacga agaggacagc    2100
cacgactacg acgtggcgct gttgcagctc gaccacccgg tggtgcgctc ggccgccgtg    2160
cgtccagtct gcctgcccgc cgcgctccac ttcttcgaac ccggcctgca ctgctggatc    2220
actggctggg gcgccctgcg cgaaggcggc cccaccagca atgctctgca gaaagtggac    2280
gtgcagttga tcccacagga cctgtgcagc gaggcctatc gctaccaggt gacgccacgc    2340
atgctgtgtg ccggctaccg caagggcaag aaggatgcct gccaggtgga ctcgggtggt    2400
ccgctggtat gcaaggcact cagtggccgc tggttcctgg cagggctggt cagctggggc    2460
ctgggctgtg gccggcctaa ctacttcggc gtctacaccc gcatcacagg tgtgatcggc    2520
tggatccagc aagtggtgac ctgaggaact gccccctgc agagcaggtc ccacctcttg    2580
gactcagaga gcccagggca attgccaagc aggggggacaa gtattctggg gggaggggg    2640 cgcgagcagg ccctgtggtg gcaggaggtg gcatcttgtc ttgtccctga tgtctgctcc    2700
agtgatggca ggaggatgga ggagtgccag cagctggggg tcaagacgtc ccctagggac    2760
ccaggcccac acccagccct tctgcctccc gattctctct cctctgtccc cttcctccac    2820
tgctgcctat tgcaaggaag tggctcagca gcaagaatgc tggctctacg tccccaggag    2880
tgtctgagct gtgccccact ctgtacagag gctgcttggg cagccttgcc tctagagagc    2940
agatgccagc ttcggaagcc cctggtctaa cttgggatct gggaatggaa ggtgcccca    3000 taggaggga ccctcacagc cccggggact gccaggtggg ccggctgcca ccgtaagcca    3060
aaaaaggtgg ggaagccctg actccaaggt ccttgcccca ccctgcctg ccacctggcc    3120 cctcacagcc cagaccctca ccggcaggtg agctcagctg ccctttggaa taaagctgcc    3180
tgatccaa                                                            3188

<210> SEQ ID NO 6
<211> LENGTH: 3212
<212> TYPE: DNA
<213> ORGANISM: Homo sapiens

<400> SEQUENCE: 6
tttttttttt tttttttttt tgatcaggca gctttattcc aaagggcagc tgagctcacc     60
tcccagtgag ggtctgggct gtgagggccc aggtggcagg caggggtggg gcaaggaccc    120
tggagtcagg acttccccac cttttggctt acagtggcag caggcccacc tggcagtctc    180
cagggctctg agggtcccct ccgatgggag caccttccat tcccagatcc caagttagac    240
caggggcttc cgaagctgga atctgctctc tggaggcaag gctgcccaaa cagcctctgt    300
acagagtggg gcgcacctca gacactcctc gggatgtaga accagcattc ttgctgctga    360
gccactgcct tgcattaggc agcagtggag gaagggacg gaggagagag aattgggagg    420
cagaagggct gggtgtgggc ctgggtcctc aggggacgtc ttgaccccca gctgctggca    480
cttctccatc ctcctgccat cactggagca gacatcaggg acgagacaag atgccacctc    540
```

```
ctgccaccac agggcctgct ctctccccca cccccgcca gaatacttgt cccctgctt     600 ggcagttgcc ctgggctctc tgagtccagg aggtgggccc tgctttgcag gggggcagtt     660
cctcaggtca ccacttgctg gatccagctg atcacacctg tgatgcgggt gtagacgccg     720
aagtagttag gccggccaca gcccaggccc cagctgacca gccccgccag gaaccagcgg     780
ccactgagtg ccttgcacac cagcggacca cctgagtcac cctgacaggc atccttcttg     840
cccttgcggt agccggcaca cagcatgcgt ggcgtcacct ggtagcgata gacctcgctg     900
cacaggtcct gtgggatcaa ctgcacatcc actttctgca gagcgttgct gatggggccg     960
ccctcgcgca aggcgcccca gcccgtaatc cagcagtgca ggccgggctc gaagaagtgg    1020
gagcgcgcgg gcaggcagac ggggcgcacg gcggccgagc gcaccaccgg gtggtcgagc    1080
tgcagcagcg ccacgtcgta gtcatggctg tcctcttcgt ggtacgggtg caggagcagg    1140
cggctcacct tgaaggacac ctctccaggc cagcgcgagt tctgccacac cttgcccagg    1200
aacacggtcc acagcaccgt ggaggccatg ctgtcctcct ggaagcagtg ggcagctgtt    1260
atcacccagc ggtcagcgat gagggccccc ccacagatgt gtcgaccccg aacctggagg    1320
ctggcctgcc atggccactc accctcggag gacacagctc caccaacaat gcggctggag    1380
gggccctgga ggccacagtc acagtgctcc tcatccgagc cgtccctgca gtcgggccgc    1440
ccatcacact gcgggttggg cttcttcacg cagctccggt cctcacactg gaaggtgaat    1500
gtcccacatg cacccccttc ctggcactgc tcttcgtcgc tgccgttgag acaatcaggc    1560
tgcccatcac agaccttggg cagtgagatg catgtgctgt cctctttgca ctggaatgtg    1620
gctctgcaaa cgcagtttct ctcatccagg ccgttgggc agtccttgac cccatcacag    1680
gcagggacac agagtccatt cacagaacag aggaactctc cagggcaggg gtccgactgg    1740
ttgtacaagc catagtgcac ccgcacaccg ggcccggtga gggagatctg ggaggtgaag    1800
ttgatggtga tcccggccgt ggccaccacg gggatcctct cggcgtaggg ctgcaggatg    1860
cgcaagccac acagcctcct gttctggatc gtccactggc cctgggtgca cggcaaatca    1920
tacttctgcc tcctcagtgc ataggcatca aaccagaggg ccaagccgta gtccagagag    1980
ggcaccgtga ggtgccagga gcagtgggtt tgggcgagt agtagctggg gaagtacggg    2040
gtgctgagga cgccctggga gtcgagcctg ttgtccagcg tcaggttcac ttcacaggcc    2100
tggaagacca ccgctgcac ggagagcacg aaggggtcgt agtagctgtg caggcccttc    2160
ttccagacga ccgccatgat ggccccgac gccagaacct ccaccacggg ctcctggcgg    2220
ctgcagccgt acaccgaggt gatgagcctc ttctccaggg gccggccac gtcatacatg    2280 gccagtcggt cccggcactc tgccagcgtc cactccagcc ggagtttgag catgaggtcc    2340 ttgggggccct gcaggtgcca caggcagctg gaggccaggt ggtcaggccc cttcagccgg    2400
aggacctggc cctggcccac gtagctgtag cggtaacaac ccagcgtgga attcaatgca    2460
gctatgtctt tcacactggc ttccaggatc actaggccct cggggtccac ttcgtactcg    2520
gccctgtagg ggacggcagc cgagctgttg actgtggaca gcagctcctc caccagcagt    2580
gcctgcacca cctcggggct cagcatcagc cggcggtgct cggggatttg gagaatgaac    2640
cagaagaagc aggtgagggg tccctcccca aggaataga cggagctgga gttgtagtaa    2700
gttcccaggc gggtgctggt gatgagctcc ttgagcatct tctgggcttt ggcggtttca    2760
ctgcggaagg cactagattc ccggcgggta agatcctggg agaagtggcg attgagtaca    2820
cgcagactgc ctgagtacac ctggctgacc atcacctccg ccttgtaccc taggaaatac    2880
```

| | |
|---|---:|
| cagagtagca ccccgccga agccagcacg agcagggcca gcagcacaaa caggggcacc | 2940 |
| aggcggaggt agccccgggc ttttctcttg gagtcctcac aggccttgaa catcccctcc | 3000 |
| ggctccgctt cctcgccatc acctccgtcc cctgcccgc cagccacctg ggggcctcg | 3060 |
| gccacgggca tccttttgga gtggaagagt aacaacatca ggcggcagtg actgcaagtg | 3120 |
| ggtgccgaga cagctcacag aggagggaag tgcatctcag gtcagctcgc accagagggc | 3180 |
| aggcaccaga gctggactgg gtctggctca ag | 3212 |

<210> SEQ ID NO 7
<211> LENGTH: 3206
<212> TYPE: DNA
<213> ORGANISM: Mus musculus

<400> SEQUENCE: 7

| | |
|---|---:|
| tttttttttt tttttcagtg tcagggcttg gtcaagtgct ttattcccag aacagacagt | 60 |
| gggcctccag tgaatggcag ggaggcccct gtagcaggca gagcttcagc aggcatctgc | 120 |
| agctgaggct gcccggtgat ttggcttaga gtacagccca cttggcagac tcaagggctc | 180 |
| tgatagagcc ttgataggag gccttcttt ctctgtgcag ttcccccaag aggcttttgc | 240 |
| aaggggaagg attctttctt tcctacagag acccggaggc caaggtcatg gccgccagac | 300 |
| cccactccaa aacagtggta ggagcaggga ggggaaagga ctagaataag aaagggttag | 360 |
| aagtgaaacc tagccgaggc tggccctgg acctcaggag gcatcctaac caccagctga | 420 |
| catccttctc tgtactgtca ctggggtagg cctgagggaa acaggcctta gcagggtcac | 480 |
| ttgccccaga atacttgtgt cctggctggg tggacaccct gaacttggcc tggaggcagg | 540 |
| tccagctctg tagaacagcc ctcaggtcag cacctgctgg atccagttga tcacacgtgt | 600 |
| gacacgggtg tagacgccaa agaaattggg tcggccacag cccaggcccc agctaaccaa | 660 |
| ccctgccagg aaccagcggc cactgggctc cctgcaaacc agtgggcctc cagagtcacc | 720 |
| ctggcaggca tctttcttgc ccttgcgta gccagcacag agcatgcgtg gggacacctg | 780 |
| gtagcggtag gcctcactgc agaggtcctg agggaccagc tgtacgtcca ccttctgcag | 840 |
| ggtgttgctc accggaccac cctctcgctg ggctccccag cctgtgatcc agcagtgctg | 900 |
| gcctggctca aagaagtggg agcgggcagg caggcagacg gggcgcacag tggccgagta | 960 |
| caccacgggg tggtcgagct gcagcagggc acgtcgtag tcatggctgt cctcctcgtg | 1020 |
| gtacgggtgc aggaacagac ggctcacctt gaaggacacc tcgcctggcc agcgcgagtt | 1080 |
| ctgccgcatc tttcccagga acacggtcca cagcttcggg gaggccatgc tgtcctcctg | 1140 |
| gaagcagtgg gcggccgtta tgacccagcg gtcagcgatg agagcccccc cacagatgtg | 1200 |
| tcgaccccga atctggaggc tggcctgcca tggccactca ccctcggagg acacggtccc | 1260 |
| gcccacaata cggctggaga ggccctggag gccacagtca cagtgttgct catctgagcc | 1320 |
| gtctctgcaa tctgactggc cgtcacactc tgggttgggc ttcttcacac agctccggtc | 1380 |
| ctcacactgg aaagtgaatg tcccacaggg cactccttct tggcactgtt cttcgtcact | 1440 |
| gccattgaga cagtcgggct gccggtcaca gactctaggc agtgaaatgc acgtgctgtc | 1500 |
| ctcttggcac tggaacatgg ctctgcagac acagtttctc tcatccaggc cattgggca | 1560 |
| gtccttgatc ccgtcacacg cagggacaca cagtccattc acagagcaga ggaactcacc | 1620 |
| agggcagggg tctgattggt tgtacaagct gtagtacact tgcacacccg ggcctgtgag | 1680 |
| ggagatctgg gaggtgaagt tgatggtgac accatctgag gccaccatgg ggatcctctc | 1740 |
| agcatatggc tgcagggtac ggaagccaca cagcctcctg ttctggatca tccactggcc | 1800 |

```
ctgagtacac agtcggttgt acttctgcct cctcagtgcg taggcatcga accagagcgc    1860
caagccgtag tccagagagg gtaccgtgag atgccaggag cagtgggtac tgggagagta    1920
gtaactgggg tagtagggtg tacggaggaa gccctgtgtg tccagccggc cctccagtgt    1980
caggttcacc tggcagtcct ggaaggccac agacttcact gagagcagga aagggtcata    2040
gtagctatgc atgcccttt tccacaccac ggccatgacg gagcccgatg ccagcacctc     2100
catcacaggt tcctggcggc tgcacccata gaccgaggtg ataagtctct tctccagggg    2160
cccagctgcg tcgtacatcg ccaccctgtc tctgcaatcg acccgggtcc actccagccg    2220
cactttgatc atgaggtctt cgggcccttg cagatgccac aggcagcttg tggtctgctg    2280
gtcaggcccc ttcaatggga ggacctggcc tgggttcaca tagctgtagc gataacagcc    2340
cagcgtggaa ttcagtacga ctatgtcgtt cacactggct tccaggatca ccaggccttc    2400
cgggtccacc tcatattcgg tcttatagga agccagggtt gagctgttgg acagtagctc    2460
atccaccagg agctcgcgca ctacttcagg gctcagggtc agtcgctggt actcagggat    2520
gtcaaggata aaccagaaga agcaggtgag gggtccctcc ccaaaggagt agacagaact    2580
agagttgtag taagtaccca ggcgggtgct ggcaaccagt tcttggagca tcttctgggc    2640
tttggcagat tcactgcgga aagcaataga ctcccgtcgg cccaggtcct gggagaaatg    2700
acggttgagc acccggaggc tgccagagta cacctggctt acggtcactt ccgctttgta    2760
ccctaggaaa taccaaagca tgaccctgc tgagaccagc gcagccaaga ccagcaacag     2820
tggcgtgaag cggacgtagt cccggttttt tctcttggtg tttttgggg gcttgaactt     2880 cccctctggc tcagcagctt cctctccatc acccgcatcg ccctgaccat cagccgcttg    2940
ggggacctcg gtggtgggca tcctggtaga acaggggagc tggaaacatc tcggcatctt    3000
caagagtgga aggtaggtgc cgggcctgca cacaggcctg gaggcctctg tttatccagg    3060
ccaaggtctt tccacccca actgccagc ttaggttgga tcaatggcct ggagccatgg      3120
ctggggtgtc tggcccttgt cccttgtggc ctgtggcccc aagttccatg ggcctctcct    3180
gtcaggtcca gggcgacaat gaaact                                         3206
```

<210> SEQ ID NO 8
<211> LENGTH: 2999
<212> TYPE: DNA
<213> ORGANISM: Rattus norvegicus

<400> SEQUENCE: 8

```
gcttggccaa ctgctttatt tccggaacag acagtgggcc tccagtgaat ggcagggagg      60
gccctgtagc aggcagagca cagcaggcac ccgcagctga ggctgcccca tgatttggct     120
tacggtatgg ccctacttgg cagtctcaag ggctctgaca gagccttgat agaggcacct     180
tctttctcgg atccagttcc ccctagaggc ttttgcaagg ggaaggaatc ttactttccc     240
acagaccttg gaaccagcat cattgccacc agacccacc ccaaaacagc agtaggaggg      300
gagaggggaa aggactagaa taagaaaggg ttggaagtga agccgagctg aggctagccc     360
ctggaggcat cctaaccacc agctgacatc cttctctgta ctgtccctgg ggtaggcatg     420
aggggacagg ccttagcagg gtcgctcgcc ccagaatact tgtgccctgg ctgggtggtc     480
acctgggctc cttgcaaacc agtgggcctc cagagtcgcc ctggcaggca tctttcttgc     540
ccttgcgata accagcacag agcatgcgtg gggtcacctg gtaacggtag gcctcattgc     600
acaggtcctg agggatcagt tgcacatcca ccttctgaag ggtgctgcta ccaggaccac     660
```

| | |
|---|---|
| cctctcgctg ggctccccag cctgtgatcc agcagtgctg gcctggctca aagaagtgag | 720 |
| agcgtgcggg caggcagacg gggcgcacgg tggccgagta caccacaggg tggtccagct | 780 |
| gcagcagggc cacgtcgtag tcatggctgt cctcctcatg atacgggtgc aggaacaggc | 840 |
| ggctcacctt gaaggacacc tcgcccggcc agcgtgaatt ctgccgcatc tttcccagaa | 900 |
| acacggtcca cagcctcggg gaggccatgc tgtcctcctg gaagcagtga gcggctgtta | 960 |
| tgacccagcg gtcagcgatg agagcccccc cacagatgtg tcgacccgga atctggagac | 1020 |
| tggcctgcca gggccactca ccctccgagg acatggcccc gcccacaatg cggctggagg | 1080 |
| ggccctggag gccacagtca cagtgctcct catcccgagcc atccctgcag tctgcctgcc | 1140 |
| cgtcacactc ggggttgggc ttcttcacac agctccggtc ctcacactgg aaagtgaatg | 1200 |
| tcccacaggg cactccttct tggcactgct cttcgtcgct accattgaga cagtcgggct | 1260 |
| gccggtcaca gactctcggc agtgagatgc acgtgctgtc ctcttggcac tggaacatgg | 1320 |
| ctctgcagac acagttcctc tcatccaggc cgttggggca gtccttgatt ccgtcacaag | 1380 |
| cagggacaca caatccattc acagagcaga ggaactctcc agggcagggg tctgattggt | 1440 |
| tgtacaagct gtagtacact tgcacacccg ggcctgtgag ggagatctgg gaggtgaagt | 1500 |
| tgatggtgat accatccgag gccaccacgg ggatcctctc agcatatggc tgcagggtac | 1560 |
| ggaagccaca tagcctcctg ttctggatca tccactggcc ctgagtacat agtaggttgt | 1620 |
| acttctgcct cctcagtgca taggcgtcaa accagagtgc caagccatag tccagagagg | 1680 |
| gaaccgtgag atgccaggag cagtgggtac tgggcgagta gtaactgggg tagtagggtg | 1740 |
| tacgaggaa gccctgtgga tccagccggc cttccagggt caggttcacc tggcagtcct | 1800 |
| ggaaggccac agacttcact gagagcagaa aagggtcata gaagctatgc aagcccttct | 1860 |
| tccacaccac ggccatgaca gagcccgacg ccagcacctc catcacgggt tcctggcggc | 1920 |
| tgcacccata gaccgaggtg ataagtctct tctccagggg cccagctgcg tcgtacatcg | 1980 |
| ccaccctgtc tctgcaatca acccgagtcc actctagctg cactttgagc atgaggtcct | 2040 |
| cgggcccctg caggtgccac aggcagctag tggtctgctg gtcgggcccc ctcaaccgga | 2100 |
| ggacctggcc cgggttcacg tagctgtagc ggtaacagcc cagcgtggaa ttcagtacga | 2160 |
| ctatgtcgtt cacgctggct tctagtatca ccaggccttc cgggtccacc tcatattcgg | 2220 |
| tcctatagga agccaaggct gagctgttgg acagtagctc acccaccagg agctcgcgca | 2280 |
| ccacctcagg gctcagggtc agtcgctggt actcggggat gtcaaggatg aaccagaaga | 2340 |
| agcagataag gggtccctcc ccaaaggcgt agatggaact ggagttgtag taagtaccca | 2400 |
| agcgggtgct ggcaaccagc tcttggaaca tcttctgggc tttggcagtt tcagtgcgga | 2460 |
| aagcaataga ctcccgtcgg gccaagtcct gtgaaaaatg gcggttgagc acccggaggc | 2520 |
| tgccagagta cacctggctt atggtcactt ccgccttgta cctaggaaa taccagagca | 2580 |
| tgactcctgc cgaagccaac gcagccaaga ccagcaacag tggtgtgaag cggacgtagt | 2640 |
| ccctgtcttt tctcttggcg tttctggggg ccttgaacac cccctctggc tctgcagctt | 2700 |
| cctctccatc acctccatca ccctgaccac cagctgcttg ggaacctca gcggtgggca | 2760 |
| tcctggtaga cagggagc tggaaacatc ttggcatctt caagagtgga aggtaggtgc | 2820 |
| tgggcctgaa cacaggcctg gaggcctctg tttatccagg ccaaggtctc tccacccaca | 2880 |
| actggccagc ttaggttgga tcaatagcct ggaaccatga ctggggtgtc tggcccttgt | 2940 |
| ccctcgtggc ctgtggcccc aagttccatg ggcctcctgt caggtccagg acggacaat | 2999 |

<210> SEQ ID NO 9
<211> LENGTH: 2440
<212> TYPE: DNA
<213> ORGANISM: Macaca mulatta

<400> SEQUENCE: 9

| | | | | | |
|---|---|---|---|---|---|
| gaggtgggac | ctgctctgca | gggggggcagt | tcctcaggtc | accacttgct | ggatccagcc | 60 |
| gatcacacct | gtgatgcggg | tgtagacgcc | gaagtagtta | ggccggccac | agcccaggcc | 120 |
| ccagctgacc | agccctgcca | ggaaccagcg | gccactgagt | gccttgcata | ccagcggacc | 180 |
| acccgagtca | ccctggcagg | catccttctt | gcccttgcgg | tagccggcac | acagcatgcg | 240 |
| tggcgtcacc | tggtagcgat | aggcctcgct | gcacaggtcc | tgtgggatca | actgcacgtc | 300 |
| cactttctgc | agagcattgc | tggtggggcc | gccttcgcgc | agggcgcccc | agccagtgat | 360 |
| ccagcagtga | aggccgggtt | cgaagaagtg | ggagcgcgcg | ggcaggcaga | ctggacgcac | 420 |
| ggcggccgag | cgcaccaccg | ggtggtcgag | ctgcaacagc | gccacgtcgt | agtcgtggct | 480 |
| gtcctcttcg | tgatacggat | gcaggagtag | gcggctcacc | ttgaaggaca | cctctccagg | 540 |
| ccagcgcgag | ttctgccaca | ccttgcccag | gaacaccgtc | acagcgccg | gggaggccat | 600 |
| gctgtcctcc | tggaagcaat | gggcagctgt | tatcacccag | cggtcagcga | tgagggcgcc | 660 |
| cccacagatg | tgtcgacccc | gaacctggag | gctggcctgc | catggccact | caccctcgga | 720 |
| ggacacggcc | ccaccaacaa | tgcgactgga | ggggccctgg | aggccacagt | cacagtgctg | 780 |
| ctcgtctgag | ccgtccctgc | agtcgggccg | cccatcacac | tgtgggttgg | gcttcttcac | 840 |
| gcagctctgg | tcctcacact | ggaaggtgaa | tgtcccgcag | gcacccctt | cctggcaccg | 900 |
| ctcttcatcg | ctgccgttga | acagtcagg | ctgcccgtca | cagaccttaa | gcagtgagat | 960 |
| gcacgtgctg | tcctcttggc | actggaatgt | ggctctgcaa | acgcagtttc | tctcatccag | 1020 |
| gccgttgggg | cagtccttga | ccccatcaca | ggcagggacg | cagagtccgt | tcacagagca | 1080 |
| gaggaactct | ccagggcagg | ggtccgactg | gttgtacaag | ccatagtgca | cccgcacacc | 1140 |
| aggccctgtg | agggagatct | gggaggtgaa | attgatggtg | atgccggccg | tggccaccac | 1200 |
| ggggatcctc | tcggcgtaag | gctgcaggat | gcgcaggcca | cacagcctcc | tgttctggat | 1260 |
| cgtccactgg | ccctgggtgc | acggcaaatc | atacttctgc | ctccgcagtg | cgtaggcgtc | 1320 |
| aaaccagagg | gccaagccgt | agtccagaga | gggcaccgtg | aggtgccagg | agcagtgggt | 1380 |
| tcggggcgag | tagtagctgg | ggaagtacgg | ggtgctgagg | acgccctggg | agtccagcct | 1440 |
| gtcatccagc | gtcaggttta | cctcgcaggc | ctggaagacc | accgactgca | cggagagcat | 1500 |
| aaaggggtcg | tagtagctgt | gcaggcccctt | cttccagacc | accgccatga | tggccccga | 1560 |
| tgccaggact | tccaccacag | gctcctggcg | gctgcagcca | tacaccgagg | tgatgagcct | 1620 |
| cttctccagg | ggcccagcca | cgtcatacat | ggccagtcgg | tccggcact | cggccagcgt | 1680 |
| ccactccagc | cggagtttca | gcatgaggtc | ttcggggccc | tgcaggtgcc | acaggcagct | 1740 |
| ggaggccagg | tggtcgggtc | ccttcagccg | gaggacctga | ccctggccca | cgtagctgta | 1800 |
| gcggtaacaa | cccagcgtgg | aattcagtgc | agctatgtct | ttcacactgg | cttctaggat | 1860 |
| cactaggccc | tcggggtcca | cttcgtactc | ggccctgtag | gggacagccg | ccgagctgtt | 1920 |
| gactgtggac | agcagctcct | ccaccagcag | tgcctgcacc | acctcgggc | tcagcatcag | 1980 |
| ccggcggtgc | tcggggattt | ggagaatgaa | ccagaagaag | caggtgagcg | gtccctcccc | 2040 |
| aaaggaatag | acgagctgg | agttgtaata | agttcccagg | cgggtgctgg | cgatgagctc | 2100 |
| cttgagcatc | ttctgggctt | tggcggtttc | actgcggaag | gcactggatt | cccggcgggt | 2160 |

-continued

| | |
|---|---|
| aagatcctgg gagaagtggc gattgagcac gcgcaggctg cctgagtaca cctggctgac | 2220 |
| cgtcacctcc gccttgtacc ctaggaaata ccagagtagc acccccactg aagtcagcac | 2280 |
| aaccagggtc agccacaggg gcgccaggcg gaggtagccc cgggcttttc tcttggagtc | 2340 |
| ctcacgggcc tcgaacatcc cctctggctc cgcttcctcg ccatcacctc cgtcccctg | 2400 |
| cccaccagcc acctgggggg ccttggccac aggcatcctg | 2440 |

<210> SEQ ID NO 10
<211> LENGTH: 3188
<212> TYPE: DNA
<213> ORGANISM: Macaca mulatta

<400> SEQUENCE: 10

| | |
|---|---|
| ttggatcagg cagctttatt ccaaagggca gctgagctca cctgccggtg agggtctggg | 60 |
| ctgtgagggg ccaggtggca ggcaggggtg gggcaaggac cttggagtca gggcttcccc | 120 |
| acctttttg gcttacggtg gcagccggcc cacctggcag tccccggggc tgtgagggtc | 180 |
| ccctcctatg ggggcacctt ccattcccag atcccaagtt agaccagggg cttccgaagc | 240 |
| tggcatctgc tctctagagg caaggctgcc caagcagcct ctgtacagag tggggcacag | 300 |
| ctcagacact cctggggacg tagagccagc attcttgctg ctgagccact tccttgcaat | 360 |
| aggcagcagt ggaggaaggg gacagaggag agagaatcgg gaggcagaag ggctgggtgt | 420 |
| gggcctgggt ccctagggga cgtcttgacc cccagctgct ggcactcctc catcctcctg | 480 |
| ccatcactgg agcagacatc agggacaaga caagatgcca cctcctgcca ccacagggcc | 540 |
| tgctcgcgcc cccctccccc cagaatactt gtccccctgc ttggcaattg ccctgggctc | 600 |
| tctgagtcca agaggtggga cctgctctgc aggggggcag ttcctcaggt caccacttgc | 660 |
| tggatccagc cgatcacacc tgtgatgcgg gtgtagacgc cgaagtagtt aggccggcca | 720 |
| cagcccaggc cccagctgac cagccctgcc aggaaccagc ggccactgag tgccttgcat | 780 |
| accagcggac cacccgagtc accctggcag gcatccttct tgcccttgcg gtagccggca | 840 |
| cacagcatgc gtggcgtcac ctggtagcga taggcctcgc tgcacaggtc ctgtgggatc | 900 |
| aactgcacgt ccactttctg cagagcattg ctggtggggc cgccttcgcg cagggcgccc | 960 |
| cagccagtga tccagcagtg caggccgggt tcgaagaagt gggagcgcgc gggcaggcag | 1020 |
| actgacgca cggcggccga gcgcaccacc gggtggtcga gctgcaacag cgccacgtcg | 1080 |
| tagtcgtggc tgtcctcttc gtgatacgga tgcaggagta ggcggctcac cttgaaggac | 1140 |
| acctctccag gccagcgcga gttctgccac accttgccca ggaacaccgt ccacagcgcc | 1200 |
| ggggaggcca tgctgtcctc ctggaagcaa tgggcagctg ttatcaccca gcggtcagcg | 1260 |
| atgagggcgc cccacagat gtgtcgaccc cgaacctgga ggctggcctg ccatggccac | 1320 |
| tcaccctcgg aggacacggc cccaccaaca atgcgactgg aggggccctg gaggccacag | 1380 |
| tcacagtgct gctcgtctga gccgtccctg cagtcgggcc gcccatcaca ctgtgggttg | 1440 |
| ggcttcttca cgcagctctg gtcctcacac tggaaggtga atgtcccgca gggcacccct | 1500 |
| tcctggcacc gctcttcatc gctgccgttg agacagtcag gctgcccgtc acagaccta | 1560 |
| agcagtgaga tgcacgtgct gtcctcttgg cactggaatg tggctctgca aacgcagttt | 1620 |
| ctctcatcca ggccgttggg gcagtccttg accccatcac aggcagggac gcagagtccg | 1680 |
| ttcacagagc agaggaactc tccagggcag gggtccgact ggttgtacaa gccatagtgc | 1740 |
| acccgcacac caggccctgt gagggagatc tgggaggtga aattgatggt gatgccggcc | 1800 |
| gtggccacca cggggatcct ctcggcgtaa ggctgcagga tgcgcaggcc acacagcctc | 1860 |

```
ctgttctgga tcgtccactg gccctgggtg cacggcaaat catacttctg cctccgcagt    1920
gcgtaggcgt caaaccagag ggccaagccg tagtccagag agggcaccgt gaggtgccag    1980
gagcagtggg ttcggggcga gtagtagctg gggaagtacg gggtgctgag gacgccctgg    2040
gagtccagcc tgtcatccag cgtcaggttt acctcgcagg cctggaagac caccgactgc    2100
acggagagca taaaggggtc gtagtagctg tgcaggccct tcttccagac caccgccatg    2160
atggcccccg atgccaggac ttccaccaca ggctcctggc ggctgcagcc atacaccgag    2220
gtgatgagcc tcttctccag gggcccagcc acgtcataca tggccagtcg gtcccggcac    2280
tcggccagcc tccactccag ccggagtttc agcatgaggt cttcggggcc tgcaggtgc    2340 cacaggcagc tggaggccag gtggtcgggt cccttcagcc ggaggacctg accctggccc    2400
acgtagctgt agcggtaaca acccagcgtg gaattcagtg cagctatgtc tttcacactg    2460
gcttctagga tcactaggcc ctcggggtcc acttcgtact cggccctgta ggggacagcc    2520
gccgagctgt tgactgtgga cagcagctcc tccaccagca gtgcctgcac cacctcgggg    2580
ctcagcatca gccggcggtg ctcggggatt tggagaatga accagaagaa gcaggtgagc    2640
ggtccctccc caaaggaata gacggagctg gagttgtaat aagttcccag gcgggtgctg    2700
gcgatgagct ccttgagcat cttctgggct ttggcggttt cactgcggaa ggcactggat    2760
tcccggcggg taagatcctg ggagaagtgg cgattgagca cgcgcaggct gcctgagtac    2820
acctggctga ccgtcacctc cgccttgtac cctaggaaat accagagtag caccccact    2880 gaagtcagca caaccagggt cagccacagg ggcgccaggc ggaggtagcc ccgggctttt    2940
ctcttggagt cctcacgggc ctcgaacatc ccctctggct ccgcttcctc gccatcacct    3000
ccgtccccct gcccaccagc cacctggggg gccttggcca caggcatcct ttcagagtgg    3060
aagagtaaca acatcaggcg gcagtgaccg gaagtgggtg ccgagacagt tcacagagga    3120
gcgaagtgca tctcaaggca gctcaccccca gagggcaggc accagagctg gactgggtgt    3180
ggctcaag                                                              3188
```

<210> SEQ ID NO 11
<211> LENGTH: 16
<212> TYPE: PRT
<213> ORGANISM: Unknown
<220> FEATURE:
<221> NAME/KEY: source
<223> OTHER INFORMATION: /note="Description of Unknown: Exemplary
      hydrophobic membrane translocation peptide"

<400> SEQUENCE: 11

Ala Ala Val Ala Leu Leu Pro Ala Val Leu Ala Leu Leu Ala Pro
1               5                   10                  15

<210> SEQ ID NO 12
<211> LENGTH: 11
<212> TYPE: PRT
<213> ORGANISM: Unknown
<220> FEATURE:
<221> NAME/KEY: source
<223> OTHER INFORMATION: /note="Description of Unknown: RFGF
      analogue peptide"

<400> SEQUENCE: 12

Ala Ala Leu Leu Pro Val Leu Leu Ala Ala Pro
1               5                   10

<210> SEQ ID NO 13

```
<211> LENGTH: 13
<212> TYPE: PRT
<213> ORGANISM: Human immunodeficiency virus

<400> SEQUENCE: 13

Gly Arg Lys Lys Arg Arg Gln Arg Arg Pro Pro Gln
1               5                   10

<210> SEQ ID NO 14
<211> LENGTH: 16
<212> TYPE: PRT
<213> ORGANISM: Drosophila sp.

<400> SEQUENCE: 14

Arg Gln Ile Lys Ile Trp Phe Gln Asn Arg Arg Met Lys Trp Lys Lys
1               5                   10                  15

<210> SEQ ID NO 15
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 15
cuuacgcuga guacuucgat t                                            21

<210> SEQ ID NO 16
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 16
ucgaaguacu cagcguaagt t                                            21

<210> SEQ ID NO 17
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
uggccuggag agguguccuu c                                            21

<210> SEQ ID NO 18
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 18
ggggugcuac ucugguauuu c                                              21

<210> SEQ ID NO 19
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
caacggccug gaugagagaa a                                              21

<210> SEQ ID NO 20
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
aucgccacuu cucccaggau c                                              21

<210> SEQ ID NO 21
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
gguggcagga gguggcaucu u                                              21

<210> SEQ ID NO 22
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
gaccgacugg ccauguauga c                                              21

<210> SEQ ID NO 23
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
ggugugcggg ugcacuaugg c                                              21

<210> SEQ ID NO 24
<211> LENGTH: 21
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
ggccuggaug agagaaacug c                                              21

<210> SEQ ID NO 25
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
cucugguauu uccuagggua c                                              21

<210> SEQ ID NO 26
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
gccccugguc uaacuuggga u                                              21

<210> SEQ ID NO 27
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
gaggcagaag uaugauuugc c                                              21

<210> SEQ ID NO 28
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
aagccagugu gaaagacaua g                                              21

<210> SEQ ID NO 29
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
gccgggaccg acuggccaug u                                              21
```

```
<210> SEQ ID NO 30
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
cuccagguuc ggggucgaca c                                          21

<210> SEQ ID NO 31
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
agccccuggu cuaacuuggg a                                          21

<210> SEQ ID NO 32
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
ucgccacuuc ucccaggauc u                                          21

<210> SEQ ID NO 33
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
acucugguau uuccuagggu a                                          21

<210> SEQ ID NO 34
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
ucgcugaccg cugggugaua a                                          21

<210> SEQ ID NO 35
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 35
gccccaacgg ccuggaugag a                                            21

<210> SEQ ID NO 36
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
gccaagcagg gggacaagua u                                            21

<210> SEQ ID NO 37
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
uccccuacag ggccgaguac g                                            21

<210> SEQ ID NO 38
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38 cugguuguu accgcuacag c                                             21

<210> SEQ ID NO 39
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
cuggccugga gagguguccu u                                            21

<210> SEQ ID NO 40
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
gugcgggugc acuauggcuu g                                            21

<210> SEQ ID NO 41
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
uggcaggagg uggcaucuug u                                              21

<210> SEQ ID NO 42
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
cccuacaggg ccgaguacga a                                              21

<210> SEQ ID NO 43
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
accugcuucu ucugguucau u                                              21

<210> SEQ ID NO 44
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
ugccugugau ggggucaagg a                                              21

<210> SEQ ID NO 45
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
cagcuucgga agccccuggu c                                              21

<210> SEQ ID NO 46
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
```
ccccuggucu aacuugggau c    21

<210> SEQ ID NO 47
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
ugcuucuucu gguucauucu c    21

<210> SEQ ID NO 48
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
cccaacggcc uggaugagag a    21

<210> SEQ ID NO 49
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
aagggccugc acagcuacua c    21

<210> SEQ ID NO 50
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
gucuaacuug ggaucuggga a    21

<210> SEQ ID NO 51
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
agcuucggaa gccccugguc u    21

<210> SEQ ID NO 52
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
ccagugugaa agacauagcu g                                              21

<210> SEQ ID NO 53
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
ccagguucgg ggucgacaca u                                              21

<210> SEQ ID NO 54
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
uccacgcugg guuguuaccg c                                              21

<210> SEQ ID NO 55
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
ugccaagcag ggggacaagu a                                              21

<210> SEQ ID NO 56
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
auccagaaca ggaggcugug u                                              21

<210> SEQ ID NO 57
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
uucaccuccc agaucucccu c                                              21

<210> SEQ ID NO 58

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
ccuccgaggg ugaguggcca u                                              21

<210> SEQ ID NO 59
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
uccagaacag gaggcugugu g                                              21

<210> SEQ ID NO 60
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
guguccuccg agggugagug g                                              21

<210> SEQ ID NO 61
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61 uucgggucg acacaucugu g                                               21

<210> SEQ ID NO 62
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
ucggggucga cacaucugug g                                              21

<210> SEQ ID NO 63
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
```

-continued ugcuuccagg aggacagcau g                                              21

<210> SEQ ID NO 64
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
ucugguauuu ccuaggguac a                                              21

<210> SEQ ID NO 65
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
uugaaggaca ccucuccagg cca                                            23

<210> SEQ ID NO 66
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
aggaaauacc agaguagcac ccc                                            23

<210> SEQ ID NO 67
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
aguuucucuc auccaggccg uug                                            23

<210> SEQ ID NO 68
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
aagauccugg gagaaguggc gau                                            23

<210> SEQ ID NO 69
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 69
acaagaugcc accuccugcc acc                                              23

<210> SEQ ID NO 70
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
acgucauaca uggccagucg guc                                              23

<210> SEQ ID NO 71
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
aagccauagu gcacccgcac acc                                              23

<210> SEQ ID NO 72
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
acgcaguuuc ucucauccag gcc                                              23

<210> SEQ ID NO 73
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
uuguacccua ggaaauacca gag                                              23

<210> SEQ ID NO 74
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
agaucccaag uuagaccagg ggc                                              23
```

```
<210> SEQ ID NO 75
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
acggcaaauc auacuucugc cuc                                            23

<210> SEQ ID NO 76
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
agcuaugucu uucacacugg cuu                                            23

<210> SEQ ID NO 77
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
auacauggcc agucgguccc ggc                                            23

<210> SEQ ID NO 78
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
augugucgac cccgaaccug gag                                            23

<210> SEQ ID NO 79
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
gaucccaagu uagaccaggg gcu                                            23

<210> SEQ ID NO 80
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 80
uaagauccug ggagaagugg cga                                              23

<210> SEQ ID NO 81
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
uguacccuag gaaauaccag agu                                              23

<210> SEQ ID NO 82
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
uguuaucacc cagcggucag cga                                              23

<210> SEQ ID NO 83
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
ucucucaucc aggccguugg ggc                                              23

<210> SEQ ID NO 84
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
gaauacuugu cccccugcuu ggc                                              23

<210> SEQ ID NO 85
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
uucguacucg gcccuguagg gga                                              23

<210> SEQ ID NO 86
<211> LENGTH: 23
<212> TYPE: RNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 86
uagcuguagc gguaacaacc cag                                           23

<210> SEQ ID NO 87
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
ugaaggacac cucuccaggc cag                                           23

<210> SEQ ID NO 88
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
uacaagccau agugcacccg cac                                           23

<210> SEQ ID NO 89
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
agacaagaug ccaccuccug cca                                           23

<210> SEQ ID NO 90
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
acuucguacu cggcccugua ggg                                           23

<210> SEQ ID NO 91
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
agaaugaacc agaagaagca ggu                                           23
```

<210> SEQ ID NO 92
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
aguccuugac cccaucacag gca                                          23

<210> SEQ ID NO 93
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
uagaccaggg gcuuccgaag cug                                          23

<210> SEQ ID NO 94
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
cagaucccaa guuagaccag ggg                                          23

<210> SEQ ID NO 95
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
uggagaauga accagaagaa gca                                          23

<210> SEQ ID NO 96
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
uuucucucau ccaggccguu ggg                                          23

<210> SEQ ID NO 97
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
ucguaguagc ugugcaggcc cuu                                          23

<210> SEQ ID NO 98
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
cauucccaga ucccaaguua gac                                          23

<210> SEQ ID NO 99
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
uuagaccagg ggcuuccgaa gcu                                          23

<210> SEQ ID NO 100
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
ugcagcuaug ucuuucacac ugg                                          23

<210> SEQ ID NO 101
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
agaugugucg accccgaacc ugg                                          23

<210> SEQ ID NO 102
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
uagcgguaac aacccagcgu gga                                          23

<210> SEQ ID NO 103
<211> LENGTH: 23
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
aauacuuguc ccccugcuug gca                                              23

<210> SEQ ID NO 104
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
ccacacagcc uccuguucug gau                                              23

<210> SEQ ID NO 105
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
gugagggaga ucugggaggu gaa                                              23

<210> SEQ ID NO 106
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
ccauggccac ucacccucgg agg                                              23

<210> SEQ ID NO 107
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
gccacacagc cuccuguucu gga                                              23

<210> SEQ ID NO 108
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
ggccacucac ccucggagga cac                                              23
```

<210> SEQ ID NO 109
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 109
cccacagaug ugucgacccc gaa                                           23

<210> SEQ ID NO 110
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 110
ccccacagau gugucgaccc cga                                           23

<210> SEQ ID NO 111
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 111
gccaugcugu ccuccuggaa gca                                           23

<210> SEQ ID NO 112
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 112
uguacccuag gaaauaccag agu                                           23

<210> SEQ ID NO 113
<211> LENGTH: 21
<212> TYPE: RNA
<213> ORGANISM: Homo sapiens

<400> SEQUENCE: 113
uggccuggag agguguccuu c                                             21

<210> SEQ ID NO 114
<211> LENGTH: 21
<212> TYPE: RNA
<213> ORGANISM: Homo sapiens

<400> SEQUENCE: 114
ggggugcuac ucugguauuu c                                             21

<210> SEQ ID NO 115

```
<211> LENGTH: 21
<212> TYPE: RNA
<213> ORGANISM: Homo sapiens

<400> SEQUENCE: 115
caacggccug gaugagagaa a                                              21

<210> SEQ ID NO 116
<211> LENGTH: 21
<212> TYPE: RNA
<213> ORGANISM: Homo sapiens

<400> SEQUENCE: 116
aucgccacuu cucccaggau c                                              21

<210> SEQ ID NO 117
<211> LENGTH: 21
<212> TYPE: RNA
<213> ORGANISM: Homo sapiens

<400> SEQUENCE: 117
gguggcagga gguggcaucu u                                              21

<210> SEQ ID NO 118
<211> LENGTH: 21
<212> TYPE: RNA
<213> ORGANISM: Homo sapiens

<400> SEQUENCE: 118
gaccgacugg ccauguauga c                                              21

<210> SEQ ID NO 119
<211> LENGTH: 21
<212> TYPE: RNA
<213> ORGANISM: Homo sapiens

<400> SEQUENCE: 119
ggugugcggg ugcacuaugg c                                              21

<210> SEQ ID NO 120
<211> LENGTH: 21
<212> TYPE: RNA
<213> ORGANISM: Homo sapiens

<400> SEQUENCE: 120
ggccuggaug agagaaacug c                                              21

<210> SEQ ID NO 121
<211> LENGTH: 21
<212> TYPE: RNA
<213> ORGANISM: Homo sapiens

<400> SEQUENCE: 121
cucugguauu uccuagggua c                                              21

<210> SEQ ID NO 122
<211> LENGTH: 21
<212> TYPE: RNA
<213> ORGANISM: Homo sapiens

<400> SEQUENCE: 122
gccccugguc uaacuuggga u                                              21
```

```
<210> SEQ ID NO 123
<211> LENGTH: 21
<212> TYPE: RNA
<213> ORGANISM: Homo sapiens

<400> SEQUENCE: 123
gaggcagaag uaugauuugc c                                              21

<210> SEQ ID NO 124
<211> LENGTH: 21
<212> TYPE: RNA
<213> ORGANISM: Homo sapiens

<400> SEQUENCE: 124
aagccagugu gaaagacaua g                                              21

<210> SEQ ID NO 125
<211> LENGTH: 21
<212> TYPE: RNA
<213> ORGANISM: Homo sapiens

<400> SEQUENCE: 125
gccgggaccg acuggccaug u                                              21

<210> SEQ ID NO 126
<211> LENGTH: 21
<212> TYPE: RNA
<213> ORGANISM: Homo sapiens

<400> SEQUENCE: 126
cuccagguuc ggggucgaca c                                              21

<210> SEQ ID NO 127
<211> LENGTH: 21
<212> TYPE: RNA
<213> ORGANISM: Homo sapiens

<400> SEQUENCE: 127
agccccuggu cuaacuuggg a                                              21

<210> SEQ ID NO 128
<211> LENGTH: 21
<212> TYPE: RNA
<213> ORGANISM: Homo sapiens

<400> SEQUENCE: 128
ucgccacuuc ucccaggauc u                                              21

<210> SEQ ID NO 129
<211> LENGTH: 21
<212> TYPE: RNA
<213> ORGANISM: Homo sapiens

<400> SEQUENCE: 129
acucugguau uuccuagggu a                                              21

<210> SEQ ID NO 130
<211> LENGTH: 21
<212> TYPE: RNA
<213> ORGANISM: Homo sapiens

<400> SEQUENCE: 130
ucgcugaccg cuggugaua a                                               21
```

```
<210> SEQ ID NO 131
<211> LENGTH: 21
<212> TYPE: RNA
<213> ORGANISM: Homo sapiens

<400> SEQUENCE: 131
gccccaacgg ccuggaugag a                                              21

<210> SEQ ID NO 132
<211> LENGTH: 21
<212> TYPE: RNA
<213> ORGANISM: Homo sapiens

<400> SEQUENCE: 132
gccaagcagg gggacaagua u                                              21

<210> SEQ ID NO 133
<211> LENGTH: 21
<212> TYPE: RNA
<213> ORGANISM: Homo sapiens

<400> SEQUENCE: 133
uccccuacag ggccgaguac g                                              21

<210> SEQ ID NO 134
<211> LENGTH: 21
<212> TYPE: RNA
<213> ORGANISM: Homo sapiens

<400> SEQUENCE: 134
cuggguuguu accgcuacag c                                              21

<210> SEQ ID NO 135
<211> LENGTH: 21
<212> TYPE: RNA
<213> ORGANISM: Homo sapiens

<400> SEQUENCE: 135
cuggccugga gagguguccu u                                              21

<210> SEQ ID NO 136
<211> LENGTH: 21
<212> TYPE: RNA
<213> ORGANISM: Homo sapiens

<400> SEQUENCE: 136
gugcgggugc acuauggcuu g                                              21

<210> SEQ ID NO 137
<211> LENGTH: 21
<212> TYPE: RNA
<213> ORGANISM: Homo sapiens

<400> SEQUENCE: 137
uggcaggagg uggcaucuug u                                              21

<210> SEQ ID NO 138
<211> LENGTH: 21
<212> TYPE: RNA
<213> ORGANISM: Homo sapiens

<400> SEQUENCE: 138
cccuacaggg ccgaguacga a                                              21
```

```
<210> SEQ ID NO 139
<211> LENGTH: 21
<212> TYPE: RNA
<213> ORGANISM: Homo sapiens

<400> SEQUENCE: 139
accugcuucu ucugguucau u                                              21

<210> SEQ ID NO 140
<211> LENGTH: 21
<212> TYPE: RNA
<213> ORGANISM: Homo sapiens

<400> SEQUENCE: 140
ugccugugau ggggucaagg a                                              21

<210> SEQ ID NO 141
<211> LENGTH: 21
<212> TYPE: RNA
<213> ORGANISM: Homo sapiens

<400> SEQUENCE: 141
cagcuucgga agccccuggu c                                              21

<210> SEQ ID NO 142
<211> LENGTH: 21
<212> TYPE: RNA
<213> ORGANISM: Homo sapiens

<400> SEQUENCE: 142
ccccuggucu aacuugggau c                                              21

<210> SEQ ID NO 143
<211> LENGTH: 21
<212> TYPE: RNA
<213> ORGANISM: Homo sapiens

<400> SEQUENCE: 143
ugcuucuucu gguucauucu c                                              21

<210> SEQ ID NO 144
<211> LENGTH: 21
<212> TYPE: RNA
<213> ORGANISM: Homo sapiens

<400> SEQUENCE: 144
cccaacggcc uggaugagag a                                              21

<210> SEQ ID NO 145
<211> LENGTH: 21
<212> TYPE: RNA
<213> ORGANISM: Homo sapiens

<400> SEQUENCE: 145
aagggccugc acagcuacua c                                              21

<210> SEQ ID NO 146
<211> LENGTH: 21
<212> TYPE: RNA
<213> ORGANISM: Homo sapiens

<400> SEQUENCE: 146
```
gucuaacuug ggaucuggga a                                                    21

<210> SEQ ID NO 147
<211> LENGTH: 21
<212> TYPE: RNA
<213> ORGANISM: Homo sapiens

<400> SEQUENCE: 147
agcuucggaa gccccugguc u                                                    21

<210> SEQ ID NO 148
<211> LENGTH: 21
<212> TYPE: RNA
<213> ORGANISM: Homo sapiens

<400> SEQUENCE: 148
ccagugugaa agacauagcu g                                                    21

<210> SEQ ID NO 149
<211> LENGTH: 21
<212> TYPE: RNA
<213> ORGANISM: Homo sapiens

<400> SEQUENCE: 149
ccagguucgg ggucgacaca u                                                    21

<210> SEQ ID NO 150
<211> LENGTH: 21
<212> TYPE: RNA
<213> ORGANISM: Homo sapiens

<400> SEQUENCE: 150
uccacgcugg guuguuaccg c                                                    21

<210> SEQ ID NO 151
<211> LENGTH: 21
<212> TYPE: RNA
<213> ORGANISM: Homo sapiens

<400> SEQUENCE: 151
ugccaagcag ggggacaagu a                                                    21

<210> SEQ ID NO 152
<211> LENGTH: 21
<212> TYPE: RNA
<213> ORGANISM: Homo sapiens

<400> SEQUENCE: 152
auccagaaca ggaggcugug u                                                    21

<210> SEQ ID NO 153
<211> LENGTH: 21
<212> TYPE: RNA
<213> ORGANISM: Homo sapiens

<400> SEQUENCE: 153
uucaccuccc agaucucccu c                                                    21

<210> SEQ ID NO 154
<211> LENGTH: 21
<212> TYPE: RNA
<213> ORGANISM: Homo sapiens

<400> SEQUENCE: 154
ccuccgaggg ugaguggcca u               21

<210> SEQ ID NO 155
<211> LENGTH: 21
<212> TYPE: RNA
<213> ORGANISM: Homo sapiens

<400> SEQUENCE: 155
uccagaacag gaggcugugu g               21

<210> SEQ ID NO 156
<211> LENGTH: 21
<212> TYPE: RNA
<213> ORGANISM: Homo sapiens

<400> SEQUENCE: 156
guguccuccg agggugagug g               21

<210> SEQ ID NO 157
<211> LENGTH: 21
<212> TYPE: RNA
<213> ORGANISM: Homo sapiens

<400> SEQUENCE: 157
uucggggucg acacaucugu g               21

<210> SEQ ID NO 158
<211> LENGTH: 21
<212> TYPE: RNA
<213> ORGANISM: Homo sapiens

<400> SEQUENCE: 158
ucggggucga cacaucugug g               21

<210> SEQ ID NO 159
<211> LENGTH: 21
<212> TYPE: RNA
<213> ORGANISM: Homo sapiens

<400> SEQUENCE: 159
ugcuuccagg aggacagcau g               21

<210> SEQ ID NO 160
<211> LENGTH: 21
<212> TYPE: RNA
<213> ORGANISM: Homo sapiens

<400> SEQUENCE: 160
ucugguauuu ccuaggguac a               21

<210> SEQ ID NO 161
<211> LENGTH: 23
<212> TYPE: RNA
<213> ORGANISM: Homo sapiens

<400> SEQUENCE: 161
uugaaggaca ccucuccagg cca             23

<210> SEQ ID NO 162
<211> LENGTH: 23
<212> TYPE: RNA
<213> ORGANISM: Homo sapiens

```
<400> SEQUENCE: 162
aggaaauacc agaguagcac ccc                                              23

<210> SEQ ID NO 163
<211> LENGTH: 23
<212> TYPE: RNA
<213> ORGANISM: Homo sapiens

<400> SEQUENCE: 163
aguuucucuc auccaggccg uug                                              23

<210> SEQ ID NO 164
<211> LENGTH: 23
<212> TYPE: RNA
<213> ORGANISM: Homo sapiens

<400> SEQUENCE: 164
aagauccugg gagaaguggc gau                                              23

<210> SEQ ID NO 165
<211> LENGTH: 23
<212> TYPE: RNA
<213> ORGANISM: Homo sapiens

<400> SEQUENCE: 165
acaagaugcc accuccugcc acc                                              23

<210> SEQ ID NO 166
<211> LENGTH: 23
<212> TYPE: RNA
<213> ORGANISM: Homo sapiens

<400> SEQUENCE: 166
acgucauaca uggccagucg guc                                              23

<210> SEQ ID NO 167
<211> LENGTH: 23
<212> TYPE: RNA
<213> ORGANISM: Homo sapiens

<400> SEQUENCE: 167
aagccauagu gcacccgcac acc                                              23

<210> SEQ ID NO 168
<211> LENGTH: 23
<212> TYPE: RNA
<213> ORGANISM: Homo sapiens

<400> SEQUENCE: 168
acgcaguuuc ucucauccag gcc                                              23

<210> SEQ ID NO 169
<211> LENGTH: 23
<212> TYPE: RNA
<213> ORGANISM: Homo sapiens

<400> SEQUENCE: 169
uuguacccua ggaaauacca gag                                              23

<210> SEQ ID NO 170
<211> LENGTH: 23
<212> TYPE: RNA
<213> ORGANISM: Homo sapiens
```

```
<400> SEQUENCE: 170
agaucccaag uuagaccagg ggc                                              23

<210> SEQ ID NO 171
<211> LENGTH: 23
<212> TYPE: RNA
<213> ORGANISM: Homo sapiens

<400> SEQUENCE: 171
acggcaaauc auacuucugc cuc                                              23

<210> SEQ ID NO 172
<211> LENGTH: 23
<212> TYPE: RNA
<213> ORGANISM: Homo sapiens

<400> SEQUENCE: 172
agcuaugucu uucacacugg cuu                                              23

<210> SEQ ID NO 173
<211> LENGTH: 23
<212> TYPE: RNA
<213> ORGANISM: Homo sapiens

<400> SEQUENCE: 173
auacauggcc agucggcccc ggc                                              23

<210> SEQ ID NO 174
<211> LENGTH: 23
<212> TYPE: RNA
<213> ORGANISM: Homo sapiens

<400> SEQUENCE: 174
augugucgac cccgaaccug gag                                              23

<210> SEQ ID NO 175
<211> LENGTH: 23
<212> TYPE: RNA
<213> ORGANISM: Homo sapiens

<400> SEQUENCE: 175
gaucccaagu uagaccaggg gcu                                              23

<210> SEQ ID NO 176
<211> LENGTH: 23
<212> TYPE: RNA
<213> ORGANISM: Homo sapiens

<400> SEQUENCE: 176
uaagauccug ggagaagugg cga                                              23

<210> SEQ ID NO 177
<211> LENGTH: 23
<212> TYPE: RNA
<213> ORGANISM: Homo sapiens

<400> SEQUENCE: 177
uguacccuag gaaauaccag agu                                              23

<210> SEQ ID NO 178
<211> LENGTH: 23
<212> TYPE: RNA
```

```
<213> ORGANISM: Homo sapiens

<400> SEQUENCE: 178
uguuaucacc cagcggucag cga                                          23

<210> SEQ ID NO 179
<211> LENGTH: 23
<212> TYPE: RNA
<213> ORGANISM: Homo sapiens

<400> SEQUENCE: 179
ucucucaucc aggccguugg ggc                                          23

<210> SEQ ID NO 180
<211> LENGTH: 23
<212> TYPE: RNA
<213> ORGANISM: Homo sapiens

<400> SEQUENCE: 180
gaauacuugu cccccugcuu ggc                                          23

<210> SEQ ID NO 181
<211> LENGTH: 23
<212> TYPE: RNA
<213> ORGANISM: Homo sapiens

<400> SEQUENCE: 181
uucguacucg gcccuguagg gga                                          23

<210> SEQ ID NO 182
<211> LENGTH: 23
<212> TYPE: RNA
<213> ORGANISM: Homo sapiens

<400> SEQUENCE: 182
uagcuguagc gguaacaacc cag                                          23

<210> SEQ ID NO 183
<211> LENGTH: 23
<212> TYPE: RNA
<213> ORGANISM: Homo sapiens

<400> SEQUENCE: 183
ugaaggacac cucuccaggc cag                                          23

<210> SEQ ID NO 184
<211> LENGTH: 23
<212> TYPE: RNA
<213> ORGANISM: Homo sapiens

<400> SEQUENCE: 184
uacaagccau agugcacccg cac                                          23

<210> SEQ ID NO 185
<211> LENGTH: 23
<212> TYPE: RNA
<213> ORGANISM: Homo sapiens

<400> SEQUENCE: 185
agacaagaug ccaccuccug cca                                          23

<210> SEQ ID NO 186
<211> LENGTH: 23
```

```
<212> TYPE: RNA
<213> ORGANISM: Homo sapiens

<400> SEQUENCE: 186
acuucguacu cggcccugua ggg                                              23

<210> SEQ ID NO 187
<211> LENGTH: 23
<212> TYPE: RNA
<213> ORGANISM: Homo sapiens

<400> SEQUENCE: 187
agaaugaacc agaagaagca ggu                                              23

<210> SEQ ID NO 188
<211> LENGTH: 23
<212> TYPE: RNA
<213> ORGANISM: Homo sapiens

<400> SEQUENCE: 188
aguccuugac cccaucacag gca                                              23

<210> SEQ ID NO 189
<211> LENGTH: 23
<212> TYPE: RNA
<213> ORGANISM: Homo sapiens

<400> SEQUENCE: 189
uagaccaggg gcuuccgaag cug                                              23

<210> SEQ ID NO 190
<211> LENGTH: 23
<212> TYPE: RNA
<213> ORGANISM: Homo sapiens

<400> SEQUENCE: 190
cagaucccaa guuagaccag ggg                                              23

<210> SEQ ID NO 191
<211> LENGTH: 23
<212> TYPE: RNA
<213> ORGANISM: Homo sapiens

<400> SEQUENCE: 191
uggagaauga accagaagaa gca                                              23

<210> SEQ ID NO 192
<211> LENGTH: 23
<212> TYPE: RNA
<213> ORGANISM: Homo sapiens

<400> SEQUENCE: 192
uuucucucau ccaggccguu ggg                                              23

<210> SEQ ID NO 193
<211> LENGTH: 23
<212> TYPE: RNA
<213> ORGANISM: Homo sapiens

<400> SEQUENCE: 193
ucguaguagc ugugcaggcc cuu                                              23

<210> SEQ ID NO 194
```

```
<211> LENGTH: 23
<212> TYPE: RNA
<213> ORGANISM: Homo sapiens

<400> SEQUENCE: 194
cauucccaga ucccaaguua gac                                              23

<210> SEQ ID NO 195
<211> LENGTH: 23
<212> TYPE: RNA
<213> ORGANISM: Homo sapiens

<400> SEQUENCE: 195
uuagaccagg ggcuuccgaa gcu                                              23

<210> SEQ ID NO 196
<211> LENGTH: 23
<212> TYPE: RNA
<213> ORGANISM: Homo sapiens

<400> SEQUENCE: 196
ugcagcuaug ucuuucacac ugg                                              23

<210> SEQ ID NO 197
<211> LENGTH: 23
<212> TYPE: RNA
<213> ORGANISM: Homo sapiens

<400> SEQUENCE: 197
agaugugucg accccgaacc ugg                                              23

<210> SEQ ID NO 198
<211> LENGTH: 23
<212> TYPE: RNA
<213> ORGANISM: Homo sapiens

<400> SEQUENCE: 198
uagcgguaac aacccagcgu gga                                              23

<210> SEQ ID NO 199
<211> LENGTH: 23
<212> TYPE: RNA
<213> ORGANISM: Homo sapiens

<400> SEQUENCE: 199
aauacuuguc ccccugcuug gca                                              23

<210> SEQ ID NO 200
<211> LENGTH: 23
<212> TYPE: RNA
<213> ORGANISM: Homo sapiens

<400> SEQUENCE: 200
ccacacagcc uccuguucug gau                                              23

<210> SEQ ID NO 201
<211> LENGTH: 23
<212> TYPE: RNA
<213> ORGANISM: Homo sapiens

<400> SEQUENCE: 201
gugagggaga ucugggaggu gaa                                              23
```

-continued

```
<210> SEQ ID NO 202
<211> LENGTH: 23
<212> TYPE: RNA
<213> ORGANISM: Homo sapiens

<400> SEQUENCE: 202
ccauggccac ucacccucgg agg                                              23

<210> SEQ ID NO 203
<211> LENGTH: 23
<212> TYPE: RNA
<213> ORGANISM: Homo sapiens

<400> SEQUENCE: 203
gccacacagc cuccuguucu gga                                              23

<210> SEQ ID NO 204
<211> LENGTH: 23
<212> TYPE: RNA
<213> ORGANISM: Homo sapiens

<400> SEQUENCE: 204
ggccacucac ccucggagga cac                                              23

<210> SEQ ID NO 205
<211> LENGTH: 23
<212> TYPE: RNA
<213> ORGANISM: Homo sapiens

<400> SEQUENCE: 205
cccacagaug ugucgacccc gaa                                              23

<210> SEQ ID NO 206
<211> LENGTH: 23
<212> TYPE: RNA
<213> ORGANISM: Homo sapiens

<400> SEQUENCE: 206
ccccacagau gugucgaccc cga                                              23

<210> SEQ ID NO 207
<211> LENGTH: 23
<212> TYPE: RNA
<213> ORGANISM: Homo sapiens

<400> SEQUENCE: 207
gccaugcugu ccuccuggaa gca                                              23

<210> SEQ ID NO 208
<211> LENGTH: 23
<212> TYPE: RNA
<213> ORGANISM: Homo sapiens

<400> SEQUENCE: 208
uguacccuag gaaauaccag agu                                              23

<210> SEQ ID NO 209
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 209
ugguauuucc uagggua cat t                                              21

<210> SEQ ID NO 210
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 210
uguacccuag gaaauaccat t                                               21

<210> SEQ ID NO 211
<211> LENGTH: 21
<212> TYPE: RNA
<213> ORGANISM: Homo sapiens

<400> SEQUENCE: 211
ggugcuacuc ugguauuccc u                                               21

<210> SEQ ID NO 212
<211> LENGTH: 21
<212> TYPE: RNA
<213> ORGANISM: Homo sapiens

<400> SEQUENCE: 212
ucugguauuu ccuagggua c a                                              21

<210> SEQ ID NO 213
<211> LENGTH: 21
<212> TYPE: RNA
<213> ORGANISM: Homo sapiens

<400> SEQUENCE: 213
cugguauuuc cuagggua ca a                                              21

<210> SEQ ID NO 214
<211> LENGTH: 21
<212> TYPE: RNA
<213> ORGANISM: Homo sapiens

<400> SEQUENCE: 214
ugguauuucc uagggua caa a                                              21

<210> SEQ ID NO 215
<211> LENGTH: 21
<212> TYPE: RNA
<213> ORGANISM: Homo sapiens

<400> SEQUENCE: 215
gguauuuccu aggguacaag a                                               21

<210> SEQ ID NO 216
<211> LENGTH: 19
```

```
<212> TYPE: RNA
<213> ORGANISM: Homo sapiens

<400> SEQUENCE: 216
ugguauuucc uaggguaca                                              19

<210> SEQ ID NO 217
<211> LENGTH: 21
<212> TYPE: RNA
<213> ORGANISM: Homo sapiens

<400> SEQUENCE: 217
guauuuccua ggguacaagg a                                           21

<210> SEQ ID NO 218
<211> LENGTH: 21
<212> TYPE: RNA
<213> ORGANISM: Homo sapiens

<400> SEQUENCE: 218 auuccuagg guacaaggcg a                                            21

<210> SEQ ID NO 219
<211> LENGTH: 21
<212> TYPE: RNA
<213> ORGANISM: Homo sapiens

<400> SEQUENCE: 219 uuccuaggg uacaaggcgg a                                            21

<210> SEQ ID NO 220
<211> LENGTH: 21
<212> TYPE: RNA
<213> ORGANISM: Homo sapiens

<400> SEQUENCE: 220
cgccacuucu cccaggaucu u                                           21

<210> SEQ ID NO 221
<211> LENGTH: 21
<212> TYPE: RNA
<213> ORGANISM: Homo sapiens

<400> SEQUENCE: 221
gccacuucuc ccaggaucuu a                                           21

<210> SEQ ID NO 222
<211> LENGTH: 21
<212> TYPE: RNA
<213> ORGANISM: Homo sapiens

<400> SEQUENCE: 222
cugcuucuuc ugguucauuc u                                           21

<210> SEQ ID NO 223
<211> LENGTH: 21
<212> TYPE: RNA
<213> ORGANISM: Homo sapiens

<400> SEQUENCE: 223
cuucuucugg uucauucuc a                                            21

<210> SEQ ID NO 224
```

```
<211> LENGTH: 21
<212> TYPE: RNA
<213> ORGANISM: Homo sapiens

<400> SEQUENCE: 224
cccuacaggg ccgaguacga a                                              21

<210> SEQ ID NO 225
<211> LENGTH: 21
<212> TYPE: RNA
<213> ORGANISM: Homo sapiens

<400> SEQUENCE: 225
cuacagggcc gaguacgaag u                                              21

<210> SEQ ID NO 226
<211> LENGTH: 21
<212> TYPE: RNA
<213> ORGANISM: Homo sapiens

<400> SEQUENCE: 226
gccaguguga aagacauagc u                                              21

<210> SEQ ID NO 227
<211> LENGTH: 21
<212> TYPE: RNA
<213> ORGANISM: Homo sapiens

<400> SEQUENCE: 227
agugugaaag acauagcugc a                                              21

<210> SEQ ID NO 228
<211> LENGTH: 21
<212> TYPE: RNA
<213> ORGANISM: Homo sapiens

<400> SEQUENCE: 228
cacgcugggu uguuaccgcu a                                              21

<210> SEQ ID NO 229
<211> LENGTH: 21
<212> TYPE: RNA
<213> ORGANISM: Homo sapiens

<400> SEQUENCE: 229
ggguuguuac cgcuacagcu a                                              21

<210> SEQ ID NO 230
<211> LENGTH: 21
<212> TYPE: RNA
<213> ORGANISM: Homo sapiens

<400> SEQUENCE: 230
cgggaccgac uggccaugua u                                              21

<210> SEQ ID NO 231
<211> LENGTH: 21
<212> TYPE: RNA
<213> ORGANISM: Homo sapiens

<400> SEQUENCE: 231
ccgacuggcc auguaugacg u                                              21
```

```
<210> SEQ ID NO 232
<211> LENGTH: 21
<212> TYPE: RNA
<213> ORGANISM: Homo sapiens

<400> SEQUENCE: 232
gggccugcac agcuacuacg a                                             21

<210> SEQ ID NO 233
<211> LENGTH: 21
<212> TYPE: RNA
<213> ORGANISM: Homo sapiens

<400> SEQUENCE: 233
ggcagaagua ugauuugccg u                                             21

<210> SEQ ID NO 234
<211> LENGTH: 21
<212> TYPE: RNA
<213> ORGANISM: Homo sapiens

<400> SEQUENCE: 234
ccagaacagg aggcugugug g                                             21

<210> SEQ ID NO 235
<211> LENGTH: 21
<212> TYPE: RNA
<213> ORGANISM: Homo sapiens

<400> SEQUENCE: 235
cagaacagga ggcugugugg c                                             21

<210> SEQ ID NO 236
<211> LENGTH: 21
<212> TYPE: RNA
<213> ORGANISM: Homo sapiens

<400> SEQUENCE: 236
caccucccag aucucccuca c                                             21

<210> SEQ ID NO 237
<211> LENGTH: 21
<212> TYPE: RNA
<213> ORGANISM: Homo sapiens

<400> SEQUENCE: 237
caccucccag aucucccuca a                                             21

<210> SEQ ID NO 238
<211> LENGTH: 21
<212> TYPE: RNA
<213> ORGANISM: Homo sapiens

<400> SEQUENCE: 238
ugugcgggug cacuauggcu u                                             21

<210> SEQ ID NO 239
<211> LENGTH: 21
<212> TYPE: RNA
<213> ORGANISM: Homo sapiens

<400> SEQUENCE: 239
gcgggugcac uauggcuugu a                                             21
```

```
<210> SEQ ID NO 240
<211> LENGTH: 21
<212> TYPE: RNA
<213> ORGANISM: Homo sapiens

<400> SEQUENCE: 240
ccccugcccu ggagaguucc u                                              21

<210> SEQ ID NO 241
<211> LENGTH: 21
<212> TYPE: RNA
<213> ORGANISM: Homo sapiens

<400> SEQUENCE: 241
cccugcccug gagaguuccu a                                              21

<210> SEQ ID NO 242
<211> LENGTH: 21
<212> TYPE: RNA
<213> ORGANISM: Homo sapiens

<400> SEQUENCE: 242
ccugcccugg agaguuccuc u                                              21

<210> SEQ ID NO 243
<211> LENGTH: 21
<212> TYPE: RNA
<213> ORGANISM: Homo sapiens

<400> SEQUENCE: 243
cugcccugga gaguuccucu a                                              21

<210> SEQ ID NO 244
<211> LENGTH: 21
<212> TYPE: RNA
<213> ORGANISM: Homo sapiens

<400> SEQUENCE: 244
ccugugaugg ggucaaggac u                                              21

<210> SEQ ID NO 245
<211> LENGTH: 21
<212> TYPE: RNA
<213> ORGANISM: Homo sapiens

<400> SEQUENCE: 245
ggacugcccc aacggccugg a                                              21

<210> SEQ ID NO 246
<211> LENGTH: 21
<212> TYPE: RNA
<213> ORGANISM: Homo sapiens

<400> SEQUENCE: 246
acugccccaa cggccuggau a                                              21

<210> SEQ ID NO 247
<211> LENGTH: 21
<212> TYPE: RNA
<213> ORGANISM: Homo sapiens

<400> SEQUENCE: 247
cugccccaac ggccuggaug a                                              21
```

<210> SEQ ID NO 248
<211> LENGTH: 21
<212> TYPE: RNA
<213> ORGANISM: Homo sapiens

<400> SEQUENCE: 248
ugccccaacg gccuggauga a                                              21

<210> SEQ ID NO 249
<211> LENGTH: 21
<212> TYPE: RNA
<213> ORGANISM: Homo sapiens

<400> SEQUENCE: 249
gccccaacgg ccuggaugag a                                              21

<210> SEQ ID NO 250
<211> LENGTH: 21
<212> TYPE: RNA
<213> ORGANISM: Homo sapiens

<400> SEQUENCE: 250
ccccaacggc cuggaugaga a                                              21

<210> SEQ ID NO 251
<211> LENGTH: 21
<212> TYPE: RNA
<213> ORGANISM: Homo sapiens

<400> SEQUENCE: 251
cccaacggcc uggaugagag a                                              21

<210> SEQ ID NO 252
<211> LENGTH: 21
<212> TYPE: RNA
<213> ORGANISM: Homo sapiens

<400> SEQUENCE: 252
caacggccug gaugagagaa a                                              21

<210> SEQ ID NO 253
<211> LENGTH: 21
<212> TYPE: RNA
<213> ORGANISM: Homo sapiens

<400> SEQUENCE: 253
acggccugga ugagagaaac u                                              21

<210> SEQ ID NO 254
<211> LENGTH: 21
<212> TYPE: RNA
<213> ORGANISM: Homo sapiens

<400> SEQUENCE: 254
ccuggaugag agaaacugcg u                                              21

<210> SEQ ID NO 255
<211> LENGTH: 21
<212> TYPE: RNA
<213> ORGANISM: Homo sapiens

<400> SEQUENCE: 255

```
cacugugacu guggccucca a                                               21

<210> SEQ ID NO 256
<211> LENGTH: 21
<212> TYPE: RNA
<213> ORGANISM: Homo sapiens

<400> SEQUENCE: 256
guccuccgag ggugaguggc c                                               21

<210> SEQ ID NO 257
<211> LENGTH: 21
<212> TYPE: RNA
<213> ORGANISM: Homo sapiens

<400> SEQUENCE: 257
cuccgagggu gaguggccau a                                               21

<210> SEQ ID NO 258
<211> LENGTH: 21
<212> TYPE: RNA
<213> ORGANISM: Homo sapiens

<400> SEQUENCE: 258
uccgagggug aguggccaug g                                               21

<210> SEQ ID NO 259
<211> LENGTH: 21
<212> TYPE: RNA
<213> ORGANISM: Homo sapiens

<400> SEQUENCE: 259
ccagguucgg ggucgacaca u                                               21

<210> SEQ ID NO 260
<211> LENGTH: 21
<212> TYPE: RNA
<213> ORGANISM: Homo sapiens

<400> SEQUENCE: 260
agguucgggg ucgacacauc u                                               21

<210> SEQ ID NO 261
<211> LENGTH: 21
<212> TYPE: RNA
<213> ORGANISM: Homo sapiens

<400> SEQUENCE: 261
cggggucgac acaucugugg g                                               21

<210> SEQ ID NO 262
<211> LENGTH: 21
<212> TYPE: RNA
<213> ORGANISM: Homo sapiens

<400> SEQUENCE: 262
cggggucgac acaucugugg a                                               21

<210> SEQ ID NO 263
<211> LENGTH: 21
<212> TYPE: RNA
<213> ORGANISM: Homo sapiens

<400> SEQUENCE: 263
```
ggggucgaca caucuguggg g                           21

<210> SEQ ID NO 264
<211> LENGTH: 21
<212> TYPE: RNA
<213> ORGANISM: Homo sapiens

<400> SEQUENCE: 264
ggggucgaca caucuguggg a                           21

<210> SEQ ID NO 265
<211> LENGTH: 21
<212> TYPE: RNA
<213> ORGANISM: Homo sapiens

<400> SEQUENCE: 265
gggucgacac aucugugggg a                           21

<210> SEQ ID NO 266
<211> LENGTH: 21
<212> TYPE: RNA
<213> ORGANISM: Homo sapiens

<400> SEQUENCE: 266
gcugaccgcu gggugauaac a                           21

<210> SEQ ID NO 267
<211> LENGTH: 21
<212> TYPE: RNA
<213> ORGANISM: Homo sapiens

<400> SEQUENCE: 267
cuuccaggag gacagcaugg c                           21

<210> SEQ ID NO 268
<211> LENGTH: 21
<212> TYPE: RNA
<213> ORGANISM: Homo sapiens

<400> SEQUENCE: 268
ggccuggaga ggguguccuuc a                          21

<210> SEQ ID NO 269
<211> LENGTH: 21
<212> TYPE: RNA
<213> ORGANISM: Homo sapiens

<400> SEQUENCE: 269
gccuggagag guguccuuca a                           21

<210> SEQ ID NO 270
<211> LENGTH: 21
<212> TYPE: RNA
<213> ORGANISM: Homo sapiens

<400> SEQUENCE: 270
ccaagcaggg ggacaaguau u                           21

<210> SEQ ID NO 271
<211> LENGTH: 21
<212> TYPE: RNA
<213> ORGANISM: Homo sapiens -continued

<400> SEQUENCE: 271 caagcaggggg gacaaguauu c                                          21

<210> SEQ ID NO 272
<211> LENGTH: 21
<212> TYPE: RNA
<213> ORGANISM: Homo sapiens

<400> SEQUENCE: 272
uggcaggagg uggcaucuug u                                           21

<210> SEQ ID NO 273
<211> LENGTH: 21
<212> TYPE: RNA
<213> ORGANISM: Homo sapiens

<400> SEQUENCE: 273
gcaggaggug gcaucuuguc u                                           21

<210> SEQ ID NO 274
<211> LENGTH: 21
<212> TYPE: RNA
<213> ORGANISM: Homo sapiens

<400> SEQUENCE: 274
gcuucggaag ccccuggucu a                                           21

<210> SEQ ID NO 275
<211> LENGTH: 21
<212> TYPE: RNA
<213> ORGANISM: Homo sapiens

<400> SEQUENCE: 275
cuucggaagc cccuggucua a                                           21

<210> SEQ ID NO 276
<211> LENGTH: 21
<212> TYPE: RNA
<213> ORGANISM: Homo sapiens

<400> SEQUENCE: 276
ccccuggucu aacuugggau c                                           21

<210> SEQ ID NO 277
<211> LENGTH: 21
<212> TYPE: RNA
<213> ORGANISM: Homo sapiens

<400> SEQUENCE: 277
cccuggucua acuugggauc u                                           21

<210> SEQ ID NO 278
<211> LENGTH: 21
<212> TYPE: RNA
<213> ORGANISM: Homo sapiens

<400> SEQUENCE: 278
ccuggucuaa cuugggaucu g                                           21

<210> SEQ ID NO 279
<211> LENGTH: 21
<212> TYPE: RNA
<213> ORGANISM: Homo sapiens

```
<400> SEQUENCE: 279
cuaacuuggg aucgggaau g                                              21

<210> SEQ ID NO 280
<211> LENGTH: 23
<212> TYPE: RNA
<213> ORGANISM: Homo sapiens

<400> SEQUENCE: 280
aggaaauacc agaguagcac ccc                                           23

<210> SEQ ID NO 281
<211> LENGTH: 23
<212> TYPE: RNA
<213> ORGANISM: Homo sapiens

<400> SEQUENCE: 281
uguacccuag gaaauaccag agu                                           23

<210> SEQ ID NO 282
<211> LENGTH: 23
<212> TYPE: RNA
<213> ORGANISM: Homo sapiens

<400> SEQUENCE: 282
uuguacccua ggaaauacca gag                                           23

<210> SEQ ID NO 283
<211> LENGTH: 23
<212> TYPE: RNA
<213> ORGANISM: Homo sapiens

<400> SEQUENCE: 283
uuuguacccu aggaaauacc aga                                           23

<210> SEQ ID NO 284
<211> LENGTH: 23
<212> TYPE: RNA
<213> ORGANISM: Homo sapiens

<400> SEQUENCE: 284
ucuuguaccc uaggaaauac cag                                           23

<210> SEQ ID NO 285
<211> LENGTH: 19
<212> TYPE: RNA
<213> ORGANISM: Homo sapiens

<400> SEQUENCE: 285
uguacccuag gaaauacca                                                19

<210> SEQ ID NO 286
<211> LENGTH: 23
<212> TYPE: RNA
<213> ORGANISM: Homo sapiens

<400> SEQUENCE: 286
uccuuguacc cuaggaaaua cca                                           23

<210> SEQ ID NO 287
<211> LENGTH: 23
<212> TYPE: RNA
```

```
<213> ORGANISM: Homo sapiens

<400> SEQUENCE: 287
ucgccuugua cccuaggaaa uac                                              23

<210> SEQ ID NO 288
<211> LENGTH: 23
<212> TYPE: RNA
<213> ORGANISM: Homo sapiens

<400> SEQUENCE: 288
uccgccuugu acccuaggaa aua                                              23

<210> SEQ ID NO 289
<211> LENGTH: 23
<212> TYPE: RNA
<213> ORGANISM: Homo sapiens

<400> SEQUENCE: 289
aagauccugg gagaaguggc gau                                              23

<210> SEQ ID NO 290
<211> LENGTH: 23
<212> TYPE: RNA
<213> ORGANISM: Homo sapiens

<400> SEQUENCE: 290
uaagauccug ggagaagugg cga                                              23

<210> SEQ ID NO 291
<211> LENGTH: 23
<212> TYPE: RNA
<213> ORGANISM: Homo sapiens

<400> SEQUENCE: 291
agaaugaacc agaagaagca ggu                                              23

<210> SEQ ID NO 292
<211> LENGTH: 23
<212> TYPE: RNA
<213> ORGANISM: Homo sapiens

<400> SEQUENCE: 292
uggagaauga accagaagaa gca                                              23

<210> SEQ ID NO 293
<211> LENGTH: 23
<212> TYPE: RNA
<213> ORGANISM: Homo sapiens

<400> SEQUENCE: 293
uucguacucg gcccuguagg gga                                              23

<210> SEQ ID NO 294
<211> LENGTH: 23
<212> TYPE: RNA
<213> ORGANISM: Homo sapiens

<400> SEQUENCE: 294
acuucguacu cggcccugua ggg                                              23

<210> SEQ ID NO 295
<211> LENGTH: 23
```

```
<212> TYPE: RNA
<213> ORGANISM: Homo sapiens

<400> SEQUENCE: 295
agcuaugucu uucacacugg cuu                                              23

<210> SEQ ID NO 296
<211> LENGTH: 23
<212> TYPE: RNA
<213> ORGANISM: Homo sapiens

<400> SEQUENCE: 296
ugcagcuaug ucuuucacac ugg                                              23

<210> SEQ ID NO 297
<211> LENGTH: 23
<212> TYPE: RNA
<213> ORGANISM: Homo sapiens

<400> SEQUENCE: 297
uagcgguaac aacccagcgu gga                                              23

<210> SEQ ID NO 298
<211> LENGTH: 23
<212> TYPE: RNA
<213> ORGANISM: Homo sapiens

<400> SEQUENCE: 298
uagcuguagc gguaacaacc cag                                              23

<210> SEQ ID NO 299
<211> LENGTH: 23
<212> TYPE: RNA
<213> ORGANISM: Homo sapiens

<400> SEQUENCE: 299
auacauggcc agucggaccc ggc                                              23

<210> SEQ ID NO 300
<211> LENGTH: 23
<212> TYPE: RNA
<213> ORGANISM: Homo sapiens

<400> SEQUENCE: 300
acgucauaca uggccagucg guc                                              23

<210> SEQ ID NO 301
<211> LENGTH: 23
<212> TYPE: RNA
<213> ORGANISM: Homo sapiens

<400> SEQUENCE: 301
ucguaguagc ugugcaggcc cuu                                              23

<210> SEQ ID NO 302
<211> LENGTH: 23
<212> TYPE: RNA
<213> ORGANISM: Homo sapiens

<400> SEQUENCE: 302
acggcaaauc auacuucugc cuc                                              23

<210> SEQ ID NO 303
```

-continued

```
<211> LENGTH: 23
<212> TYPE: RNA
<213> ORGANISM: Homo sapiens

<400> SEQUENCE: 303
ccacacagcc uccuguucug gau                                              23

<210> SEQ ID NO 304
<211> LENGTH: 23
<212> TYPE: RNA
<213> ORGANISM: Homo sapiens

<400> SEQUENCE: 304
gccacacagc cuccuguucu gga                                              23

<210> SEQ ID NO 305
<211> LENGTH: 23
<212> TYPE: RNA
<213> ORGANISM: Homo sapiens

<400> SEQUENCE: 305
gugagggaga ucugggaggu gaa                                              23

<210> SEQ ID NO 306
<211> LENGTH: 23
<212> TYPE: RNA
<213> ORGANISM: Homo sapiens

<400> SEQUENCE: 306
uugagggaga ucugggaggu gaa                                              23

<210> SEQ ID NO 307
<211> LENGTH: 23
<212> TYPE: RNA
<213> ORGANISM: Homo sapiens

<400> SEQUENCE: 307
aagccauagu gcacccgcac acc                                              23

<210> SEQ ID NO 308
<211> LENGTH: 23
<212> TYPE: RNA
<213> ORGANISM: Homo sapiens

<400> SEQUENCE: 308
uacaagccau agugcacccg cac                                              23

<210> SEQ ID NO 309
<211> LENGTH: 23
<212> TYPE: RNA
<213> ORGANISM: Homo sapiens

<400> SEQUENCE: 309
aggaacucuc cagggcaggg guc                                              23

<210> SEQ ID NO 310
<211> LENGTH: 23
<212> TYPE: RNA
<213> ORGANISM: Homo sapiens

<400> SEQUENCE: 310
uaggaacucu ccagggcagg ggu                                              23
```

```
<210> SEQ ID NO 311
<211> LENGTH: 23
<212> TYPE: RNA
<213> ORGANISM: Homo sapiens

<400> SEQUENCE: 311
agaggaacuc uccagggcag ggg                                              23

<210> SEQ ID NO 312
<211> LENGTH: 23
<212> TYPE: RNA
<213> ORGANISM: Homo sapiens

<400> SEQUENCE: 312
uagaggaacu cuccagggca ggg                                              23

<210> SEQ ID NO 313
<211> LENGTH: 23
<212> TYPE: RNA
<213> ORGANISM: Homo sapiens

<400> SEQUENCE: 313
aguccuugac cccaucacag gca                                              23

<210> SEQ ID NO 314
<211> LENGTH: 23
<212> TYPE: RNA
<213> ORGANISM: Homo sapiens

<400> SEQUENCE: 314
uccaggccgu uggggcaguc cuu                                              23

<210> SEQ ID NO 315
<211> LENGTH: 23
<212> TYPE: RNA
<213> ORGANISM: Homo sapiens

<400> SEQUENCE: 315
uauccaggcc guuggggcag ucc                                              23

<210> SEQ ID NO 316
<211> LENGTH: 23
<212> TYPE: RNA
<213> ORGANISM: Homo sapiens

<400> SEQUENCE: 316
ucauccaggc cguuggggca guc                                              23

<210> SEQ ID NO 317
<211> LENGTH: 23
<212> TYPE: RNA
<213> ORGANISM: Homo sapiens

<400> SEQUENCE: 317
uucauccagg ccguuggggc agu                                              23

<210> SEQ ID NO 318
<211> LENGTH: 23
<212> TYPE: RNA
<213> ORGANISM: Homo sapiens

<400> SEQUENCE: 318
ucucauccag gccguugggg cag                                              23
```

```
<210> SEQ ID NO 319
<211> LENGTH: 23
<212> TYPE: RNA
<213> ORGANISM: Homo sapiens

<400> SEQUENCE: 319
uucucaucca ggccguuggg gca                                              23

<210> SEQ ID NO 320
<211> LENGTH: 23
<212> TYPE: RNA
<213> ORGANISM: Homo sapiens

<400> SEQUENCE: 320
ucucucaucc aggccguugg ggc                                              23

<210> SEQ ID NO 321
<211> LENGTH: 23
<212> TYPE: RNA
<213> ORGANISM: Homo sapiens

<400> SEQUENCE: 321
uuucucucau ccaggccguu ggg                                              23

<210> SEQ ID NO 322
<211> LENGTH: 23
<212> TYPE: RNA
<213> ORGANISM: Homo sapiens

<400> SEQUENCE: 322
aguuucucuc auccaggccg uug                                              23

<210> SEQ ID NO 323
<211> LENGTH: 23
<212> TYPE: RNA
<213> ORGANISM: Homo sapiens

<400> SEQUENCE: 323
acgcaguuuc ucucauccag gcc                                              23

<210> SEQ ID NO 324
<211> LENGTH: 23
<212> TYPE: RNA
<213> ORGANISM: Homo sapiens

<400> SEQUENCE: 324
uuggaggcca cagucacagu gcu                                              23

<210> SEQ ID NO 325
<211> LENGTH: 23
<212> TYPE: RNA
<213> ORGANISM: Homo sapiens

<400> SEQUENCE: 325
ggccacucac ccucggagga cac                                              23

<210> SEQ ID NO 326
<211> LENGTH: 23
<212> TYPE: RNA
<213> ORGANISM: Homo sapiens

<400> SEQUENCE: 326
uauggccacu cacccucgga gga                                              23
```

```
<210> SEQ ID NO 327
<211> LENGTH: 23
<212> TYPE: RNA
<213> ORGANISM: Homo sapiens

<400> SEQUENCE: 327
ccauggccac ucacccucgg agg                                        23

<210> SEQ ID NO 328
<211> LENGTH: 23
<212> TYPE: RNA
<213> ORGANISM: Homo sapiens

<400> SEQUENCE: 328
augugucgac cccgaaccug gag                                        23

<210> SEQ ID NO 329
<211> LENGTH: 23
<212> TYPE: RNA
<213> ORGANISM: Homo sapiens

<400> SEQUENCE: 329
agaugugucg accccgaacc ugg                                        23

<210> SEQ ID NO 330
<211> LENGTH: 23
<212> TYPE: RNA
<213> ORGANISM: Homo sapiens

<400> SEQUENCE: 330
cccacagaug ugucgaccccc gaa                                       23

<210> SEQ ID NO 331
<211> LENGTH: 23
<212> TYPE: RNA
<213> ORGANISM: Homo sapiens

<400> SEQUENCE: 331
uccacagaug ugucgacccc gaa                                        23

<210> SEQ ID NO 332
<211> LENGTH: 23
<212> TYPE: RNA
<213> ORGANISM: Homo sapiens

<400> SEQUENCE: 332
ccccacagau gugucgaccc cga                                        23

<210> SEQ ID NO 333
<211> LENGTH: 23
<212> TYPE: RNA
<213> ORGANISM: Homo sapiens

<400> SEQUENCE: 333
ucccacagau gugucgaccc cga                                        23

<210> SEQ ID NO 334
<211> LENGTH: 23
<212> TYPE: RNA
<213> ORGANISM: Homo sapiens

<400> SEQUENCE: 334
```

```
uccccacaga uguguocgacc ccg                                              23

<210> SEQ ID NO 335
<211> LENGTH: 23
<212> TYPE: RNA
<213> ORGANISM: Homo sapiens

<400> SEQUENCE: 335
uguuaucacc cagcggucag cga                                               23

<210> SEQ ID NO 336
<211> LENGTH: 23
<212> TYPE: RNA
<213> ORGANISM: Homo sapiens

<400> SEQUENCE: 336
gccaugcugu ccuccuggaa gca                                               23

<210> SEQ ID NO 337
<211> LENGTH: 23
<212> TYPE: RNA
<213> ORGANISM: Homo sapiens

<400> SEQUENCE: 337
ugaaggacac cucuccaggc cag                                               23

<210> SEQ ID NO 338
<211> LENGTH: 23
<212> TYPE: RNA
<213> ORGANISM: Homo sapiens

<400> SEQUENCE: 338
uugaaggaca ccucuccagg cca                                               23

<210> SEQ ID NO 339
<211> LENGTH: 23
<212> TYPE: RNA
<213> ORGANISM: Homo sapiens

<400> SEQUENCE: 339
aauacuuguc ccccugcuug gca                                               23

<210> SEQ ID NO 340
<211> LENGTH: 23
<212> TYPE: RNA
<213> ORGANISM: Homo sapiens

<400> SEQUENCE: 340
gaauacuugu cccccugcuu ggc                                               23

<210> SEQ ID NO 341
<211> LENGTH: 23
<212> TYPE: RNA
<213> ORGANISM: Homo sapiens

<400> SEQUENCE: 341
acaagaugcc accuccugcc acc                                               23

<210> SEQ ID NO 342
<211> LENGTH: 23
<212> TYPE: RNA
<213> ORGANISM: Homo sapiens

<400> SEQUENCE: 342
```

```
agacaagaug ccaccuccug cca                                          23

<210> SEQ ID NO 343
<211> LENGTH: 23
<212> TYPE: RNA
<213> ORGANISM: Homo sapiens

<400> SEQUENCE: 343
uagaccaggg gcuuccgaag cug                                          23

<210> SEQ ID NO 344
<211> LENGTH: 23
<212> TYPE: RNA
<213> ORGANISM: Homo sapiens

<400> SEQUENCE: 344
uuagaccagg ggcuuccgaa gcu                                          23

<210> SEQ ID NO 345
<211> LENGTH: 23
<212> TYPE: RNA
<213> ORGANISM: Homo sapiens

<400> SEQUENCE: 345
gaucccaagu uagaccaggg gcu                                          23

<210> SEQ ID NO 346
<211> LENGTH: 23
<212> TYPE: RNA
<213> ORGANISM: Homo sapiens

<400> SEQUENCE: 346
agaucccaag uuagaccagg ggc                                          23

<210> SEQ ID NO 347
<211> LENGTH: 23
<212> TYPE: RNA
<213> ORGANISM: Homo sapiens

<400> SEQUENCE: 347
cagaucccaa guuagaccag ggg                                          23

<210> SEQ ID NO 348
<211> LENGTH: 23
<212> TYPE: RNA
<213> ORGANISM: Homo sapiens

<400> SEQUENCE: 348
cauucccaga ucccaaguua gac                                          23

<210> SEQ ID NO 349
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 349
```

```
ugguauuucc uaggguacat t                                              21

<210> SEQ ID NO 350
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 350
ucugguauuu ccuaggguac a                                              21

<210> SEQ ID NO 351
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351
gccuggagag guguccuuca a                                              21

<210> SEQ ID NO 352
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 352
cugguauuuc cuaggguaca a                                              21

<210> SEQ ID NO 353
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 353
gcaggaggug gcaucuuguc u                                              21

<210> SEQ ID NO 354
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 354
gggccugcac agcuacuacg a                                              21

<210> SEQ ID NO 355
<211> LENGTH: 21
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 355
caccucccag aucucccuca c                                              21

<210> SEQ ID NO 356
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 356
ggugcuacuc ugguauuucc u                                              21

<210> SEQ ID NO 357
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 357
cccuggucua acuugggauc u                                              21

<210> SEQ ID NO 358
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 358
gcugaccgcu gggugauaac a                                              21

<210> SEQ ID NO 359
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 359
cuacagggcc gaguacgaag u                                              21

<210> SEQ ID NO 360
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 360
cuaacuuggg aucugggaau g                                              21

<210> SEQ ID NO 361
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 361
uccgagggug aguggccaug g                                              21

<210> SEQ ID NO 362
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 362
acggccugga ugagagaaac u                                              21

<210> SEQ ID NO 363
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 363
ggcagaagua ugauuugccg u                                              21

<210> SEQ ID NO 364
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 364
cccaacggcc uggaugagag a                                              21

<210> SEQ ID NO 365
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 365
cugcuucuuc ugguucauuc u                                              21

<210> SEQ ID NO 366
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 366
```

```
cuucggaagc cccuggucua a                                              21
```

<210> SEQ ID NO 367
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 367

```
cagaacagga ggcugugugg c                                              21
```

<210> SEQ ID NO 368
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 368

```
cgccacuucu cccaggaucu u                                              21
```

<210> SEQ ID NO 369
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 369

```
gccaguguga aagacauagc u                                              21
```

<210> SEQ ID NO 370
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 370

```
caagcagggg gacaaguauu c                                              21
```

<210> SEQ ID NO 371
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 371

```
ccugugaugg ggucaaggac u                                              21
```

<210> SEQ ID NO 372
<211> LENGTH: 21
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 372
agugugaaag acauagcugc a                                            21

<210> SEQ ID NO 373
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 373
guccuccgag ggugaguggc c                                            21

<210> SEQ ID NO 374
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 374
uggcaggagg uggcaucuug u                                            21

<210> SEQ ID NO 375
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 375
cgggaccgac uggccaugua u                                            21

<210> SEQ ID NO 376
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 376
cccuacaggg ccgaguacga a                                            21

<210> SEQ ID NO 377
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 377
gcuucggaag ccccuggucu a                                            21
```

```
<210> SEQ ID NO 378
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 378
agguucgggg ucgacacauc u                                              21

<210> SEQ ID NO 379
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 379
cggggucgac acaucugugg g                                              21

<210> SEQ ID NO 380
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 380
ccgacuggcc auguaugacg u                                              21

<210> SEQ ID NO 381
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 381
ccagguucgg ggucgacaca u                                              21

<210> SEQ ID NO 382
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 382
ggguuguuac cgcuacagcu a                                              21

<210> SEQ ID NO 383
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 383
ccuggucuaa cuugggaucu g                                              21

<210> SEQ ID NO 384
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 384
cacgcugggu uguuaccgcu a                                              21

<210> SEQ ID NO 385
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 385
ggggucgaca caucuguggg g                                              21

<210> SEQ ID NO 386
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 386
ugugcgggug cacuauggcu u                                              21

<210> SEQ ID NO 387
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 387
ccccuggucu aacuugggau c                                              21

<210> SEQ ID NO 388
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 388
ggccuggaga gguguccuuc a                                              21

<210> SEQ ID NO 389
<211> LENGTH: 21
<212> TYPE: RNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 389
cuucuucugg uucauucucc a                                              21

<210> SEQ ID NO 390
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 390
ccaagcaggg ggacaaguau u                                              21

<210> SEQ ID NO 391
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 391
cuuccaggag gacagcaugg c                                              21

<210> SEQ ID NO 392
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 392
ccuggaugag agaaacugcg u                                              21

<210> SEQ ID NO 393
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 393
gccacuucuc ccaggaucuu a                                              21

<210> SEQ ID NO 394
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 394
gcgggugcac uauggcuugu a                                              21
```

<210> SEQ ID NO 395
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 395
caacggccug gaugagagaa a         21

<210> SEQ ID NO 396
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 396
ccagaacagg aggcugugug g         21

<210> SEQ ID NO 397
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 397
gggucgacac aucugugggg a         21

<210> SEQ ID NO 398
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 398
ccccaacggc cuggaugaga a         21

<210> SEQ ID NO 399
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 399
gccccaacgg ccuggaugag a         21

<210> SEQ ID NO 400
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 400
cugcccugga gaguuccucu a                                        21

<210> SEQ ID NO 401
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401
cggggucgac acaucugugg a                                        21

<210> SEQ ID NO 402
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402
uuuccuaggg uacaaggcgg a                                        21

<210> SEQ ID NO 403
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403
acugccccaa cggccuggau a                                        21

<210> SEQ ID NO 404
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 404
ggggucgaca caucuguggg a                                        21

<210> SEQ ID NO 405
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 405
cugccccaac ggccuggaug a                                        21

<210> SEQ ID NO 406
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
auuuccuagg guacaaggcg a                                            21

<210> SEQ ID NO 407
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 407
ccccugcccu ggagaguucc u                                            21

<210> SEQ ID NO 408
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 408
cccugcccug gagaguuccu a                                            21

<210> SEQ ID NO 409
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 409
cacugugacu guggccucca a                                            21

<210> SEQ ID NO 410
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 410
ggacugcccc aacggccugg a                                            21

<210> SEQ ID NO 411
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 411
gguauuuccu aggguacaag a                                            21
```

<210> SEQ ID NO 412
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 412
caccucccag aucucccuca a                                              21

<210> SEQ ID NO 413
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 413
ugguauuucc uaggguacaa a                                              21

<210> SEQ ID NO 414
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 414
guauuuccua gggucaagg a                                               21

<210> SEQ ID NO 415
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 415
cuccgagggu gaguggccau a                                              21

<210> SEQ ID NO 416
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 416
ugccccaacg gccuggauga a                                              21

<210> SEQ ID NO 417
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

```
                              Synthetic oligonucleotide"

<400> SEQUENCE: 417
ccugcccugg agaguuccuc u                                              21

<210> SEQ ID NO 418
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 418
uguacccuag gaaauaccat t                                              21

<210> SEQ ID NO 419
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 419
uguacccuag gaaauaccag agu                                            23

<210> SEQ ID NO 420
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 420
uugaaggaca ccucuccagg cca                                            23

<210> SEQ ID NO 421
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 421
uuguacccua ggaaauacca gag                                            23

<210> SEQ ID NO 422
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 422
agacaagaug ccaccuccug cca                                            23
```

<210> SEQ ID NO 423
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 423
ucguaguagc ugugcaggcc cuu                                            23

<210> SEQ ID NO 424
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 424
gugagggaga ucugggaggu gaa                                            23

<210> SEQ ID NO 425
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 425
aggaaauacc agaguagcac ccc                                            23

<210> SEQ ID NO 426
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 426
agaucccaag uuagaccagg ggc                                            23

<210> SEQ ID NO 427
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 427
uguuaucacc cagcggucag cga                                            23

<210> SEQ ID NO 428
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

```
                         Synthetic oligonucleotide"

<400> SEQUENCE: 428
acuucguacu cggcccugua ggg                                         23

<210> SEQ ID NO 429
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 429
cauucccaga ucccaaguua gac                                         23

<210> SEQ ID NO 430
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 430
ccauggccac ucaccucgg agg                                          23

<210> SEQ ID NO 431
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 431
aguuucucuc auccaggccg uug                                         23

<210> SEQ ID NO 432
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 432
acggcaaauc auacuucugc cuc                                         23

<210> SEQ ID NO 433
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 433
ucucucaucc aggccguugg ggc                                         23

<210> SEQ ID NO 434
<211> LENGTH: 23
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 434
agaaugaacc agaagaagca ggu                                              23

<210> SEQ ID NO 435
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 435
uuagaccagg ggcuuccgaa gcu                                              23

<210> SEQ ID NO 436
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 436
gccacacagc cuccuguucu gga                                              23

<210> SEQ ID NO 437
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 437
aagauccugg gagaaguggc gau                                              23

<210> SEQ ID NO 438
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 438
agcuaugucu uucacacugg cuu                                              23

<210> SEQ ID NO 439
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 439
```
gaauacuugu cccccugcuu ggc                                      23

<210> SEQ ID NO 440
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 440
aguccuugac cccaucacag gca                                      23

<210> SEQ ID NO 441
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 441
ugcagcuaug ucuuucacac ugg                                      23

<210> SEQ ID NO 442
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 442
ggccacucac ccucggagga cac                                      23

<210> SEQ ID NO 443
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 443
acaagaugcc accuccugcc acc                                      23

<210> SEQ ID NO 444
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 444
auacauggcc agucgguccc ggc                                      23

<210> SEQ ID NO 445
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 445
uucguacucg gcccuguagg gga                                               23

<210> SEQ ID NO 446
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 446
uagaccaggg gcuuccgaag cug                                               23

<210> SEQ ID NO 447
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 447
agaugugucg accccgaacc ugg                                               23

<210> SEQ ID NO 448
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 448
cccacagaug ugucgacccc gaa                                               23

<210> SEQ ID NO 449
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 449
acgucauaca uggccagucg guc                                               23

<210> SEQ ID NO 450
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 450
augugucgac cccgaaccug gag                                               23

<210> SEQ ID NO 451

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 451
uagcuguagc gguaacaacc cag                                               23

<210> SEQ ID NO 452
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 452
cagaucccaa guuagaccag ggg                                               23

<210> SEQ ID NO 453
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 453
uagcgguaac aacccagcgu gga                                               23

<210> SEQ ID NO 454
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 454
ccccacagau gugucgaccc cga                                               23

<210> SEQ ID NO 455
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 455
aagccauagu gcacccgcac acc                                               23

<210> SEQ ID NO 456
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 456
```
gaucccaagu uagaccaggg gcu                                           23

<210> SEQ ID NO 457
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 457
ugaaggacac cucuccaggc cag                                           23

<210> SEQ ID NO 458
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 458
uggagaauga accagaagaa gca                                           23

<210> SEQ ID NO 459
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 459
aauacuuguc ccccugcuug gca                                           23

<210> SEQ ID NO 460
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 460
gccaugcugu ccuccuggaa gca                                           23

<210> SEQ ID NO 461
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 461
acgcaguuuc ucucauccag gcc                                           23

<210> SEQ ID NO 462
<211> LENGTH: 23
<212> TYPE: RNA
<213> ORGANISM: Artificial Sequence
<220> FEATURE:

-continued

```
<221> NAME/KEY: source
<223> OTHER INFORMATION: /note="Description of Artificial Sequence:
      Synthetic oligonucleotide"

<400> SEQUENCE: 462
uaagauccug ggagaagugg cga                                              23

<210> SEQ ID NO 463
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 463
uacaagccau agugcacccg cac                                              23

<210> SEQ ID NO 464
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 464
uuucucucau ccaggccguu ggg                                              23

<210> SEQ ID NO 465
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 465
ccacacagcc uccuguucug gau                                              23

<210> SEQ ID NO 466
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 466
uccccacaga ugugucgacc ccg                                              23

<210> SEQ ID NO 467
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 467
uucucaucca ggccguuggg gca                                              23
```

```
<210> SEQ ID NO 468
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 468
ucucauccag gccguugggg cag                                              23

<210> SEQ ID NO 469
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 469
uagaggaacu cuccagggca ggg                                              23

<210> SEQ ID NO 470
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 470
uccacagaug ugucgacccc gaa                                              23

<210> SEQ ID NO 471
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 471
uccgccuugu acccuaggaa aua                                              23

<210> SEQ ID NO 472
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 472
uauccaggcc guugggcag ucc                                               23

<210> SEQ ID NO 473
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 473
ucccacagau gugucgaccc cga                                          23

<210> SEQ ID NO 474
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 474
ucauccaggc cguuggggca guc                                          23

<210> SEQ ID NO 475
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 475
ucgccuugua cccuaggaaa uac                                          23

<210> SEQ ID NO 476
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 476
aggaacucuc cagggcaggg guc                                          23

<210> SEQ ID NO 477
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 477
uaggaacucu ccagggcagg ggu                                          23

<210> SEQ ID NO 478
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 478
uuggaggcca cagucacagu gcu                                          23

<210> SEQ ID NO 479
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 479
uccaggccgu ugggggcaguc cuu                                              23

<210> SEQ ID NO 480
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 480
ucuuguaccc uaggaaauac cag                                               23

<210> SEQ ID NO 481
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 481
uugagggaga ucugggaggu gaa                                               23

<210> SEQ ID NO 482
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
uuuguacccu aggaaauacc aga                                               23

<210> SEQ ID NO 483
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 483
uccuuguacc cuaggaaaua cca                                               23

<210> SEQ ID NO 484
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 484
uauggccacu cacccucgga gga                                               23
```

<210> SEQ ID NO 485
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 485
uucauccagg ccguuggggc agu                                         23

<210> SEQ ID NO 486
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 486
agaggaacuc uccagggcag ggg                                         23

<210> SEQ ID NO 487
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 487
cugguauuuc cuaggguaca a                                           21

<210> SEQ ID NO 488
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 488
cugguauuuc cuaggguaca a                                           21

<210> SEQ ID NO 489
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 489
cugguauuuc cuagggtaca a                                           21

<210> SEQ ID NO 490
<211> LENGTH: 21
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 490
cugguauuuc cuaggguaca a                                            21

<210> SEQ ID NO 491
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 491
cugguauuuc cuaggguaca a                                            21

<210> SEQ ID NO 492
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 492
cugguauuuc cuaggguaca a                                            21

<210> SEQ ID NO 493
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 493
gguauuuccu aggguacaa                                               19

<210> SEQ ID NO 494
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 494
cugguauuuc cuaggguaca a                                            21

<210> SEQ ID NO 495
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 495
cugguauuuc cuaggguaca a                                            21
```

<210> SEQ ID NO 496
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 496
cugguauuuc cuaggguaca a                                         21

<210> SEQ ID NO 497
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 497
cugguauuuc cuaggguaca a                                         21

<210> SEQ ID NO 498
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 498
cugguauuuc cuaggguaca a                                         21

<210> SEQ ID NO 499
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 499
cugguauuuc cuaggguaca a                                         21

<210> SEQ ID NO 500
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 500
cugguauuuc cuaggguaca a                                         21

<210> SEQ ID NO 501
<211> LENGTH: 21
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 501
cugguauuuc cuaggguaca a                                              21

<210> SEQ ID NO 502
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 502
cugguauuuc cuaggguaca a                                              21

<210> SEQ ID NO 503
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 503
cugguauuuc cuaggguaca a                                              21

<210> SEQ ID NO 504
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 504
cugguauuuc cuaggguaca a                                              21

<210> SEQ ID NO 505
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 505
cugguauuuc cuaggguaca a                                              21

<210> SEQ ID NO 506
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 506
cugguauuuc cuaggguaca a                                              21
```

<210> SEQ ID NO 507
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 507
cugguauuuc cuaggguaca a                                              21

<210> SEQ ID NO 508
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 508
cugguauuuc cuaggguaca a                                              21

<210> SEQ ID NO 509
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 509
cugguauuuc cuaggguaca a                                              21

<210> SEQ ID NO 510
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 510
cugguauuuc cuaggguaca a                                              21

<210> SEQ ID NO 511
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 511
cugguauuuc cuaggguaca a                                              21

<210> SEQ ID NO 512
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

```
<400> SEQUENCE: 512
cugguauuuc cuaggguaca a                                              21

<210> SEQ ID NO 513
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513
cugguauuuc cuaggguaca a                                              21

<210> SEQ ID NO 514
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 514
cugguauuuc cuaggguaca a                                              21

<210> SEQ ID NO 515
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 515
cugguauuuc cuaggguaca a                                              21

<210> SEQ ID NO 516
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 516
cugguauuuc cuaggguaca a                                              21

<210> SEQ ID NO 517
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 517
cugguauuuc cuagggtaca a                                               21

<210> SEQ ID NO 518
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 518
cugguauuuc cuagggitaca a                                              21

<210> SEQ ID NO 519
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 519
cugguauuuc cuaggguaca a                                               21

<210> SEQ ID NO 520
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 520
cugguauuuc cuaggguaca a                                               21

<210> SEQ ID NO 521
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 521
cugguauuuc cuaggguaca a                                               21

<210> SEQ ID NO 522
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 522
cugguauuuc cuaggguaca a                                               21
```

```
<210> SEQ ID NO 523
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (17)..(17)
<223> OTHER INFORMATION: Thymidine-glycol nucleic acid (GNA) S-Isomer

<400> SEQUENCE: 523
cugguauuuc cuagggtaca a                                               21

<210> SEQ ID NO 524
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 524
cugguauuuc cuaggguaca a                                               21

<210> SEQ ID NO 525
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 525
cugguauuuc cuaggguaca a                                               21

<210> SEQ ID NO 526
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 526
cugguauuuc cuaggguaca a                                               21

<210> SEQ ID NO 527
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 527
```
cugguauuuc cuagggtaca a                                              21

<210> SEQ ID NO 528
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 528
cugguauuuc cuaggguaca a                                              21

<210> SEQ ID NO 529
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 529
cugguauuuc cuaggguaca a                                              21

<210> SEQ ID NO 530
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 530
cugguauuuc ctaggguaca a                                              21

<210> SEQ ID NO 531
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 531
cugguauuuc ctaggguaca a                                              21

<210> SEQ ID NO 532
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

```
<400> SEQUENCE: 532
cugguauuuc ctaggguaca a                                              21

<210> SEQ ID NO 533
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 533
cugguauuuc cuaggguaca a                                              21

<210> SEQ ID NO 534
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 534
cugguauuuc cuaggguaca a                                              21

<210> SEQ ID NO 535
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 535
cugguauuuc cuagggtaca a                                              21

<210> SEQ ID NO 536
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 536
cugguauuuc cuaggguaca a                                              21

<210> SEQ ID NO 537
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 537
cugguauuuc cuagguaca a                                               21

<210> SEQ ID NO 538
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 538
cugguauuuc cuaggguaca a                                              21

<210> SEQ ID NO 539
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 539
cugguauuuc cuaggguaca a                                              21

<210> SEQ ID NO 540
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 540
cugguauuuc cuaggguaca a                                              21

<210> SEQ ID NO 541
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 541
cugguauuuc cuaggguaca a                                              21

<210> SEQ ID NO 542
<211> LENGTH: 21
<212> TYPE: DNA
<213> ORGANISM: Artificial Sequence
<220> FEATURE:
<221> NAME/KEY: source
```

<223> OTHER INFORMATION: /note="Description of Artificial Sequence:
       Synthetic oligonucleotide"
<220> FEATURE:
<221> NAME/KEY: source
<223> OTHER INFORMATION: /note="Description of Combined DNA/RNA
       Molecule: Synthetic oligonucleotide"

<400> SEQUENCE: 542
cugguauuuc ctaggguaca a                                               21

<210> SEQ ID NO 543
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 543
cugguauuuc cuaggguaca a                                               21

<210> SEQ ID NO 544
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 544
uuguacccua ggaaauacca gag                                             23

<210> SEQ ID NO 545
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 545
uuguacccua ggaaauacca gag                                             23

<210> SEQ ID NO 546
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 546
uuguacccua ggaaauacca gag                                             23

<210> SEQ ID NO 547
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 547
uuguacccua ggaaauacca gag                                    23

<210> SEQ ID NO 548
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 548
uuguacccua ggaaauacca gag                                    23

<210> SEQ ID NO 549
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 549
uuguacccua ggaaauacca gag                                    23

<210> SEQ ID NO 550
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 550
uuguacccua ggaaauacca g                                      21

<210> SEQ ID NO 551
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 551
uuguacccua ggaaauacca gag                                    23

<210> SEQ ID NO 552
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 552
uuguacccua ggaaauacca gag                                    23

<210> SEQ ID NO 553
<211> LENGTH: 23
<212> TYPE: RNA
<213> ORGANISM: Artificial Sequence
<220> FEATURE:
<221> NAME/KEY: source -continued
<223> OTHER INFORMATION: /note="Description of Artificial Sequence:
      Synthetic oligonucleotide"

<400> SEQUENCE: 553
uuguacccua ggaaauacca gag                                              23

<210> SEQ ID NO 554
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 554
uuguacccua ggaaauacca gag                                              23

<210> SEQ ID NO 555
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 555
uuguacccua ggaaauacca gag                                              23

<210> SEQ ID NO 556
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 556
uuguacccua ggaaauacca gag                                              23

<210> SEQ ID NO 557
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 557
uuguacccua ggaaauacca gag                                              23

<210> SEQ ID NO 558
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 558
uuguacccua ggaaauacca gag                                              23

<210> SEQ ID NO 559

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 559
uuguacccua ggaaauacca gag                                              23

<210> SEQ ID NO 560
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 560
uuguacccua ggaaauacca gag                                              23

<210> SEQ ID NO 561
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 561
uuguacccua ggaaauacca gag                                              23

<210> SEQ ID NO 562
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 562
uuguacccua ggaaauacca gag                                              23

<210> SEQ ID NO 563
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 563
uuguacccua ggaaauacca gag                                              23

<210> SEQ ID NO 564
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 564
```
uuguacccua ggaaauacca gag					23

<210> SEQ ID NO 565
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 565
uuguacccua ggaaauacca gag					23

<210> SEQ ID NO 566
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 566
uuguacccua ggaaauacca gag					23

<210> SEQ ID NO 567
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 567
uuguacccua ggaaauacca gag					23

<210> SEQ ID NO 568
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 568
uuguacccua ggaaauacca gag					23

<210> SEQ ID NO 569
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 569
uuguacccua ggaaauacca gag					23

<210> SEQ ID NO 570
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 570
uuguacccua ggaaauacca gag                                          23

<210> SEQ ID NO 571
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 571
uuguacccua ggaaauacca gag                                          23

<210> SEQ ID NO 572
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 572
uuguacccua ggaaauacca gag                                          23

<210> SEQ ID NO 573
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 573
uuguacccua ggaaauacca gag                                          23

<210> SEQ ID NO 574
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 574
uuguacccua ggaaauacca gag                                          23

<210> SEQ ID NO 575
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
uuguacccua ggaaauacca gag                                          23
```

-continued

```
<210> SEQ ID NO 576
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 576
uuguacccua ggaaauacca gag                                              23

<210> SEQ ID NO 577
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 577
uuguacccua ggaaauacca gag                                              23

<210> SEQ ID NO 578
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 578
uuguacccua ggaaauacca gag                                              23

<210> SEQ ID NO 579
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 579
uuguacccua ggaaauacca gag                                              23

<210> SEQ ID NO 580
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 580
uuguacccua ggaaauacca gag                                              23

<210> SEQ ID NO 581
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 581
uuguacccua ggaaauacca gag                                              23

<210> SEQ ID NO 582
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 582
uuguacccua ggaaauacca gag                                              23

<210> SEQ ID NO 583
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 583
uuguacccua ggaaauacca gag                                              23

<210> SEQ ID NO 584
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 584
uuguacccua ggaaauacca gag                                              23

<210> SEQ ID NO 585
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 585
uuguacccua ggaaauacca gag                                              23

<210> SEQ ID NO 586
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 586
uuguacccua ggaaauacca gag                                              23

<210> SEQ ID NO 587
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 587
uuguacccua ggaaauacca gag                                              23

<210> SEQ ID NO 588
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 588
uuguacccua ggaaauacca gag                                              23

<210> SEQ ID NO 589
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589
uuguacccua ggaaauacca gag                                              23

<210> SEQ ID NO 590
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 590
uuguacccua ggaaauacca gag                                              23

<210> SEQ ID NO 591
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 591
uuguacccua ggaaauacca gag                                              23

<210> SEQ ID NO 592
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592
uuguacccua ggaaauacca gag                                              23
```

<210> SEQ ID NO 593
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 593
uuguacccua ggaaauacca gag                                              23

<210> SEQ ID NO 594
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 594
uuguacccua ggaaauacca gag                                              23

<210> SEQ ID NO 595
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 595
uuguacccua ggaaauacca gag                                              23

<210> SEQ ID NO 596
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 596
uuguacccua ggaaauacca gag                                              23

<210> SEQ ID NO 597
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 597
uuguacccua ggaaauacca gag                                              23

<210> SEQ ID NO 598
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 598
uuguacccua ggaaauacca gag                                          23

<210> SEQ ID NO 599
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 599
uuguacccua ggaaauacca gag                                          23

<210> SEQ ID NO 600
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 600
uuguacccua ggaaauacca gag                                          23

<210> SEQ ID NO 601
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 601
cugguauuuc cuaggguaca a                                            21

<210> SEQ ID NO 602
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 602
cugguauuuc cuaggguaca a                                            21

<210> SEQ ID NO 603
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 603
cugguauuuc cuagggtaca a                                            21
```

```
<210> SEQ ID NO 604
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 604
cugguauuuc cuaggguaca a                                                21

<210> SEQ ID NO 605
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 605
cugguauuuc cuaggguaca a                                                21

<210> SEQ ID NO 606
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 606
cugguauuuc cuaggguaca a                                                21

<210> SEQ ID NO 607
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 607
gguauuuccu aggguacaa                                                   19

<210> SEQ ID NO 608
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 608
cugguauuuc cuaggguaca a                                                21

<210> SEQ ID NO 609
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 609
cugguauuuc cuaggguaca a                                      21

<210> SEQ ID NO 610
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 610
cugguauuuc cuaggguaca a                                      21

<210> SEQ ID NO 611
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 611
cugguauuuc cuaggguaca a                                      21

<210> SEQ ID NO 612
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 612
cugguauuuc cuaggguaca a                                      21

<210> SEQ ID NO 613
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 613
cugguauuuc cuaggguaca a                                      21

<210> SEQ ID NO 614
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614
cugguauuuc cuaggguaca a                                      21
```

<210> SEQ ID NO 615
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615
cugguauuuc cuaggguaca a                                                 21

<210> SEQ ID NO 616
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616
cugguauuuc cuaggguaca a                                                 21

<210> SEQ ID NO 617
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 617
cugguauuuc cuaggguaca a                                                 21

<210> SEQ ID NO 618
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 618
cugguauuuc cuaggguaca a                                                 21

<210> SEQ ID NO 619
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 619
cugguauuuc cuaggguaca a                                                 21

<210> SEQ ID NO 620
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 620
cugguauuuc cuaggguaca a                                              21

<210> SEQ ID NO 621
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 621
cugguauuuc cuaggguaca a                                              21

<210> SEQ ID NO 622
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 622
cugguauuuc cuaggguaca a                                              21

<210> SEQ ID NO 623
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 623
cugguauuuc cuaggguaca a                                              21

<210> SEQ ID NO 624
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 624
cugguauuuc cuaggguaca a                                              21

<210> SEQ ID NO 625
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 625
cugguauuuc cuaggguaca a                                              21

<210> SEQ ID NO 626
<211> LENGTH: 21
<212> TYPE: RNA
```

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 626
cugguauuuc cuaggguaca a                                              21

<210> SEQ ID NO 627
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 627
cugguauuuc cuaggguaca a                                              21

<210> SEQ ID NO 628
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 628
cugguauuuc cuaggguaca a                                              21

<210> SEQ ID NO 629
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 629
cugguauuuc cuaggguaca a                                              21

<210> SEQ ID NO 630
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 630
cugguauuuc cuaggguaca a                                              21

<210> SEQ ID NO 631
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<220> FEATURE:
<221> NAME/KEY: source
<223> OTHER INFORMATION: /note="Description of Combined DNA/RNA
      Molecule: Synthetic oligonucleotide"

<400> SEQUENCE: 631
cugguauuuc cuagggtaca a                                              21

<210> SEQ ID NO 632
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 632
cugguauuuc cuaggguaca a                                              21

<210> SEQ ID NO 633
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 633
cugguauuuc cuaggguaca a                                              21

<210> SEQ ID NO 634
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 634
cugguauuuc cuaggguaca a                                              21

<210> SEQ ID NO 635
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 635
cugguauuuc cuaggguaca a                                              21

<210> SEQ ID NO 636
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 636
cugguauuuc cuaggguaca a                                              21

<210> SEQ ID NO 637
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (17)..(17)
<223> OTHER INFORMATION: Thymidine-glycol nucleic acid (GNA) S-Isomer

<400> SEQUENCE: 637
cugguauuuc cuagggtaca a                                              21

<210> SEQ ID NO 638
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 638
cugguauuuc cuaggguaca a                                              21

<210> SEQ ID NO 639
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 639
cugguauuuc cuaggguaca a                                              21

<210> SEQ ID NO 640
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 640
cugguauuuc cuaggguaca a                                              21

<210> SEQ ID NO 641
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 641
cugguauuuc cuagggtaca a                                              21

<210> SEQ ID NO 642
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 642
cugguauuuc cuaggguaca a                                              21

<210> SEQ ID NO 643
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 643
cugguauuuc cuaggguaca a                                              21

<210> SEQ ID NO 644
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 644
cugguauuuc ctaggguaca a                                              21

<210> SEQ ID NO 645
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 645
cugguauuuc ctaggguaca a                                              21

<210> SEQ ID NO 646
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 646
cugguauuuc ctaggguaca a                                              21

<210> SEQ ID NO 647
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 647
cugguauuuc cuaggguaca a                                              21

<210> SEQ ID NO 648
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 648
cugguauuuc cuaggguaca a                                              21

<210> SEQ ID NO 649
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 649
cugguauuuc cuagggtaca a                                              21

<210> SEQ ID NO 650
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 650
cugguauuuc cuaggguaca a                                              21

<210> SEQ ID NO 651
<211> LENGTH: 21
<212> TYPE: DNA
<213> ORGANISM: Artificial Sequence -continued

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 651
cugguauuuc cuaggguaca a                                              21

<210> SEQ ID NO 652
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 652
cugguauuuc cuaggguaca a                                              21

<210> SEQ ID NO 653
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 653
cugguauuuc cuaggguaca a                                              21

<210> SEQ ID NO 654
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 654
cugguauuuc cuaggguaca a                                              21

<210> SEQ ID NO 655
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 655
cugguauuuc cuaggguaca a                                              21

<210> SEQ ID NO 656
```

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 656
cugguauuuc ctagggguaca a                                              21

<210> SEQ ID NO 657
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 657
cugguauuuc cuaggguaca a                                               21

<210> SEQ ID NO 658
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 658
uuguacccua ggaaauacca gag                                             23

<210> SEQ ID NO 659
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 659
uuguacccua ggaaauacca gag                                             23

<210> SEQ ID NO 660
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 660
uuguacccua ggaaauacca gag                                             23

<210> SEQ ID NO 661
<211> LENGTH: 23
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 661
uuguacccua ggaaauacca gag                                              23

<210> SEQ ID NO 662
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 662
uuguacccua ggaaauacca gag                                              23

<210> SEQ ID NO 663
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 663
uuguacccua ggaaauacca gag                                              23

<210> SEQ ID NO 664
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 664
uuguacccua ggaaauacca g                                                21

<210> SEQ ID NO 665
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 665
uuguacccua ggaaauacca gag                                              23

<210> SEQ ID NO 666
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 666
uuguacccua ggaaauacca gag                                              23

<210> SEQ ID NO 667
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 667
uuguacccua ggaaauacca gag                                              23

<210> SEQ ID NO 668
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 668
uuguacccua ggaaauacca gag                                              23

<210> SEQ ID NO 669
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 669
uuguacccua ggaaauacca gag                                              23

<210> SEQ ID NO 670
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 670
uuguacccua ggaaauacca gag                                              23

<210> SEQ ID NO 671
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 671
uuguacccua ggaaauacca gag                                              23

<210> SEQ ID NO 672
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 672
```
uuguacccua ggaaauacca gag                                              23

<210> SEQ ID NO 673
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 673
uuguacccua ggaaauacca gag                                              23

<210> SEQ ID NO 674
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 674
uuguacccua ggaaauacca gag                                              23

<210> SEQ ID NO 675
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 675
uuguacccua ggaaauacca gag                                              23

<210> SEQ ID NO 676
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 676
uuguacccua ggaaauacca gag                                              23

<210> SEQ ID NO 677
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 677
uuguacccua ggaaauacca gag                                              23

<210> SEQ ID NO 678
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 678
uuguacccua ggaaauacca gag                                              23

<210> SEQ ID NO 679
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 679
uuguacccua ggaaauacca gag                                              23

<210> SEQ ID NO 680
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 680
uuguacccua ggaaauacca gag                                              23

<210> SEQ ID NO 681
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 681
uuguacccua ggaaauacca gag                                              23

<210> SEQ ID NO 682
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 682
uuguacccua ggaaauacca gag                                              23

<210> SEQ ID NO 683
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 683
uuguacccua ggaaauacca gag                                              23
```

```
<210> SEQ ID NO 684
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 684
uuguacccua ggaaauacca gag                                            23

<210> SEQ ID NO 685
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 685
uuguacccua ggaaauacca gag                                            23

<210> SEQ ID NO 686
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 686
uuguacccua ggaaauacca gag                                            23

<210> SEQ ID NO 687
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 687
uuguacccua ggaaauacca gag                                            23

<210> SEQ ID NO 688
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 688
uuguacccua ggaaauacca gag                                            23

<210> SEQ ID NO 689
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 689
uuguacccua ggaaauacca gag                                              23

<210> SEQ ID NO 690
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 690
uuguacccua ggaaauacca gag                                              23

<210> SEQ ID NO 691
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 691
uuguacccua ggaaauacca gag                                              23

<210> SEQ ID NO 692
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 692
uuguacccua ggaaauacca gag                                              23

<210> SEQ ID NO 693
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 693
uuguacccua ggaaauacca gag                                              23

<210> SEQ ID NO 694
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 694
uuguacccua ggaaauacca gag                                              23

<210> SEQ ID NO 695
<211> LENGTH: 23
<212> TYPE: RNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 695
uuguacccua ggaaauacca gag                                             23

<210> SEQ ID NO 696
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 696
uuguacccua ggaaauacca gag                                             23

<210> SEQ ID NO 697
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 697
uuguacccua ggaaauacca gag                                             23

<210> SEQ ID NO 698
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 698
uuguacccua ggaaauacca gag                                             23

<210> SEQ ID NO 699
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 699
uuguacccua ggaaauacca gag                                             23

<210> SEQ ID NO 700
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 700
uuguacccua ggaaauacca gag                                             23
```

<210> SEQ ID NO 701
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 701
uuguacccua ggaaauacca gag        23

<210> SEQ ID NO 702
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 702
uuguacccua ggaaauacca gag        23

<210> SEQ ID NO 703
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 703
uuguacccua ggaaauacca gag        23

<210> SEQ ID NO 704
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 704
uuguacccua ggaaauacca gag        23

<210> SEQ ID NO 705
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 705
uuguacccua ggaaauacca gag        23

<210> SEQ ID NO 706
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 706
uuguacccua ggaaauacca gag                                              23

<210> SEQ ID NO 707
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 707
uuguacccua ggaaauacca gag                                              23

<210> SEQ ID NO 708
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 708
uuguacccua ggaaauacca gag                                              23

<210> SEQ ID NO 709
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 709
uuguacccua ggaaauacca gag                                              23

<210> SEQ ID NO 710
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 710
uuguacccua ggaaauacca gag                                              23

<210> SEQ ID NO 711
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 711
uuguacccua ggaaauacca gag                                              23

<210> SEQ ID NO 712
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 712
uuguacccua ggaaauacca gag                                             23

<210> SEQ ID NO 713
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 713
uuguacccua ggaaauacca gag                                             23

<210> SEQ ID NO 714
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 714
uuguacccua ggaaauacca gag                                             23

<210> SEQ ID NO 715
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 715
ugagccagac ccaguccagt t                                               21

<210> SEQ ID NO 716
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 716
gacccagucc agcucuggut t                                               21

<210> SEQ ID NO 717
<211> LENGTH: 21
<212> TYPE: DNA
<213> ORGANISM: Artificial Sequence
```

-continued

<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 717
cucuggugcc ugcccucugt t                                              21

<210> SEQ ID NO 718
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 718
gcccucuggu gcgagcugat t                                              21

<210> SEQ ID NO 719
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 719
ggugcgagcu gaccugagat t                                              21

<210> SEQ ID NO 720
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 720
ugaccugaga ugcacuucct t                                              21

<210> SEQ ID NO 721
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 721
ugcacuuccc uccucugugt t                                    21

<210> SEQ ID NO 722
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 722
cugugagcug ucucggcact t                                    21

<210> SEQ ID NO 723
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 723
gucucggcac ccacuugcat t                                    21

<210> SEQ ID NO 724
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 724
ccacuugcag ucacugccgt t                                    21

<210> SEQ ID NO 725
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 725
gucacugccg ccugauguut t                                    21

-continued

<210> SEQ ID NO 726
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 726
gccugauguu guuacucuut t                                              21

<210> SEQ ID NO 727
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 727
uuacucuucc acuccaaaat t                                              21

<210> SEQ ID NO 728
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 728
acuccaaaag gaugcccgut t                                              21

<210> SEQ ID NO 729
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 729
ugcccguggc cgaggcccct t                                              21

<210> SEQ ID NO 730
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:

```
                             Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 730
uggccgaggc ccccaggut t                                               21

<210> SEQ ID NO 731
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 731
ccagguggcu ggcgggcagt t                                              21

<210> SEQ ID NO 732
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 732
gcgggcaggg ggacggaggt t                                              21

<210> SEQ ID NO 733
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 733
ggacggaggu gauggcgagt t                                              21

<210> SEQ ID NO 734
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 734
```

-continued gugauggcga ggaagcggat t                                               21

<210> SEQ ID NO 735
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 735
gaagcggagc cggaggggat t                                               21

<210> SEQ ID NO 736
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 736
gccggagggg auguucaagt t                                               21

<210> SEQ ID NO 737
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 737
uguucaaggc cugugaggat t                                               21

<210> SEQ ID NO 738
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 738
cugugaggac uccaagagat t                                               21

<210> SEQ ID NO 739
<211> LENGTH: 21
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 739
acuccaagag aaaagcccgt t                                           21

<210> SEQ ID NO 740
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 740
gcccggggcu accuccgcct t                                           21

<210> SEQ ID NO 741
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 741
accuccgccu ggugccccut t                                           21

<210> SEQ ID NO 742
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 742
gccuggugcc ccuguuugut t                                           21

<210> SEQ ID NO 743
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 743
uguuugugcu gcuggcccut t                                                 21

<210> SEQ ID NO 744
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 744
ugcuggcccu gcucgugcut t                                                 21

<210> SEQ ID NO 745
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 745
gcucgugcug gcuucggcgt t                                                 21

<210> SEQ ID NO 746
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 746
ucggcggggg ugcuacucut t                                                 21

<210> SEQ ID NO 747
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 747 cggcggggu gcuacucugt t                                                  21
```

```
<210> SEQ ID NO 748
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 748
ggcgggggug cuacucuggt t                                            21

<210> SEQ ID NO 749
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 749 gcggggugc uacucuggut t                                             21

<210> SEQ ID NO 750
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 750
cgggggugcu acucugguau t                                            21

<210> SEQ ID NO 751
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 751
gggggugcua cucugguaut t                                            21

<210> SEQ ID NO 752
<211> LENGTH: 21
<212> TYPE: DNA
<213> ORGANISM: Artificial Sequence
<220> FEATURE:
<221> NAME/KEY: source
```

-continued

<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 752
gggugcuacu cugguauuut t                                              21

<210> SEQ ID NO 753
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 753
ggugcuacuc ugguauuuct t                                              21

<210> SEQ ID NO 754
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 754
gugcuacucu gguauuucct t                                              21

<210> SEQ ID NO 755
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 755
gcuacucugg uauuuccuat t                                              21

<210> SEQ ID NO 756
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

```
<400> SEQUENCE: 756
cuacucuggu auuccuagt t                                               21

<210> SEQ ID NO 757
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 757
uacucuggua uuccuaggt t                                               21

<210> SEQ ID NO 758
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 758
acucugguau uccuagggt t                                               21

<210> SEQ ID NO 759
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 759
cucugguauu uccuagggut t                                              21

<210> SEQ ID NO 760
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 760
cugguauuuc cuaggguact t                                              21

<210> SEQ ID NO 761
<211> LENGTH: 21
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 761
guauuuccua ggguacaagt t                                              21

<210> SEQ ID NO 762
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 762
uauuuccuag gguacaaggt t                                              21

<210> SEQ ID NO 763
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 763
auuuccuagg guacaaggct t                                              21

<210> SEQ ID NO 764
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 764
uuuccuaggg uacaaggcgt t                                              21

<210> SEQ ID NO 765
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 765
uuccuagggu acaaggcggt t                                              21

<210> SEQ ID NO 766
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 766
ccuaggguac aaggcggagt t                                              21

<210> SEQ ID NO 767
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 767
cuaggguaca aggcggaggt t                                              21

<210> SEQ ID NO 768
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 768
uaggguacaa ggcggaggut t                                              21

<210> SEQ ID NO 769
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 769
aggguacaag gcggaggugt t                                              21
```

<210> SEQ ID NO 770
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 770
ggguacaagg cggaggugat t                                              21

<210> SEQ ID NO 771
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 771
gguacaaggc ggaggugaut t                                              21

<210> SEQ ID NO 772
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 772
guacaaggcg gaggugaugt t                                              21

<210> SEQ ID NO 773
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 773
uacaaggcgg aggugauggt t                                              21

<210> SEQ ID NO 774
<211> LENGTH: 21
<212> TYPE: DNA
<213> ORGANISM: Artificial Sequence
<220> FEATURE:

-continued

<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 774
acaaggcgga ggugauggut t                                             21

<210> SEQ ID NO 775
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 775
caaggcggag gugaugguct t                                             21

<210> SEQ ID NO 776
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 776
aaggcggagg ugauggucat t                                             21

<210> SEQ ID NO 777
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 777
aggcggaggu gauggucagt t                                             21

<210> SEQ ID NO 778
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonuclectide"

-continued

<400> SEQUENCE: 778
ugauggucag ccagguguat t                                              21

<210> SEQ ID NO 779
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 779
ccagguguac ucaggcagut t                                              21

<210> SEQ ID NO 780
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 780
gcagucugcg uguacucaat t                                              21

<210> SEQ ID NO 781
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 781
gcguguacuc aaucgccact t                                              21

<210> SEQ ID NO 782
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 782
ucgccacuuc ucccaggaut t                                              21

<210> SEQ ID NO 783

-continued

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 783
cucccaggau cuuacccgct t                                               21

<210> SEQ ID NO 784
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 784
uacccgccgg gaaucuagut t                                               21

<210> SEQ ID NO 785
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 785
ccgggaaucu agugccuuct t                                               21

<210> SEQ ID NO 786
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 786
agugccuucc gcagugaaat t                                               21

<210> SEQ ID NO 787
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 787
gugaaaccgc caaagcccat t                                              21

<210> SEQ ID NO 788
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 788
cgccaaagcc cagaagaugt t                                              21

<210> SEQ ID NO 789
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 789
cagaagaugc ucaaggagct t                                              21

<210> SEQ ID NO 790
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 790
ucaaggagcu caucaccagt t                                              21

<210> SEQ ID NO 791
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 791
```
accagcaccc gccugggaat t                                        21

<210> SEQ ID NO 792
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 792
gccugggaac uuacuacaat t                                        21

<210> SEQ ID NO 793
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 793
gaacuuacua caacuccagt t                                        21

<210> SEQ ID NO 794
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 794
aacuccagcu ccgucuauut t                                        21

<210> SEQ ID NO 795
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 795
ccgucuauuc cuuuggggat t                                        21

<210> SEQ ID NO 796
<211> LENGTH: 21
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 796
uuggggaggg accccucact t                                              21

<210> SEQ ID NO 797
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 797
ccccucaccu gcuucuucut t                                              21

<210> SEQ ID NO 798
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 798
cugcuucuuc ugguucauut t                                              21

<210> SEQ ID NO 799
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 799
cugguucauu cuccaaauct t                                              21

<210> SEQ ID NO 800
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

-continued

Molecule: Synthetic oligonucleotide"

<400> SEQUENCE: 800
ucuccaaauc cccgagcact t                                            21

<210> SEQ ID NO 801
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"
<220> FEATURE:
<221> NAME/KEY: source
<223> OTHER INFORMATION: /note="Description of Combined DNA/RNA
        Molecule: Synthetic oligonucleotide"

<400> SEQUENCE: 801
ccgagcaccg ccggcugaut t                                            21

<210> SEQ ID NO 802
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"
<220> FEATURE:
<221> NAME/KEY: source
<223> OTHER INFORMATION: /note="Description of Combined DNA/RNA
        Molecule: Synthetic oligonucleotide"

<400> SEQUENCE: 802
ggcugaugcu gagccccgat t                                            21

<210> SEQ ID NO 803
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"
<220> FEATURE:
<221> NAME/KEY: source
<223> OTHER INFORMATION: /note="Description of Combined DNA/RNA
        Molecule: Synthetic oligonucleotide"

<400> SEQUENCE: 803
ugagccccga gguggugcat t                                            21

<210> SEQ ID NO 804
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"
<220> FEATURE:
<221> NAME/KEY: source
<223> OTHER INFORMATION: /note="Description of Combined DNA/RNA
        Molecule: Synthetic oligonucleotide"

<400> SEQUENCE: 804
uggugcaggc acugcuggut t                                            21

```
<210> SEQ ID NO 805
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 805
aggcacugcu gguggaggat t                                            21

<210> SEQ ID NO 806
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 806
guggaggagc ugcuguccat t                                            21

<210> SEQ ID NO 807
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 807
uguccacagu caacagcuct t                                            21

<210> SEQ ID NO 808
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 808
ucaacagcuc ggcugccgut t                                            21

<210> SEQ ID NO 809
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

```
                        Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 809
ucggcugccg uccccuacat t                                              21

<210> SEQ ID NO 810
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 810
aguggacccc gagggccuat t                                              21

<210> SEQ ID NO 811
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 811
agggccuagu gauccuggat t                                              21

<210> SEQ ID NO 812
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 812
uagugauccu ggaagccagt t                                              21

<210> SEQ ID NO 813
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 813
```
aagccagugu gaaagacaut t                                              21

<210> SEQ ID NO 814
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 814
ugaaagacau agcugcauut t                                              21

<210> SEQ ID NO 815
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 815
ugcauugaau uccacgcugt t                                              21

<210> SEQ ID NO 816
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 816
cuacagcuac gugggccagt t                                              21

<210> SEQ ID NO 817
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 817
cuacgugggc cagggccagt t                                              21

<210> SEQ ID NO 818
<211> LENGTH: 21
<212> TYPE: DNA

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 818
agggccaggu ccuccggcut t                                            21

<210> SEQ ID NO 819
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 819
ccggcugaag gggccugact t                                            21

<210> SEQ ID NO 820
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 820
gggccugacc accuggccut t                                            21

<210> SEQ ID NO 821
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 821
ccaccuggcc uccagcugct t                                            21

<210> SEQ ID NO 822
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 822
ccagcugccu guggcaccut t                                            21

<210> SEQ ID NO 823
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 823
cuguggcacc ugcagggcct t                                            21

<210> SEQ ID NO 824
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 824
cugcagggcc ccaaggacct t                                            21

<210> SEQ ID NO 825
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 825
ccaaggaccu caugcucaat t                                            21

<210> SEQ ID NO 826
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 826
ugcucaaacu ccggcuggat t                                            21
```

-continued

<210> SEQ ID NO 827
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 827
ccggcuggag uggacgcugt t                                              21

<210> SEQ ID NO 828
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 828
gacgcuggca gagugccggt t                                              21

<210> SEQ ID NO 829
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 829
ggcagagugc cgggaccgat t                                              21

<210> SEQ ID NO 830
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 830
accgacuggc cauguaugat t                                              21

<210> SEQ ID NO 831
<211> LENGTH: 21
<212> TYPE: DNA
<213> ORGANISM: Artificial Sequence
<220> FEATURE:
<221> NAME/KEY: source -continued
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 831
ccauguauga cguggccggt t                                           21

<210> SEQ ID NO 832
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 832
guggccgggc cccuggagat t                                           21

<210> SEQ ID NO 833
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 833
cccuggagaa gaggcucaut t                                           21

<210> SEQ ID NO 834
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 834
agaagaggcu caucaccuct t                                           21

<210> SEQ ID NO 835
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

-continued

```
<400> SEQUENCE: 835
accucggugu acggcugcat t                                              21

<210> SEQ ID NO 836
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 836
acggcugcag ccgccaggat t                                              21

<210> SEQ ID NO 837
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 837
gccgccagga gcccguggut t                                              21

<210> SEQ ID NO 838
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 838
agcccguggu ggagguucut t                                              21

<210> SEQ ID NO 839
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 839
guggagguuc uggcgucggt t                                              21

<210> SEQ ID NO 840
<211> LENGTH: 21
```

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 840
uggcgucggg ggccaucaut t                                      21

<210> SEQ ID NO 841
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 841
ccaucauggc ggucgucugt t                                      21

<210> SEQ ID NO 842
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 842
gcggucgucu ggaagaaggt t                                      21

<210> SEQ ID NO 843
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 843
ggaagaaggg ccugcacagt t                                      21

<210> SEQ ID NO 844
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

-continued

<210> SEQ ID NO 844 (implied continuation)
<221> NAME/KEY: source
<223> OTHER INFORMATION: /note="Description of Combined DNA/RNA
      Molecule: Synthetic oligonucleotide"

<400> SEQUENCE: 844
ccugcacagc uacuacgact t    21

<210> SEQ ID NO 845
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 845
acuacgaccc cuucgugcut t    21

<210> SEQ ID NO 846
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 846
ccuucgugcu cuccgugcat t    21

<210> SEQ ID NO 847
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 847
ccgugcagcc gguggucuut t    21

<210> SEQ ID NO 848
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 848 cggugguuu ccaggccugt t    21

<210> SEQ ID NO 849
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 849
aggccuguga agugaaccut t                                             21

<210> SEQ ID NO 850
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 850
aagugaaccu gacgcuggat t                                             21

<210> SEQ ID NO 851
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 851
gacgcuggac aacaggcuct t                                             21

<210> SEQ ID NO 852
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 852
acaacaggcu cgacucccat t                                             21

<210> SEQ ID NO 853
<211> LENGTH: 21
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 853
acucccaggg cguccucagt t                                              21

<210> SEQ ID NO 854
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 854
ccccguacuu ccccagcuat t                                              21

<210> SEQ ID NO 855
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 855
uuccccagcu acuacucgct t                                              21

<210> SEQ ID NO 856
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 856
acuacucgcc ccaaacccat t                                              21

<210> SEQ ID NO 857
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 857
cccaaaccca cugcuccugt t                                       21

<210> SEQ ID NO 858
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 858
gcuccuggca ccucacggut t                                       21

<210> SEQ ID NO 859
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 859
accucacggu gcccucucut t                                       21

<210> SEQ ID NO 860
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 860
cucucuggac uacggcuugt t                                       21

<210> SEQ ID NO 861
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 861
gacuacggcu uggcccucut t                                       21

<210> SEQ ID NO 862

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 862
cccucugguu ugaugccuat t                                            21

<210> SEQ ID NO 863
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 863
guuugaugcc uaugcacugt t                                            21

<210> SEQ ID NO 864
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 864
gcacugagga ggcagaagut t                                            21

<210> SEQ ID NO 865
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 865
ggaggcagaa guaugauuut t                                            21

<210> SEQ ID NO 866
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 866
augauuugcc gugcacccat t                                              21

<210> SEQ ID NO 867
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 867
ugcacccagg gccaguggat t                                              21

<210> SEQ ID NO 868
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 868
gccaguggac gauccagaat t                                              21

<210> SEQ ID NO 869
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 869
ggacgaucca gaacaggagt t                                              21

<210> SEQ ID NO 870
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 870
```

```
acaggaggcu guguggcuut t                                          21
```

<210> SEQ ID NO 871
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 871

```
cuguguggcu ugcgcaucct t                                          21
```

<210> SEQ ID NO 872
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 872

```
ugcgcauccu gcagcccuat t                                          21
```

<210> SEQ ID NO 873
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 873

```
agcccuacgc cgagaggaut t                                          21
```

<210> SEQ ID NO 874
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 874

```
ccgagaggau ccccguggut t                                          21
```

<210> SEQ ID NO 875
<211> LENGTH: 21
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 875
ccgugguggc cacggccggt t                                             21

<210> SEQ ID NO 876
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 876
ccacggccgg gaucaccaut t                                             21

<210> SEQ ID NO 877
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 877
ggaucaccau caacuucact t                                             21

<210> SEQ ID NO 878
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 878
ucaacuucac cucccagaut t                                             21

<210> SEQ ID NO 879
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

Molecule: Synthetic oligonucleotide"

<400> SEQUENCE: 879
cccagaucuc ccucaccggt t                                          21

<210> SEQ ID NO 880
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 880
cccucaccgg gcccggugut t                                          21

<210> SEQ ID NO 881
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 881
cccggugugc gggugcacut t                                          21

<210> SEQ ID NO 882
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 882
gcuuguacaa ccagucggat t                                          21

<210> SEQ ID NO 883
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 883
acaaccaguc ggaccccugt t                                          21

-continued

<210> SEQ ID NO 884
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 884
accccugccc uggagaguut t                                              21

<210> SEQ ID NO 885
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 885
ccuggagagu uccucuguut t                                              21

<210> SEQ ID NO 886
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 886
ucuguucugu gaauggacut t                                              21

<210> SEQ ID NO 887
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 887
gaauggacuc ugugucccut t                                              21

<210> SEQ ID NO 888
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:

-continued

```
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 888
cugugucccu gccugugaut t                                            21

<210> SEQ ID NO 889
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 889
cugccuguga uggggucaat t                                            21

<210> SEQ ID NO 890
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 890
ggucaaggac ugccccaact t                                            21

<210> SEQ ID NO 891
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 891
ugccccaacg gccuggaugt t                                            21

<210> SEQ ID NO 892
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 892
```

```
cggccuggau gagagaaact t                                              21
```

<210> SEQ ID NO 893
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 893

```
gagagaaacu gcguuugcat t                                              21
```

<210> SEQ ID NO 894
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 894

```
uuugcagagc cacauuccat t                                              21
```

<210> SEQ ID NO 895
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 895

```
gccacauucc agugcaaagt t                                              21
```

<210> SEQ ID NO 896
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 896

```
gugcaaagag gacagcacat t                                              21
```

<210> SEQ ID NO 897
<211> LENGTH: 21
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 897
gaggacagca caugcaucut t                                         21

<210> SEQ ID NO 898
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 898
gcaucucacu gcccaaggut t                                         21

<210> SEQ ID NO 899
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 899
gcccaagguc ugugaugggt t                                         21

<210> SEQ ID NO 900
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 900
ugugaugggc agccugauut t                                         21

<210> SEQ ID NO 901
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 901
gcagccugau ugucucaact t                                               21

<210> SEQ ID NO 902
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 902
gucucaacgg cagcgacgat t                                               21

<210> SEQ ID NO 903
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 903
gcgacgaaga gcagugccat t                                               21

<210> SEQ ID NO 904
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 904
agcagugcca ggaagggut t                                                21

<210> SEQ ID NO 905
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 905
gaaggggugc caugugggat t                                               21
```

```
<210> SEQ ID NO 906
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 906
ccauguggga cauucaccut t                                             21

<210> SEQ ID NO 907
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 907
cauucaccuu ccagugugat t                                             21

<210> SEQ ID NO 908
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 908
cagugugagg accggagcut t                                             21

<210> SEQ ID NO 909
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 909
gaccggagcu gcgugaagat t                                             21

<210> SEQ ID NO 910
<211> LENGTH: 21
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 910
cugcgugaag aagcccaact t                                                 21

<210> SEQ ID NO 911
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 911
agcccaaccc gcagugugat t                                                 21

<210> SEQ ID NO 912
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 912
cagugugaug ggcggcccgt t                                                 21

<210> SEQ ID NO 913
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 913
gcggcccgac ugcagggact t                                                 21

<210> SEQ ID NO 914
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 914
cugcagggac ggcucggaut t                                              21

<210> SEQ ID NO 915
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 915
acggcucgga ugaggagcat t                                              21

<210> SEQ ID NO 916
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 916
ugaggagcac ugugacugut t                                              21

<210> SEQ ID NO 917
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 917
cugugacugu ggccuccagt t                                              21

<210> SEQ ID NO 918
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 918
gccuccaggg ccccuccagt t                                              21

<210> SEQ ID NO 919
<211> LENGTH: 21
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 919
ccccuccagc cgcauuguut t                                             21

<210> SEQ ID NO 920
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 920
ccgcauuguu gguggagcut t                                             21

<210> SEQ ID NO 921
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 921
guggagcugu guccuccgat t                                             21

<210> SEQ ID NO 922
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 922
cuccgagggu gaguggccat t                                             21

<210> SEQ ID NO 923
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 923
gggugagugg ccauggcagt t                                              21

<210> SEQ ID NO 924
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 924
auggcaggcc agccuccagt t                                              21

<210> SEQ ID NO 925
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 925
ccuccagguu cggggucgat t                                              21

<210> SEQ ID NO 926
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 926
gguucggggu cgacacauct t                                              21

<210> SEQ ID NO 927
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 927
acaucugugg gggggcccut t                                              21
```

<210> SEQ ID NO 928
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 928 guggggggc ccucaucgct t                                          21

<210> SEQ ID NO 929
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 929
aucgcugacc gcugggugat t                                         21

<210> SEQ ID NO 930
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 930
accgcugggu gauaacagct t                                         21

<210> SEQ ID NO 931
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 931
ugauaacagc ugcccacugt t                                         21

<210> SEQ ID NO 932
<211> LENGTH: 21
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 932
cccacugcuu ccaggaggat t                                              21

<210> SEQ ID NO 933
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 933
ccaggaggac agcauggcct t                                              21

<210> SEQ ID NO 934
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 934
acagcauggc cuccacggut t                                              21

<210> SEQ ID NO 935
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 935
ccacggugcu guggaccgut t                                              21

<210> SEQ ID NO 936
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

-continued

```
<400> SEQUENCE: 936
ggaccguguu ccugggcaat t                                              21

<210> SEQ ID NO 937
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 937
uccugggcaa gguguggcat t                                              21

<210> SEQ ID NO 938
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 938
guguggcaga acucgcgcut t                                              21

<210> SEQ ID NO 939
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 939
gaacucgcgc uggccuggat t                                              21

<210> SEQ ID NO 940
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 940
ggccuggaga gguguccuut t                                              21

<210> SEQ ID NO 941
```

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 941
agguguccuu caaggugagt t                                              21

<210> SEQ ID NO 942
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 942
caaggugagc cgccugcuct t                                              21

<210> SEQ ID NO 943
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 943
gccugcuccu gcacccguat t                                              21

<210> SEQ ID NO 944
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 944
gcacccguac cacgaagagt t                                              21

<210> SEQ ID NO 945
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<220> FEATURE:
<221> NAME/KEY: source
<223> OTHER INFORMATION: /note="Description of Combined DNA/RNA
      Molecule: Synthetic oligonucleotide"

<400> SEQUENCE: 945
ccacgaagag gacagccaut t                                              21

<210> SEQ ID NO 946
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 946
aggacagcca ugacuacgat t                                              21

<210> SEQ ID NO 947
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 947
acuacgacgu ggcgcugcut t                                              21

<210> SEQ ID NO 948
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 948
uggcgcugcu gcagcucgat t                                              21

<210> SEQ ID NO 949
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 949
agcucgacca cccgguggut t                                                   21

<210> SEQ ID NO 950
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 950
ccgguggugc gcucggccgt t                                                   21

<210> SEQ ID NO 951
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 951
ugcgcucggc cgccgugcgt t                                                   21

<210> SEQ ID NO 952
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 952
ccgugcgccc cgucugccut t                                                   21

<210> SEQ ID NO 953
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 953
ccgucugccu gcccgcgcgt t                                                   21

<210> SEQ ID NO 954
<211> LENGTH: 21
<212> TYPE: DNA
<213> ORGANISM: Artificial Sequence -continued

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 954
ccgcgcgcuc ccacuucuut t                                             21

<210> SEQ ID NO 955
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 955
cccacuucuu cgagcccggt t                                             21

<210> SEQ ID NO 956
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 956
gagcccggcc ugcacugcut t                                             21

<210> SEQ ID NO 957
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 957
ggccugcacu gcuggauuat t                                             21

<210> SEQ ID NO 958
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

Molecule: Synthetic oligonucleotide"

<400> SEQUENCE: 958
uggauuacgg gcugggcgt t                                    21

<210> SEQ ID NO 959
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 959 gcugggcgc cuugcgcgat t                                    21

<210> SEQ ID NO 960
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 960
ugcgcgaggg cggccccaut t                                   21

<210> SEQ ID NO 961
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 961
agggcggccc caucagcaat t                                   21

<210> SEQ ID NO 962
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 962
ucagcaacgc ucugcagaat t                                   21

```
<210> SEQ ID NO 963
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 963
ugcagaaagu ggaugugcat t                                              21

<210> SEQ ID NO 964
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 964
aaguggaugu gcaguugaut t                                              21

<210> SEQ ID NO 965
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 965
gcaguugauc ccacaggact t                                              21

<210> SEQ ID NO 966
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 966
cacaggaccu gugcagcgat t                                              21

<210> SEQ ID NO 967
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 967
gcagcgaggu cuaucgcuat t                                              21

<210> SEQ ID NO 968
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 968
gucuaucgcu accaggugat t                                              21

<210> SEQ ID NO 969
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 969
ccaggugacg ccacgcaugt t                                              21

<210> SEQ ID NO 970
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 970
ccacgcaugc ugugugccgt t                                              21

<210> SEQ ID NO 971
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 971

-continued cugugugccg gcuaccgcat t                                        21

<210> SEQ ID NO 972
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 972
accgcaaggg caagaaggat t                                        21

<210> SEQ ID NO 973
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 973
gcaagaagga ugccugucat t                                        21

<210> SEQ ID NO 974
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 974
gccugucagg gugacucagt t                                        21

<210> SEQ ID NO 975
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 975
gugacucagg ugguccgcut t                                        21

<210> SEQ ID NO 976
<211> LENGTH: 21
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 976
gugguccgcu ggugugcaat t                                           21

<210> SEQ ID NO 977
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 977
uggugugcaa ggcacucagt t                                           21

<210> SEQ ID NO 978
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 978
gcacucagug gccgcuggut t                                           21

<210> SEQ ID NO 979
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 979
gccgcugguu ccuggcgggt t                                           21

<210> SEQ ID NO 980
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 980
uccuggcggg gcuggucagt t                                              21

<210> SEQ ID NO 981
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 981
gcuggucagc uggggccugt t                                              21

<210> SEQ ID NO 982
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 982
gggccugggc uguggccggt t                                              21

<210> SEQ ID NO 983
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 983
ggcuguggcc ggccuaacut t                                              21

<210> SEQ ID NO 984
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 984
cuaacuacuu cggcgucuat t                                              21
```

<210> SEQ ID NO 985
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 985
cggcgucuac acccgcauct t                                         21

<210> SEQ ID NO 986
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 986
acacccgcau cacaggugut t                                         21

<210> SEQ ID NO 987
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 987
acagguguga ucagcuggat t                                         21

<210> SEQ ID NO 988
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 988
ucagcuggau ccagcaagut t                                         21

<210> SEQ ID NO 989
<211> LENGTH: 21
<212> TYPE: DNA
<213> ORGANISM: Artificial Sequence
<220> FEATURE:
<221> NAME/KEY: source -continued
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 989
cagcaagugg ugaccugagt t              21

<210> SEQ ID NO 990
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 990
ugaccugagg aacugcccct t              21

<210> SEQ ID NO 991
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 991
ggaacugccc cccugcaaat t              21

<210> SEQ ID NO 992
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 992
cugcaaagca gggcccacct t              21

<210> SEQ ID NO 993
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

```
<400> SEQUENCE: 993
gcagggccca ccuccuggat t                                              21

<210> SEQ ID NO 994
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 994
ccuccuggac ucagagagct t                                              21

<210> SEQ ID NO 995
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 995
cucagagagc ccagggcaat t                                              21

<210> SEQ ID NO 996
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 996
ccagggcaac ugccaagcat t                                              21

<210> SEQ ID NO 997
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 997
ggacaaguau ucuggcgggt t                                              21

<210> SEQ ID NO 998
<211> LENGTH: 21
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 998
cuggcggggg gugggggagt t                                           21

<210> SEQ ID NO 999
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 999
ggguggggga gagagcaggt t                                           21

<210> SEQ ID NO 1000
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1000
agagagcagg cccuguggut t                                           21

<210> SEQ ID NO 1001
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1001
cccuguggug gcaggaggut t                                           21

<210> SEQ ID NO 1002
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

<221> NAME/KEY: source
<223> OTHER INFORMATION: /note="Description of Combined DNA/RNA
      Molecule: Synthetic oligonucleotide"

<400> SEQUENCE: 1002
ggaggtggca ucuugucuct t                                              21

<210> SEQ ID NO 1003
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1003
caucuugucu cgucccugat t                                              21

<210> SEQ ID NO 1004
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1004
cccugauguc ugcuccagut t                                              21

<210> SEQ ID NO 1005
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1005
cugcuccagu gauggcaggt t                                              21

<210> SEQ ID NO 1006
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1006
auggcaggag gauggagaat t                                              21

<210> SEQ ID NO 1007
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1007
ggauggagaa gugccagcat t                                       21

<210> SEQ ID NO 1008
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1008
ugccagcagc uggggucat t                                        21

<210> SEQ ID NO 1009
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1009 agcuggggu caagacguct t                                        21

<210> SEQ ID NO 1010
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1010
ucaagacguc cccugaggat t                                       21

<210> SEQ ID NO 1011
<211> LENGTH: 21
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1011
cccugaggac ccaggcccat t                                        21

<210> SEQ ID NO 1012
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1012
gcccacaccc agcccuucut t                                        21

<210> SEQ ID NO 1013
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1013
agcccuucug ccucccaaut t                                        21

<210> SEQ ID NO 1014
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1014
ccucccaauu cucucuccut t                                        21

<210> SEQ ID NO 1015
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

-continued

<400> SEQUENCE: 1015
cucucuccuc cgucccuut t                                              21

<210> SEQ ID NO 1016
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1016 uccgucccu uccuccacut t                                              21

<210> SEQ ID NO 1017
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1017
cuuccuccac ugcugccuat t                                             21

<210> SEQ ID NO 1018
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1018
cugccuaaug caaggcagut t                                             21

<210> SEQ ID NO 1019
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1019
gcaaggcagu ggcucagcat t                                             21

<210> SEQ ID NO 1020

-continued

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1020
uggcucagca gcaagaaugt t                                              21

<210> SEQ ID NO 1021
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1021
caagaaugcu gguucuacat t                                              21

<210> SEQ ID NO 1022
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1022
ugguucuaca ucccgaggat t                                              21

<210> SEQ ID NO 1023
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1023
cccgaggagu gucugaggut t                                              21

<210> SEQ ID NO 1024
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<220> FEATURE:
<221> NAME/KEY: source
<223> OTHER INFORMATION: /note="Description of Combined DNA/RNA
      Molecule: Synthetic oligonucleotide"

<400> SEQUENCE: 1024
gucugaggug cgccccacut t                                              21

<210> SEQ ID NO 1025
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1025
gccccacucu guacagaggt t                                              21

<210> SEQ ID NO 1026
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1026
cuguacagag gcuguuuggt t                                              21

<210> SEQ ID NO 1027
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1027
cuguuugggc agccuugcct t                                              21

<210> SEQ ID NO 1028
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1028

-continued cuugccucca gagagcagat t                                                                 21

<210> SEQ ID NO 1029
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1029
uccagagagc agauuccagu t                                                                 21

<210> SEQ ID NO 1030
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1030
gauuccagcu ucggaagcct t                                                                 21

<210> SEQ ID NO 1031
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1031
gaauggaagg ugcucccaut t                                                                 21

<210> SEQ ID NO 1032
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1032
gugcucccau cggaggggat t                                                                 21

<210> SEQ ID NO 1033
<211> LENGTH: 21
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1033
ucggagggga cccucagagt t                                              21

<210> SEQ ID NO 1034
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1034
cccucagagc ccuggagact t                                              21

<210> SEQ ID NO 1035
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1035
gagacugcca ggugggccut t                                              21

<210> SEQ ID NO 1036
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1036
aggugggccu gcugccacut t                                              21

<210> SEQ ID NO 1037
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

Molecule: Synthetic oligonucleotide"

<400> SEQUENCE: 1037
cugccacugu aagccaaaat t                                              21

<210> SEQ ID NO 1038
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1038
cuguaagcca aaaggugggt t                                              21

<210> SEQ ID NO 1039
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1039
guggggaagu ccugacucct t                                              21

<210> SEQ ID NO 1040
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1040
ccugacucca ggguccuugt t                                              21

<210> SEQ ID NO 1041
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1041
ggguccuugc cccaccccut t                                              21

-continued

```
<210> SEQ ID NO 1042
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1042
gccccacccc ugccugccat t                                             21

<210> SEQ ID NO 1043
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1043
ccugccaccu gggcccucat t                                             21

<210> SEQ ID NO 1044
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1044
cugggcccuc acagcccagt t                                             21

<210> SEQ ID NO 1045
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1045
ucacagccca gacccucact t                                             21

<210> SEQ ID NO 1046
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 1046
cucacuggga ggugagcuct t                                              21

<210> SEQ ID NO 1047
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1047
ggugagcuca gcugcccuut t                                              21

<210> SEQ ID NO 1048
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1048
uggaauaaag cugccugaut t                                              21

<210> SEQ ID NO 1049
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1049
cuggacuggg ucuggcucat t                                              21

<210> SEQ ID NO 1050
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1050
```
accagagcug gacuggguct t                                              21

<210> SEQ ID NO 1051
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1051
cagagggcag gcaccagagt t                                              21

<210> SEQ ID NO 1052
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1052
ucagcucgca ccagagggct t                                              21

<210> SEQ ID NO 1053
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1053
ucucagguca gcucgcacct t                                              21

<210> SEQ ID NO 1054
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1054
ggaagugcau cucaggucat t                                              21

<210> SEQ ID NO 1055
<211> LENGTH: 21
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1055
cacagaggag ggaagugcat t                                              21

<210> SEQ ID NO 1056
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1056
gugccgagac agcucacagt t                                              21

<210> SEQ ID NO 1057
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1057
ugcaaguggg ugccgagact t                                              21

<210> SEQ ID NO 1058
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1058
cggcagugac ugcaaguggt t                                              21

<210> SEQ ID NO 1059
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 1059
aacaucaggc ggcagugact t                                              21

<210> SEQ ID NO 1060
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1060
aagaguaaca acaucaggct t                                              21

<210> SEQ ID NO 1061
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1061
uuuuggagug gaagaguaat t                                              21

<210> SEQ ID NO 1062
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1062
acgggcaucc uuuuggagut t                                              21

<210> SEQ ID NO 1063
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1063
ggggccucgg ccacgggcat t                                              21
```

```
<210> SEQ ID NO 1064
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1064 accuggggggg ccucggccat t                                             21

<210> SEQ ID NO 1065
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1065
cugcccgcca gccaccuggt t                                              21

<210> SEQ ID NO 1066
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1066
ccuccguccc ccugcccgct t                                              21

<210> SEQ ID NO 1067
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1067
cucgccauca ccuccgucct t                                              21

<210> SEQ ID NO 1068
<211> LENGTH: 21
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1068
uccgcuuccu cgccaucact t                                              21

<210> SEQ ID NO 1069
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1069
uccccuccgg cuccgcuuct t                                              21

<210> SEQ ID NO 1070
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1070
cuugaacauc cccuccggct t                                              21

<210> SEQ ID NO 1071
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1071
uccucacagg ccuugaacat t                                              21

<210> SEQ ID NO 1072
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

-continued

```
<400> SEQUENCE: 1072
ucucuuggag uccucacagt t                                              21

<210> SEQ ID NO 1073
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1073
cgggcuuuuc ucuuggagut t                                              21

<210> SEQ ID NO 1074
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1074
ggcggaggua gccccgggct t                                              21

<210> SEQ ID NO 1075
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1075
aggggcacca ggcggaggut t                                              21

<210> SEQ ID NO 1076
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1076
acaaacaggg gcaccaggct t                                              21

<210> SEQ ID NO 1077
<211> LENGTH: 21
```

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1077
agggccagca gcacaaacat t                                                21

<210> SEQ ID NO 1078
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1078
agcacgagca gggccagcat t                                                21

<210> SEQ ID NO 1079
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1079
cgccgaagcc agcacgagct t                                                21

<210> SEQ ID NO 1080
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1080
agaguagcac ccccgccgat t                                                21

<210> SEQ ID NO 1081
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:

-continued

```
<221> NAME/KEY: source
<223> OTHER INFORMATION: /note="Description of Combined DNA/RNA
      Molecule: Synthetic oligonucleotide"

<400> SEQUENCE: 1081
cagaguagca cccccgccgt t                                              21

<210> SEQ ID NO 1082
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1082
ccagaguagc acccccgcct t                                              21

<210> SEQ ID NO 1083
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1083
accagaguag cacccccgct t                                              21

<210> SEQ ID NO 1084
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1084
uaccagagua gcacccccgt t                                              21

<210> SEQ ID NO 1085
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1085
auaccagagu agcaccccct t                                              21
```

<210> SEQ ID NO 1086
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1086
aaauaccaga guagcaccct t                                          21

<210> SEQ ID NO 1087
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1087
gaaauaccag aguagcacct t                                          21

<210> SEQ ID NO 1088
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1088
ggaaauacca gaguagcact t                                          21

<210> SEQ ID NO 1089
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1089
uaggaaauac cagaguagct t                                          21

<210> SEQ ID NO 1090
<211> LENGTH: 21
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1090
cuaggaaaua ccagaguagt t                                              21

<210> SEQ ID NO 1091
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1091
ccuaggaaau accagaguat t                                              21

<210> SEQ ID NO 1092
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1092
cccuaggaaa uaccagagut t                                              21

<210> SEQ ID NO 1093
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1093
acccuaggaa auaccagagt t                                              21

<210> SEQ ID NO 1094
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

<400> SEQUENCE: 1094
guacccuagg aaauaccagt t				21

<210> SEQ ID NO 1095
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1095
cuuguacccu aggaaauact t				21

<210> SEQ ID NO 1096
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1096
ccuuguaccc uaggaaauat t				21

<210> SEQ ID NO 1097
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1097
gccuuguacc cuaggaaaut t				21

<210> SEQ ID NO 1098
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1098
cgccuuguac ccuaggaaat t				21

<210> SEQ ID NO 1099

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1099
ccgccuugua cccuaggaat t                                                   21

<210> SEQ ID NO 1100
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1100
cuccgccuug uacccuaggt t                                                   21

<210> SEQ ID NO 1101
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1101
ccuccgccuu guacccuagt t                                                   21

<210> SEQ ID NO 1102
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1102
accuccgccu uguacccuat t                                                   21

<210> SEQ ID NO 1103
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<220> FEATURE:
<221> NAME/KEY: source
<223> OTHER INFORMATION: /note="Description of Combined DNA/RNA
      Molecule: Synthetic oligonucleotide"

<400> SEQUENCE: 1103
caccuccgcc uuguacccut t                                               21

<210> SEQ ID NO 1104
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1104
ucaccuccgc cuuguaccct t                                               21

<210> SEQ ID NO 1105
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1105
aucaccuccg ccuuguacct t                                               21

<210> SEQ ID NO 1106
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1106
caucaccucc gccuuguact t                                               21

<210> SEQ ID NO 1107
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1107
ccaucaccuc cgccuuguat t                    21

<210> SEQ ID NO 1108
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1108
accaucaccu ccgccuugut t                    21

<210> SEQ ID NO 1109
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1109
gaccaucacc uccgccuugt t                    21

<210> SEQ ID NO 1110
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1110
ugaccaucac cuccgccuut t                    21

<210> SEQ ID NO 1111
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1111
cugaccauca ccuccgccut t                    21

<210> SEQ ID NO 1112
<211> LENGTH: 21
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1112
uacaccuggc ugaccaucat t                                              21

<210> SEQ ID NO 1113
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1113
acugccugag uacaccuggt t                                              21

<210> SEQ ID NO 1114
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1114
uugaguacac gcagacugct t                                              21

<210> SEQ ID NO 1115
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1115
guggcgauug aguacacgct t                                              21

<210> SEQ ID NO 1116
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

-continued

Molecule: Synthetic oligonucleotide"

<400> SEQUENCE: 1116
auccugggag aaguggcgat t                                     21

<210> SEQ ID NO 1117
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1117
gcggguaaga uccugggagt t                                     21

<210> SEQ ID NO 1118
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1118
acuagauucc cggcggguat t                                     21

<210> SEQ ID NO 1119
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1119
gaaggcacua gauucccggt t                                     21

<210> SEQ ID NO 1120
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1120
uuucacugcg gaaggcacut t                                     21

```
<210> SEQ ID NO 1121
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1121
ugggcuuugg cgguuucact t                                              21

<210> SEQ ID NO 1122
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1122
caucuucugg gcuuuggcgt t                                              21

<210> SEQ ID NO 1123
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1123
gcuccuugag caucuucugt t                                              21

<210> SEQ ID NO 1124
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1124
cuggugauga gcuccuugat t                                              21

<210> SEQ ID NO 1125
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1125
uucccaggcg ggugcugguu t                                              21

<210> SEQ ID NO 1126
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1126
uuguaguaag uucccaggct t                                              21

<210> SEQ ID NO 1127
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1127
cuggaguugu aguaaguuct t                                              21

<210> SEQ ID NO 1128
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1128
aauagacgga gcuggaguut t                                              21

<210> SEQ ID NO 1129
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1129
uccccaaagg aauagacggt t                                              21

<210> SEQ ID NO 1130
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1130
gugagggguc ccucccccaat t                                             21

<210> SEQ ID NO 1131
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1131
agaagaagca ggugaggggt t                                              21

<210> SEQ ID NO 1132
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1132
aaugaaccag aagaagcagt t                                              21

<210> SEQ ID NO 1133
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1133
gauuuggaga augaaccagt t                                              21

<210> SEQ ID NO 1134
<211> LENGTH: 21
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1134
gugcucgggg auuuggagat t                                              21

<210> SEQ ID NO 1135
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1135
aucagccggc ggugcucggt t                                              21

<210> SEQ ID NO 1136
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1136
ucggggcuca gcaucagcct t                                              21

<210> SEQ ID NO 1137
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1137
ugcaccaccu cggggcucat t                                              21

<210> SEQ ID NO 1138
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source

```
<223> OTHER INFORMATION: /note="Description of Combined DNA/RNA
      Molecule: Synthetic oligonucleotide"

<400> SEQUENCE: 1138
accagcagug ccugcaccat t                                              21

<210> SEQ ID NO 1139
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1139
uccuccacca gcagugccut t                                              21

<210> SEQ ID NO 1140
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1140
uggacagcag cuccuccact t                                              21

<210> SEQ ID NO 1141
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1141
gagcuguuga cuguggacat t                                              21

<210> SEQ ID NO 1142
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1142
acggcagccg agcuguugat t                                              21
```

```
<210> SEQ ID NO 1143
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1143
uguaggggac ggcagccgat t                                             21

<210> SEQ ID NO 1144
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1144
uaggcccucg ggguccacut t                                             21

<210> SEQ ID NO 1145
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1145
uccaggauca cuaggcccut t                                             21

<210> SEQ ID NO 1146
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1146
cuggcuucca ggaucacuat t                                             21

<210> SEQ ID NO 1147
<211> LENGTH: 21
<212> TYPE: DNA
<213> ORGANISM: Artificial Sequence
<220> FEATURE:
<221> NAME/KEY: source
```

-continued

```
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1147
augucuuuca cacuggcuut t                                              21

<210> SEQ ID NO 1148
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1148
aaugcagcua ugucuuucat t                                              21

<210> SEQ ID NO 1149
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1149
cagcguggaa uucaaugcat t                                              21

<210> SEQ ID NO 1150
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1150
cuggcccacg uagcuguagt t                                              21

<210> SEQ ID NO 1151
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 1151
cuggcccugg cccacguagu t                                              21

<210> SEQ ID NO 1152
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1152
agccggagga ccuggcccut t                                              21

<210> SEQ ID NO 1153
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1153
gucaggcccc uucagccggt t                                              21

<210> SEQ ID NO 1154
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1154
aggccaggug gucaggccct t                                              21

<210> SEQ ID NO 1155
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1155
gcagcuggag gccagguggt t                                              21

<210> SEQ ID NO 1156
<211> LENGTH: 21
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1156
aggugccaca ggcagcuggt t                                              21

<210> SEQ ID NO 1157
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1157
ggcccugcag gugccacagt t                                              21

<210> SEQ ID NO 1158
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1158
gguccuuggg gcccugcagt t                                              21

<210> SEQ ID NO 1159
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1159
uugagcauga gguccuuggt t                                              21

<210> SEQ ID NO 1160
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

<221> NAME/KEY: source
<223> OTHER INFORMATION: /note="Description of Combined DNA/RNA
      Molecule: Synthetic oligonucleotide"

<400> SEQUENCE: 1160
uccagccgga guuugagcat t                                              21

<210> SEQ ID NO 1161
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1161
cagcguccac uccagccggt t                                              21

<210> SEQ ID NO 1162
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1162
ccggcacucu gccagcguct t                                              21

<210> SEQ ID NO 1163
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1163
ucggucccgg cacucugcct t                                              21

<210> SEQ ID NO 1164
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1164
ucauacaugg ccagucggut t                                              21

```
<210> SEQ ID NO 1165
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1165
ccggccacgu cauacauggt t                                              21

<210> SEQ ID NO 1166
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1166
ucuccagggg cccggccact t                                              21

<210> SEQ ID NO 1167
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1167
augagccucu ucuccagggt t                                              21

<210> SEQ ID NO 1168
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1168
gaggugauga gccucuuucut t                                             21

<210> SEQ ID NO 1169
<211> LENGTH: 21
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1169
ugcagccgua caccgaggut t                                              21

<210> SEQ ID NO 1170
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1170
uccuggcggc ugcagccgut t                                              21

<210> SEQ ID NO 1171
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1171
accacgggcu ccuggcggct t                                              21

<210> SEQ ID NO 1172
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1172
agaaccucca ccacgggcut t                                              21

<210> SEQ ID NO 1173
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

<400> SEQUENCE: 1173
ccgacgccag aaccuccact t                    21

<210> SEQ ID NO 1174
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1174
augauggccc ccgacgccat t                    21

<210> SEQ ID NO 1175
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1175
cagacgaccg ccaugauggt t                    21

<210> SEQ ID NO 1176
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1176
ccuucuucca gacgaccgct t                    21

<210> SEQ ID NO 1177
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1177
cugugcaggc ccuucuucct t                    21

<210> SEQ ID NO 1178

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1178
gucguaguag cugugcaggt t                                              21

<210> SEQ ID NO 1179
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1179
agcacgaagg ggucguagut t                                              21

<210> SEQ ID NO 1180
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1180
ugcacggaga gcacgaaggt t                                              21

<210> SEQ ID NO 1181
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1181
aagaccaccg gcugcacggt t                                              21

<210> SEQ ID NO 1182
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<220> FEATURE:
<221> NAME/KEY: source
<223> OTHER INFORMATION: /note="Description of Combined DNA/RNA
      Molecule: Synthetic oligonucleotide"

<400> SEQUENCE: 1182
caggccugga agaccaccgt t                                              21

<210> SEQ ID NO 1183
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1183
agguucacuu cacaggccut t                                              21

<210> SEQ ID NO 1184
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1184
uccagcguca gguucacuut t                                              21

<210> SEQ ID NO 1185
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1185
gagccuguug uccagcguct t                                              21

<210> SEQ ID NO 1186
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1186
ugggagucga gccuguugut t                                              21

<210> SEQ ID NO 1187
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1187
cugaggacgc ccugggagut t                                              21

<210> SEQ ID NO 1188
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1188
uagcugggga aguacggggt t                                              21

<210> SEQ ID NO 1189
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1189
gcgaguagua gcuggggaat t                                              21

<210> SEQ ID NO 1190
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1190
uggguuuggg gcgaguagut t                                              21

<210> SEQ ID NO 1191
<211> LENGTH: 21
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1191
caggagcagu ggguuugggt t                                              21

<210> SEQ ID NO 1192
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1192
accgugaggu gccaggagct t                                              21

<210> SEQ ID NO 1193
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1193
agagagggca ccgugaggut t                                              21

<210> SEQ ID NO 1194
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1194
caagccguag uccagagagt t                                              21

<210> SEQ ID NO 1195
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

Molecule: Synthetic oligonucleotide"

<400> SEQUENCE: 1195
agagggccaa gccguaguct t                                               21

<210> SEQ ID NO 1196
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1196
uaggcaucaa accagagggt t                                               21

<210> SEQ ID NO 1197
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1197
cagugcauag gcaucaaact t                                               21

<210> SEQ ID NO 1198
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1198
acuucugccu ccucagugct t                                               21

<210> SEQ ID NO 1199
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1199
aaaucauacu ucugccucct t                                               21

```
<210> SEQ ID NO 1200
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1200
ugggugcacg gcaaaucaut t                                              21

<210> SEQ ID NO 1201
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1201
uccacuggcc cugggugcat t                                              21

<210> SEQ ID NO 1202
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1202
uucuggaucg uccacuggct t                                              21

<210> SEQ ID NO 1203
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1203
cuccuguucu ggaucgucct t                                              21

<210> SEQ ID NO 1204
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

```
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1204
aagccacaca gccuccugut t                                              21

<210> SEQ ID NO 1205
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1205
ggaugcgcaa gccacacagt t                                              21

<210> SEQ ID NO 1206
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1206
uagggcugca ggaugcgcat t                                              21

<210> SEQ ID NO 1207
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1207
auccucucgg cguagggcut t                                              21

<210> SEQ ID NO 1208
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1208
```

-continued

```
accacgggga uccucucggt t                                      21

<210> SEQ ID NO 1209
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1209
ccggccgugg ccaccacggt t                                      21

<210> SEQ ID NO 1210
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1210
auggugaucc cggccguggt t                                      21

<210> SEQ ID NO 1211
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1211
gugaaguuga uggugaucct t                                      21

<210> SEQ ID NO 1212
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1212
aucugggagg ugaaguugat t                                      21

<210> SEQ ID NO 1213
<211> LENGTH: 21
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1213
ccggugaggg agaucugggt t                                            21

<210> SEQ ID NO 1214
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1214
acaccgggcc cggugagggt t                                            21

<210> SEQ ID NO 1215
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1215
agugcacccg cacaccgggt t                                            21

<210> SEQ ID NO 1216
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1216
uccgacuggu uguacaagct t                                            21

<210> SEQ ID NO 1217
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 1217
caggggaccg acugguugut t                                              21

<210> SEQ ID NO 1218
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1218
aacucuccag ggcagggut t                                               21

<210> SEQ ID NO 1219
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1219
aacagaggaa cucuccaggt t                                              21

<210> SEQ ID NO 1220
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1220
aguccauuca cagaacagat t                                              21

<210> SEQ ID NO 1221
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1221
agggacacag aguccauuct t                                              21
```

<210> SEQ ID NO 1222
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 1222
aucacaggca gggacacagt t                                              21

<210> SEQ ID NO 1223
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 1223
uugaccccau cacaggcagt t                                              21

<210> SEQ ID NO 1224
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 1224 guugggcag uccuugacct t                                               21

<210> SEQ ID NO 1225
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 1225
cauccaggcc guugggcat t                                               21

<210> SEQ ID NO 1226
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1226
guuucucuca uccaggccgt t                                            21

<210> SEQ ID NO 1227
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1227
ugcaaacgca guuucucuct t                                            21

<210> SEQ ID NO 1228
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1228
uggaaugugg cucugcaaat t                                            21

<210> SEQ ID NO 1229
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1229
cuuugcacug gaauguggct t                                            21

<210> SEQ ID NO 1230
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

```
<400> SEQUENCE: 1230
ugugcugucc ucuuugcact t                                              21

<210> SEQ ID NO 1231
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1231
agaugcaugu gcuguccuct t                                              21

<210> SEQ ID NO 1232
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1232
accuugggca gugagaugct t                                              21

<210> SEQ ID NO 1233
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1233
cccaucacag accuugggct t                                              21

<210> SEQ ID NO 1234
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1234
aaucaggcug cccaucacat t                                              21

<210> SEQ ID NO 1235
<211> LENGTH: 21
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1235
guugagacaa ucaggcugct t                                              21

<210> SEQ ID NO 1236
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1236
ucgucgcugc cguugagact t                                              21

<210> SEQ ID NO 1237
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1237
uggcacugcu cuucgucgct t                                              21

<210> SEQ ID NO 1238
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1238
accccuuccu ggcacugcut t                                              21

<210> SEQ ID NO 1239
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

<221> NAME/KEY: source
<223> OTHER INFORMATION: /note="Description of Combined DNA/RNA
      Molecule: Synthetic oligonucleotide"

<400> SEQUENCE: 1239
ucccacaugg caccccuuct t          21

<210> SEQ ID NO 1240
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1240
aggugaaugu cccacauggt t          21

<210> SEQ ID NO 1241
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1241
ucacacugga aggugaaugt t          21

<210> SEQ ID NO 1242
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1242
agcuccgguc cucacacugt t          21

<210> SEQ ID NO 1243
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1243
ucuucacgca gcuccgguct t          21

<210> SEQ ID NO 1244
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1244
guugggcuuc uucacgcagt t                                            21

<210> SEQ ID NO 1245
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1245
ucacacugcg gguugggcut t                                            21

<210> SEQ ID NO 1246
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1246
cgggccgccc aucacacugt t                                            21

<210> SEQ ID NO 1247
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1247
gucccugcag ucgggccgct t                                            21

<210> SEQ ID NO 1248
<211> LENGTH: 21
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1248
auccgagccg ucccugcagt t                                              21

<210> SEQ ID NO 1249
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1249
ugcuccucau ccgagccgut t                                              21

<210> SEQ ID NO 1250
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1250
acagucacag ugcuccucat t                                              21

<210> SEQ ID NO 1251
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1251
cuggaggcca cagucacagt t                                              21

<210> SEQ ID NO 1252
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

<400> SEQUENCE: 1252
cuggaggggc ccuggaggct t                                              21

<210> SEQ ID NO 1253
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1253
aacaaugcgg cuggaggggt t                                              21

<210> SEQ ID NO 1254
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1254
agcuccacca acaaugcggt t                                              21

<210> SEQ ID NO 1255
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1255
ucggaggaca cagcuccact t                                              21

<210> SEQ ID NO 1256
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1256
uggccacuca cccucggagt t                                              21

<210> SEQ ID NO 1257

-continued

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1257
cugccauggc cacucaccct t                                              21

<210> SEQ ID NO 1258
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1258
cuggaggcug gccugccaut t                                              21

<210> SEQ ID NO 1259
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1259
ucgaccccga accuggaggt t                                              21

<210> SEQ ID NO 1260
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1260
gaugugucga ccccgaacct t                                              21

<210> SEQ ID NO 1261
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 1261 agggccccc cacagaugut t                                                    21

<210> SEQ ID NO 1262
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1262
gcgaugaggg cccccccact t                                                   21

<210> SEQ ID NO 1263
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1263
ucacccagcg gucagcgaut t                                                   21

<210> SEQ ID NO 1264
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1264
gcuguuauca cccagcggut t                                                   21

<210> SEQ ID NO 1265
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1265
```

```
cagugggcag cuguuaucat t                                        21
```

<210> SEQ ID NO 1266
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1266

```
uccuccugga agcagugggt t                                        21
```

<210> SEQ ID NO 1267
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1267

```
ggccaugcug uccuccuggt t                                        21
```

<210> SEQ ID NO 1268
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1268

```
accguggagg ccaugcugut t                                        21
```

<210> SEQ ID NO 1269
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1269

```
acgguccaca gcaccguggt t                                        21
```

<210> SEQ ID NO 1270
<211> LENGTH: 21
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1270
uugcccagga acacgguccu t                                              21

<210> SEQ ID NO 1271
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1271
ugccacaccu ugcccaggat t                                              21

<210> SEQ ID NO 1272
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1272
agcgcgaguu cugccacact t                                              21

<210> SEQ ID NO 1273
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1273
uccaggccag cgcgaguuct t                                              21

<210> SEQ ID NO 1274
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

Molecule: Synthetic oligonucleotide"

<400> SEQUENCE: 1274
aaggacaccu cuccaggcct t                                    21

<210> SEQ ID NO 1275
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1275
cucaccuuga aggacaccut t                                    21

<210> SEQ ID NO 1276
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1276
gagcaggcgg cucaccuugt t                                    21

<210> SEQ ID NO 1277
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1277
uacgggugca ggagcaggct t                                    21

<210> SEQ ID NO 1278
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1278
cucuucgugg uacgggugct t                                    21

-continued

<210> SEQ ID NO 1279
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1279
auggcugucc ucuucguggt t                                            21

<210> SEQ ID NO 1280
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1280
ucguagucau ggcuguccut t                                            21

<210> SEQ ID NO 1281
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1281
agcagcgcca cgucguagut t                                            21

<210> SEQ ID NO 1282
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1282
ucgagcugca gcagcgccat t                                            21

<210> SEQ ID NO 1283
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:

```
          Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1283
accaccgggu ggucgagcut t                                              21

<210> SEQ ID NO 1284
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1284
cggccgagcg caccaccggt t                                              21

<210> SEQ ID NO 1285
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1285
cgcacggcgg ccgagcgcat t                                              21

<210> SEQ ID NO 1286
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1286
aggcagacgg ggcgcacggt t                                              21

<210> SEQ ID NO 1287
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1287
```
cgcgcgggca ggcagacggt t                                              21

<210> SEQ ID NO 1288
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1288
aagaaguggg agcgcgcggt t                                              21

<210> SEQ ID NO 1289
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1289
ccgggcucga agaagugggt t                                              21

<210> SEQ ID NO 1290
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1290
agcagugcag gccgggcuct t                                              21

<210> SEQ ID NO 1291
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1291
uaauccagca gugcaggcct t                                              21

<210> SEQ ID NO 1292
<211> LENGTH: 21
<212> TYPE: DNA

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1292
cgccccagcc cguaauccat t                                                    21

<210> SEQ ID NO 1293
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1293
ucgcgcaagg cgccccagct t                                                    21

<210> SEQ ID NO 1294
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1294
auggggccgc ccucgcgcat t                                                    21

<210> SEQ ID NO 1295
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1295
uugcugaugg ggccgcccut t                                                    21

<210> SEQ ID NO 1296
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

<223> OTHER INFORMATION: /note="Description of Combined DNA/RNA
      Molecule: Synthetic oligonucleotide"

<400> SEQUENCE: 1296
uucugcagag cguugcugat t                                              21

<210> SEQ ID NO 1297
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1297
ugcacaucca cuuucugcat t                                              21

<210> SEQ ID NO 1298
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1298
aucaacugca cauccacuut t                                              21

<210> SEQ ID NO 1299
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1299
guccuguggg aucaacugct t                                              21

<210> SEQ ID NO 1300
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1300
ucgcugcaca gguccugugt t                                              21

```
<210> SEQ ID NO 1301
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1301
uagcgauaga ccucgcugct t                                              21

<210> SEQ ID NO 1302
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1302
ucaccuggua gcgauagact t                                              21

<210> SEQ ID NO 1303
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1303
caugcguggc gucaccuggt t                                              21

<210> SEQ ID NO 1304
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1304
cggcacacag caugcguggt t                                              21

<210> SEQ ID NO 1305
<211> LENGTH: 21
<212> TYPE: DNA
<213> ORGANISM: Artificial Sequence
<220> FEATURE:
<221> NAME/KEY: source
```

-continued

<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1305
ugcgguagcc ggcacacagt t					21

<210> SEQ ID NO 1306
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1306
uccuucuugc ccuugcggut t					21

<210> SEQ ID NO 1307
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1307
ugacaggcau ccuucuugct t					21

<210> SEQ ID NO 1308
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1308
cugagucacc cugacaggct t					21

<210> SEQ ID NO 1309
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1309
agcggaccac cugagucact t						21

<210> SEQ ID NO 1310
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1310
uugcacacca gcggaccact t						21

<210> SEQ ID NO 1311
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1311
cugagugccu ugcacaccat t						21

<210> SEQ ID NO 1312
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1312
accagcggcc acugagugct t						21

<210> SEQ ID NO 1313
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1313
cccgccagga accagcggct t						21

<210> SEQ ID NO 1314
<211> LENGTH: 21

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1314
cugaccagcc ccgccaggat t                                              21

<210> SEQ ID NO 1315
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1315
caggccccag cugaccagct t                                              21

<210> SEQ ID NO 1316
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1316
ccggccacag cccaggccct t                                              21

<210> SEQ ID NO 1317
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1317
aguuaggccg gccacagcct t                                              21

<210> SEQ ID NO 1318
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 1318
uagacgccga aguaguuagt t                                              21

<210> SEQ ID NO 1319
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1319
gaugcgggug uagacgccgt t                                              21

<210> SEQ ID NO 1320
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1320
acaccuguga ugcgggugut t                                              21

<210> SEQ ID NO 1321
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1321
uccagcugau cacaccugut t                                              21

<210> SEQ ID NO 1322
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1322
acuugcugga uccagcugat t                                              21
```

<210> SEQ ID NO 1323
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1323
cucaggucac cacuugcugt t                                              21

<210> SEQ ID NO 1324
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1324
ggggcaguuc cucaggucat t                                              21

<210> SEQ ID NO 1325
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1325
uuugcagggg ggcaguucct t                                              21

<210> SEQ ID NO 1326
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1326
ggugggcccu gcuuugcagt t                                              21

<210> SEQ ID NO 1327
<211> LENGTH: 21
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1327
uccaggaggu gggcccugct t                                              21

<210> SEQ ID NO 1328
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1328
gcucucugag uccaggaggt t                                              21

<210> SEQ ID NO 1329
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1329
uugcccuggg cucucugagt t                                              21

<210> SEQ ID NO 1330
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligoncueotide"

<400> SEQUENCE: 1330
ugcuuggcag uugcccuggt t                                              21

<210> SEQ ID NO 1331
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

<400> SEQUENCE: 1331
cccgccagaa uacuugucct t                                                  21

<210> SEQ ID NO 1332
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1332 cuccccacc ccccgccagt t                                                   21

<210> SEQ ID NO 1333
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1333
ccugcucucu cccccaccct t                                                  21

<210> SEQ ID NO 1334
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1334
accacagggc cugcucucut t                                                  21

<210> SEQ ID NO 1335
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1335
accuccugcc accacagggt t                                                  21

<210> SEQ ID NO 1336

-continued

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1336
gagacaagau gccaccucct t                                              21

<210> SEQ ID NO 1337
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1337
ucagggacga gacaagaugt t                                              21

<210> SEQ ID NO 1338
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1338
acuggagcag acaucagggt t                                              21

<210> SEQ ID NO 1339
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1339
ccugccauca cuggagcagt t                                              21

<210> SEQ ID NO 1340
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 1340
uucuccaucc uccugccaut t                                              21

<210> SEQ ID NO 1341
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1341
ugcuggcacu ucuccaucct t                                              21

<210> SEQ ID NO 1342
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1342 ugaccccag cugcuggcat t                                               21

<210> SEQ ID NO 1343
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1343
gacgucuuga cccccagcut t                                              21

<210> SEQ ID NO 1344
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1344
```
uccucagggg acgucuugat t                                          21

<210> SEQ ID NO 1345
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1345
ugggccuggg uccucagggt t                                          21

<210> SEQ ID NO 1346
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1346
agaagggcug gguguggct t                                           21

<210> SEQ ID NO 1347
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1347
auugggaggc agaagggcut t                                          21

<210> SEQ ID NO 1348
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1348
aggagagaga auugggaggt t                                          21

<210> SEQ ID NO 1349
<211> LENGTH: 21
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1349
aaggggacgg aggagagagt t                                              21

<210> SEQ ID NO 1350
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1350
aguggaggaa ggggacggat t                                              21

<210> SEQ ID NO 1351
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1351
uaggcagcag uggaggaagt t                                              21

<210> SEQ ID NO 1352
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1352
acugccuugc auuaggcagt t                                              21

<210> SEQ ID NO 1353
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

```
                  Molecule: Synthetic oligonucleotide"

<400> SEQUENCE: 1353
ugcugagcca cugccuugct t                                              21

<210> SEQ ID NO 1354
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1354
cauucuugcu gcugagccat t                                              21

<210> SEQ ID NO 1355
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1355
uguagaacca gcauucuugt t                                              21

<210> SEQ ID NO 1356
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1356
uccucgggau guagaaccat t                                              21

<210> SEQ ID NO 1357
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1357
accucagaca cuccucgggt t                                              21
```

-continued

<210> SEQ ID NO 1358
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 1358 agugggggcgc accucagact t                                        21

<210> SEQ ID NO 1359
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 1359
ccucuguaca gaguggggct t                                         21

<210> SEQ ID NO 1360
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 1360
ccaaacagcc ucuguacagt t                                         21

<210> SEQ ID NO 1361
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 1361
ggcaaggcug cccaaacagt t                                         21

<210> SEQ ID NO 1362
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:

```
                              Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1362
ucugcucucu ggaggcaagt t                                                    21

<210> SEQ ID NO 1363
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1363
cuggaaucug cucucuggat t                                                    21

<210> SEQ ID NO 1364
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1364
ggcuuccgaa gcuggaauct t                                                    21

<210> SEQ ID NO 1365
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1365
augggagcac cuuccauuct t                                                    21

<210> SEQ ID NO 1366
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1366
```
uccccuccga ugggagcact t                               21

<210> SEQ ID NO 1367
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1367
cucugagggu ccccuccgat t                               21

<210> SEQ ID NO 1368
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1368
gucuccaggg cucugagggt t                               21

<210> SEQ ID NO 1369
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1369
aggcccaccu ggcagucuct t                               21

<210> SEQ ID NO 1370
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1370
aguggcagca ggcccaccut t                               21

<210> SEQ ID NO 1371
<211> LENGTH: 21
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1371
uuuuggcuua caguggcagt t                                               21

<210> SEQ ID NO 1372
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1372
cccaccuuuu ggcuuacagt t                                               21

<210> SEQ ID NO 1373
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1373
ggagucagga cuuccccact t                                               21

<210> SEQ ID NO 1374
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1374
caaggacccu ggagucaggt t                                               21

<210> SEQ ID NO 1375
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

-continued

<223> OTHER INFORMATION: /note="Description of Combined DNA/RNA
      Molecule: Synthetic oligonucleotide"

<400> SEQUENCE: 1375 aggggtggggg caaggaccct t                                              21

<210> SEQ ID NO 1376
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1376
uggcaggcag gggugggct t                                                21

<210> SEQ ID NO 1377
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1377
ugagggccca gguggcaggt t                                               21

<210> SEQ ID NO 1378
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1378
cugggcugug agggcccagt t                                               21

<210> SEQ ID NO 1379
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<220> FEATURE:
<221> NAME/KEY: source
<223> OTHER INFORMATION: /note="Description of Combined DNA/RNA
      Molecule: Synthetic oligonucleotide"

<400> SEQUENCE: 1379
gugagggucu gggcugugat t                                              21

<210> SEQ ID NO 1380
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1380
gagcucaccu cccagugagt t                                              21

<210> SEQ ID NO 1381
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1381
aagggcagcu gagcucacct t                                              21

<210> SEQ ID NO 1382
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1382
aucaggcagc uuuauuccat t                                              21
```